(12) United States Patent
Sumi

(10) Patent No.: US 9,326,748 B2
(45) Date of Patent: *May 3, 2016

(54) CLINICAL APPARATUSES

(76) Inventor: Chikayoshi Sumi, Tokorozawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,779

(22) Filed: Jun. 25, 2012

(65) Prior Publication Data

US 2012/0278005 A1 Nov. 1, 2012

Related U.S. Application Data

(63) Continuation of application No. 11/334,089, filed on Jan. 18, 2006, now Pat. No. 8,211,019.

(30) Foreign Application Priority Data

| Jan. 21, 2005 | (JP) | 2005-014774 |
| Jan. 26, 2005 | (JP) | 2005-018871 |
| Feb. 14, 2005 | (JP) | 2005-036466 |
| May 11, 2005 | (JP) | 2005-138825 |
| Aug. 17, 2005 | (JP) | 2005-236918 |
| Nov. 9, 2005 | (JP) | 2005-324413 |

(51) Int. Cl.
*A61B 8/08* (2006.01)
*G01S 7/52* (2006.01)
*G01S 15/89* (2006.01)
(Continued)

(52) U.S. Cl.
CPC .................. *A61B 8/08* (2013.01); *A61B 5/0051* (2013.01); *A61B 5/0053* (2013.01); *A61B 5/7239* (2013.01); *A61B 8/485* (2013.01); *G01S 7/52042* (2013.01); *G01S 7/52095* (2013.01);
(Continued)

(58) Field of Classification Search
CPC ........ A61B 8/08; A61B 8/485; A61B 5/7239; A61B 7/52095; A61B 5/0051; A61B 5/015; G01S 7/52042; G01S 7/52095; G01S 15/8906; G01S 15/8984; G01S 15/582
USPC .............. 600/442–443, 449, 437; 73/789–860
See application file for complete search history.

(56) References Cited

U.S. PATENT DOCUMENTS 5,460,178 A 10/1995 Hudon et al.
5,555,534 A 9/1996 Maslak et al.
(Continued)

FOREIGN PATENT DOCUMENTS

| JP | 07-055775 | 3/1995 |
| JP | 2001-518342 | 10/2001 |
| WO | WO 99/17660 | 4/1999 |

*Primary Examiner* — Bo J Peng
(74) *Attorney, Agent, or Firm* — Holtz, Holtz & Volek PC

(57) ABSTRACT

A clinical apparatus includes a storage to store strain data, strain rate data, or acceleration data measured in a ROI (region of interest); and a data processor to calculate a stress, a stress tensor, a stress tensor component, an inertia, a mean normal stress, a pressure, a mechanical source, an elastic constant, a visco elastic constant, a viscosity, or a density of an arbitrary point within the ROI. The data processor calculates the stress, the stress tensor, the stress tensor component, the inertia, the mean normal stress, the pressure, or the mechanical source based on an equation representing a relation between (i) the stress, the stress tensor, the stress tensor component, the inertia, the mean normal stress, the pressure, or the mechanical source, (ii) the elastic constant, the visco elastic constant, the viscosity, or the density, and (iii) the measured strain data, the strain rate data, or the acceleration data.

29 Claims, 26 Drawing Sheets

(51) Int. Cl.
*A61B 5/00* (2006.01)
*A61B 5/01* (2006.01)
*G01S 15/58* (2006.01)

(52) U.S. Cl.
CPC ......... *G01S15/8906* (2013.01); *G01S 15/8984* (2013.01); *A61B 5/015* (2013.01); *G01S 15/582* (2013.01)

(56) References Cited

U.S. PATENT DOCUMENTS

| | | |
|---|---|---|
| 6,213,947 B1 | 4/2001 | Phillips |
| 2004/0034304 A1 | 2/2004 | Sumi |
| 2006/0052696 A1* | 3/2006 | Shiina et al. ................ 600/437 |
| 2006/0058661 A1 | 3/2006 | Hirama |

* cited by examiner

FIG.2
ULTRASOUND
OSCILLATOR
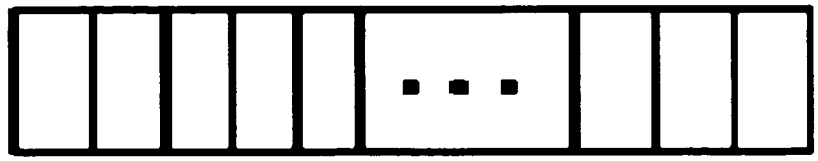
1D ARRAYED ULTRASOUND OSCILLATORS
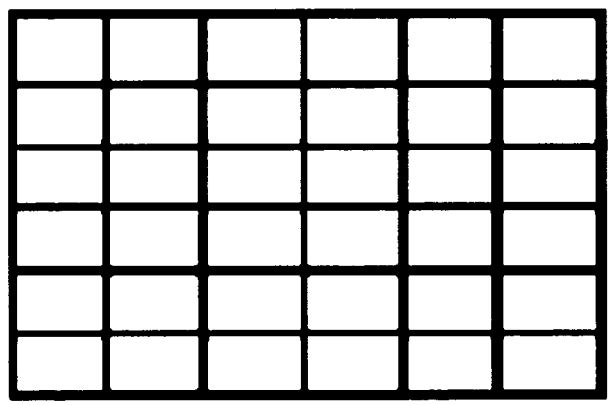
2D ARRAYED ULTRASOUND OSCILLATORS

METHOD 1-3 (METHOD 2-3, METHOD 3-3) : START OF MEASUREMENT OF DISPLACEMENT VECTOR DISTRIBUTION d(x,y,z) IN SOI, ROI (i = 1)

---

PROCESS 1: AT EACH POINT (x,y,z) IN SOI, ROI
- PROCESS 1 OF METHOD 1-1 (2-1, 3-1):
  PHASE MATCHING USING (SMOOTHED) I-1TH ESTIMATE $D_{i-1}$
  ($D_0$: INITIAL VALUE)
- PROCESS 2 OF METHOD 1-1 (2-1, 3-1):
  ESTIMATE OF RESIDUAL DISPLACEMENT VECTOR $u_i$
- POSSIBILITY OF DIVERGENCE OF PHASE MATCHING IN SOI, ROI?
        YES => PROCESS 2
        NO:  => METHOD 1-1 (2-1, 3-1)

---

PROCESS 2: UPDATE OF ESTIMATE
       OF DISPLACEMENT VECTOR DISTRIBUTION:
- $d_i(x,y,z)$ = (SMOOTHED) $d_{i-1}(x,y,z)$ + $u_i(x,y,z)$
- SMOOTHING OF $d_i(x,y,z)$
     [LOW PASS FILTERING, MEDIAN FILTERING]
   OVER SOI, ROI,
  OR OVER SPACE, REGION CENTERED ON THE SPACE, REGION
   WHERE THE POSSIBILITY IS DETECTED

---

PROCESS 3: MAKE SPATIAL RESOLUTION HIGH ?
     YES: MAKE LOCAL REGION SIZE SMALL
     NO:  LEAVE LOCAL REGION SIZE

---

PROCESS 4: TERMINATE OF ITERATIVE ESTIMATION ?
    YES:                  => END
    NO: i = i + 1         => PROCESS 1

FIG.13

```
┌─────────────────────────────────────────────────────────────┐
│ METHOD 1-4 (METHOD 2-4, METHOD 3-4): START OF MEASUREMENT   │
│ OF DISPLACEMENT VECTOR DISTRIBUTION d(x,y,z) IN SOI, ROI    │
│ (i = 1)                                                     │
└─────────────────────────────────────────────────────────────┘
                              ↓
┌─────────────────────────────────────────────────────────────┐
│ PROCESS 1: AT EACH POINT (x,y,z) IN SOI, ROI                │
│   · PROCESS 1 OF METHOD 1-1 (2-1, 3-1):                     │
│       PHASE MATCHING USING (SMOOTHED) i-1TH ESTIMATE $d_{i-1}$ │
│       ($d_0$: INITIAL VALUE)                                │
│   · ESTIMATE OF RESIDUAL DISPLACEMENT VECTOR                │
│     DISTRIBUTION $u_i(x,y,z)$ UTILIZING LEAST-SQUARES       │
│     METHOD, REGULARIZATION METHOD                           │
│       TO COPE WITH LARGE DISPLACEMENT:                      │
│         (i)   UNWRAP OF PHASE                               │
│         (ii)  UTILIZATION OF CROSS-CORRELATION METHOD       │
│         (iii) THIN OUT ULTRASOUND DATA                      │
└─────────────────────────────────────────────────────────────┘
                              ↓
┌─────────────────────────────────────────────────────────────┐
│ PROCESS 2: UPDATE OF ESTIMATE                               │
│             OF DISPLACEMENT VECTOR DISTRIBUTION:            │
│   · $d_i(x,y,z)$ = (SMOOTHED) $d_{i-1}(x,y,z)$ + $u_i(x,y,z)$ │
│   · OCCASIONALLY, SMOOTHING OF $d_i(x,y,z)$                 │
│         [LOW PASS FILTERING, MEDIAN FILTERING]              │
└─────────────────────────────────────────────────────────────┘
                              ↓
┌─────────────────────────────────────────────────────────────┐
│ PROCESS 3: MAKE SPATIAL RESOLUTION HIGH ?                   │
│         YES: MAKE LOCAL REGION SIZE SMALL                   │
│         NO:  LEAVE LOCAL REGION SIZE                        │
└─────────────────────────────────────────────────────────────┘
                              ↓
┌─────────────────────────────────────────────────────────────┐
│ PROCESS 4: TERMINATE OF ITERATIVE ESTIMATION ?              │
│         YES:                => END                          │
│         NO:  i = i + 1      => PROCESS 1                    │
└─────────────────────────────────────────────────────────────┘
```

FIG.21

```
START OF MEASUREMENT OF DISPLACEMENT VECTOR DISTRIBUTION
IN SOI, ROI
TARGET OF METHOD 4-1, METHOD 5-1: SPACE OF INTEREST (SOI)
TARGET OF METHOD 6-1: REGION OF INTEREST (ROI)
```
↓
```
PROCESS 1: AT EACH ROI OR LINE OF INTEREST
    2D DISPLACEMENT VECTOR MEASUREMENT IN 2D ROI
            (METHOD 2-1 OR 2-2 OR 2-3 OR 2-4 OR 2-5)
  OR
    ONE DIRECTION DISPLACEMENT COMPONENT DISTRIBUTION IN
    1D ROI (METHOD 3-1 OR 3-2 OR 3-3 OR 3-4 OR 3-5)
```
↓
```
MEASUREMENT OVER SOI, ROI
```

START OF MEASUREMENT OF DISPLACEMENT VECTOR DISTRIBUTION
d(x,y,z) IN SOI, ROI (i = 1)
METHOD 4-2 BASED ON METHOD 2-2 (2D DISPLACEMENT VECTOR
      MEASUREMENT IN 2D ROI)
METHOD 5-2 BASED ON METHOD 3-2 (ONE DIRECTION
      DISPLACEMENT COMPONENT DISTRIBUTION IN 1D ROI)
METHOD 6-2 BASED ON METHOD 3-2

---

PROCESS 1:
TARGET OF METHOD 4-2, METHOD 5-2: SPACE OF INTEREST (SOI)
TARGET OF METHOD 6-2: REGION OF INTEREST (ROI)

AT EACH POINT (x,y,z) IN SOI, ROI
    PROCESS 1 OF METHOD 2-1, 3-1:
        PHASE MATCHING USING (SMOOTHED) i-1TH ESTIMATE
        $d_{i-1}(x,y,z)$ ($d_0(x,y,z)$: INITIAL VALUE)
    ESTIMATE OF RESIDUAL DISPLACEMENT VECTOR $u_i(x,y,z)$
THUS, RESIDUAL DISPLACEMENT VECTOR DISTRIBUTION
$u_i(x,y,z)$ IS OBTAINED IN SOI, ROI.

---

PROCESS 2: UPDATE OF ESTIMATE
           OF DISPLACEMENT VECTOR DISTRIBUTION:
  · $d_i(x,y,z)$ = (SMOOTHED) $d_{i-1}(x,y,z)$ + $u_i(x,y,z)$
  · SMOOTHING OF $d_i(x,y,z)$
        [LOW PASS FILTERING, MEDIAN FILTERING]

---

PROCESS 3: MAKE SPATIAL RESOLUTION HIGH ?
        YES: MAKE LOCAL REGION SIZE SMALL
        NO:  LEAVE LOCAL REGION SIZE

---

PROCESS 4: TERMINATE OF ITERATIVE ESTIMATION ?
    YES:                  => END
    NO:  i = i + 1   => PROCESS 1

FIG.23

```
START OF MEASUREMENT OF DISPLACEMENT VECTOR DISTRIBUTION
d(x,y,z) IN SOI, ROI (i = 1)
METHOD 4-3 BASED ON METHOD 2-3 (2D DISPLACEMENT VECTOR
     MEASUREMENT IN 2D ROI)
METHOD 5-3 BASED ON METHOD 3-3 (ONE DIRECTION
     DISPLACEMENT COMPONENT DISTRIBUTION IN 1D ROI)
METHOD 6-3 BASED ON METHOD 3-3
```
↓
```
PROCESS 1:
   TARGET OF METHOD 4-3, METHOD 5-3: SPACE OF INTEREST (SOI)
   TARGET OF METHOD 6-3: REGION OF INTEREST (ROI)

· AT EACH POINT (x,y,z) IN SOI, ROI

PROCESS 1 OF METHOD 2-1, 3-1:
       PHASE MATCHING USING (SMOOTHED) i-1TH ESTIMATE
       di-1(x,y,z)  (d0(x,y,z): INITIAL VALUE)
   ESTIMATE OF RESIDUAL DISPLACEMENT VECTOR ui(x,y,z)
THUS, RESIDUAL DISPLACEMENT VECTOR DISTRIBUTION
ui(x,y,z) IS OBTAINED IN SOI, ROI.

·POSSIBILITY OF DIVERGENCE OF PHASE MATCHING
   IN SOI, ROI?
          YES  =>  PROCESS 2
          NO:  =>  METHOD 4-1 (5-1, 6-1)
```
↓
```
PROCESS 2: UPDATE OF ESTIMATE
            OF DISPLACEMENT VECTOR DISTRIBUTION:

· di(x,y,z) = (SMOOTHED) di-1(x,y,z) + ui(x,y,z)

· SMOOTHING OF di(x,y,z)
       [LOW PASS FILTERING, MEDIAN FILTERING]
```
↓
```
PROCESS 3: MAKE SPATIAL RESOLUTION HIGH ?
         YES: MAKE LOCAL REGION SIZE SMALL
         NO:  LEAVE LOCAL REGION SIZE
```
↓
```
PROCESS 4: TERMINATE OF ITERATIVE ESTIMATION ?
       YES:                  =>  END
       NO:  i = i + 1        =>  PROCESS 1
```

FIG.24

START OF MEASUREMENT OF DISPLACEMENT VECTOR DISTRIBUTION
d(x,y,z) IN SOI, ROI (i = 1)
METHOD 4-4 BASED ON METHOD 2-4 (2D DISPLACEMENT VECTOR
    MEASUREMENT IN 2D ROI)
METHOD 5-4 BASED ON METHOD 3-4 (ONE DIRECTION
    DISPLACEMENT COMPONENT DISTRIBUTION IN 1D ROI)
METHOD 6-4 BASED ON METHOD 3-4

PROCESS 1:
- AT EACH POINT (x,y,z) IN SOI, ROI
    PROCESS 1 OF METHOD 2-1, 3-1:
        PHASE MATCHING USING (SMOOTHED) i-1TH ESTIMATE
        $d_{i-1}(x,y,z)$ ($d_0(x,y,z)$: INITIAL VALUE)
- ESTIMATE OF RESIDUAL DISPLACEMENT VECTOR
    DISTRIBUTION $u_i(x,y,z)$ IN SOI, ROI UTILIZING
    LEAST-SQUARES METHOD, REGULARIZATION METHOD

PROCESS 2: UPDATE OF ESTIMATE
            OF DISPLACEMENT VECTOR DISTRIBUTION:
- $d_i(x,y,z)$ = (SMOOTHED) $d_{i-1}(x,y,z)$ + $u_i(x,y,z)$
- OCCASIONALLY, SMOOTHING OF $d_i(x,y,z)$
    [LOW PASS FILTERING, MEDIAN FILTERING]

PROCESS 3: MAKE SPATIAL RESOLUTION HIGH ?
        YES: MAKE LOCAL REGION SIZE SMALL
        NO:  LEAVE LOCAL REGION SIZE

PROCESS 4: TERMINATE OF ITERATIVE ESTIMATION ?
        YES:              => END
        NO: i = i + 1    => PROCESS 1

FIG.25

```
START OF MEASUREMENT OF DISPLACEMENT VECTOR DISTRIBUTION
d(x,y,z) IN SOI, ROI (i = 1)
METHOD 4-5 BASED ON METHOD 2-5 (2D DISPLACEMENT VECTOR
      MEASUREMENT IN 2D ROI)
METHOD 5-5 BASED ON METHOD 3-5 (ONE DIRECTION
      DISPLACEMENT COMPONENT DISTRIBUTION IN 1D ROI)
METHOD 6-5 BASED ON METHOD 3-5
```

↓

```
PROCESS 1:
· AT EACH POINT (x,y,z) IN SOI, ROI
    PROCESS 1 OF METHOD 2-1, 3-1:
        PHASE MATCHING USING (SMOOTHED) i-1TH ESTIMATE
        di-1(x,y,z) (d0(x,y,z): INITIAL VALUE)
· ESTIMATE OF RESIDUAL DISPLACEMENT VECTOR
    DISTRIBUTION ui(x,y,z) IN SOI, ROI UTILIZING
    LEAST-SQUARES METHOD, REGULARIZATION METHOD
·POSSIBILITY OF DIVERGENCE OF PHASE MATCHING
    IN SOI, ROI?
          YES  =>  PROCESS 2
          NO:  =>  METHOD 4-1 (5-1, 6-1)
```

↓

```
PROCESS 2: UPDATE OF ESTIMATE
            OF DISPLACEMENT VECTOR DISTRIBUTION:
· di(x,y,z) = (SMOOTHED) di-1(x,y,z) + ui(x,y,z)
· OCCASIONALLY, SMOOTHING OF di(x,y,z)
        [LOW PASS FILTERING, MEDIAN FILTERING]
```

↓

```
PROCESS 3: MAKE SPATIAL RESOLUTION HIGH ?
        YES: MAKE LOCAL REGION SIZE SMALL
        NO:  LEAVE LOCAL REGION SIZE
```

↓

```
PROCESS 4: TERMINATE OF ITERATIVE ESTIMATION ?
      YES:                 => END
      NO:  i = i + 1       => PROCESS 1
```

CLINICAL APPARATUSES

This is a Continuation Application of U.S. application Ser. No. 11/334,089 now U.S. Pat. No. 8211019, filed Jan. 18, 2006, the entire contents of which are incorporated herein by reference.

BACKGROUND OF THE INVENTION

1. Field of the Invention

The present invention relates to apparatuses and methods for low-destructively or low-invasively measuring mechanical properties within object such as structures, substances, materials, living tissues (liver, prostate, breast, bone, etc). For instance, measured can be, due to applied stress and/or vibration by arbitrary mechanical sources, the generated displacement vector, strain tensor, strain rate tensor, acceleration vector or velocity vector within the body. Furthermore, from the measured deformation data, the following constants can be measured, i.e., elastic constants such as shear modulus, Poisson's ratio, etc., visco elastic constants such as visco shear modulus, visco Poisson's ratio, etc., delay times or relaxation times relating these elastic constants and visco elastic constants, or density.

In typical applied fields, e.g., in a medical field such as ultra sonic diagnosis, nuclear magnetic resonance diagnosis, light diagnosis, radio therapeutics, the present methods and apparatuses can be applied for monitoring tissue degeneration, i.e., treatment effectiveness. Otherwise, on structures, substances, materials, living tissues, measured static and/or dynamic mechanical properties can be utilized for evaluation, examination, diagnosis, etc.

2. Description of a Related Art

For instance, in the medical field (liver, prostate, breast, bone, etc.), lesions are proposed to be treated by cryotherapy, or by applying radioactive ray, high intensity focus ultrasound, laser, electromagnetic RF wave, microwave, etc. In these cases, the treatment effectiveness is proposed to be monitored. Moreover, chemotherapy effectiveness is also proposed to be monitored (anti-cancer drug, ethanol, etc). For instance, for radiotherapy etc., the treatment effectiveness can be monitored by low-invasively measuring degeneration (including temperature change) of the lesion. Otherwise, due to applied stress to the tissue part of interest including lesions, the generated deformations and deformation changes are measured, from which the pathological states of the tissue are evaluated such as elastic constants etc. Thus, based on the measured distinct pathological states, the part of interest is diagnosed, or treatment effectiveness is observed.

Temperature is known to have high correlations with elastic constants, visco elastic constants, delay times or relaxation times relating elastic constants and visco elastic constants, density, etc. Therefore, by measuring the following constants, the temperature distribution can be measured, i.e., elastic constants such as shear modulus, Poisson's ratio, etc., visco elastic constants such as visco shear modulus, visco Poisson's ratio, etc., delay times or relaxation times relating these elastic constants and visco elastic constants, or density.

In the past, the elastic constants and visco elastic constants have been measured by applying stresses at many points and by measuring the responses such as stresses and strains. That is, a stress meter and/or a strain meter are used, and sensitivity analysis is numerically performed with utilization of the finite difference method or finite element method. Otherwise, in addition to the elastic constants, the visco elastic constants such as visco shear modulus, visco Poisson's ratio, etc. has also been measured by estimating the shear wave propagation velocity generated by applying vibrations.

The disadvantages of the past measurement technique is that the past technique requires many independent deformation fields generated by mechanical sources outside the target body. However, if there exist internal mechanical sources and/or mechanical sources are uncontrollable, the technique becomes unavailable. That is, the past technique requires all information about mechanical sources, such as positions, force directions, force magnitudes, etc. Moreover, the technique requires stress data and strain data at the target body surface, and requires whole body model (using the finite difference method or finite element method). Furthermore, the spatial resolutions of measured elastic constants and visco elastic constants from the shear wave velocity are very low.

In other monitoring techniques for the temperature, evaluated are nuclear magnetic resonance frequencies, electric impedances, ultrasound velocities, etc. However, these techniques require other physical properties of the target tissue to measure the temperature. If the degeneration occurs in the region, the physical properties also change; thus causing severe limitations of the temperature measurement.

On the other hand, a medical ultrasound diagnosis apparatus can low-invasively image a tissue distribution by converting ultrasonic echo signals (echo signals) to images, after transmitting ultrasonic pulses to target tissue and receiving the echo signals by ultrasound transducer. Thus, by ultrasonically measuring the tissue displacements generated due to arbitrary mechanical sources or by measuring the generated tissue strains, tissue elastic constants, etc., the differences of these between lesion and normal tissue can be observed low-invasively. For instance, measured within the body can be, due to applied stress and/or vibration by arbitrary mechanical sources, the generated displacement vector, strain tensor, strain rate tensor, acceleration vector, velocity vector, etc. Furthermore, from the measured deformation data, the following constants can be measured, elastic constants such as shear modulus, Poisson's ratio, etc., visco elastic constants such as visco shear modulus, visco Poisson's ratio, etc., delay times or relaxation times relating these elastic constants and visco elastic constants, or density.

Then, in the past, the tissue displacement has been proposed to be measured to low-invasively diagnose the tissue and lesion by evaluating the echo signal changes of more than one time transmitting signal. The strain distribution is obtained from the measured displacement distribution, based on which the distribution of pathological states of tissue have been proposed to be diagnosed (Japanese Patent Application Publication JP-A-7-55775, JP-A-2001-518342). Specifically, a 3-dimensional (3D), 2D, or 1D region of interest (ROI) is set in the target body, and distributions of three, two, or one displacement components are measured, from which in addition to the strain tensor distribution, the elastic constant distributions, etc. are also numerically obtained.

In addition to the ultrasound transducer, as the displacement (strain) sensor, utilized can be known contact or non-contact sensors such as electromagnetic wave (including light) detector etc. As mechanical sources, compressor and vibrator can be, transducer-mounted apparatuses, not transducer-mounted ones, internal heart motion, respiratory motion, etc. If the ROI is deformed by ultrasound transmitted from sensor, there may not require other mechanical sources except for the sensor. In addition to the stationary elastic constants, the difference of the tissue pathological states includes dynamic changes of elastic constants, temperature due to treatment, etc.

However, as the classical tissue displacement measurement methods assume that tissue deforms or is deformed only in the axial (beam) direction, even when tissue also moves in lateral (scan) direction, the classical method has low axial displacement measurement accuracy. That is, the displacement was determined only by 1D axial processing of the ultrasound echo signals (hereafter, echo signal includes rf echo signal, quadrate detection signal, envelop detection signal, and complex signal).

Recently, the displacement accuracy is improved by us through development of 2D displacement vector measurement method, i.e., the phase gradient estimation method of the 2D echo cross-spectrum based on so-called the 2D cross-correlation processing and the least squares processing. This method can suitably cope with internal, uncontrollable mechanical sources (e.g., heart motion, respiratory motion, blood vessel motion, body motion, etc).

However, strictly speaking, the measurement accuracy of actual 3D tissue displacement becomes low because the method can measure by 2D processing of echo signals two displacement components or by 1D processing one displacement component.

Particularly, as the echo signal has a narrow bandwidth and has no carrier frequency in the lateral direction, the lateral displacement measurement accuracy and spatial resolution are much lower compared with axial ones. Thus, the low lateral measurement accuracy degrades the 3D displacement vector measurement and the 3D strain tensor measurement.

Furthermore, when a large displacement requires to be handled, before estimating the gradient of the cross-spectrum phase, i.e., the phase must be unwrapped. Otherwise, the displacement must be coarsely estimated by cross-correlation method as the multiples of sampling intervals. Thus, the measurement process had become complex one.

SUMMARY OF THE INVENTION

The first purpose of the present invention is to provide apparatuses and methods for low-destructively measuring mechanical properties within object such as structures, substances, materials, living tissues (liver, prostate, breast, bone, etc.) even if there exists internal and/or uncontrollable mechanical sources. The first purpose of the present invention is, for instance, for diagnosing and monitoring treatment effectiveness on living tissue, to provide the measurement technique of following constants, elastic constants such as shear modulus, Poisson's ratio, etc., visco elastic constants such as visco shear modulus, visco Poisson's ratio, etc., delay times or relaxation times relating these elastic constants and visco elastic constants, or density.

The second purpose of the present invention is to provide the low-invasive treatment technique with utilization of low-invasive measurement of the following constants, elastic constants such as shear modulus, Poisson's ratio, etc., visco elastic constants such as visco shear modulus, visco Poisson's ratio, etc., delay times or relaxation times relating these elastic constants and visco elastic constants, or density.

The third purpose of the present invention is to improve the measurement accuracy of displacement vector distribution generated in 3D, 2D (including or not including beam direction), or 1D (beam direction or scan direction) ROI in the target body when the gradient of the echo cross-spectrum phase is estimated. The cross-spectrum can also be estimated by Fourier's transform of the echo cross-correlation function.

The fourth purpose of the present invention is to simplify the calculation process such that the process does not require to unwrap the cross-spectrum phase nor to utilize the cross-correlation method; thus reducing calculation amount and shortening calculation time.

The fifth purpose of the present invention is to improve the measurement accuracy of the lateral displacements (orthogonal directions to beam direction).

In the preferred, embodiment of the present invention, the above-described purposes are achieved.

All the displacement measurement methods related to the present invention enable to measure the local displacement vector or local displacement vector components from the phases of the ultrasound echo signals acquired from the target as the responses to more than one time transmitted ultrasound.

One method measures the displacement vector component from the gradient of the cross-spectrum phase evaluated from the echo signals acquired at two different time, i.e., before and after tissue deformation. The 3D processing yields, from 3D cross-spectrum phase $\theta(\omega x, \omega y, \omega z)$, the accurate measurements of 3D displacement vectors $(d=(dx, dy, dz)^T)$ in 3D ROI, and consequently, yields the measurements of the more accurate displacement vector components compared with the corresponding components measured by 2D processing (using 2D cross-spectrum phase: $\theta(\omega x, \omega y)$, or $\theta(\omega y, \omega z)$, or $\theta(\omega x, \omega z)$) and 1D processing (using 1D cross-spectrum phase: $\theta(\omega x)$, or $\theta(\omega y)$, or $\theta(\omega z)$).

When measuring displacement from the gradient of the echo cross-spectrum phase, to realize the more accurate measurement accuracy, the least squares method can be applied with utilization as the weight function of the squares of the cross-spectrum usually normalized by the cross-spectrum power. In order to stabilize the measurement, the regularization method can also be applied, by which a priori information can be incorporated, i.e., about within the ROI the magnitude of the unknown displacement vector, spatial continuity and differentiability of the unknown displacement vector distribution, etc. The regularization parameter depends on time-space dimension of the ROI, direction of the unknown displacement component, position of the unknown displacement vector, etc. Otherwise, the regularization can also utilize the mechanical properties of tissue (e.g., incompressibility) and the compatibility conditions of displacement vector distribution and displacement component distribution.

Moreover, to reduce the calculation amount and shorten the calculation time of the displacement vector, the invented multidimensional autocorrelation method or Doppler method can be used, in which by generating plural complex signals from one set of echo signals, the derived independent equations are simultaneously solved. In addition, to increase the measurement accuracy of the lateral displacements of all the multidimensional measurement methods, invented lateral Gaussian envelope cosine modulation (LGECM) can be performed. Furthermore, to increase the number of the simultaneous equations, the different lateral modulation frequencies can also be realized from the same one set of echo signals. The basic and harmonic components of the echo signal can also be used.

The displacement measurement apparatus related to the present invention can be equipped with the following means: displacement (strain) sensor (transducer to transmit ultrasounds to the target, and detect echo signals generated in the target), relative position controller and relative direction controller between the sensor and the target, means of transmitting/receiving (transmitter of driving signals sent to the sensor, and receiver of the echo signals detected by the sensor), means of data processing (controller of the driving signals, and processor of the received echo signals), and means of data storing (storage of echo signals, measured deformation data).

The means of data processing also measures the local displacement vector or the local displacement vector components from the phases of the ultrasound echo signals acquired from the target as the responses to more than one time transmitted ultrasound utilizing the stated displacement measurement methods.

The strain tensor measurement apparatus related to the first point of view of the present invention can be equipped with the displacement measurement apparatus, and the means of data processing that can yield strain tensor components by spatial differential filtering with suitable a cutoff frequency in spatial domain or frequency domain the measured 3D, or 2D displacement vector components, or measured one direction displacement component in the 3D, 2D, or 1D ROI. The means of data processing can also yield strain rate tensor components, acceleration vector components, or velocity vector components by time differential filtering with a suitable cutoff frequency in time domain or frequency domain the measured time series of displacement components, or strain components.

The strain tensor measurement method related to the present invention also enable to directly measure the local strain tensor or the local strain tensor components from the phases of the ultrasound echo signals acquired from the target as the responses to more than one time transmitted ultrasound.

The strain tensor measurement apparatus related to the second point of view of the present invention can be equipped with the following means: displacement (strain) sensor (transducer to transmit ultrasounds to the target, and detect echo signals generated in the target), relative position controller and relative direction controller between the sensor and the target, means of transmitting/receiving (transmitter of driving signals sent to the sensor, and receiver of the echo signals detected at the sensor), means of data processing (controller of the driving signals, and processor of the received echo signals), and means of data storing (storage of echo signals, measured deformation data).

The means of data processing also directly measures the local strain tensor or the local strain tensor components utilizing the stated direct strain measurement methods from the phases of the ultrasound echo signals acquired from the target as the responses to more than one time transmitted ultrasound.

The elasticity and visco-elasticity constants measurement apparatus related to the first point of view of the present invention can be equipped with the following means: means of data storing (storage of at least one of strain tensor data, strain rate tensor data, acceleration vector data, elastic constants, visco elastic constants, or density measured in the ROI set in the target), and means of calculating elastic and visco elastic constants (calculator of at least one of elastic constants, visco elastic constants, or density of arbitrary point in the ROI from at least one of the measured strain tensor data, strain rate tensor data, or acceleration vector data).

The means of calculating elastic and visco elastic constants numerically determines at least one of the elastic constants, visco elastic constants, or density from the first order partial differential equations relating at least one of the elastic constants, visco elastic constants, or density to at least one of the strain tensor data, strain rate tensor data, acceleration vector data. Time delays or relaxation times can also be determined by ratio of the corresponding elastic constant and visco elastic constant.

The elasticity and visco-elasticity constants measurement apparatus related to the second point of view of the present invention can be equipped with the following means: means of data storing (storage of at least one of strain tensor data, strain rate tensor data, acceleration vector data, elastic constants, visco elastic constants, or density measured in the ROI including lesions), means of calculating elastic and visco elastic constants (calculator of at least one of elastic constants, visco elastic constants, or density of arbitrary point in the ROI from at least one of the measured strain tensor data, strain rate tensor data, or acceleration vector data), and means of output of degeneration information on parts including the lesions (output means of degeneration information based on calculated at least one of the elastic constants, visco elastic constants, or density).

The means of calculating elastic and visco elastic constants numerically determines at least one of the elastic constants, visco elastic constants, or the density from the first order partial differential equations relating at least one of the elastic constants, visco elastic constants, or density to at least one of the strain tensor data, strain rate tensor data, acceleration vector data.

The elasticity and visco-elasticity constants measurement apparatus-based treatment apparatus related to the present invention can be equipped with the following means: treatment transducer arrayed with more than one oscillator, means (circuit) of treatment transmitting (transmitter of driving signals to each oscillator of the treatment transducer array), diagnosis transducer arrayed with more than one oscillator, means (circuit) of diagnosis transmitting (transmitter of driving signals sent to each oscillator of the diagnosis transducer array), means (circuit) of receiving (receiver of the echo signals detected at the oscillators of the transducers and matcher of the echo signals based on their phases), means of calculating elastic and visco elastic constants (calculator of at least one of elastic constants, visco elastic constants, or density from the matched echo signals), means of output of degeneration information on parts including the lesions (output means of degeneration information based on calculated at least one of the elastic constants, visco elastic constants, or density), controller of the means (circuit) of treatment transmitting, means (circuit) of diagnosis transmitting, means (circuit) of receiving, and means of calculating elastic and visco elastic constants, and the input means of commands and conditions into the controller.

The controller can be not only equipped with functions for controlling the means (circuit) of diagnosis transmitting and means (circuit) of receiving based on the commands and the conditions, but also equipped with functions for deforming the ROI in the target based on the commands and the conditions, and for controlling the means (circuit) of treatment transmitting based on the commands and the conditions to control the treatment ultrasound beam transmitted from the treatment transducer.

The means of calculating elastic and visco elastic constants obtains the matched echo signals in the ROI based on the commands given by the controller, and calculates at least one of the strain tensor data, strain rate tensor data, or acceleration vector data in the ROI, and subsequently calculates from these deformation data at least one of elastic constants, visco elastic constants, or density in the ROI.

Here, controlled of treatment ultrasound beam can be the beam focus position, treatment term, treatment interval, ultrasound beam power, ultrasound beam strength, transmit term, beam shape (apodization), etc. The oscillators can serve both as treatment ones and diagnosis ones.

BRIEF DESCRIPTION OF THE DRAWINGS

FIG. 2 shows illustration of a displacement (strain) sensor applicable to the present invention;

FIG. 12 shows flowchart of method of 3D displacement vector distribution in 3D space (method 1-3), that of method of 2D displacement vector distribution in 2D region (method 2-3), that of method of one direction displacement component distribution in 1D region (method 3-3);

FIG. 13 shows flowchart of method of 3D displacement vector distribution in 3D space (method 1-4), that of method of 2D displacement vector distribution in 2D region (method 2-4), that of method of one direction displacement component distribution in 1D region (method 3-4);

FIG. 21 shows flowchart of method of 2D displacement vector distribution in 3D space (method 4-1), that of method of one direction displacement component distribution in 3D space (method 5-1), and that of method of one direction displacement component distribution in 2D region (method 6-1);

FIG. 22 shows flowchart of method of 2D displacement vector distribution in 3D space (method 4-2), that of method of one direction displacement component distribution in 3D space (method 5-2), and that of method of one direction displacement component distribution in 2D region (method 6-2);

FIG. 23 shows flowchart of method of 2D displacement vector distribution in 3D space (method 4-3), that of method of one direction displacement component distribution in 3D space (method 5-3), and that of method of one direction displacement component distribution in 2D region (method 6-3);

FIG. 24 shows flowchart of method of 2D displacement vector distribution in 3D space (method 4-4), that of method of one direction displacement component distribution in 3D space (method 5-4), and that of method of one direction displacement component distribution in 2D region (method 6-4);

FIG. 25 shows flowchart of method of 2D displacement vector distribution in 3D space (method 4-5), that of method of one direction displacement component distribution in 3D space (method 5-5), and that of method of one direction displacement component distribution in 2D region (method 6-5);

DESCRIPTION OF THE PREFERRED EMBODIMENTS

The following is explanation in detail of conduct forms of the present invention with referring to figures.

Figure 1:
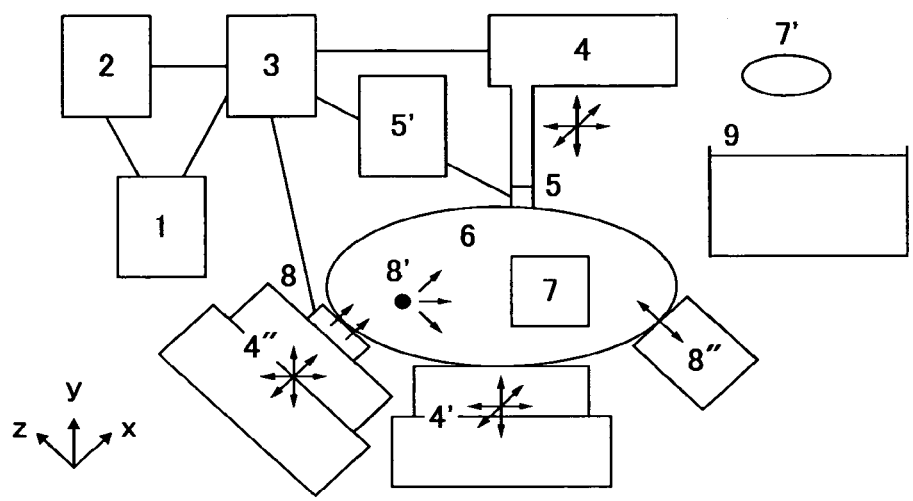
FIG. 1 shows a schematic representation of a global frame of displacement vector and strain tensor measurement apparatus, and elasticity and visco-elasticity constants measurement apparatus, related to one of conduct forms of the present invention.

FIG. 1 shows a schematic representation of a global frame of the displacement vector and strain tensor measurement apparatus, and the elasticity and visco-elasticity constants measurement apparatus, related to one of conduct forms of the present invention. This apparatus measures in 3D, 2D, or 1D ROI 7 set in the measurement object 6 the displacement vector component distributions, strain tensor component distributions, their time-space partial derivative distributions, etc. to obtain the strain tensor field, strain rate tensor field, acceleration vector etc., from which this apparatus measures the following constant distributions, i.e., elastic constants such as shear modulus, Poisson's ratio, etc., visco elastic constants such as visco shear modulus, visco Poisson's ratio, etc., delay times or relaxation times relating these elastic constants and visco elastic constants, or density.

As shown in FIG. 1, the displacement (strain) sensor can be directly contacted to the object surface, or suitable medium can be put between the sensor and object. On this conduct form, as the displacement (strain) sensor, ultrasound transducer is used. The transducer can have 1D or 2D array of oscillators.

The distance between the object 6 and displacement (strain) sensor 5 can be mechanically controlled by the position controller 4. Moreover, the relative distance between the object 6 and displacement (strain) sensor 5 can be mechanically controlled by the position controller 4'. Ultrasound transmitter (ultrasound pulser) 5' is equipped to drive the displacement (strain) sensor 5, and 5' also serves as the output controller, i.e., the receiver with amplifiers of echo signals detected at the displacement (strain) sensor 5. Furthermore, the mechanical source 8 can be equipped to apply static compression, vibration, etc., and mechanical position controller 4" can also be equipped.

Output echo signals of the output controller 5' are stored at storage 2, passing through measurement controller 3. The echo signals stored at the storage 2 are read out by the data processor 1, and displacement vector component distributions (time series) or strain tensor component distributions (time series) are directly calculated and obtained of arbitrary time in the ROI 7, and the further calculated and obtained are their time-space partial derivatives, i.e., the strain tensor component distributions (time series), strain rate tensor component distributions (time series), acceleration vector component distributions (time series), velocity vector component distributions (time series) etc. That is, after the displacement vector component distributions are calculated in the ROI 7, the strain tensor component distributions (time series) are obtained by implementing a 3D, 2D, or 1D spatial differential filter to the obtained displacement vector component distributions (time series). The cutoff frequencies of all the filters used in the present invention can be set different values freely at each point at each time in each spatio-temporal direction as those of usual filters. The acceleration vector component distributions (time series) are obtained by implementing a time differential filter twice to the measured displacement vector component distributions (time series). The strain rate tensor component distributions (time series) are obtained by implementing a spatial differential filter to the velocity vector component distributions (time series) obtained by implementing a time differential filter to the displacement vector component distributions (time series), or by implementing a time differential filter once to the measured strain tensor component distributions (time series). Moreover, when the strain tensor component distributions (time series) are directly calculated of the ROI 7 and obtained, the strain rate tensor component distributions (times series) are obtained by implementing a time differential filter to the measured strain tensor component distributions (time series). Furthermore, this data processor 1 calculates the following constant distributions, i.e., elastic constants such as shear modulus, Poisson's ratio, etc., visco elastic constants such as visco shear modulus, visco Poisson's ratio, etc., delay times or relaxation times relating these elastic constants and visco elastic constants, or density from the measured distributions of strain tensor components (time series), strain rate tensor components (time series), acceleration vector components (time series), etc. These calculated results are stored at the storage 2.

The measurement controller 3 controls the data processor 1, the position controller 4 and 4", and the transmitting/output controller 5'. The position controller 4' is not utilized when the object 6 is spatially fixed. When the displacement (strain) sensor 5 is electronic scan type, the position controller 4 is not always utilized. That is, it may be possible to measure 6 without mechanical scanning. The displacement (strain) sensor 5 may be contacted on the object 6, or may not. That is, the displacement (strain) sensor 5 and object 6 may be dipped in or immersed in water tank, for instance, when monitoring the treatment effectiveness of High Intensity Focus Ultrasound (HIFU).

Figure 3:
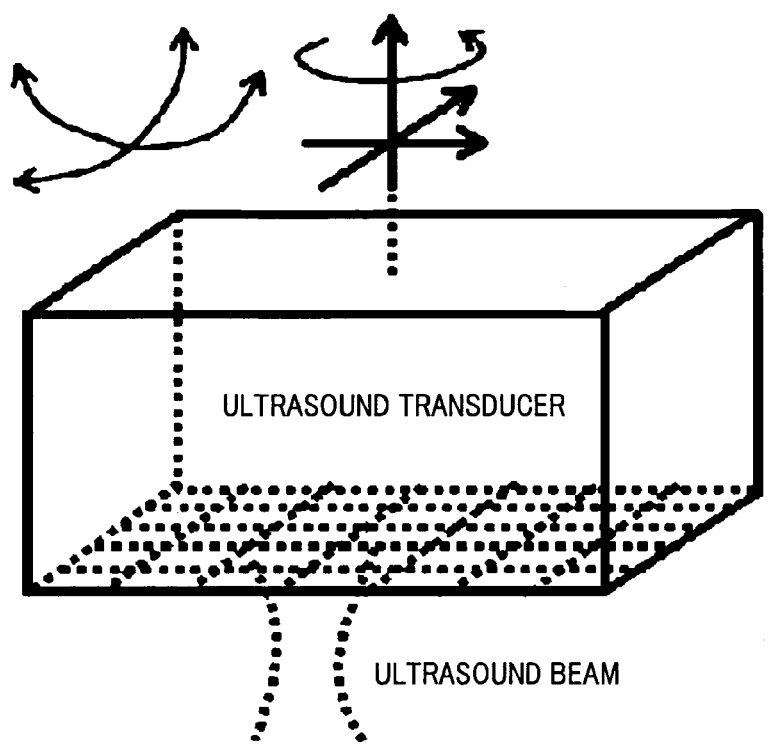
FIG. 3 shows illustration of mechanical scan movements of the displacement (strain) sensor.

The position controller 4 mechanically controls the relative position between the displacement (strain) sensor 5 and object 6. Specifically, the position controller 4 realizes vertical, horizon, turn, and fan direction scan movements (FIG. 3). The output of the transmitting/output controller 5' is also stored at storage 2 successively or with set time intervals. The data processor 1 controls the transmitting/output controller 5', and acquires the echo's basic wave components, n-th harmonic wave components (n equals from 2 to N), or all the components in 3D, 2D, or 1D ROI 7, and implements the below-described data processing to yield the displacement data, strain data, strain rate data, or acceleration data, and stores these measured data in the storage 2.

The transmitting/output controller 5' and the data processor 1 obeys the commands of measurement controller 3, and carry out synthetic aperture processing, e.g., transmitting fixed focusing process, multi-transmitting fixed focusing process, receiving dynamic focusing process, etc. Furthermore, the transmitting/output controller 5' and the data processor 1 carry out apodization process of ultrasound signals, i.e., weighting process on each ultrasound transmitted/received at each oscillator to sharpen the synthesized ultrasound beam, and carry out beam steering process to acquire the echo signals of 3D, 2D, or 1D ROI.

Next explanation is in detail about displacement and strain measurement apparatus related to conduct forms of the present invention.

On this conduct form, as the displacement (strain) sensor 5, the following type ultrasound transducers can be utilized, i.e., 2D array being mechanical scan possible, 2D array being electronic scan possible, 1D array being mechanical scan possible, and 1D array being electronic scan possible.

On this conduct form, synthetic aperture processing can be performed. Also beam steering can be performed. When the beam steering is performed, the measured displacement component distributions and strain tensor component distributions are spatially interpolated, after which the measured displacement component distributions (time series) and strain tensor component distributions (time series) are time-spatially differentiated to yield the strain tensor component distributions (time series), strain rate tensor component distributions (time series), acceleration vector component distributions (time series), and velocity vector component distributions (time series).

Figure 4:
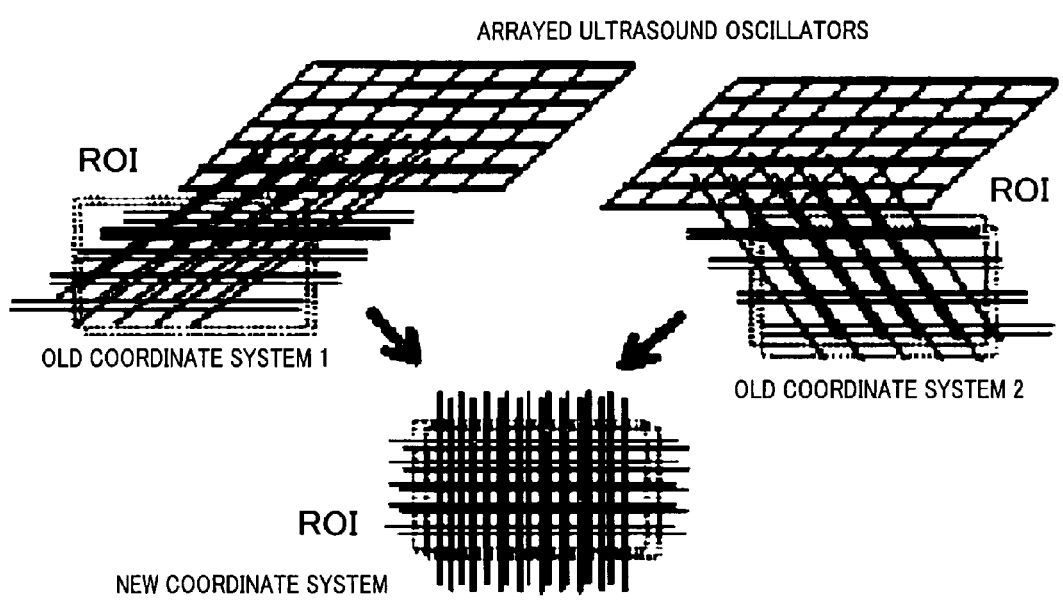
FIG. 4 shows illustration of beam steering, and spatial interpolation of measured two displacement vector component distributions.
Figure 5:
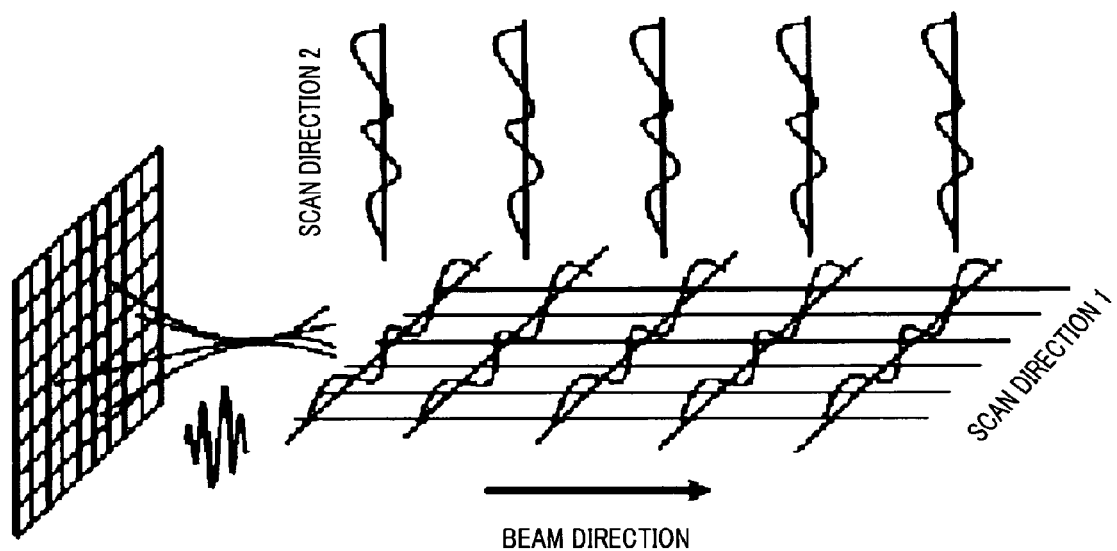
FIG. 5 shows illustration of sinusoidal modulation of the ultrasound in scan directions.
Figure 6:
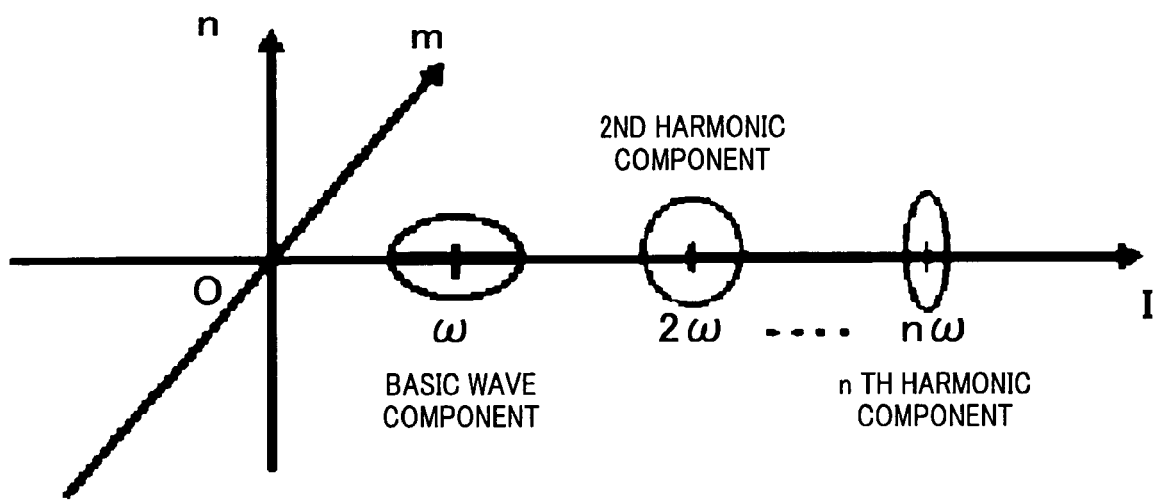
FIG. 6 shows illustration of a basic (n=1) wave component and n-th harmonic wave components (n equals from 2 to N) of ultrasound echo signal.

As measurement of the beam direction is considerably accurate compared with that of the orthogonal scan direction, to yield high accuracy displacement vector measurement, mechanical scan and/or beam steering can be performed. That is, echo data are acquired by performing mechanical scan and/or beam steering such that ultrasound beams are transmitted in more than three different directions when measuring 3D displacement vector, in more than two different directions when measuring 2D displacement vector, and in more than one direction when measuring 1D displacement component. From two echo data acquired by transmitting the ultrasound beams in same direction, accurately the distribution of displacement component in beam direction is measured, by which accurate 3D or 2D displacement vector distribution can be obtained (e.g., FIG. 4). The 1D axial displacement measurement can also be performed to yield the displacement vector instead of the multidimensional measurement. Otherwise, by using one element of the ultrasound array for transmitting ultrasound (during scan or not) and by using one or plural elements of the ultrasound array for receiving echo, beam forming is performed in more than three different directions when measuring 3D displacement vector, in more than two different directions when measuring 2D displacement vector, and in more than one direction when measuring 1D displacement component. The beam forming can also be performed only at receiving. From two echo data acquired by forming beams in same direction, accurately the distribution of displacement component in beam direction is measured, by which accurate 3D or 2D displacement vector distribution can be obtained. This enables to reduce the time for transmitting/receiving. The 1D axial displacement measurement can also be performed to yield the displacement vector instead of the multidimensional measurement. Moreover, by transmitting ultrasound using one element of the ultrasound array and by receiving echo using one or plural elements of the ultrasound array, beam forming is performed in more than six different directions when measuring 3D strain tensor, in more than three different directions when measuring 2D strain tensor, and in more than one direction when measuring 1D strain component. From two echo data acquired by forming beams in same direction, accurately the distribution of strain component in beam direction is measured, by which accurate 3D or 2D strain tensor distribution can be obtained. The 1D axial measurement can also be performed to yield the strain tensor instead of the multidimensional measurement. Otherwise, the displacement vector or strain tensor can be measured using the superimposed echo signals obtained by multi-directional beam forming. The 1D axial measurement can also be performed instead of the multidimensional measurement (the same below). Otherwise, the displacement vector or strain tensor can be measured using the quadrate-detected or enveloped-detected, superimposed echo signals. Otherwise, the displacement vector or strain tensor can be measured using the superimposed, quadrate-detected or enveloped-detected echo signals. These superimposed echo signals can also be used to yield an ultrasound image. Here, for transmitting described above, plural elements can also be used. Moreover, the beam can also be transmitted to different direction from that of the receiving. Moreover, beam forming may not be performed at transmitting, or only apodization may be performed. The apodization may also not be performed. When measuring the displacement or strain components more than the unknown number of the displacement or strain components, a least squares method is used. At the time, by incorporating the reliability of the measurements into the displacement vector measurement, a weighted least squares method is used together with the correlation or power of the local echo data.

However, to obtain the final displacement vector distribution, the displacement vector distributions having the different discrete coordinates must be converted to ones having one new discrete coordinate. That is, by interpolating the displacement component distributions measured on the old discrete coordinates, the displacement components can be obtained at each point of the new discrete coordinate. For instance, displacement component distribution is Fourier's transformed, which is multiplied with complex exponential such that the phase is shifted. Thus, realized is spatial shifting of the displacement component distribution.

On this conduct form, received echo signals can be sinusoidally modulated in scan directions. For instance, there exist J. A. Jensen's method ("A new method for estimation of velocity vectors", IEEE Transactions on Ultrasonics, Ferroelectrics, and Frequency Control, vol. 45, no. 3, pp. 837-850, May 1998) and M. E. Anderson's method (Multi-dimensional velocity estimation with ultrasound using spatial quadrature," IEEE Transactions on Ultrasonics, Ferroelectrics, and Frequency Control, vol. 45, no. 3, pp. 852-861, May 1998). However, in Jensen's method, the finite aperture must be apodized by sin c functions. Moreover, in Anderson's method, it is difficult to design the modulation frequency and bandwidth. In the present invention, the lateral Gaussian envelope cosine modulation method is presented. In the method, by apodizing and focusing (spherical, cylindrical or axicon focussing) the received echo signals, at each depth x, the lateral (y) point spread function (PSF) is designed as a Gaussian type, i.e., $A\exp(-y^2/(2\sigma_y^2))\cos(2\pi f_y y)$, or the lateral (yz-plane) PSF is designed as $A\exp((-y^2/(2\sigma_y^2))+(-z^2/(2\sigma_z^2)))\cos(2\pi f_y y)\cos(2\pi f_z z)$. Here, $\sigma_y$ corresponds to the lateral (y) beam width, $\sigma_z$ corresponds to the lateral (z) beam width, $f_y$ corresponds to the lateral (y) modulation frequency, $f_z$ corresponds to the lateral (z) modulation frequency. These lateral modulation can also be realized at transmitting.

When realizing the lateral (y) PSF, $A\exp(-y^2/(2\sigma_y^2))\cos(2\pi f_y y)$, the apodization is performed for each depth x using the proportional weight values expressed by $1/(2\lambda x)\{\exp[-(2\pi)^2(y/(\lambda x)+f_y+f_a)^2 a\sigma_y^2/2]+\exp[-(2\pi)^2(y/(\lambda x)-f_y-f_a)^2 a\sigma_y^2/2]\}$. Here, $\lambda$ is the ultrasound wavelength, and $f_a$ and a are respectively parameters that are introduced to compensate the errors of the realized modulation frequency fy and bandwidth By due to the inappropriateness of Fraunhofer's approximations. When realizing the lateral (yz-plane) PSF, $A\exp((-y^2/(2\sigma_y^2))+(-z^2/(2\sigma_z^2)))\cos(2\pi f_y y)\cos(2\pi f_z z)$, the apodization is performed for each depth x using the proportional weight values expressed by $1/(4\lambda x)\{\exp[-(2\pi)^2(y/(\lambda x)+f_y+f_a)^2 a\sigma_y^2/2-(2\pi)^2(z/(\lambda x)+f_z+f_b)^2 b\sigma_z^2/2]+\exp[-(2\pi)^2(y/(\lambda x)+f_y+f_a)^2 a\sigma_y^2/2-(2\pi)^2(z/(\lambda x)-f_z-f_b)^2 b\sigma_z^2/2]+\exp[-(2\pi)^2(y/(\lambda x)-f_y-f_a)^2 a\sigma_y^2/2-(2\pi)^2(z/(\lambda x)+f_z+f_b)^2 b\sigma_z^2/2]+\exp[-(2\pi)^2(y/(\lambda x)-f_y-f_a)^2 a\sigma_y^2/2-(2\pi)^2(z/(\lambda x)-f_z-f_b)^2 b\sigma_z^2/2]\}$. Here, $f_b$ and b are respectively are respectively parameters that are introduced to compensate the errors of the realized modulation frequency fz and bandwidth Bz due to the inappropriateness of Fraunhofer's approximations.

The sinusoidal modulation frequency is better to be higher. However, as this modulation shifts in frequency domain in the scan direction the band determined by beam width, based on the sampling theorem the modulation frequency requires to be set such that the highest frequency becomes less than the half of the sampling frequency determined by beam pitch.

Thus, improved is measurement accuracies of displacement component distributions in the scan directions being orthogonal to beam direction.

By these processes, the obtained ultrasound echo signals in 3D, 2D or 1D ROI can be effectively utilized, i.e., the basic wave component, harmonic wave components (The carrier frequency higher, improved is measurement accuracy of the displacement component in the beam direction. The carrier frequency higher, the beam width narrower. Thus, as the bandwidth in the scan direction is wider compared with the basic component wave, also improved is measurement accuracy of the displacement component in the scan direction), or all the wave components due to low SNRs of only harmonic wave components.

That is, the below-described displacement and strain measurement methods (1-1 to 1-5, 2-1 to 2-5, 3-1 to 3-5, 4-1 to 4-5, 5-1 to 5-5, 6-1 to 6-5) can utilize the ultrasound echo signals such as only extracted the basic wave components, only extracted the n-th harmonic wave components (n equals from 2 to N) or these combinations.

These stated displacement and strain measurement methods are based on iterative update of the displacement estimate utilizing the estimated remaining error data (i.e., the estimated residual displacement data). The initial estimate is set based on the a priori knowledge about measurement target, i.e., the displacement distribution, strain distribution, strain rate distribution, acceleration distribution or velocity distribution. Finally obtained are accurate displacement vector distribution (time series), displacement vector component distributions (time series), strain tensor distribution (time series), strain tensor component distributions (time series), strain rate tensor distribution (time series), strain rate tensor component distributions (time series), acceleration vector distribution (time series), acceleration vector component distributions (time series), velocity vector distribution (time series), or velocity vector component distributions (time series). However, when stressing on real-time processing, the measurement can be finished by only one estimation.

During the iterative estimation of the displacement vector and residual displacement vector, when estimation errors are detected a priori at the points of time-space magnitude and time-space continuity, for instance, the estimates can be truncated by compulsion such that the estimates range from the smallest value to the largest value set a priori, or such that the difference between the estimates of the neighboring points settles within the range set a priori.

On these stated iterative displacement and strain measurement methods, all the methods for estimating the residual displacement vector or displacement vector components utilize the phases of the ultrasound echo signals acquired at more than one time as an index. First of all, one of these methods is used to explain the iterative methods, i.e., the method that estimates the displacement from the gradient of the phase of the cross-spectrum obtained from two ultrasound echo signals.

The displacement and strain measurement methods can be implemented each for the extracted basic wave signals and n-th harmonic wave components (n equals from 2 to N). In this case, the final measurement result can be obtained by evaluating the mean displacement data weighted by the power of the cross-spectrums etc.

In addition, when measuring the displacement from the gradient of the cross-spectrum phase by utilizing the least squares method, the data processor also utilize the regularization method based on the a priori knowledge, which improves the stability, accuracy, and spatial resolutions of the measurement of the displacement vector distribution, or the displacement vector component distributions.

In the past, when a large displacement requires to be handled, before estimating the gradient of the cross-spectrum phase, the phase had been unwrapped, or the displacement had been coarsely estimated by cross-correlation method. Thus, measurement procedure had become complex. To cope with these complexities, the measurement procedure is made simpler with no utilization of these processes by introducing a process of thinning out echo data and a process of remaking echo data interval original. Thus, the implemented soft amount and calculation time are reduced. Occasionally, the regularization may not be performed.

However, as other method, before estimating the gradient of the cross-spectrum phase, the phase can also be unwrapped, or the displacement can also be coarsely estimated by the cross-correlation method.

Also in this case, when measuring the local displacement from the gradient of the cross-spectrum phase, the a priori knowledge about the displacement distribution in the ROI can be incorporated by utilizing the regularization method, where the least squares method utilizes as the weight function the squares of the cross-spectrum usually normalized by the cross-spectrum power.

Freely, when estimating the gradient of the cross-spectrum phase, the acquired ultrasound echo signals can be thinned out in each direction with a constant intervals.

These cases handle the gradient of the local 3D, 2D or 1D cross-spectrum phase evaluated on 3D, 2D, or 1D ultrasound echo signals acquired at more than one time from 3D space, 2D or 1D region in the object. Stably measured with high accuracy and high spatial resolutions are 3D displacement vector component distributions in the 3D SOI (space of interest), 2D displacement vector component distributions in the 2D ROI, one direction displacement component distribution in the 1D ROI, 2D displacement vector component distributions or one direction displacement component distribution in the 3D SOI, or one direction displacement component distribution in the 2D ROI.

The displacement and strain measurement apparatus of the present invention measures in the 3D SOI, 2D, or 1D ROI in the object the displacement vector distribution, strain tensor distribution, strain rate tensor distribution, acceleration vector distribution, velocity vector distribution, etc. from ultrasound echo signals measured in 3D SOI, 2D or 1D ROI (referred to 3D, 2D or 1D ultrasound echo signals). The displacement and strain measurement apparatus can be equipped with:

displacement (strain) sensor (ultrasound transducer), relative position controller and relative direction controller between the sensor and the target (vertical, horizon, turn, and fan direction scan movements), transmitter (ultrasound pulser)/output controller (receiver and amplifier), means of data processing (synthetic aperture process: transmitting fixed focusing process, multi-transmitting fixed focusing process, receiving dynamic focusing process etc., apodization), means of data storing (storage of echo signals), means of (signal) data processing (calculation of displacement vector distribution, strain tensor distribution, strain rate tensor distribution, acceleration vector distribution, velocity vector distribution, etc.), and means of data storing (storage of the displacement vector distribution, strain tensor distribution, strain rate tensor distribution, acceleration vector distribution, velocity vector distribution, etc).

In this case, the means of data processing can yield the strain tensor components by implementing a spatial 3D, 2D, or 1D differential filter with a cutoff frequency or multiplying Fourier's transform of the differential filter in frequency domain to 3D displacement vector component distributions in the 3D SOI (space of interest), 2D displacement vector component distributions in the 2D ROI, one direction displacement component distribution in the 1D ROI, 2D displacement vector component distributions or one direction displacement component distribution in the 3D SOI, or one direction displacement component distribution in the 2D ROI. Moreover, by implementing a time differential filter with a cutoff frequency or multiplying Fourier's transform of the differential filter in frequency domain to time series of these, the strain rate tensor component distributions, acceleration vector component distributions, velocity vector component distributions. Moreover, the strain rate tensor component distributions can also be obtained from the directly measured strain tensor component distributions.

The displacement and strain measurement apparatus can also be equipped with a static compressor or vibrator as a mechanical source to generate at least one strain tensor field (one displacement vector field) in the 3D SOI, 2D or 1D ROI in the object. In this case, the strain tensor field (displacement vector field) generated due to body motion (heart motion, blood vessel motion, respiratory) can also be measured in the 3D SOI 2D, or 1D ROI in the object.

The following ultrasound transducer type can be utilized, i.e., the ultrasound oscillator being mechanical scan possible, electronic scan type 2D ultrasound oscillator array (occasionally being mechanical scan possible) or 1D ultrasound oscillator array (occasionally being mechanical scan possible). Thus, echo signal is synthesized one. When the displacement (strain) sensor is contacted on the object, the contacted part can also become mechanical source. That is, the displacement (strain) sensor also serves as a compressor or vibrator. When the part of lesion is dipped in or immersed in water tank to carry out treatment with High Intensity Focus Ultrasound (HIFU), the object can be non-contactly measured by dipping in or immersing the displacement (strain) sensor as well in water tank.

Moreover, when the displacement (strain) sensor is directly contacted to the object surface as a mechanical source to stably measure elastic constant distributions and visco elastic constant distributions, a suitable reference medium can be put between the sensor and object. In this case, the reference medium can also be mounted (installed) on the transducer.

Basically, the means of data processing can yield the strain tensor component distributions, stain rate tensor component distributions, acceleration vector component distributions, or velocity vector component distributions from the displacement data obtained by synthesizing the ultrasound echo in 3D SOI, 2D or 1D ROI detected by the displacement (strain) sensor, i.e., the 3D displacement vector component distributions in the 3D SOI, 2D displacement vector component distributions in the 2D ROI, one direction displacement component distribution in the 1D ROI, 2D displacement vector component distributions or one direction displacement component distribution in the 3D SOI or one direction displacement component distribution in the 2D ROI. Moreover, the strain rate tensor component distributions can also be obtained from the directly measured strain tensor component distributions.

In this case, the means of data processing can yield the displacement component distributions and strain tensor component distributions from the ultrasound echo signals acquired in each dimensional ROI with beam steering as well as synthetic aperture processing, from which obtained can be the strain tensor component distributions, strain rate tensor component distributions, acceleration vector component distributions or velocity vector component distributions.

Moreover, in this case, the means of data processing can yield the displacement component distributions and strain tensor component distributions from the ultrasound echo basic wave components, harmonic wave components, or all the components, from which obtained can be the strain tensor component distributions, strain rate tensor component distributions, acceleration vector component distributions, or velocity vector component distributions.

Here, the lateral modulation frequency is better to be higher. However, as the modulation shifts the band determined by the beam width in the scan direction in the frequency domain, based on the sampling theorem, the modulation frequency requires to be set such that the highest frequency becomes less than the half of the sampling frequency determined by beam pitch.

Furthermore, the ultrasound echo signals can also be acquired by combining these processing, i.e., synthetic aperture processing, beam steering, lateral modulation of the echo signal in scan directions. In this case, measured can also be the displacement vector component distribution from the ultrasound echo basic wave components, harmonic wave components or all the components.

When utilizing the below-described displacement and strain measurement methods, as the measurement of the beam direction is considerably accurate compared with that of the orthogonal direction (i.e., scan direction), to yield high accuracy displacement measurements, mechanical scan and/or beam steering are performed. That is, the echo data frames are acquired under object's pre- and post-deformation by performing mechanical scan and/or beam steering such that the ultrasound beams are transmitted in more than three different directions when measuring 3D displacement vector, in more than two different directions when measuring 2D displacement vector and in more than one direction when measuring one displacement component. From two echo data acquired by transmitting the ultrasound beams in same direction, accurately the distribution of displacement component in the beam direction is measured, by which the accurate 3D or 2D displacement vector distribution is obtained. To obtain the final displacement vector distribution, the displacement vector distributions having the different discrete coordinates must be converted to ones having one new discrete coordinate. That is, by interpolating the displacement component distributions measured on the old discrete coordinates, the displacement component can be obtained at each point of the new discrete coordinate. For instance, the displacement component distribution is Fourier's transformed, which is multiplied with complex exponential such that the phase is shifted. That is, spatial shifting of the displacement component distribution is realized. The strain tensor component distributions can be obtained from the displacement vector measurement data. Moreover, from the time series of these data, obtained can be the strain tensor rate component distributions, acceleration vector component distributions, velocity vector component distributions. Other displacement measurement methods and strain measurement methods can also be applied to the ultrasound echo time series data in similar ways. The 1D axial displacement measurement can also be performed to yield the displacement vector instead of the multidimensional measurement. Otherwise, by using one element of the ultrasound array for transmitting ultrasound (during scan or not) and by using one or plural elements of the ultrasound array for receiving echo, beam forming is performed in more than three different directions when measuring 3D displacement vector, in more than two different directions when measuring 2D displacement vector, and in more than one direction when measuring 1D displacement component. The beam forming can also be performed only at receiving. From two echo data acquired by forming beams in same direction, accurately the distribution of displacement component in beam direction is measured, by which accurate 3D or 2D displacement vector distribution can be obtained. This enables to reduce the time for transmitting/receiving. The 1D axial displacement measurement can also be performed to yield the displacement vector instead of the multidimensional measurement. Moreover, by transmitting ultrasound using one element of the ultrasound array and by receiving echo using one or plural elements of the ultrasound array, beam forming is performed in more than six different directions when measuring 3D strain tensor, in more than three different directions when measuring 2D strain tensor, and in more than one direction when measuring 1D strain component. From two echo data acquired by forming beams in same direction, accurately the distribution of strain component in beam direction is measured, by which accurate 3D or 2D strain tensor distribution can be obtained. The 1D axial measurement can also be performed to yield the strain tensor instead of the multidimensional measurement. Otherwise, the displacement vector or strain tensor can be measured using the superimposed echo signals obtained by multi-directional beam forming. The 1D axial measurement can also be performed instead of the multidimensional measurement (the same below). Otherwise, the displacement vector or strain tensor can be measured using the quadrate-detected or enveloped-detected, superimposed echo signals. Otherwise, the displacement vector or strain tensor can be measured using the superimposed, quadrate-detected or enveloped-detected echo signals. These superimposed echo signals can also be used to yield an ultrasound image. Here, for transmitting described above, plural elements can also be used. Moreover, the beam can also be transmitted to different direction from that of the receiving. Moreover, beam forming may not be performed at transmitting, or only apodization may be performed. The apodization may also not be performed. When measuring the displacement or strain components more than the unknown number of the displacement or strain components, a least squares method is used. At the time, by incorporating the reliability of the measurements into the displacement vector measurement, a weighted least squares method is used together with the correlation or power of the local echo data.

Next explanation is in detail about the displacement and strain measurement algorithms related to the conduct forms of the present invention. The means of data processing 1 always carries out the below-explained calculation process or their combination, or as occasion demands.

(1) Calculation process of 3D displacement vector component distribution in 3D ROI (below-described methods 1-1 to 1-5)
(2) Calculation process of 2D displacement vector component distribution in 2D ROI (below-described methods 2-1 to 2-5)
(3) Calculation process of 1D (one direction) displacement component distribution in 1D ROI (below-described methods 3-1 to 3-5)
(4) Calculation process of 2D displacement vector component distribution in 3D ROI (below-described methods 4-1 to 4-5)
(5) Calculation process of 1D (one direction) displacement component distribution in 3D ROI (below-described methods 5-1 to 5-5)
(6) Calculation process of 1D (one direction) displacement component distribution in 2D ROI (below-described methods 6-1 to 6-5)

When the beam steering is performed, at the means of data processing 1, the measured displacement vector component distributions are spatially interpolated.

With respect to displacement component distributions and strain component distributions obtained through the above calculation processes, the means of data processing 1 performs differentiation such that the followings are obtained, i.e., at each time the strain tensor component distributions, strain gradient component distributions, strain rate tensor component distributions, strain rate gradient component, acceleration vector component distributions, or velocity vector distributions. These calculated results are stored at the storage 2. Moreover, these calculated results are displayed on display apparatus such as CRT (color or gray scaled) etc in real-time or in quasi real-time.

As a static or a motion image, or a time course (difference) image, etc., the followings can be displayed, i.e., the displacement vector distribution, displacement vector component distributions, strain tensor component distributions, strain gradient component distributions, strain rate tensor component distributions, strain rate gradient component distributions, acceleration vector component distributions or velocity vector component distributions. At arbitrary points the values and their graph of the time course can also be displayed. For instance, by utilizing the ultrasound diagnosis apparatus, the spatial variations of bulk modulus and density of tissues can be displayed in real-time. Thus, the above-described static or motion image, or time course image of the displacement vector distribution etc can also be superimposed and displayed on the ultrasound image. The followings can be displayed in vector style as well, i.e., the displacement vector distribution, acceleration vector, velocity vector.

The following is explanation in detail of the displacement measurement and calculation processes.

(I) Method 1: Measurement of 3D Displacement Vector Distribution

Figure 7:
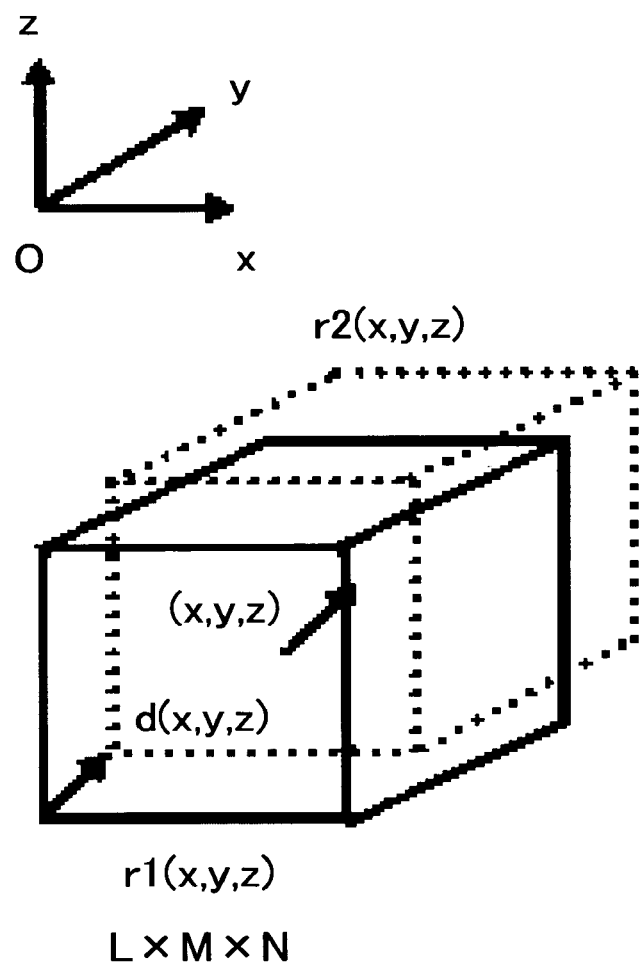
FIG. 7 shows illustration of a local 3D space centered on a point (x,y,z) in 3D ROI in pre-deformation ultrasound echo signal space, and the shifted one in post-deformation ultrasound echo signal space.
Figure 8:
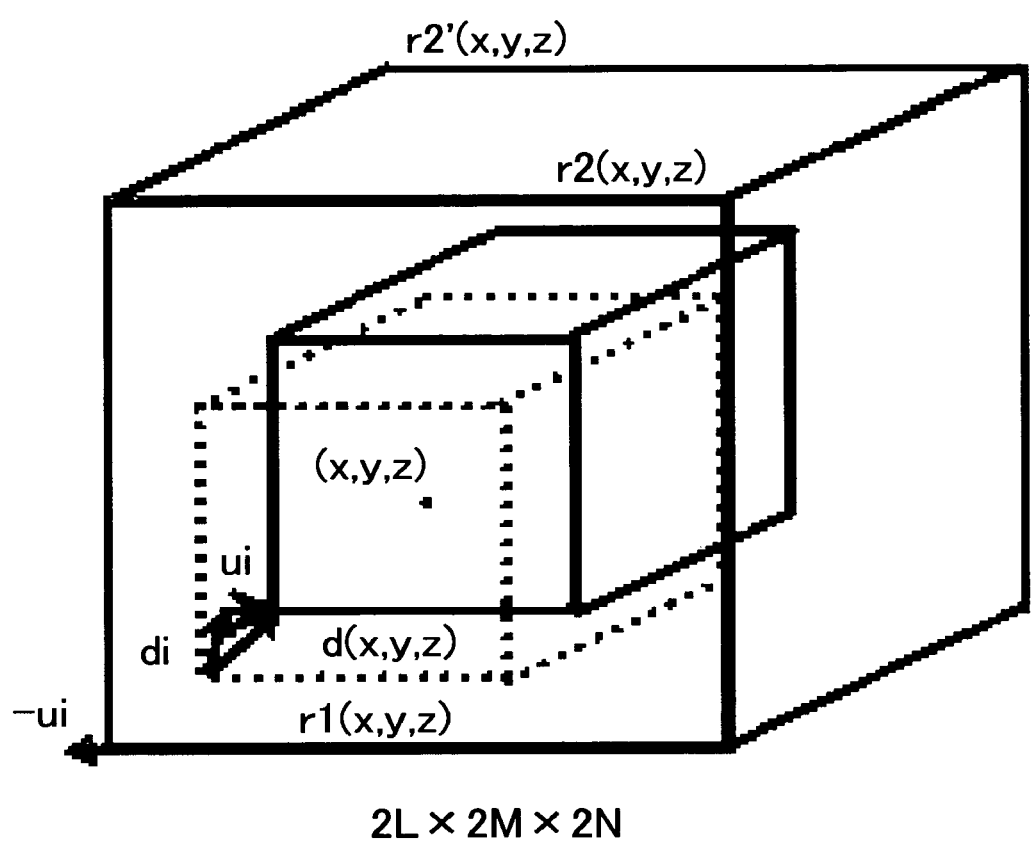
FIG. 8 shows illustration as the example of searching for local 3D ultrasound echo signal by phase matching in searching space set in post-deformation ultrasound echo signal space. That is, the corresponding local signal is searched for using pre-deformation local echo signal.
Figure 9:
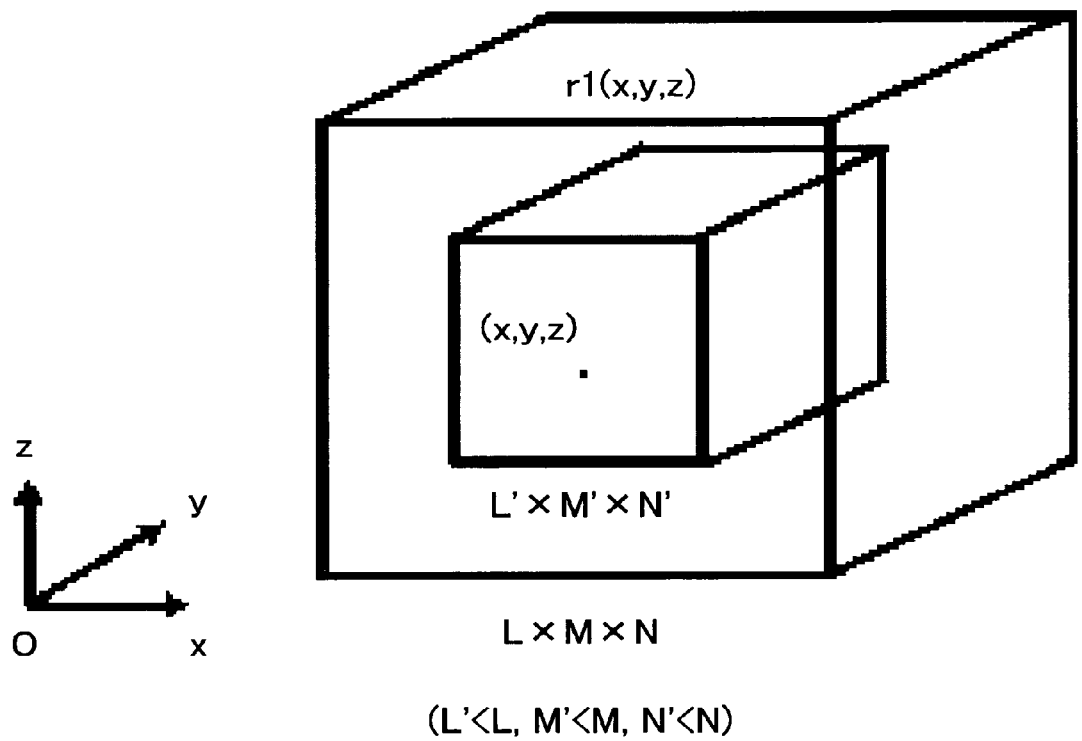
FIG. 9 shows illustration to make 3D displacement vector distribution high spatial resolution, i.e., to make local space small.

The 3D displacement vector distribution can be measured in 3D SOI 7 in the Cartesian coordinate system. The 3D ultrasound echo signals are acquired under pre-deformation and post-deformation. These echo signals are processed by the below-described methods 1-1, 1-2, 1-3, 1-4, and 1-5. That is, as shown in FIG. 7, a local space is set at each point in the pre- and post-deformation 3D echo signal, and as shown in FIG. 8, the corresponding local space is iteratively searched for in the SOI 7 using the local phase characteristics as the index. In this searching scheme, the estimated residual displacement vector is used to update the previously estimated displacement vector. When the estimated residual displacement vector is satisfied with prescribed conditions, the local space size is made small (FIG. 9). Thus, accurate 3D displacement vector measurement is realized. Here, the sampling intervals are $\Delta x$, $\Delta y$, $\Delta z$ respectively in the x, y, and z-axes.

[Method 1-1]

Figure 10:
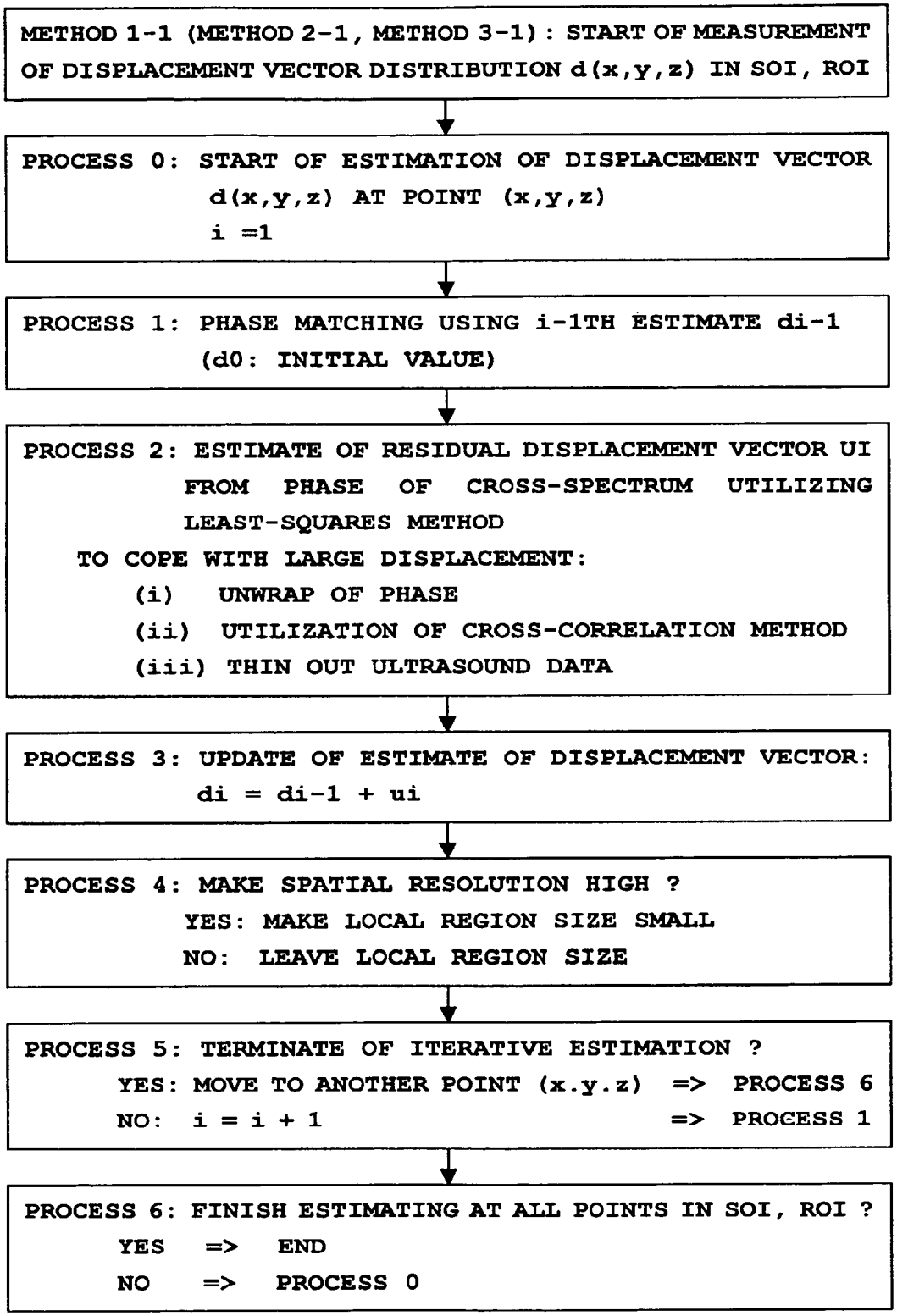
FIG. 10 shows flowchart of method of 3D displacement vector distribution in 3D space (method 1-1), that of method of 2D displacement vector distribution in 2D region (method 2-1), that of method of one direction displacement component distribution in 1D region (method 3-1)

The procedure of the method 1-1 is shown in FIG. 10. The processes 1 to 5 yields 3D displacement vector $d(x,y,z)$ [$=(dx(x,y,z), dy(x,y,z), dz(x,y,z))^T$] of an arbitrary point $(x,y,z)$ in the 3D SOI from the pre- and post-deformation local 3D echo signals $r_1(l,m,n)$ and $r_2(l,m,n)$ [$0 \le l \le L-1$, $0 \le m \le M-1$, $0 \le n \le N-1$] centered on $(x,y,z)$ of the pre- and post-deformation 3D echo signals $r_1(x,y,z)$ and $r_2(x,y,z)$. L, M, and N should be determined such that $\Delta xL$, $\Delta yM$, $\Delta zN$ are respectively at least 4 times longer than the corresponding displacement components $|dx(x,y,z)|$, $|dy(x,y,z)|$, $|dz(x,y,z)|$.

(Process 1: Phase Matching at the Point (x,y,z))

Phase matching is performed to obtain the i-th estimate $d^i(x,y,z)$ [$=(d^i x(x,y,z), d^i y(x,y,z), d^i z(x,y,z))^T$] of the 3D displacement vector $d(x,y,z)$ [$=(dx(x,y,z), dy(x,y,z), dz(x,y,z))^T$].

Searching space is set in the post-deformation echo signal space $r_2(x,y,z)$, being centered on the local space [$0 \leq l \leq L-1$, $0 \leq n \leq M-1$, $0 \leq n \leq N-1$] centered on (x,y,z) and being twice longer than the corresponding length, in order to update the i−1 th estimate $d^{i-1}(x,y,z)$ [$=(d^{i-1}x(x,y,z), d^{i-1}y(x,y,z), d^{i-1}z(x,y,z))^T$] of the 3D displacement vector $d(x,y,z)$ [$=(dx(x,y,z), dy(x,y,z), dz(x,y,z))^T$], where $$d^0(x,y,z) = \check{d}(x,y,z). \tag{1}$$

The phase of the post-deformation local echo signal is matched to the pre-deformation local echo signal by multiplying $$\exp\left\{j \frac{2\pi}{L} \frac{d_x^{i-1}(x,y,z)}{\Delta x} l + j \frac{2\pi}{M} \frac{d_y^{i-1}(x,y,z)}{\Delta y} m + j \frac{2\pi}{N} \frac{d_z^{i-1}(x,y,z)}{\Delta z} n\right\} \tag{2}$$

to the 3D Fourier's transform of this searching space echo signal $r'_2(l,m,n)$ [$0 \leq l \leq 2L-1$, $0 \leq m \leq 2M-1$, $0 \leq n \leq 2N-1$] using i-th estimate $d^{i-1}(x,y,z)$, or by multiplying $$\exp\left\{-j \frac{2\pi}{L} \frac{\bar{u}_x^{i-1}(x,y,z)}{\Delta x} l + j \frac{2\pi}{M} \frac{\bar{u}_y^{i-1}(x,y,z)}{\Delta y} m + j \frac{2\pi}{N} \frac{\bar{u}_z^{i-1}(x,y,z)}{\Delta z} n\right\} \tag{2'}$$

to the 3D Fourier's transform of the i−1 th phase-matched searching space echo signal $r'^{i-1}_2(l,m,n)$ using the estimate $\hat{u}^{i-1}(x,y,z)$ [$=(\hat{u}_x^{i-1}(x,y,z), \hat{u}_y^{i-1}(x,y,z), \hat{u}_z^{i-1}(x,y,z))^T$] [$\hat{u}^0(x,y,z) = 0$ (zero vector)] of the vector $u^{i-1}(x,y,z)$ [$=(u^{i-1}_x(x,y,z), u^{i-1}_y(x,y,z), u^{i-1}_z(x,y,z))^T$].

By carrying out the inverse Fourier's transform of this product, the post-deformation echo signal $r'_2(l,m,n)$ is obtained at the center of the searching space echo signal $r'_2(l,m,n)$, which is used at the i-th stage to estimate the 3D displacement vector $d(x,y,z)$ [$=(dx(x,y,z), dy(x,y,z), dz(x,y,z))^T$].

Alternatively, the phase of the pre-deformation local echo signal can be matched to the post-deformation local echo signal in a similar way. That is, the 3D Fourier's transform of the searching space echo signal $r'_1(l,m,n)$ [$0 \leq l \leq 2L-1$, $0 \leq m \leq 2M-1$, $0 \leq n \leq 2N-1$] centered on the point (x,y,z) in the pre-deformation echo signal space is multiplied with $$\exp\left\{-j \frac{2\pi}{L} \frac{d_x^{i-1}(x,y,z)}{\Delta x} l - j \frac{2\pi}{M} \frac{d_y^{i-1}(x,y,z)}{\Delta y} m - j \frac{2\pi}{N} \frac{d_z^{i-1}(x,y,z)}{\Delta z} n\right\}, \tag{2''}$$

or the 3D Fourier's transform of the i−1 th phase-matched searching space echo signal $r'^{i-1}_1(l,m,n)$ is multiplied with $$\exp \tag{2'''}$$

$$\left\{-j \frac{2\pi}{L} \frac{\bar{u}_x^{i-1}(x,y,z)}{\Delta x} l - j \frac{2\pi}{M} \frac{\bar{u}_y^{i-1}(x,y,z)}{\Delta y} m - j \frac{2\pi}{N} \frac{\bar{u}_z^{i-1}(x,y,z)}{\Delta z} n\right\}.$$

(Process 2: Estimation of 3D Residual Displacement Vector at the Point (x,y,z))

The local 3D echo cross-spectrum is evaluated from the 3D Fourier's transforms of the pre-deformation local. 3D ultrasound echo signal $r_1(l,m,n)$ and the phase-matched post-deformation local 3D ultrasound echo signal $r'_2(l,m,n)$.

$$S^i_{2,1}(l,m,n) = R_2^{i*}(l,m,n) R_1(l,m,n), \tag{3}$$

where * denotes conjugate.

Alternatively, when the pre-deformation local 3D ultrasound echo signal is phase-matched, the cross-spectrum of $r'_1(l,m,n)$ and $r_2(l,m,n)$ is evaluated as $$S'_{2,1}(l,m,n) = R_2^*(l,m,n) R'_1(l,m,n).$$

The cross-spectrum is represented as $$S^i_{2,1}(l,m,n) \cong |R^i_1(l,m,n)|^2 \exp \tag{4}$$

$$\left\{j \frac{2\pi}{L} \frac{u^i_x(x,y,z)}{\Delta x} l + j \frac{2\pi}{M} \frac{u^i_y(x,y,z)}{\Delta y} m + j \frac{2\pi}{N} \frac{u^i_z(x,y,z)}{\Delta z} n\right\},$$

where $0 \leq l \leq L-1$, $0 \leq m \leq M-1$, $0 \leq n \leq N-1$, and then the phase is represented as $$\theta^i(l,m,n) = \tan^{-1}\left(\frac{\text{Im}[S^i_{2,1}(l,m,n)]}{\text{Re}[S^i_{2,1}(l,m,n)]}\right), \tag{5}$$

where Re[·] and Im[·] respectively represent the real and imaginary component of "·".

The least squares method is implemented on the gradient of the phase eq. (5) weighted with squared cross-spectrum $|S_{2,1}^i(l,m,n)|_2 (=\text{Re}^2[S_{2,1}^i(l,m,n)]+\text{Im}^2[S_{2,1}^i(l,m,n)])$. That is, by minimizing the functional $$\text{error}(u^i(x,y,z)) = \tag{6}$$

$$\sum_{l,m,n} |S^i_{2,1}(l,m,n)|^2 \times \left(\theta^i(l,m,n) - u^i_x(x,y,z)\left(\frac{2\pi}{L\Delta x}\right)l - u^i_y(x,y,z)\left(\frac{2\pi}{M\Delta y}\right)m - u^i_z(x,y,z)\left(\frac{2\pi}{N\Delta z}\right)n\right)^2$$

with respect to the 3D residual vector $u^i(x,y,z)$ to be used to update the i−1 th estimate $d^{i-1}(x,y,z)$ of the 3D displacement vector $d(x,y,z)$, the estimate of $u^i(x,y,z)$ is obtained as $$\hat{u}^i(x,y,z) [=(\hat{u}_x^i(x,y,z), \hat{u}_y^i(x,y,z), \hat{u}_z^i(x,y,z))^T]. \tag{6-2}$$

Concretely, the following simultaneous equations are solved.

$$\begin{bmatrix} \sum_{l,m,n} |S_{2,1}^i(l,m,n)|^2 \left(\frac{2\pi}{L\Delta x}\right) l\theta^i(l,m,n) \\ \sum_{l,m,n} |S_{2,1}^i(l,m,n)|^2 \left(\frac{2\pi}{M\Delta y}\right) m\theta^i(l,m,n) \\ \sum_{l,m,n} |S_{2,1}^i(l,m,n)|^2 \left(\frac{2\pi}{N\Delta z}\right) n\theta^i(l,m,n) \end{bmatrix} = \tag{7}$$

$$\begin{bmatrix} \sum_{l,m,n} |S_{2,1}^i(l,m,n)|^2 \left(\frac{2\pi}{L\Delta x}\right)^2 l^2 & \sum_{l,m,n} |S_{2,1}^i(l,m,n)|^2 \left(\frac{2\pi}{L\Delta x}\right)\left(\frac{2\pi}{M\Delta y}\right) lm & \sum_{l,m,n} |S_{2,1}^i(l,m,n)|^2 \left(\frac{2\pi}{L\Delta x}\right)\left(\frac{2\pi}{N\Delta z}\right) ln \\ \sum_{l,m,n} |S_{2,1}^i(l,m,n)|^2 \left(\frac{2\pi}{L\Delta x}\right)\left(\frac{2\pi}{M\Delta y}\right) lm & \sum_{l,m,n} |S_{2,1}^i(l,m,n)|^2 \left(\frac{2\pi}{M\Delta y}\right)^2 m^2 & \sum_{l,m,n} |S_{2,1}^i(l,m,n)|^2 \left(\frac{2\pi}{M\Delta y}\right)\left(\frac{2\pi}{N\Delta z}\right) mn \\ \sum_{l,m,n} |S_{2,1}^i(l,m,n)|^2 \left(\frac{2\pi}{L\Delta z}\right)\left(\frac{2\pi}{N\Delta z}\right) ln & \sum_{l,m,n} |S_{2,1}^i(l,m,n)|^2 \left(\frac{2\pi}{M\Delta y}\right)\left(\frac{2\pi}{N\Delta z}\right) mn & \sum_{l,m,n} |S_{2,1}^i(l,m,n)|^2 \left(\frac{2\pi}{N\Delta z}\right)^2 n^2 \end{bmatrix} \times \begin{bmatrix} u_x^i(x,y,z) \\ u_y^i(x,y,z) \\ u_z^i(x,y,z) \end{bmatrix}$$

When the 3D displacement vector d(x,y,z) is large, the 3D residual displacement vector $u^i(x,y,z)$ requires to be estimated after unwrapping the phase of the cross-spectrum [eq. (3)] in the frequency domain (l,m,n).

Alternatively, when the 3D displacement vector d(x,y,z) is large, by using cross-correlation method (evaluation of the peak position of the cross-correlation function obtained as the 3D inverse Fourier's transform of the cross-spectrum [eq. (3)]) at the initial stages during iterative estimation, the 3D residual displacement vector $u^i(x,y,z)$ can be estimated without unwrapping the phase of the cross-spectrum [eq. (3)] in the frequency domain. Specifically, by using the cross-correlation method, x, y, and z components of the 3D displacement vector are respectively estimated as integer multiplications of the ultrasound echo sampling intervals $\Delta x$, $\Delta y$, $\Delta z$. For instance, with respect to the threshold values correTratio or correTdiff, after $$\frac{\|\hat{u}^i(x,y,z)\|}{\|\hat{u}^{i-1}(x,y,z)\|} \leq correTratio \tag{8}$$

or $$\|\hat{u}^i(x,y,z)\| \leq correTdiff \tag{8'}$$

is satisfied with where $\|\hat{u}^i(x,y,z)\|$ and $\|\hat{u}^{i-1}(x,y,z)\|$ are respectively the norms (magnitudes) of the i th and i−1 th estimate of the residual vector, by using the estimate of the 3D displacement vector d(x,y,z) as the initial estimate, the 3D residual displacement vector is estimated from the gradient of the phase of the cross-spectrum [eq. (3)].

Empirically it is known that after using cross-correlation method the conditions $|u^i_x(x,y,z)| \leq \Delta x/2$, $|u^i_y(x,y,z)| \leq \Delta y/2$, $|u^i_z(x,y,z)| \leq \Delta z/2$ are satisfied with. However, for enabling the estimation of the 3D residual displacement vector without unwrapping the phase of the cross-spectrum,
the necessary and sufficient condition is $$\left| \frac{u_x^i(x,y,z)}{\Delta x} + \frac{u_y^i(x,y,z)}{\Delta y} + \frac{u_z^i(x,y,z)}{\Delta z} \right| \leq 1 \tag{9}$$

or

-continued $$|u_x^i(x,y,z)| \leq \Delta x/3, \tag{9'}$$
$$|u_y^i(x,y,z)| \leq \Delta y/3, \text{ and}$$
$$|u_z^i(x,y,z)| \leq \Delta z/3.$$

Therefore, when estimating the gradient of the cross-spectrum phase after using the cross-correlation method, the acquired ultrasound echo data are thinned out with a constant interval in each direction and the reduced echo data are used such that the condition (9) or (9') is satisfied with. The iteration number i increasing, i.e., the magnitude of the 3D residual displacement vector components $u^i_x(x,y,z)$, $u^i_y(x,y,z)$, $u^i_z(x,y,z)$ decreasing, the ultrasound echo data densities are made restored in each direction. Hence, at the initial stages where estimating the gradient of the cross-spectrum phase, for instance, the ultrasound echo signals are used with one and half times or twice as a long interval as the original interval in each direction. The densities of the ultrasound echo signals are made restored in each direction, for instance, one and half times or twice per a iteration.

Alternatively, when the magnitude of the 3D displacement vector d(x,y,z) is large, at the initial stages, the acquired original ultrasound echo data can be thinned out with a constant interval in each direction and the reduced echo data can be used such that the 3D residual displacement vector can be estimated without unwrapping the phase of the cross-spectrum [eq. (3)] in the frequency domain (l,m,n). Specifically, the acquired original ultrasound echo data are thinned out with a constant interval in each direction and the reduced echo data are used such that the condition (9) or (9') is satisfied with. The iteration number i increasing, i.e., the magnitude of the 3D residual displacement vector components $u^i_x(x,y,z)$, $u^i_y(x,y,z)$, $u^i_z(x,y,z)$ decreasing, the ultrasound echo data densities are made restored in each direction, for instance, twice per a iteration. When the 3D residual displacement vector components $u^i_x(x,y,z)$, $u^i_y(x,y,z)$, $u^i_z(x,y,z)$ are estimated, if neither the condition (9) nor (9') is satisfied with, the values are truncated such that the conditions are satisfied with.

The interval of the ultrasound echo signal data are shortened, for instance, when with respect to the threshold values stepTratio or stepTdiff the condition $$\frac{\|\overline{u}^i(x,y,z)\|}{\|\overline{u}^{i-1}(x,y,z)\|} \leq stepTratio \quad (10)$$

or $$\|\overline{u}^i(x,y,z) - \overline{u}^{i-1}(x,y,z)\| \leq stepTdiff \quad (11)$$

is satisfied with, where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (10) or (10') can be applied to each direction component, and in this case the data interval is shorten in each direction. These are also applied to the below-described methods 1-2, 1-3, 1-4, and 1-5.

(Process 3: Update of the 3D Displacement Vector Estimate of the Point (x,y,z))

Thus, the i th estimate of the 3D displacement vector d(x, y,z) is evaluated as $$d^i(x,y,z) = d^{i-1}(x,y,z) + \hat{u}^i(x,y,z). \quad (11)$$

[Process 4: Condition for Heightening the Spatial Resolution of the 3D Displacement Vector Distribution Measurement (Condition for Making the Local Space Small)]

In order to make the spatial resolution high of the 3D displacement vector distribution measurement, the local space is made small during iterative estimation. The criteria is described below. The processes 1, 2 and 3 are iteratively carried out till the criteria is satisfied with. When the criteria is satisfied with, the local space is made small, for instance, the length of each side is made half. For instance, the criteria is (12) or (12') with respect to the threshold values Tratio or Tdiff.

$$\frac{\|\hat{u}^i(x,y,z)\|}{\|\hat{u}^{i-1}(x,y,z)\|} \leq Tratio \quad (12)$$

or $$\|\hat{u}^i(x,y,z) - \hat{u}^{i-1}(x,y,z)\| \leq Tdiff, \quad (12')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (12) or (12') can be applied to each direction component, and in this case the side is shorten in each direction.

(Process 5: Condition for Terminating the Iterative Estimation of the 3D Displacement Vector of the Point (x,y,z))

Described below is the criteria for terminating the iterative estimation of the 3D displacement vector of each point. The processes 1, 2 and 3 are iteratively carried out till the criteria is satisfied with. For instance, the criteria is (13) or (13') with respect to the threshold values aboveTratio or aboveTdiff.

$$\frac{\|\hat{u}^i(x,y,z)\|}{\|\hat{u}^{i-1}(x,y,z)\|} \leq aboveTratio \quad (13)$$

or $$\|\hat{u}^i(x,y,z) - \hat{u}^{i-1}(x,y,z)\| \leq aboveTdiff, \quad (13')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

(Process 6)

The 3D displacement vector component distributions are obtained by carrying out the processes 1, 2, 3, 4, and 5 at every point in the 3D SOI.

The initial estimate [eq. (1)] of the iterative estimation of the 3D displacement vector is set as zero vector if a priori data is not given about the displacement of body motion nor applied compression. Alternatively, the values accurately estimated at the neighborhood can be used (high correlation or least squares).

[Limitation of Method 1-1]

The estimate of the 3D displacement vector d(x,y,z) is iteratively updated at each point (x,y,z) in the 3D SOI. Being dependent on the SNR of the local 3D echo signal, particularly at the initial stages errors possibly occur when estimating the residual vector and then the phase matching possibly diverges. For instance, when solving eq. (7) [process 2] or detecting the peak position of the cross-correlation function [process 2], errors possibly occur.

The possibility for divergence of the phase matching is, for instance, confirmed by the condition (14) or (14') with respect to the threshold value belowTratio or BelowTdiff.

$$\frac{\|\hat{u}^i(x,y,z)\|}{\|\hat{u}^{i-1}(x,y,z)\|} \geq belowTratio \quad (14)$$

or $$\|\hat{u}^i(x,y,z) - \hat{u}^{i-1}(x,y,z)\| \geq belowTdiff, \quad (14')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

To prevent the phase matching (process 1) from diverging, in the below-described methods 1-2, 1-3, 1-4, and 1-5, by freely using the condition (14) or (14'), the estimation error is reduced of the residual vector. Thus, even if the SNR of the ultrasound echo signals are low, accurate 3D displacement vector measurement can be realized.

[Method 1-2]

Figure 11:
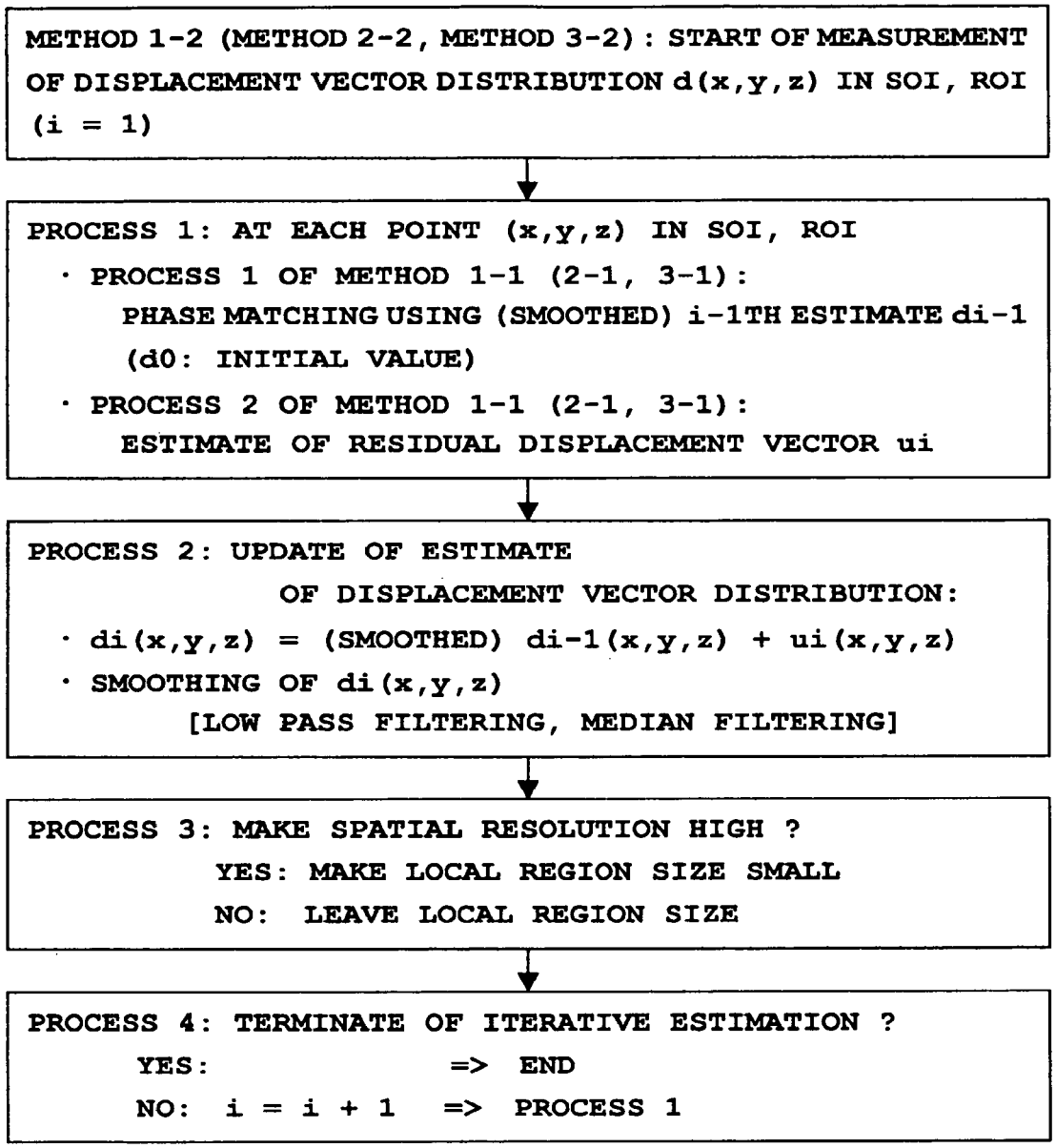
FIG. 11 shows flowchart of method of 3D displacement vector distribution in 3D space (method 1-2), that of method of 2D displacement vector distribution in 2D region (method 2-2), that of method of one direction displacement component distribution in 1D region (method 3-2)

The flowchart of the method 1-2 is shown in FIG. 11. To prevent the phase matching from diverging at the process 1 of the method 1-1, the estimation error is reduced of the residual vector. Thus, even if the SNR of the ultrasound echo signals are low, accurate 3D displacement vector measurement can be realized.

The procedure of the iterative estimation is different from that of the method 1-1. At i th estimate (i≥1), the following processes are performed.

(Process 1: Estimation of the 3D Residual Displacement Vector Distribution)

The phase matching and estimation of the 3D residual displacement vector are performed at every point (x,y,z) in the 3D SOI. That is, the processes 1 and 2 of the method 1-1 are performed once at every point in the SOI. Thus, the estimate of the 3D residual vector distribution is obtained [eq. (6-2)].

(Process 2: Update of the Estimate of the 3D Displacement Vector Distribution)

The i−1 th estimate of the 3D displacement vector distribution is updated using the i th estimate of the 3D residual vector distribution.

$$d^i(x,y,z) = \hat{d}^{i-1}(x,y,z) + \hat{u}^i(x,y,z) \quad (15)$$

Next, this estimate is 3D low pass filtered or 3D median filter to yield the estimate of the 3D displacement vector distribution:

$$\hat{d}^i(x,y,z) = LPF[d^i(x,y,z)], \text{ or } \hat{d}^i(x,y,z) = MED[d^i(x,y,z)]. \quad (16)$$

Thus, the estimation error is reduced of the residual vector compared with the process 2 of the method 1-1 [eq. (7)]. Hence, the phase matching of the process 1 of method 1-2 is performed using the smoothed estimate of the 3D displacement vector distribution.

[Process 3: Condition for Heightening the Spatial Resolution of the 3D Displacement Vector Distribution Measurement (Condition for Making the Local Space Small)]

In order to make the spatial resolution high of the 3D displacement vector distribution measurement, during the iterative estimation, the local space used for each point is made small, or the local space used over the SOI is made small.

The criteria for each point is described below. The processes 1 and 2 (method 1-2) are iteratively carried out till the criteria is satisfied with. When the criteria is satisfied with, the local space is made small, for instance, the length of each side is made half. For instance, the criteria is (17) or (17') with respect to the threshold values Tratio or Tdiff.

$$\frac{\|\hat{u}^i(x, y, z)\|}{\|\hat{u}^{i-1}(x, y, z)\|} \leq Tratio \text{ or} \tag{17}$$

$$\|\hat{u}^i(x, y, z) - \hat{u}^{i-1}(x, y, z)\| \leq Tdiff, \tag{17'}$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (17) or (17') can be applied to each direction component, and in this case the side is shorten in each direction.

The criteria over the SOI is described below. The processes 1 and 2 (method 1-2) are iteratively carried out till the criteria is satisfied with. When the criteria is satisfied with, the local space is made small, for instance, the length of each side is made half. For instance, the criteria is (18) or (18') with respect to the threshold values Tratioroi or Tdiffroi.

$$\frac{\sum_{(x,y,z) \in SOI} \|\hat{u}^i(x, y, z)\|^2}{\sum_{(x,y,z) \in SOI} \|\hat{u}^{i-1}(x, y, z)\|^2} \leq Tratioroi \text{ or} \tag{18}$$

$$\sum_{(x,y,z) \in SOI} \|\hat{u}^i(x, y, z) - \hat{u}^{i-1}(x, y, z)\| \leq Tdiffroi, \tag{18'}$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (18) or (18') can be applied to each direction component, and in this case the side is shorten in each direction.

(Process 4: Condition for Terminating the Iterative Estimation of the 3D Displacement Vector Distribution)

Described below is the criteria for terminating the iterative estimation of the 3D displacement vector distribution. The processes 1, 2 and 3 of method 1-2 are iteratively carried out till the criteria is satisfied with. For instance, the criteria is (19) or (19') with respect to the threshold values aboveTratioroi or aboveTdiffroi.

$$\frac{\sum_{(x,y,z) \in SOI} \|\hat{u}^i(x, y, z)\|^2}{\sum_{(x,y,z) \in SOI} \|\hat{u}^{i-1}(x, y, z)\|^2} \leq aboveTratioroi \text{ or} \tag{19}$$

$$\sum_{(x,y,z) \in SOI} \|\hat{u}^i(x, y, z) - \hat{u}^{i-1}(x, y, z)\| \leq aboveTdiffroi, \tag{19'}$$

where $\|\hat{u}^i(x,y,z)\|$ and $\|\hat{u}^{i-1}(x,y,z)\|$ are respectively the norms (magnitudes) of the i th and i−1 th estimates of the residual vectors.

Final estimate is obtained from eq. (15) or eq. (16).

The initial estimate [eq. (1)] of the iterative estimation of the 3D displacement vector is set as zero vector if a priori data is not given about the displacement of body motion nor applied compression. Alternatively, the values accurately estimated at the neighborhood can be used (high correlation or least squares).

[Method 1-3]

The flowchart of the method 1-3 is shown in FIG. 12. To prevent the phase matching from diverging at the process 1 of the method 1-1, the estimation error is reduced of the residual vector. Possibility of the divergence is detected from the above-described condition (14) or (14'), and by effectively utilizing the method 1-1 and 1-2, even if the SNR of the ultrasound echo signals are low, accurate 3D displacement vector measurement can be realized.

At first, the procedure of the iterative estimation is same as that of the method 1-2 (Processes 1, 2, 3, and 4). At i th estimate, the following processes are performed.

The phase matching and estimation of the 3D residual displacement vector are performed at every point (x,y,z) in the 3D SOI. That is, the processes 1 and 2 of the method 1-1 are performed once at every point in the SOI. Thus, the estimate of the 3D residual vector distribution is obtained [eq. (6-2)].

During this estimation, if neither condition (14) nor (14') is satisfied with, the method 1-1 is used. If condition (14) or (14') is satisfied with at points or spaces, in the process 2 of the method 1-2, over sufficiently large spaces centered on the points or spaces, or over the SOI, the estimate $d^i(x,y,z)$ of the 3D displacement vector $d(x,y,z)$ can be 3D low pass filtered or 3D median filtered as eq. (20).

$$\hat{d}^i(x,y,z) = LPF[d^i(x,y,z)], \text{ or } \hat{d}^i(x,y,z) = MED[d^i(x,y,z)] \tag{20}$$

Thus, the estimation error is reduced of the residual vector compared with the process 2 of the method 1-1 [eq. (7)].

Thus, the iterative estimation is terminated at the process 5 of the method 1-1 or the process 4 of the method 1-2. Hence, the final estimate is obtained from eq. (11), or eq. (15), or eq. (20).

The initial estimate [eq. (1)] of the iterative estimation of the 3D displacement vector is set as zero vector if a priori data is not given about the displacement of body motion nor applied compression. Alternatively, the values accurately estimated at neighborhood can be used (high correlation or least squares).

[Method 1-4]

The flowchart of the method 1-4 is shown in FIG. 13. To prevent the phase matching from diverging at the process 1 of the method 1-1, the estimation error is reduced of the residual vector. Thus, even if the SNR of the ultrasound echo signals are low, accurate 3D displacement vector measurement can be realized.

The procedure of the iterative estimation is different from that of the method 1-1. At the i th estimate (i≥1), the following processes are performed.

(Process 1: Estimation of the 3D Residual Displacement Vector Distribution)

The phase matching and estimation of the 3D residual displacement vector are performed at every point (x,y,z) in the 3D SOI. That is, the process 1 of the method 1-1 is performed once at every point in the SOI.

To obtain the estimate $\hat{u}^i(x,y,z)$ [$=\hat{u}_x^i(x,y,z), \hat{u}_y^i(x,y,z), \hat{u}_z^i(x,y,z))^T$] of the residual vector distribution $u^i(x,y,z)$ [$=(u^i_x(x,y,z), u^i_y(x,y,z), u^i_z(x,y,z))^T$], at every point the local 3D echo cross-spectrum is evaluated from the 3D Fourier's transforms of the pre-deformation local 3D ultrasound echo signal $r_1(l,m,n)$ and phase-matched post-deformation local 3D ultrasound echo signal $r^i_2(l,m,n)$. Alternatively, when pre-deformation local 3D ultrasound echo signal is phase-matched, at every point the cross-spectrum of $r^i_1(l,m,n)$ and $r_2(l,m,n)$ is evaluated.

The least squares method is implemented on the gradient of the phase with utilization of each weight function, i.e., the squared cross-spectrum $|S_{2,1}^i(l,m,n)|^2$, where each weight function is normalized by the power of the cross-spectrum, i.e., $$\sum_{l,m,n} |S_{2,1}^i(l,m,n)|^2.$$

Moreover, regularization method is also implemented. That is, by minimizing the following functional with respect to the vector $u^i$ comprised of the 3D residual vector distribution $u^i(x,y,z)$.

$$\text{error}(u^i) = \|a - Fu^i\|^2 + \alpha_{1i}\|u^i\|^2 + \alpha_{2i}\|Gu^i\|^2 + \alpha_{3i}\|G^T Gu^i\|^2 + \alpha_{4i}\|GG^T Gu^i\|^2 \quad (21)$$

where a: vector comprised of (x,y,z) distribution of the cross-spectrum phase $\Theta^i(l,m,n)$ weighted with the cross-spectrum $|S_{2,1}^i(l,m,n)|$ normalized by the magnitude of the cross-spectrum $$\sqrt{\sum_{l,m,n} |S_{2,1}^i(l,m,n)|^2}$$

evaluated at every point in the 3D SOI.

F: matrix comprised of (x,y,z) distribution of the Fourier's coordinate value (l,m,n) weighted with the cross-spectrum $|S_{2,1}^i(l,m,n)|$ normalized by the magnitude of the cross-spectrum $$\sqrt{\sum_{l,m,n} |S_{2,1}^i(l,m,n)|^2}$$

evaluated at every point in the 3D SOI.

$\alpha_{1i}, \alpha_{2i}, \alpha_{3i}, \alpha_{4i}$: regularization parameter (at least larger than zero)

$Gu^i$: vector comprised of the finite difference approximations of the 3D distributions of the 3D gradient components of the unknown 3D residual vector $u^i(x,y,z)$ components $$\frac{\partial}{\partial x}u^i_x(x,y,z), \frac{\partial}{\partial y}u^i_x(x,y,z), \frac{\partial}{\partial z}u^i_x(x,y,z),$$

$$\frac{\partial}{\partial x}u^i_y(x,y,z), \frac{\partial}{\partial y}u^i_y(x,y,z), \frac{\partial}{\partial z}u^i_y(x,y,z),$$

$$\frac{\partial}{\partial x}u^i_z(x,y,z), \frac{\partial}{\partial y}u^i_z(x,y,z), \frac{\partial}{\partial z}u^i_z(x,y,z)$$

$G^T Gu^i$: vector comprised of the finite difference approximations of the 3D distributions of the 3D Laplacians of the unknown 3D residual vector $u^i(x,y,z)$ components $$\frac{\partial^2}{\partial x^2}u^i_x(x,y,z) + \frac{\partial^2}{\partial y^2}u^i_x(x,y,z) + \frac{\partial^2}{\partial z^2}u^i_x(x,y,z)$$

$$\frac{\partial^2}{\partial x^2}u^i_y(x,y,z) + \frac{\partial^2}{\partial y^2}u^i_y(x,y,z) + \frac{\partial^2}{\partial z^2}u^i_y(x,y,z)$$

$$\frac{\partial^2}{\partial x^2}u^i_z(x,y,z) + \frac{\partial^2}{\partial y^2}u^i_z(x,y,z) + \frac{\partial^2}{\partial z^2}u^i_z(x,y,z)$$

$GG^T Gu^i$: vector comprised of the finite difference approximations of the 3D distributions of the 3D gradient components of the 3D Laplacians of the unknown 3D residual vector $u^i(x,y,z)$ components $$\frac{\partial}{\partial x}\left(\frac{\partial^2}{\partial x^2}u^i_x(x,y,z) + \frac{\partial^2}{\partial y^2}u^i_x(x,y,z) + \frac{\partial^2}{\partial z^2}u^i_x(x,y,z)\right),$$

$$\frac{\partial}{\partial y}\left(\frac{\partial^2}{\partial x^2}u^i_x(x,y,z) + \frac{\partial^2}{\partial y^2}u^i_x(x,y,z) + \frac{\partial^2}{\partial z^2}u^i_x(x,y,z)\right),$$

$$\frac{\partial}{\partial z}\left(\frac{\partial^2}{\partial x^2}u^i_x(x,y,z) + \frac{\partial^2}{\partial y^2}u^i_x(x,y,z) + \frac{\partial^2}{\partial z^2}u^i_x(x,y,z)\right),$$

$$\frac{\partial}{\partial x}\left(\frac{\partial^2}{\partial x^2}u^i_y(x,y,z) + \frac{\partial^2}{\partial y^2}u^i_y(x,y,z) + \frac{\partial^2}{\partial z^2}u^i_y(x,y,z)\right),$$

$$\frac{\partial}{\partial y}\left(\frac{\partial^2}{\partial x^2}u^i_y(x,y,z) + \frac{\partial^2}{\partial y^2}u^i_y(x,y,z) + \frac{\partial^2}{\partial z^2}u^i_y(x,y,z)\right),$$

$$\frac{\partial}{\partial z}\left(\frac{\partial^2}{\partial x^2}u^i_y(x,y,z) + \frac{\partial^2}{\partial y^2}u^i_y(x,y,z) + \frac{\partial^2}{\partial z^2}u^i_y(x,y,z)\right),$$

$$\frac{\partial}{\partial x}\left(\frac{\partial^2}{\partial x^2}u^i_z(x,y,z) + \frac{\partial^2}{\partial y^2}u^i_z(x,y,z) + \frac{\partial^2}{\partial z^2}u^i_z(x,y,z)\right),$$

$$\frac{\partial}{\partial y}\left(\frac{\partial^2}{\partial x^2}u^i_z(x,y,z) + \frac{\partial^2}{\partial y^2}u^i_z(x,y,z) + \frac{\partial^2}{\partial z^2}u^i_z(x,y,z)\right),$$

$$\frac{\partial}{\partial z}\left(\frac{\partial^2}{\partial x^2}u^i_z(x,y,z) + \frac{\partial^2}{\partial y^2}u^i_z(x,y,z) + \frac{\partial^2}{\partial z^2}u^i_z(x,y,z)\right),$$

As $\|u^i\|^2$, $\|Gu^i\|^2$, $\|G^T Gu^i\|^2$, $\|GG^T Gu^i\|^2$ are positive definite, error ($u^i$) has one minimum value. Thus, by solving for residual displacement vector distribution $u^i(x,y,z)$ the simultaneous equations:

$$(F^T F + \alpha_{1i}I + \alpha_{2i}G^T G + \alpha_{3i}G^T GG^T G + \alpha_{4i}G^T GG^T GG^T G)u^i = F^T a, \quad (22)$$

the estimate $\hat{u}^i(x,y,z)$ [$=(\hat{u}_x^i(x,y,z), \hat{u}_y^i(x,y,z), \hat{u}_z^i(x,y,z))^T$] of the residual vector distribution $u^i(x,y,z)$ [$=(u^i_x(x,y,z), u^i_y(x,y,z), u^i_z(x,y,z))^T$] is stably obtained. Thus, the estimation error is reduced of the residual vector.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then the position of the unknown displacement vector, direction of the unknown displacement component, direction of the partial derivative, etc.

(Process 2: Update of the Estimate of the 3D Displacement Vector Distribution)

The i−1 th estimate of the 3D displacement vector distribution is updated using i th estimate of the 3D residual vector distribution.

$$d^i(x,y,z)=\hat{d}^{i-1}(x,y,z)+\hat{u}^i(x,y,z) \quad (23)$$

Freely, this estimate can be 3D low pass filtered or 3D median filter to yield the estimate of the 3D displacement vector distribution.

$$\hat{d}^i(x,y,z)=LPF[d^i(x,y,z)], \text{ or } \hat{d}^i(x,y,z)=MED[d^i(x,y,z)] \quad (24)$$

Hence, the phase matching of the process 1 of the method 1-4 is performed using the 3D residual vector data $u^i(x,y,z)$ obtained from eq. (22), or the 3D vector data $d^i(x,y,z)$ obtained from eq. (23), or smoothed estimate obtained from eq. (24).

[Process 3: Condition for Heightening the Spatial Resolution of the 3D Displacement Vector Distribution Measurement (Condition for Making the Local Space Small)]

In order to make the spatial resolution high of the 3D displacement vector distribution measurement, during the iterative estimation, the local space used for each point is made small, or the local space used over the SOI is made small.

The criteria for each point is described below. The processes 1 and 2 of method 1-4 are iteratively carried out till the criteria is satisfied with. When the criteria is satisfied with, the local space is made small, for instance, the length of each side is made half. For instance, the criteria is (25) or (25') with respect to the threshold values Tratio or Tdiff.

$$\frac{\|\hat{u}^i(x,y,z)\|}{\|\hat{u}^{i-1}(x,y,z)\|} \leq Tratio \text{ or} \quad (25)$$

$$\|\hat{u}^i(x,y,z) - \hat{u}^{i-1}(x,y,z)\| \leq Tdiff, \quad (25')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (25) or (25') can be applied to each direction component, and in this case the side is shorten in each direction.

The criteria over the SOI is described below. The processes 1 and 2 of method 1-4 are iteratively carried out till the criteria is satisfied with. When the criteria is satisfied with, the local space is made small, for instance, the length of each side is made half. For instance, the criteria is (26) or (26') with respect to the threshold values Tratioroi or Tdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq Tratioroi \text{ or} \quad (26)$$

$$\sum_{(x,y,z)\in SOI}\|\hat{u}^i(x,y,z) - \hat{u}^{i-1}(x,y,z)\| \leq Tdiffroi, \quad (26')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (26) or (26') can be applied to each direction component, and in this case the side is shorten in each direction.

(Process 4: Condition for Terminating the Iterative Estimation of the 3D Displacement Vector Distribution)

Described below is the criteria for terminating the iterative estimation of the 3D displacement vector distribution. The processes 1, 2 and 3 of method 1-4 are iteratively carried out till the criteria is satisfied with. For instance, the criteria is (27) or (27') with respect to the threshold values aboveTratioroi or aboveTdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq aboveTratioroi \text{ or} \quad (27)$$

$$\sum_{(x,y,z)\in SOI}\|\hat{u}^i(x,y,z) - \hat{u}^{i-1}(x,y,z)\| \leq aboveTdiffroi, \quad (27')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

Final estimate is obtained from eq. (23) or eq. (24).

The initial estimate [eq. (1)] of the iterative estimation of the 3D displacement vector is set as zero vector if a priori data is not given about the displacement of body motion nor applied compression. Alternatively, the values accurately estimated at the neighborhood can be used (high correlation or least squares).

[Method 1-5]

Figure 14:
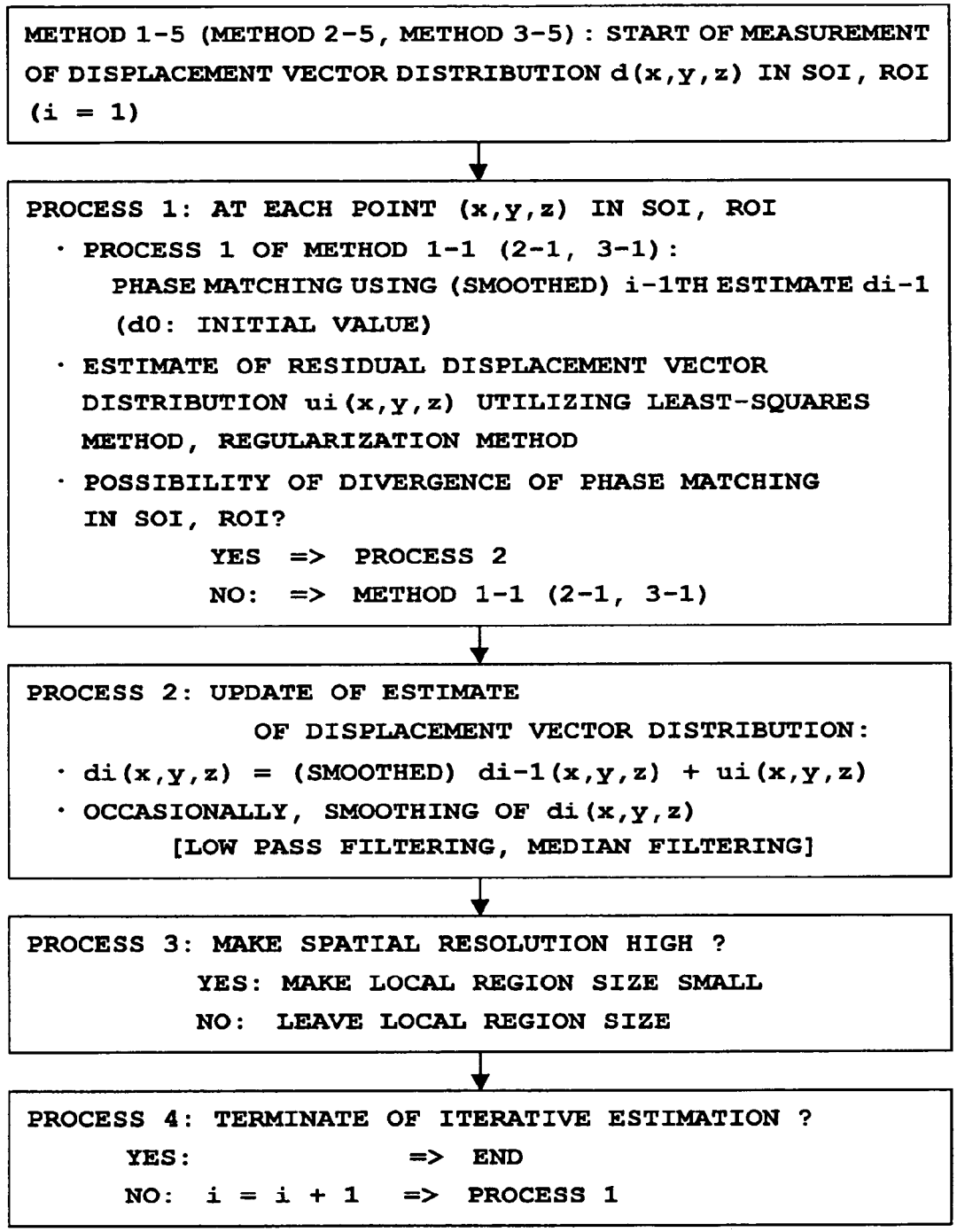
FIG. 14 shows flowchart of method of 3D displacement vector distribution in 3D space (method 1-5), that of method of 2D displacement vector distribution in 2D region (method 2-5), that of method of one direction displacement component distribution in 1D region (method 3-5)

The flowchart of the method 1-5 is shown in FIG. 14. To prevent the phase matching from diverging at the process 1 of the method 1-1, the estimation error is reduced of the residual vector. Possibility of the divergence is detected from the above-described condition (14) or (14'), and by effectively utilizing the methods 1-1 and 1-4, even if the SNR of the ultrasound echo signals are low, accurate 3D displacement vector measurement can be realized.

At first, the procedure of the iterative estimation is same as that of the method 1-4 (Processes 1, 2, 3, and 4). At the i th estimate, the following processes are performed.

The phase matching and estimation of the 3D residual displacement vector are performed at every point (x,y,z) in the 3D SOI. That is, the process 1 of the method 1-1 is performed once at every point in the SOI. Moreover, using the regularization method, stably the estimate of the 3D residual vector distribution is obtained.

During this estimation, if neither condition (14) nor (14') is satisfied with, the method 1-1 is used. If condition (14) or (14') is satisfied with at points or spaces, in the process 2 of the method 1-4, over sufficiently large spaces centered on the points or spaces, or over the SOI, the estimate $d^i(x,y,z)$ of the 3D displacement vector $d(x,y,z)$ can be 3D low pass filtered or 3D median filtered as eq. (28).

$$\hat{d}^i(x,y,z)=LPF[d^i(x,y,z)], \text{ or } \hat{d}^i(x,y,z)=MED[d^i(x,y,z)] \quad (28)$$

Thus, the estimation error is reduced of the residual vector.

Iterative estimation is terminated at the process 5 of the method 1-1 or the process 4 of the method 1-4. Hence, the final estimate is obtained from eq. (11), or eq. (23), or eq. (28).

The initial estimate [eq. (1)] of the iterative estimation of the 3D displacement vector is set as zero vector if a priori data is not given about the displacement of body motion nor applied compression. Alternatively, the values accurately estimated at the neighborhood can be used (high correlation or least squares).

Figure 15:
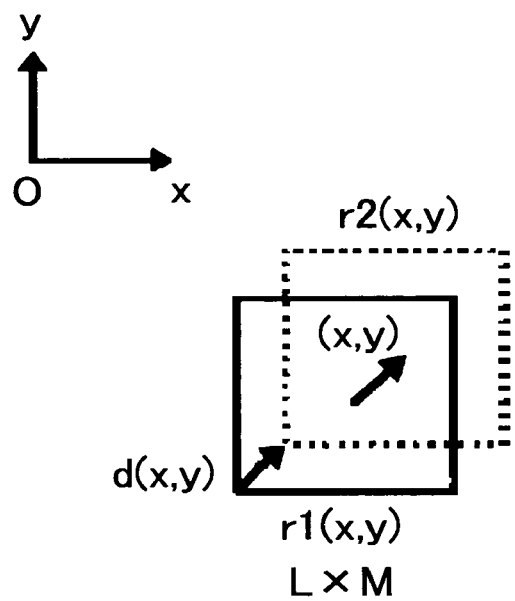
FIG. 15 shows illustration of a local 2D region centered on a point (x,y) in 2D ROI in pre-deformation ultrasound echo signal space, and the shifted one in post-deformation ultrasound echo signal space.
Figure 16:
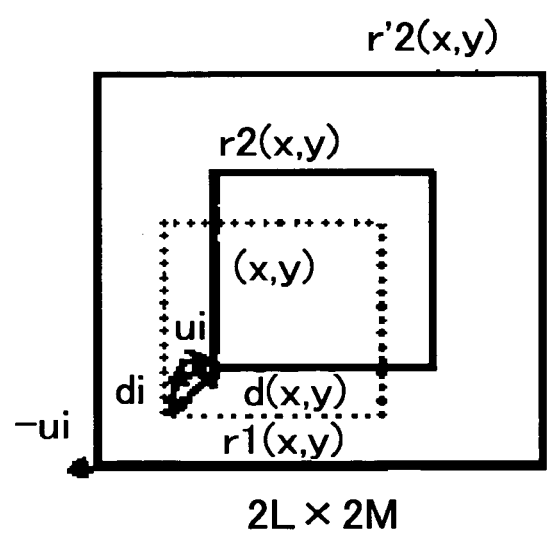
FIG. 16 shows illustration as the example of searching for local 2D ultrasound echo signal by phase matching in searching region set in post-deformation ultrasound echo signal space. That is, the corresponding local signal is searched for using pre-deformation local echo signal.
Figure 17:
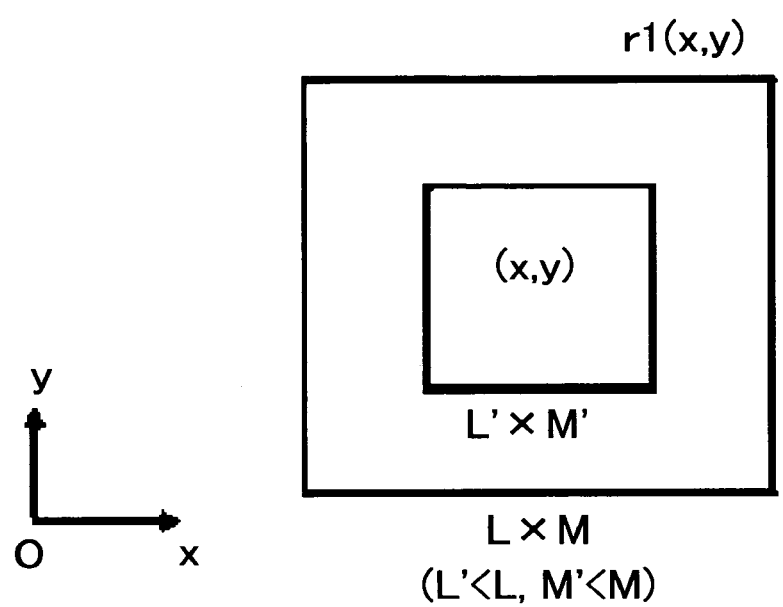
FIG. 17 shows illustration to make 2D displacement vector distribution high spatial resolution, i.e., to make local region small.

(II) Method 2: Measurement of 2D Displacement Vector Component Distribution in 2D ROI The 2D displacement vector distribution can be measured in 2D ROI 7 in the Cartesian coordinate system. The 2D ultrasound echo signals $r_1(x,y)$ and $r_2(x,y)$ are respectively acquired under pre-deformation and post-deformation. These echo signals are processed by the below-described methods 2-1, 2-2, 2-3, 2-4, and 2-5. That is, as shown in FIG. 15, a local region is set at each point in the pre- and post-deformation 2D echo signal, and as shown in FIG. 16, the corresponding local region is iteratively searched for in the ROI 7 using the local phase characteristics as the index. In this searching scheme, the estimated residual displacement vector is used to update the previously estimated displacement vector. When the estimated residual displacement vector is satisfied with prescribed conditions, the local region size is made small (FIG. 17). Thus, accurate 2D displacement vector measurement is realized. Here, the sampling intervals are $\Delta x$ and $\Delta y$ respectively in the x and y-axes.

[Method 2-1]

The procedure of the method 2-1 is shown in FIG. 10. The processes 1 to 5 yields the 2D displacement vector $d(x,y)$ $[=(dx(x,y), dy(x,y))^T]$ of an arbitrary point (x,y) in 2D ROI from the pre- and post-deformation local 2D echo signals $r_1(l,m)$ and $r_2(l,m)$ [$0 \leq l \leq L-1$, $0 \leq m \leq M-1$] centered on (x,y) of the pre- and post-deformation 2D echo signals $r_1(x,y)$ and $r_2(x,y)$. L and M should be determined such that $\Delta xL$ and $\Delta yM$ are respectively at least 4 times longer than the corresponding displacement components $|dx(x,y)|$ and $|dy(x,y)|$.

(Process 1: Phase Matching at the Point (x,y))

Phase matching is performed to obtain the i-th estimate $d^i(x,y)$ $[=(d^i x(x,y), d^i y(x,y))^T]$ of the 2D displacement vector $d(x,y)$ $[=(dx(x,y), dy(x,y))^T]$.

Searching region is set in the post-deformation echo signal space $r_2(x,y)$, being centered on the local region [$0 \leq l \leq L-1$, $0 \leq m \leq M-1$] centered on (x,y) and being twice longer than the corresponding length, in order to update the i-1 th estimate $d^{i-1}(x,y)$ $[=(d^{i-1}x(x,y), d^{i-1}y(x,y))^T]$ of the 2D displacement vector $d(x,y)$ $[=(dx(x,y), dy(x,y)^T)$, where $$d^0(x,y) = \check{d}(x,y). \tag{29}$$

The phase of the post-deformation local echo signal is matched to pre-deformation local echo signal by multiplying $$\exp\left\{ j\frac{2\pi}{L}\frac{d_x^{i-1}(x,y)}{\Delta x}l + j\frac{2\pi}{M}\frac{d_y^{i-1}(x,y)}{\Delta y}m \right\} \tag{30}$$

to the 2D Fourier's transform of this searching region echo signal $r'_2(l,m)$ [$0 \leq l \leq 2L-1$, $0 \leq m \leq 2M-1$] using the 1-th estimate $d^{i-1}(x,y)$, or by multiplying $$\exp\left\{ j\frac{2\pi}{L}\frac{\bar{u}_x^{i-1}(x,y)}{\Delta x}l + j\frac{2\pi}{M}\frac{\bar{u}_y^{i-1}(x,y)}{\Delta y}m \right\} \tag{30'}$$

to the 2D Fourier's transform of the i−1 th phase-matched searching region echo signal $r'^{i-1}{}_2(l,m)$ using the estimate $\hat{u}^{i-1}(x,y)$ $[=(\hat{u}_x^{i-1}(x,y), \hat{u}_y^{i-1}(x,y))^T][\hat{u}^0(x,y)=0$ (zero vector)] of the vector $u^{i-1}(x,y)$ $[=(u^{i-1}_x(x,y), u^{i-1}_y(x,y))^T]$.

By carrying out the inverse Fourier's transform of this product, the post-deformation echo signal $r'_2(l,m)$ is obtained at the center of the searching region echo signal $r''_2(l,m)$, which is used at the i-th stage to estimate the 2D displacement vector $d(x,y)$ $[=(dx(x,y), dy(x,y))^T]$.

Alternatively, the phase of the pre-deformation local echo signal can be matched to the post-deformation local echo signal in a similar way. That is, the 2D Fourier's transform of the searching region echo signal $r'_1(l,m)$ [$0 \leq l \leq 2L-1$, $0 \leq m \leq 2M-1$] centered on the point (x,y) in the pre-deformation echo signal region is multiplied with $$\exp\left\{ -j\frac{2\pi}{L}\frac{d_x^{i-1}(x,y)}{\Delta x}l - j\frac{2\pi}{M}\frac{d_y^{i-1}(x,y)}{\Delta y}m \right\}, \tag{30''}$$

or the 2D Fourier's transform of the i−1 th phase-matched searching region echo signal $r'^{i-1}{}_1(l,m)$ is multiplied with $$\exp\left\{ -j\frac{2\pi}{L}\frac{\bar{u}_x^{i-1}(x,y)}{\Delta x}l - j\frac{2\pi}{M}\frac{\bar{u}_y^{i-1}(x,y)}{\Delta y}m \right\}. \tag{30'''}$$

(Process 2: Estimation of 2D Residual Displacement Vector at the Point (x,y))

The local 2D echo cross-spectrum is evaluated from the 2D Fourier's transforms of the pre-deformation local 2D ultrasound echo signal $r_1(l,m)$ and phase-matched post-deformation local 2D ultrasound echo signal $r'_2(l,m)$.

$$S^i_{2,1}(l,m) = R_2^{i*}(l,m)R_1(l,m), \tag{31}$$

where * denotes conjugate.

Alternatively, when the pre-deformation local 2D ultrasound echo signal is phase-matched, the cross-spectrum of $r'^i_1(l,m)$ and $r_2(l,m)$ is evaluated as $$S^i_{2,1}(l,m) = R_2^*(l,m)R^i_1(l,m).$$

The cross-spectrum is represented as $$S^i_{2,1}(l,m) \cong |R^i_1(l,m)|^2 \exp\left\{ j\frac{2\pi}{L}\frac{u_x^i(x,y)}{\Delta x}l + j\frac{2\pi}{M}\frac{u_y^i(x,y)}{\Delta y} \right\}, \tag{32}$$

where $0 \leq l \leq L-1$, $0 \leq m \leq M-1$, and then the phase is represented as $$\theta^i(l,m) = \tan^{-1}\left( \frac{\text{Im}[S^i_{2,1}(l,m)]}{\text{Re}[S^i_{2,1}(l,m)]} \right), \tag{33}$$

where Re[·] and Im[·] respectively represent the real and imaginary component of "·".

The least squares method is implemented on the gradient of the phase eq. (33) weighted with the squared cross-spectrum $$|S_{2,1}{}^i(l,m)|^2 (=Re^2[S_{2,1}{}^i(l,m)] + Im^2[S_{2,1}{}^i(l,m)]).$$

That is, by minimizing functional:

$$\text{error}(u^i(x, y)) = \qquad (34)$$

$$\sum_{l,m} |S_{2,1}^i(l, m)|^2 \left( \theta^i(l, m) - u_x^i(x, y)\left(\frac{2\pi}{L\Delta x}\right)l - u_y^i(x, y)\left(\frac{2\pi}{M\Delta y}\right)m \right)^2$$

with respect to the 2D residual vector $u^i(x,y)$ to be used to update the i−1 th estimate $d^{i-1}(x,y)$ of the 2D displacement vector $d(x,y)$, the estimate of $u^i(x,y)$ is obtained as $$\hat{u}^i(x,y)[=(\hat{u}_x^i(x,y),\hat{u}_y^i(x,y))^T].$$

Concretely, the following simultaneous equations are solved.

$$\begin{bmatrix} \sum_{l,m} |S_{2,1}^i(l, m)|^2 \left(\frac{2\pi}{L\Delta x}\right) l\theta^i(l, m) \\ \sum_{l,m} |S_{2,1}^i(l, m)|^2 \left(\frac{2\pi}{M\Delta y}\right) m\theta^i(l, m) \end{bmatrix} = \qquad (35)$$

$$\begin{bmatrix} \sum_{l,m} |S_{2,1}^i(l, m)|^2 \left(\frac{2\pi}{L\Delta x}\right)^2 l^2 & \sum_{l,m} |S_{2,1}^i(l, m)|^2 \left(\frac{2\pi}{L\Delta x}\right)\left(\frac{2\pi}{M\Delta y}\right) lm \\ \sum_{l,m} |S_{2,1}^i(l, m)|^2 \left(\frac{2\pi}{L\Delta x}\right)\left(\frac{2\pi}{M\Delta y}\right) lm & \sum_{l,m} |S_{2,1}^i(l, m)|^2 \left(\frac{2\pi}{M\Delta y}\right)^2 m^2 \end{bmatrix} \times \begin{bmatrix} u_x^i(x, y) \\ u_y^i(x, y) \end{bmatrix}$$

When the 2D displacement vector $d(x,y)$ is large, the 2D residual displacement vector $u^i(x,y)$ needs to be estimated after unwrapping the phase of the cross-spectrum [eq. (31)] in the frequency domain (l,m).

Alternatively, when the 2D displacement vector $d(x,y)$ is large, by using the cross-correlation method (evaluation of the peak position of the cross-correlation function obtained as the 2D inverse Fourier's transform of the cross-spectrum [eq. (31)]) at the initial stages during iterative estimation, the 2D residual displacement vector $u^i(x,y)$ can be estimated without unwrapping the phase of the cross-spectrum [eq. (31)] in the frequency domain. Specifically, by using the cross-correlation method, x and y components of the 2D displacement vector are respectively estimated as integer multiplications of the ultrasound echo sampling intervals $\Delta x$, $\Delta y$. For instance, with respect to the threshold values correTratio or correTdiff, after $$\frac{\|\hat{u}^i(x, y)\|}{\|\hat{u}^{i-1}(x, y)\|} \leq \text{correTratio} \qquad (36)$$

or $$\|\hat{u}^i(x, y)\| \leq \text{correTdiff} \qquad (36')$$

is satisfied with where $\|\hat{u}^i(x,y)\|$ and $\|\hat{u}^{i-1}(x,y)\|$ are respectively the norms (magnitudes) of the i th and i−1 th estimates of the residual vectors, by using the estimate of the 2D displacement vector $d(x,y)$ as the initial estimate, the 2D residual displacement vector is estimated from the gradient of the phase of the cross-spectrum [eq. (31)].

Empirically it is known that after using the cross-correlation method the conditions $|u_x^i(x,y)| \leq \Delta x/2$, $|u_y^i(x,y)| \leq \Delta y/2$ are satisfied with. Then, the necessary and sufficient condition for enabling estimation of the 2D residual displacement vector without unwrapping the phase of the cross-spectrum $$\left| \frac{u_x^i(x, y)}{\Delta x} + \frac{u_y^i(x, y)}{\Delta y} \right| \leq 1 \qquad (37)$$

is satisfied with.

Alternatively, when the magnitude of the 2D displacement vector $d(x,y)$ is large, at initial stages, the acquired original ultrasound echo data can be thinned out with a constant interval in each direction and the reduced echo data can be used such that the 2D residual displacement vector can be estimated without unwrapping the phase of the cross-spectrum [eq. (31)] in the frequency domain (l,m). Specifically, the acquired original ultrasound echo data are thinned out with a constant interval in each direction and the reduced echo data are used such that the condition (37) or (37') is satisfied with.

$$|u_x^i(x,y)| \leq \Delta x/2 \text{ and } |u_y^i(x,y)| \leq \Delta y/2. \qquad (37')$$

The iteration number i increasing, i.e., the magnitude of the 2D residual displacement vector components $u_x^i(x,y)$, $u_y^i(x, y)$ decreasing, the ultrasound echo data densities are made restored in each direction, for instance, twice per an iteration.

The interval of the ultrasound echo signal data are shortened, for instance, when with respect to the threshold values stepTratio or stepTdiff the condition $$\frac{\|\hat{u}^i(x, y)\|}{\|\hat{u}^{i-1}(x, y)\|} \leq \text{stepTratio} \qquad (38)$$

or $$\|\hat{u}^i(x, y) - \hat{u}^{i-1}(x, y)\| \leq \text{stepTdiff} \qquad (38')$$

is satisfied with, where $\|\hat{u}^i(x,y)\|$ and $\|\hat{u}^{i-1}(x,y)\|$ are respectively the norms (magnitudes) of the i th and i−1 th estimates of the residual vectors.

The condition (38) or (38') can be applied to each direction component, and in this case the data interval is shorten in each direction. These are also applied to the below-described methods 2-2, 2-3, 2-4, and 2-5.

(Process 3: Update of the 2D Displacement Vector Estimate of the Point (x,y))

Thus, the i th estimate of the 2D displacement vector $d(x,y)$ is evaluated as $$d^i(x,y) = d^{i-1}(x,y) + \hat{u}^i(x,y). \qquad (39)$$

[Process 4: Condition for Heightening the Spatial Resolution of the 2D Displacement Vector Distribution Measurement (Condition for Making the Local Region Small)]

In order to make the spatial resolution high of the 2D displacement vector distribution measurement, the local region is made small during the iterative estimation. The criteria is below-described. The processes 1, 2 and 3 are iteratively carried out till the criteria is satisfied with. When the criteria is satisfied with, the local region is made small, for instance, the length of each side is made half. For instance, the criteria is (40) or (40') with respect to the threshold values Tratio or Tdiff.

$$\frac{\|\hat{u}^i(x, y)\|}{\|\hat{u}^{i-1}(x, y)\|} \leq Tratio \qquad (40)$$

or $$\|\hat{u}^i(x, y) - \hat{u}^{i-1}(x, y)\| \leq Tdiff, \qquad (40')$$

where $\|\hat{u}^i(x,y)\|$ and $\|\hat{u}^{i-1}(x,y)\|$ are respectively the norms (magnitudes) of the i th and i−1 th estimates of the residual vectors.

The condition (40) or (40') can be applied to each direction component, and in this case the side is shorten in each direction.

(Process 5: Condition for Terminating the Iterative Estimation of the 2D Displacement Vector of the Point (x,y))

Described below is the criteria for terminating the iterative estimation of the 2D displacement vector of each point. The processes 1, 2 and 3 are iteratively carried out till the criteria is satisfied with. For instance, the criteria is (41) or (41') with respect to threshold values aboveTratio or aboveTdiff.

$$\frac{\|\hat{u}^i(x, y)\|}{\|\hat{u}^{i-1}(x, y)\|} \leq aboveTratio \qquad (41)$$

or $$\|\hat{u}^i(x, y) - \hat{u}^{i-1}(x, y)\| \leq aboveTdiff, \qquad (41')$$

where $\|\hat{u}^i(x,y)\|$ and $\|\hat{u}^{i-1}(x,y)\|$ are respectively the norms (magnitudes) of the i th and i−1 th estimates of the residual vectors.

(Process 6)

The 2D displacement vector component distributions are obtained by carrying out processes 1, 2, 3, 4, and 5 at every point in the 2D ROI.

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Limitation of Method 2-1]

The estimate of the 2D displacement vector d(x,y) is iteratively updated at each point (x,y) in the 2D ROI. Being dependent on the SNR of the local 2D echo signals, particularly at the initial stages errors possibly occur when estimating the residual vector and then the phase matching possibly diverges. For instance, when solving eq. (35) [process 2] or detecting the peak position of the cross-correlation function [process 2], errors possibly occur.

The possibility for divergence of the phase matching is, for instance, confirmed by the condition (42) or (42') with respect to the threshold value belowTratio or BelowTdiff.

$$\frac{\|\hat{u}^i(x, y)\|}{\|\hat{u}^{i-1}(x, y)\|} \geq belowTratio \qquad (42)$$

or $$\|\hat{u}^i(x, y) - \hat{u}^{i-1}(x, y)\| \geq belowTdiff, \qquad (42')$$

where $\|\hat{u}^i(x,y)\|$ and $\|\hat{u}^{i-1}(x,y)\|$ are respectively the norms (magnitudes) of the i th and i−1 th estimates of the residual vectors.

To prevent the phase matching (process 1) from diverging, in the below-described methods 2-2, 2-3, 2-4, and 2-5, by freely using the condition (42) or (42'), estimation error is reduced of the residual vector. Thus, even if the SNR of the ultrasound echo signals are low, accurate 2D displacement vector measurement can be realized.

[Method 2-2]

The flowchart of the method 2-2 is shown in FIG. 11. To prevent the phase matching from diverging at the process 1 of the method 2-1, the estimation error is reduced of the residual vector. Thus, even if the SNR of the ultrasound echo signals are low, accurate 2D displacement vector measurement can be realized.

The procedure of the iterative estimation is different from that of the method 2-1. At i th estimate (i≥1), the following processes are performed.

(Process 1: Estimation of the 2D Residual Displacement Vector Distribution)

The phase matching and estimation of the 2D residual displacement vector are performed at every point (x,y) in the 2D ROI. That is, the processes 1 and 2 of the method 2-1 are performed once at every point in the ROI. Thus, the estimate of the 2D residual vector distribution is obtained.

(Process 2: Update of the Estimate of the 2D Displacement Vector Distribution)

The i−1 th estimate of the 2D displacement vector distribution is updated using i th estimate of the 2D residual vector distribution.

$$\hat{d}^i(x,y) = \hat{d}^{i-1}(x,y) + \hat{u}^i(x,y) \qquad (43)$$

Next, this estimate is 2D low pass filtered or 2D median filter to yield the estimate of the 2D displacement vector distribution:

$$\hat{d}^i(x,y) = LPF[\hat{d}^i(x,y)], \text{ or } \hat{d}^i(x,y) = MED[\hat{d}^i(x,y)]. \qquad (44)$$

Thus, the estimation error is reduced of the residual vector compared with the process 2 of the method 2-1 [eq. (35)]. Hence, phase matching of the process 1 of method 2-2 is performed using the smoothed estimate of the 2D displacement vector distribution.

[Process 3: Condition for Heightening the Spatial Resolution of the 2D Displacement Vector Distribution Measurement (Condition for Making the Local Region Small)]

In order to make the spatial resolution high of the 2D displacement vector distribution measurement, during the iterative estimation, the local region used for each point is made small, or the local region used over the ROI is made small.

The criteria for each point is described below. The processes 1 and 2 (method 2-2) are iteratively carried out till the criteria is satisfied with. When the criteria is satisfied with, the local region is made small, for instance, the length of each side is made half. For instance, the criteria is (45) or (45') with respect to the threshold values Tratio or Tdiff.

$$\frac{\|\hat{u}^i(x,y)\|}{\|\hat{u}^{i-1}(x,y)\|} \le Tratio \qquad (45)$$

or $$\|\hat{u}^i(x,y) - \hat{u}^{i-1}(x,y)\| \le Tdiff, \qquad (45')$$

where $\|\hat{u}^i(x,y)\|$ and $\|\hat{u}^{i-1}(x,y)\|$ are respectively the norms (magnitudes) of the i th and i−1 th estimates of the residual vectors.

The condition (45) or (45') can be applied to each direction component, and in this case the side is shorten in each direction.

The criteria over the ROI is described below. The processes 1 and 2 (method 2-2) are iteratively carried out till the criteria is satisfied with. When the criteria is satisfied with, the local region is made small, for instance, the length of each side is made half. For instance, the criteria is (46) or (46') with respect to the threshold values Tratioroi or Tdiffroi.

$$\frac{\sum_{(x,y)\in ROI}\|\hat{u}^i(x,y)\|^2}{\sum_{(x,y)\in ROI}\|\hat{u}^{i-1}(x,y)\|^2} \le Tratioroi \qquad (46)$$

or $$\sum_{(x,y)\in ROI}\|\hat{u}^i(x,y) - \hat{u}^{i-1}(x,y)\| \le Tdiffroi, \qquad (46')$$

where $\|\hat{u}^i(x,y)\|$ and $\|\hat{u}^{i-1}(x,y)\|$ are respectively the norms (magnitudes) of the i th and i−1 th estimates of the residual vectors.

The condition (46) or (46') can be applied to each direction component, and in this case the side is shorten in each direction.

(Process 4: Condition for Terminating the Iterative Estimation of the 2D Displacement Vector Distribution)

Described below is the criteria for terminating the iterative estimation of the 2D displacement vector distribution. The processes 1, 2 and 3 of method 2-2 are iteratively carried out till the criteria is satisfied with. For instance, the criteria is (47) or (47') with respect to the threshold values aboveTratioroi or aboveTdiffroi.

$$\frac{\sum_{(x,y)\in ROI}\|\hat{u}^i(x,y)\|^2}{\sum_{(x,y)\in ROI}\|\hat{u}^{i-1}(x,y)\|^2} \le aboveTratioroi \qquad (47)$$

or $$\sum_{(x,y)\in ROI}\|\hat{u}^i(x,y) - \hat{u}^{i-1}(x,y)\| \le aboveTdiffroi, \qquad (47')$$

where $\|\hat{u}^i(x,y)\|$ and $\|\hat{u}^{i-1}(x,y)\|$ are respectively the norms (magnitudes) of the i th and i−1 th estimates of the residual vectors.

Final estimate is obtained from eq. (43) or eq. (44).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Method 2-3]

The flowchart of the method 2-3 is shown in FIG. 12. To prevent the phase matching from diverging at the process 1 of the method 2-1, the estimation error is reduced of the residual vector. Possibility of the divergence is detected from the above-described condition (42) or (42'), and by effectively utilizing method 2-1 and 2-2, even if the SNR of the ultrasound echo signals are low, accurate 2D displacement vector measurement can be realized.

At first, the procedure of the iterative estimation is same as that of the method 2-2 (Processes 1, 2, 3, and 4). At i th estimate, the following processes are performed.

The phase matching and estimation of the 2D residual displacement vector are performed at every point (x,y) in the 2D ROI. That is, the processes 1 and 2 of the method 2-1 are performed once at every point in the ROI. Thus, the estimate of the 2D residual vector distribution is obtained.

During this estimation, if neither condition (42) nor (42') is satisfied with, the method 2-1 is used. If condition (42) or (42') is satisfied with at points or regions, in the process 2 of the method 2-2, over sufficiently large regions centered on the points or regions, or over the ROI, the estimate $d^i(x,y)$ of the 2D displacement vector d(x,y) can be 2D low pass filtered or 2D median filtered as eq. (48).

$$\hat{d}^i(x,y)=LPF[d^i(x,y)], \text{ or } \hat{d}^i(x,y)=MED[d^i(x,y)] \qquad (48)$$

Thus, the estimation error is reduced of the residual vector compared with the process 2 of the method 2-1 [eq. (35)].

Thus, iterative estimation is terminated at the process 5 of the method 2-1 or the process 4 of the method 2-2. Hence, the final estimate is obtained from eq. (39), or eq. (43), or eq. (48).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Method 2-4]

The flowchart of the method 2-4 is shown in FIG. 13. To prevent the phase matching from diverging at the process 1 of the method 2-1, the estimation error is reduced of the residual vector. Thus, even if the SNR of the ultrasound echo signals are low, accurate 2D displacement vector measurement can be realized.

The procedure of iterative estimation is different from that of the method 2-1. At i th estimate (i≥1), the following processes are performed.

(Process 1: Estimation of the 2D Residual Displacement Vector Distribution)

The phase matching and estimation of the 2D residual displacement vector are performed at every point (x,y) in the 2D ROI. That is, the process 1 of the method 2-1 is performed once at every point in the ROI.

To obtain the estimate $\hat{u}^i(x,y)$ [$=(\hat{u}_x^i(x,y), \hat{u}_y^i(x,y))^T$] of the residual vector distribution $u^i(x,y)$ [$=(u_x^i(x,y), u_y^i(x,y))^T$], at every point the local 2D echo cross-spectrum is evaluated from the 2D Fourier's transforms of the pre-deformation local 2D ultrasound echo signal $r_1(l,m)$ and phase-matched post-deformation local 2D ultrasound echo signal $r'_2(l,m)$. Alternatively, when the pre-deformation local 2D ultrasound echo signal is phase-matched, at every point the cross-spectrum of $r^i_1(l,m)$ and $r_2(l,m)$ is evaluated.

The least squares method is implemented on the gradient of the phase with utilization of each weight function, i.e., the squared cross-spectrum $|S_{2,1}{}^i(l,m)|^2$, where each weight function is normalized by the power of the cross-spectrum, i.e., $$\sum_{l,m} |S^i_{2,1}(l,m)|^2.$$

Moreover, regularization method is also Implemented. That is, by minimizing the following functional with respect to the vector $u^i$ comprised of the 2D residual vector distribution $u^i(x,y)$.

$$\text{error}(u^i)=\|a-Fu^i\|^2+\alpha_{1i}\|u^i\|^2+\alpha_{2i}\|Gu^i\|^2+\alpha_{3i}\|G^TGu^i\|^2+\alpha_{4i}\|GG^TGu^i\|^2 \quad (49)$$

where
- a: vector comprised of (x,y) distribution of the cross-spectrum phase $\Theta^i(l,m)$ weighted with the cross-spectrum $|S_{2,1}{}^i(l,m)|$ normalized by the magnitude of the cross-spectrum $$\sqrt{\sum_{l,m} |S^i_{2,1}(l,m)|^2}$$

evaluated at every point in the 2D ROI.
- F: matrix comprised of (x,y) distribution of the Fourier's coordinate value (l,m) weighted with the cross-spectrum $|S_{2,1}{}^i(l,m)|$ normalized by the magnitude of the cross-spectrum $$\sqrt{\sum_{l,m} |S^i_{2,1}(l,m)|^2}$$

evaluated at every point in the 2D ROI.
- $\alpha_{1i}, \alpha_{2i}, \alpha_{3i}, \alpha_{4i}$: regularization parameter (at least larger than zero)
- $Gu^i$: vector comprised of the finite difference approximations of the 213 distributions of the 2D gradient components of the unknown 2D residual vector $u^i(x,y)$ components $$\frac{\partial}{\partial x}u^i_x(x,y), \frac{\partial}{\partial y}u^i_x(x,y),$$

$$\frac{\partial}{\partial x}u^i_y(x,y), \frac{\partial}{\partial y}u^i_y(x,y)$$

$G^TGu^i$: vector comprised of the finite difference approximations of the 2D distributions of the 2D Laplacians of the unknown 2D residual vector $u^i(x,y)$ components $$\frac{\partial^2}{\partial x^2}u^i_x(x,y)+\frac{\partial^2}{\partial y^2}u^i_x(x,y)$$

$$\frac{\partial^2}{\partial x^2}u^i_y(x,y)+\frac{\partial^2}{\partial y^2}u^i_y(x,y)$$

$GG^TGu^i$: vector comprised of the finite difference approximations of the 2D distributions of the 2D gradient components of the 2D Laplacians of the unknown 2D residual vector $u^i(x,y)$ components $$\frac{\partial}{\partial x}\left(\frac{\partial^2}{\partial x^2}u^i_x(x,y)+\frac{\partial^2}{\partial y^2}u^i_x(x,y)\right),$$

$$\frac{\partial}{\partial y}\left(\frac{\partial^2}{\partial x^2}u^i_x(x,y)+\frac{\partial^2}{\partial y^2}u^i_x(x,y)\right),$$

$$\frac{\partial}{\partial x}\left(\frac{\partial^2}{\partial x^2}u^i_y(x,y)+\frac{\partial^2}{\partial y^2}u^i_y(x,y)\right),$$

$$\frac{\partial}{\partial y}\left(\frac{\partial^2}{\partial x^2}u^i_y(x,y)+\frac{\partial^2}{\partial y^2}u^i_y(x,y)\right)$$

As $\|u^i\|^2, \|Gu^i\|^2, \|G^TGu^i\|^2, \|GG^TGu^i\|^2$ are positive definite, error ($u^i$) has one minimum value. Thus, by solving for the residual displacement vector distribution $u^i(x,y)$ the simultaneous equations:

$$(F^TF+\alpha_{1i}I+\alpha_{2i}G^TG+\alpha_{3i}G^TGG^TG+\alpha_{4i}G^TGG^T GG^TG)u^i=F^Ta, \quad (50)$$

The estimate $\hat{u}^i(x,y)$ $[=(\hat{u}^i_x(x,y), \hat{u}^i_y(x,y))^T]$ of the residual vector distribution $u^i(x,y)$ $[=(\hat{u}^i_x(x,y), u^i_y(x,y))^T]$ is stably obtained. Thus, estimation error is reduced of the residual vector.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then the position of the unknown displacement vector, direction of the unknown displacement component, direction of the partial derivative, etc.

(Process 2: Update of the Estimate of the 2D Displacement Vector Distribution)

The i−1 th estimate of the 2D displacement vector distribution is updated using the i th estimate of the 2D residual vector distribution.

$$d^i(x,y)=\hat{d}^{i-1}(x,y)+\hat{u}^i(x,y) \quad (51)$$

Freely, this estimate can be 2D low pass filtered or 2D median filter to yield the estimate of the 2D displacement vector distribution.

$$\hat{d}^i(x,y)=LPF[d^i(x,y)], \text{ or } \hat{d}^i(x,y)=MED[d^i(x,y)] \quad (52)$$

Hence, the phase matching of the process 1 of method 2-4 is performed using the 2D residual vector data $u^i(x,y)$ obtained from eq. (50), or the 2D vector data $d^i(x,y)$ obtained from eq. (51), or smoothed estimate obtained from eq. (52).

[Process 3: Condition for Heightening the Spatial Resolution of the 2D Displacement Vector Distribution Measurement (Condition for Making the Local Region Small)]

In order to make the spatial resolution high of the 2D displacement vector distribution measurement, during the iterative estimation, the local region used for each point is made small, or the local region used over the ROI is made small.

The criteria for each point is described below. The processes 1 and 2 of method 2-4 are iteratively carried out till the criteria is satisfied with. When the criteria is satisfied with, the local region is made small, for instance, the length of each side is made half. For instance, the criteria is (25) or (25') with respect to the threshold values Tratio or Tdiff.

$$\frac{\|\hat{u}^i(x,y)\|}{\|\hat{u}^{i-1}(x,y)\|} \leq Tratio \quad (53)$$

or $$\|\hat{u}^i(x,y) - \hat{u}^{i-1}(x,y)\| \leq Tdiff, \quad (53')$$

where $\|\hat{u}^i(x,y)\|$ and $\|\hat{u}^{i-1}(x,y)\|$ are respectively the norms (magnitudes) of the i th and i−1 th estimates of the residual vectors.

The condition (53) or (53') can be applied to each direction component, and in this case the side is shorten in each direction.

The criteria over the ROI is described below. The processes 1 and 2 of the method 2-4 are iteratively carried out till the criteria is satisfied with. When the criteria is satisfied with, the local region is made small, for instance, the length of each side is made half. For instance, the criteria is (54) or (54') with respect to the threshold values Tratioroi or Tdiffroi.

$$\frac{\sum_{(x,y)\in ROI} \|\hat{u}^i(x,y)\|^2}{\sum_{(x,y)\in ROI} \|\hat{u}^{i-1}(x,y)\|^2} \leq Tratioroi \quad (54)$$

or $$\sum_{(x,y)\in ROI} \|\hat{u}^i(x,y) - \hat{u}^{i-1}(x,y)\| \leq Tdiffroi, \quad (54')$$

where $\|\hat{u}^i(x,y)\|$ and $\|\hat{u}^{i-1}(x,y)\|$ are respectively the norms (magnitudes) of the i th and i−1 th estimates of the residual vectors.

The condition (54) or (54') can be applied to each direction component, and in this case the side is shorten in each direction.

(Process 4: Condition for Terminating the Iterative Estimation of the 2D Displacement Vector Distribution)

Described below is the criteria for terminating the iterative estimation of the 2D displacement vector distribution. The processes 1, 2 and 3 of the method 2-4 are iteratively carried out till the criteria is satisfied with. For instance, the criteria is (55) or (55') with respect to the threshold values aboveTratioroi or aboveTdiffroi.

$$\frac{\sum_{(x,y)\in ROI} \|\hat{u}^i(x,y)\|^2}{\sum_{(x,y)\in ROI} \|\hat{u}^{i-1}(x,y)\|^2} \leq aboveTratioroi \quad (55)$$

or $$\sum_{(x,y)\in ROI} \|\hat{u}^i(x,y) - \hat{u}^{i-1}(x,y)\| \leq aboveTdiffroi, \quad (55')$$

where $\|\hat{u}^i(x,y)\|$ and $\|\hat{u}^{i-1}(x,y)\|$ are respectively the norms (magnitudes) of the i th and i−1 th estimates of the residual vectors.

Final estimate is obtained from eq. (51) or eq. (52).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Method 2-5]

The flowchart of the method 2-5 is shown in FIG. 14. To prevent the phase matching from diverging at the process 1 of the method 2-1, the estimation error is reduced of the residual vector. Possibility of the divergence is detected from the above-described condition (42) or (42'), and by effectively utilizing methods 2-1 and 2-4, even if the SNR of the ultrasound echo signals are low, accurate 2D displacement vector measurement can be realized.

At first, the procedure of the iterative estimation is same as that of the method 2-4 (Processes 1, 2, 3, and 4). At the i th estimate, the following processes are performed.

The phase matching and estimation of the 2D residual displacement vector are performed at every point (x,y) in the 2D ROI. That is, the process 1 of the method 2-1 is performed once at every point in the ROI. Moreover, using the regularization method, stably the estimate of the 2D residual vector distribution is obtained.

i−1 th estimate $\hat{d}^{i-1}(x,y)$ of 2D displacement vector distribution d(x,y).

i th estimate $\hat{u}^i(x,y)$ of 2D residual vector distribution $u^i(x,y)$.

During this estimation, if neither condition (42) nor (42') is satisfied with, the method 2-1 is used. If the condition (42) or (42') is satisfied with at the points or regions, in the process 2 of the method 2-4, over sufficiently large regions centered on the points or regions, or over the ROI, the estimate $d^i(x,y)$ of the 2D displacement vector d(x,y) can be 2D low pass filtered or 2D median filtered as eq. (56).

$$\hat{d}^i(x,y) = LPF[d^i(x,y)], \text{ or } \hat{d}^i(x,y) = MED[d^i(x,y)] \quad (56)$$

Thus, the estimation error is reduced of the residual vector.

The iterative estimation is terminated at the process 5 of the method 2-1 or the process 4 of the method 2-4. Hence, the final estimate is obtained from eq. (39), or eq. (51), or eq. (56).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

Figure 18:
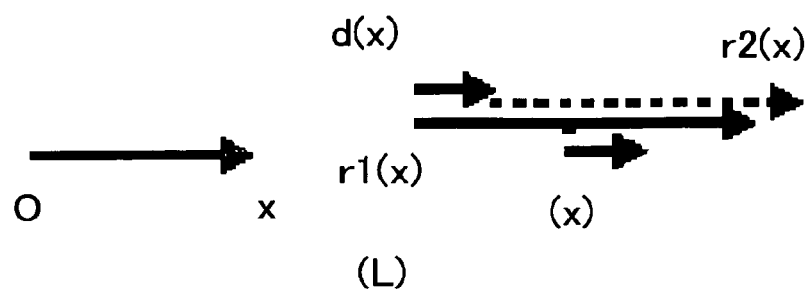
FIG. 18 shows illustration of a local 1D region centered on a point (x) in 1D ROI in pre-deformation ultrasound echo signal space, and the shifted one in post-deformation ultrasound echo signal space.
Figure 19:
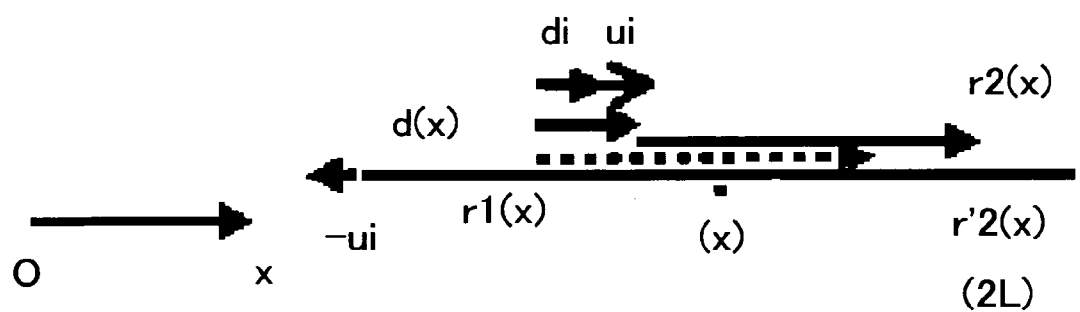
FIG. 19 shows illustration as the example of searching for local 1D ultrasound echo signal by phase matching in searching region set in post-deformation ultrasound echo signal space. That is, the corresponding local signal is searched for using pre-deformation local echo signal.
Figure 20:
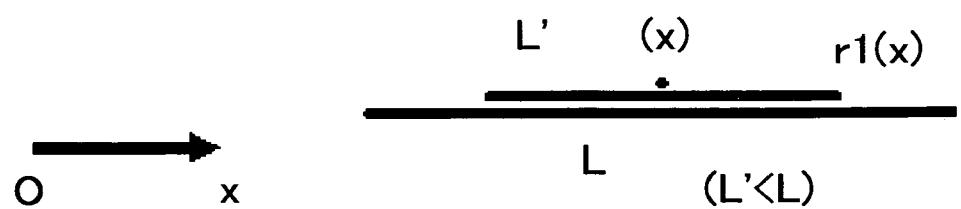
FIG. 20 shows illustration to make one direction displacement component distribution high spatial resolution, i.e., to make local region small.

(III) Method 3: Measurement of 1D (One Direction) Displacement Component Distribution in 1D ROI The 1D displacement component distribution can be measured in 1D ROI 7 in the Cartesian coordinate system. The 1D ultrasound echo signals $r_1(x)$ and $r_2(x)$ are respectively acquired under the pre-deformation and post-deformation. These echo signals are processed by the below-described methods 3-1, 3-2, 3-3, 3-4, and 3-5. That is, as shown in FIG. 18, a local region is set at each point in the pre- and post-deformation 1D echo signal, and as shown in FIG. 19, the corresponding local region is iteratively searched for in the ROI 7 using the local phase characteristics as the index. In this searching scheme, the estimated residual displacement component is used to update the previously estimated displacement component. When the estimated residual displacement component is satisfied with prescribed conditions, the local region size is made small (FIG. 20). Thus, accurate 1D displacement component measurement is realized. Here, the sampling interval is $\Delta x$ in the x-axis.

[Method 3-1]

The procedure of the method 3-1 is shown in FIG. 10. The processes 1 to 5 yield 1D displacement component dx(x) of an arbitrary point x in 1D ROI from the pre- and post-deformation local 1D echo signals $r_1(l)$ and $r_2(l)$ [$0 \leq l \leq L-1$] centered on x of the pre- and post-deformation 1D echo signals $r_1(x)$ and $r_2(x)$. L should be determined such that $\Delta xL$ is at least 4 times longer than the displacement component $|dx(x)|$.

(Process 1: Phase Matching at the Point x)

Phase matching is performed to obtain the i-th estimate $d^i x(x)$ of the 1D displacement component $dx(x)$.

Searching region is set in the post-deformation echo signal space $r_2(x)$, being centered on the local region $[0 \leq l \leq L-1]$ centered on x and being twice longer than the local region length, in order to update the i−1 th estimate $d^{i-1} x(x)$ of the 1D displacement component $dx(x)$, where $$dx^0(x) = \check{d}x(x). \tag{57}$$

The phase of the post-deformation local echo signal is matched to the pre-deformation local echo signal by multiplying $$\exp\left\{ j \frac{2\pi}{L} \frac{d_x^{i-1}(x)}{\Delta x} l \right\} \tag{58}$$

to 1D Fourier's transform of this searching region echo signal $r'_2(l)$ $[0 \leq l \leq 2L-1]$ using 1-th estimate $dx^{i-1}(x)$, or by multiplying $$\exp\left\{ j \frac{2\pi}{L} \frac{\hat{u}_x^{i-1}(x)}{\Delta x} l \right\} \tag{58'}$$

to the 1D Fourier's transform of the i−1 th phase-matched searching region echo signal $r'^{i-1}_2(l)$ using the estimate $\hat{u}_x^{i-1}(x)$ $[\hat{u}_x^0(x)=0$ (zero)$]$ of the component $u^{i-1}_x(x)$.

By carrying out the inverse Fourier's transform of this product, the post-deformation echo signal $r'_2(l)$ is obtained at the center of the searching region echo signal $r'^i_2(l)$, which is used at i-th stage to estimate the 1D displacement component $dx(x)$.

Alternatively, the phase of the pre-deformation local echo signal can be matched to the post-deformation local echo signal in a similar way. That is, the 1D Fourier's transform of the searching region echo signal $r'_1(l)$ $[0 \leq l \leq 2L-1]$ centered on the point x in the pre-deformation echo signal region is multiplied with $$\exp\left\{ -j \frac{2\pi}{L} \frac{d_x^{i-1}(x)}{\Delta x} l \right\}, \tag{58''}$$

or the 1D Fourier's transform of the i−1 th phase-matched searching region echo signal $r'^{i-1}_1(l)$ is multiplied with $$\exp\left\{ -j \frac{2\pi}{L} \frac{\hat{u}_x^{i-1}(x)}{\Delta x} l \right\}. \tag{58'''}$$

(Process 2: Estimation of 1D Residual Displacement Component at the Point x)

The local 1D echo cross-spectrum is evaluated from the 1D Fourier's transforms of the pre-deformation local 1D ultrasound echo signal $r_1(l)$ and phase-matched post-deformation local 1D ultrasound echo signal $r'_2(l)$.

$$S^i_{2,1}(l) = R_2^{i*}(l) R_1(l), \tag{59}$$

where * denotes conjugate.

Alternatively, when the pre-deformation local 1D ultrasound echo signal is phase-matched, the cross-spectrum of $r'^j_1(l)$ and $r_2(l)$ is evaluated as $$S^i_{2,1}(l) = R_2^*(l) R_1^i(l).$$

The cross-spectrum is represented as $$S^i_{2,1}(l) \cong |R_1^i(l)|^2 \exp\left\{ j \frac{2\pi}{L} \frac{u_x^i(x)}{\Delta x} l \right\}, \tag{60}$$

where $0 \leq l \leq L-1$,
and then the phase is represented as $$\theta^i(l) = \tan^{-1}\left( \frac{\text{Im}[S^i_{2,1}(l)]}{\text{Re}[S^i_{2,1}(l)]} \right), \tag{61}$$

where $\text{Re}[\cdot]$ and $\text{Im}[\cdot]$ respectively represent the real and imaginary component of "·".

The least squares method is implemented on the gradient of the phase eq. (61) weighted with the squared cross-spectrum $|S_{2,1}^i(l)|^2 *(=\text{Re}^2[S_{2,1}^i(l)]^2 + \text{Im}^2[S_{2,1}^i(l)])$. That is, by minimizing the functional:

$$\text{error}(u_x^i(x)) = \sum_l |S^i_{2,1}(l)|^2 \left( \theta^i(l) - u_x^i(x)\left(\frac{2\pi}{L\Delta x}\right) l \right)^2 \tag{62}$$

with respect to the 1D residual component $u_x^i(x)$ to be used to update the i−1 th estimate $dx^{i-1}(x)$ of the 1D displacement component $dx(x)$, the estimate of $u_x^i(x)$ is obtained as $\hat{u}_x^i(x)$. Concretely, the following equation is solved.

$$\sum_l |S^i_{2,1}(l)|^2 \left(\frac{2\pi}{L\Delta x}\right) l \theta^i(l) = \sum_l |S^i_{2,1}(l)|^2 \left(\frac{2\pi}{L\Delta x}\right)^2 l^2 u_x^i(x) \tag{63}$$

When the 1D displacement component $dx(x)$ is large, the 1D residual displacement component $u_x^i(x)$ needs to be estimated after unwrapping the phase of the cross-spectrum [eq. (59)] in the frequency domain l.

Alternatively, when the 1D displacement component $dx(x)$ is large, by using the cross-correlation method (evaluation of the peak position of the cross-correlation function obtained as 1D inverse Fourier's transform of the cross-spectrum [eq. (59)]) at the initial stages during iterative estimation, the 1D residual displacement component $u_x^i(x)$ can be estimated without unwrapping the phase of the cross-spectrum [eq. (59)] in the frequency domain. Specifically, by using the cross-correlation method, x component of the 1D displacement component is estimated as integer multiplication of the ultrasound echo sampling interval $\Delta x$. For instance, with respect to the threshold values correTratio or correTdiff, after $$\frac{\|\hat{u}_x^i(x)\|}{\|\hat{u}_x^{i-1}(x)\|} \leq \text{correTratio or} \tag{64}$$

$$\|\hat{u}_x^i(x)\| \leq \text{correTdiff} \tag{64'}$$

is satisfied with where $\|\hat{u}_x^i(x)\|$ and $\|\hat{u}_x^{i-1}(x)\|$ are respectively the norms (magnitudes) of the i th and i−1 th estimates of the residual components, by using the estimate of the 1D displacement component dx(x) as the initial estimate, the 1D residual displacement component is estimated from the gradient of the phase of the cross-spectrum [eq. (59)].

Empirically it is known that after using the cross-correlation method the condition $|u_x^i(x)|\Delta x/2$ is satisfied with. Then, the necessary and sufficient condition for enable estimation of the 1D residual displacement component without unwrapping the phase of the cross-spectrum $$\left|\frac{u_x^i(x)}{\Delta x}\right| \leq 1 \tag{65}$$

is satisfied with.

Alternatively, when the magnitude of the 1D displacement component dx(x) is large, at the initial stages, the acquired original ultrasound echo data can be thinned out with a constant interval in the direction and the reduced echo data can be used such that the 1D residual displacement component can be estimated without unwrapping the phase of the cross-spectrum [eq. (59)] in the frequency domain 1. Specifically, the acquired original ultrasound echo data are thinned out with a constant interval in the direction and the reduced echo data are used such that the condition (65) or (65') is satisfied with.

$$|u_x^i(x)| \leq \Delta x/2 \tag{65'}$$

The iteration number i increasing, i.e., the magnitude of the 1D residual displacement component $u_x^i(x)$ decreasing, the ultrasound echo data density is made restored in the direction, for instance, twice per an iteration.

The interval of the ultrasound echo signal data are shortened, for instance, when with respect to the threshold values stepTratio or stepTdiff the condition $$\frac{\|\hat{u}_x^i(x)\|}{\|\hat{u}_x^{i-1}(x)\|} \leq stepTratio \text{ or} \tag{66}$$

$$\|\hat{u}_x^i(x) - \hat{u}_x^{i-1}(x)\| \leq stepTdiff \tag{66'}$$

is satisfied with, where $\|\hat{u}_x^i(x)\|$ and $\|\hat{u}_x^{i-1}(x)\|$ are respectively the norms (magnitudes) of the i th and i−1 th estimates of the residual components.

(Process 3: Update of the 1D Displacement Component Estimate of the Point x)

Thus, the i th estimate of the 1D displacement component dx(x) is evaluated as $$dx^i(x) = dx^{i-1}(x) + \hat{u}_x^i(x). \tag{67}$$

[Process 4: Condition for Heightening the Spatial Resolution of the 1D Displacement Component Distribution Measurement (Condition for Making the Local Region Small)]

In order to make the spatial resolution high of the 1D displacement component distribution measurement, the local region is made small during the iterative estimation. The criteria is described below. The processes 1, 2 and 3 are iteratively carried out till the criteria is satisfied with. When the criteria is satisfied with, the local region is made small, for instance, the length of the local region is made half. For instance, the criteria is (68) or (68') with respect to the threshold values Tratio or Tdiff.

$$\frac{\|\hat{u}_x^i(x)\|}{\|\hat{u}_x^{i-1}(x)\|} \leq Tratio \text{ or} \tag{68}$$

$$\|\hat{u}_x^i(x) - \hat{u}_x^{i-1}(x)\| \leq Tdiff, \tag{68'}$$

where $\|\hat{u}_x^i(x)\|$ and $\|\hat{u}_x^{i-1}(x)\|$ are respectively the norms (magnitudes) of the i th and i−1 th estimates of the residual components.

(Process 5: Condition for Terminating the Iterative Estimation of the 1D Displacement Component of the Point x)

Described below is the criteria for terminating the iterative estimation of the 1D displacement component of each point. The processes 1, 2 and 3 are iteratively carried out till the criteria is satisfied with. For instance, the criteria is (69) or (69') with respect to the threshold values aboveTratio or aboveTdiff.

$$\frac{\|\hat{u}_x^i(x)\|}{\|\hat{u}_x^{i-1}(x)\|} \leq aboveTratio \text{ or} \tag{69}$$

$$\|\hat{u}_x^i(x) - \hat{u}_x^{i-1}(x)\| \leq aboveTdiff, \tag{69'}$$

where $\|\hat{u}_x^i(x)\|$ and $\|\hat{u}_x^{i-1}(x)\|$ are respectively the norms (magnitudes) of the i th and i−1 th estimates of the residual components.

(Process 6)

The 1D displacement component distribution is obtained by carrying out the processes 1, 2, 3, 4, and 5 at every point in the 1D ROI.

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Limitation of Method 3-1]

The estimate of the 1D displacement component dx(x) is iteratively updated at each point x in the 1D ROI. Being dependent on the SNR of the local 1D echo signals, particularly at the initial stages errors possibly occur when estimating the residual component and then phase matching possibly diverges. For instance, when solving eq. (63) [process 2] or detecting the peak position of the cross-correlation function [process 2], errors possibly occur The possibility for divergence of the phase matching is, for instance, confirmed by the condition (70) or (70') with respect to the threshold value belowTratio or BelowTdiff.

$$\frac{\|\hat{u}_x^i(x)\|}{\|\hat{u}_x^{i-1}(x)\|} \geq belowTratio \text{ or} \tag{70}$$

$$\|\hat{u}_x^i(x) - \hat{u}_x^{i-1}(x)\| \geq belowTdiff, \tag{70'}$$

where $\|\hat{u}_x^i(x)\|$ and $\|\hat{u}_x^{i-1}(x)\|$ are respectively the norms (magnitudes) of the i th and i−1 th estimates of the residual components.

To prevent the phase matching (process 1) from diverging, in the below-described methods 3-2, 3-3, 3-4, and 3-5, by freely using the condition (70) or (70'), the estimation error is reduced of the residual component. Thus, even if the SNR of the ultrasound echo signals are low, accurate 1D displacement component measurement can be realized.

[Method 3-2]

The flowchart of the method 3-2 is shown in FIG. 11. To prevent the phase matching from diverging at the process 1 of the method 3-1, the estimation error is reduced of the residual component. Thus, even if the SNR of the ultrasound echo signals are low, accurate 1D displacement component measurement can be realized.

The procedure of the iterative estimation is different from that of the method 3-1. At the i th estimate (i≥1), the following processes are performed.

(Process 1: Estimation of the 1D Residual Displacement Component Distribution)

The phase matching and estimation of the 1D residual displacement component are performed at every point x in the 1D ROI. That is, the processes 1 and 2 of the method 3-1 are performed once at every point in the ROI. Thus, the estimate of the 1D residual component distribution is obtained.

(Process 2: Update of the Estimate of the 1D Displacement Component Distribution)

The i−1 th estimate of the 1D displacement component distribution is updated using the i th estimate of the 1D residual component distribution.

$$dx^i(x) = \hat{d}_x^{i-1}(x) + \hat{u}_x^i(x) \tag{71}$$

Next, this estimate is 1D low pass filtered or 1D median filter to yield the estimate of the 1D displacement component distribution:

$$\hat{d}_x^i(x) = LPF[dx^i(x)], \text{ or } \hat{d}_x^i(x) = MED[dx^i(x)]. \tag{72}$$

Thus, the estimation error is reduced of the residual component compared with the process 2 of the method 3-1 [eq. (63)]. Hence, the phase matching of the process 1 of the method 3-2 is performed using the smoothed estimate of the 1D displacement component distribution.

[Process 3: Condition for Heightening the Spatial Resolution of the 1D Displacement Component Distribution Measurement (Condition for Making the Local Region Small)]

In order to make the spatial resolution high of the 1D displacement component distribution measurement, during the iterative estimation, the local region used for each point is made small, or the local region used over the ROI is made small.

The criteria for each point is described below. The processes 1 and 2 (method 3-2) are iteratively carried out till the criteria is satisfied with. When the criteria is satisfied with, the local region is made small, for instance, the length of the local region is made half. For instance, the criteria is (73) or (73') with respect to the threshold values Tratio or Tdiff.

$$\frac{\|\hat{u}_x^i(x)\|}{\|\hat{u}_x^{i-1}(x)\|} \leq Tratio \text{ or} \tag{73}$$

$$\|\hat{u}_x^i(x) - \hat{u}_x^{i-1}(x)\| \leq Tdiff, \tag{73'}$$

where $\|\hat{u}_x^i(x)\|$ and $\|\hat{u}_x^{i-1}(x)\|$ are respectively the norms (magnitudes) of the i th and i−1 th estimates of the residual components.

The criteria over the ROI is described below. The processes 1 and 2 (method 3-2) are iteratively carried out till the criteria is satisfied with. When the criteria is satisfied with, the local region is made small, for instance, the length of the local region is made half. For instance, the criteria is (74) or (74') with respect to threshold values Tratioroi or Tdiffroi.

$$\frac{\sum_{x \in ROI} \|\hat{u}_x^i(x)\|^2}{\sum_{x \in ROI} \|\hat{u}_x^{i-1}(x)\|^2} \leq Tratioroi \text{ or} \tag{74}$$

$$\sum_{x \in ROI} \|\hat{u}_x^i(x) - \hat{u}_x^{i-1}(x)\| \leq Tdiffroi, \tag{74'}$$

where $\|\hat{u}_x^i(x)\|$ and $\|\hat{u}_x^{i-1}(x)\|$ are respectively the norms (magnitudes) of the i th and i−1 th estimates of the residual components.

(Process 4: Condition for Terminating the Iterative Estimation of the 1D Displacement Component Distribution)

Described below is the criteria for terminating the iterative estimation of the 1D displacement component distribution. The processes 1, 2 and 3 of the method 3-2 are iteratively carried out till the criteria is satisfied with. For instance, the criteria is (75) or (75') with respect to the threshold values aboveTratioroi or aboveTdiffroi.

$$\frac{\sum_{x \in ROI} \|\hat{u}_x^i(x)\|^2}{\sum_{x \in ROI} \|\hat{u}_x^{i-1}(x)\|^2} \leq aboveTratioroi \text{ or} \tag{75}$$

$$\sum_{x \in ROI} \|\hat{u}_x^i(x) - \hat{u}_x^{i-1}(x)\| \leq aboveTdiffroi, \tag{75'}$$

where $\|\hat{u}_x^i(x)\|$ and $\|\hat{u}_x^{i-1}(x)\|$ are respectively the norms (magnitudes) of the i th and i−1 th estimates of the residual components.

Final estimate is obtained from eq. (71) or eq. (72).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 3-3]

The flowchart of the method 3-3 is shown in FIG. 12. To prevent the phase matching from diverging at the process 1 of the method 3-1, the estimation error is reduced of the residual component. Possibility of the divergence is detected from the above-described condition (70) or (70'), and by effectively utilizing the methods 3-1 and 3-2, even if the SNR of the ultrasound echo signals are low, accurate 1D displacement component measurement can be realized.

At first, the procedure of the iterative estimation is same as that of the method 3-2 (Processes 1, 2, 3, and 4). At the i th estimate, the following processes are performed.

Thye phase matching and estimation of the 1D residual displacement component are performed at every point x in the 1D ROI. That is, the processes 1 and 2 of the method 3-1 are performed once at every point in the ROI. Thus, the estimate of the 1D residual component distribution is obtained.

During this estimation, if neither condition (70) nor (70') is satisfied with, the method 3-1 is used. If condition (70) or (70') is satisfied with at the points or regions, in the process 2 of the method 3-2, over sufficiently large regions centered on the points or regions, or over the ROI, the estimate $dx^i(x)$ of the 1D displacement component $dx(x)$ can be 1D low pass filtered or 1D median filtered as eq. (76).

$$\hat{d}_x^i(x) = LPF[dx^i(x)], \text{ or } \hat{d}_x^i(x) = MED[dx^i(x)] \tag{76}$$

Thus, the estimation error is reduced of the residual component compared with the process 2 of the method 3-1 [eq. (63)].

Thus, the iterative estimation is terminated at the process 5 of the method 3-1 or the process 4 of the method 3-2. Hence, the final estimate is obtained from eq. (67), or eq. (71), or eq. (76).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 3-4]

The flowchart of the method 3-4 is shown in FIG. 13. To prevent the phase matching from diverging at the process 1 of the method 3-1, the estimation error is reduced of the residual component. Thus, even if the SNR of the ultrasound echo signals are low, accurate 1D displacement component measurement can be realized.

The procedure of the iterative estimation is different from that of the method 3-1. At the i th estimate (i≥1), the following processes are performed.

(Process 1: Estimation of the 1D Residual Displacement Component Distribution)

The phase matching and estimation of the 1D residual displacement component are performed at every point x in the 1D ROI. That is, the process 1 of the method 3-1 is performed once at every point in the ROI.

To obtain the estimate $\hat{u}_x^i(x)$ of the residual component distribution $u_x^i(x)$, at every point the local 1D echo cross-spectrum is evaluated from the 1D Fourier's transforms of the pre-deformation local 1D ultrasound echo signal $r_1(l)$ and phase-matched post-deformation local 1D ultrasound echo signal $r'_2(l)$. Alternatively, when pre-deformation local 1D ultrasound echo signal is phase-matched, at every point the cross-spectrum of $r'_1(l)$ and $r_2(l)$ is evaluated.

The least squares method is implemented on the gradient of the phase with utilization of each weight function, i.e., the squared cross-spectrum $|S_{2,1}^i(l)|^2$, where each weight function is normalized by the power of the cross-spectrum, i.e., $$\sum_l |S_{2,1}^i(l)|^2.$$

Moreover, the regularization method is also implemented. That is, by minimizing the following functional with respect to the vector $u^i$ comprised of the 1D residual component distribution $u_x^i(x)$.

$$\text{error}(u^i) = \|a - Fu^i\|^2 + \alpha_{1i}\|u^i\|^2 + \alpha_{2i}\|Gu^i\|^2 + \alpha_{3i}\|G^TGu^i\|^2 + \alpha_{4i}\|GG^TGu^i\|^2 \quad (77)$$

where a: vector comprised of x distribution of the cross-spectrum phase $\Theta^i(l)$ weighted with the cross-spectrum $|S_{2,1}^i(l)|$ normalized by the magnitude of the cross-spectrum $$\sqrt{\sum_l |S_{2,1}^i(l)|^2}$$

evaluated at every point in the 1D ROI.

F: matrix comprised of x distribution of the Fourier's coordinate value l weighted with the cross-spectrum $|S_{2,1}^i(l)|$ normalized by the magnitude of the cross-spectrum $$\sqrt{\sum_l |S_{2,1}^i(l)|^2}$$

evaluated at every point in the 1D ROI.

$\alpha_{1i}, \alpha_{2i}, \alpha_{3i}, \alpha_{4i}$: regularization parameter (at least larger than zero)

$Gu^i$: vector comprised of the finite difference approximations of the 1D distribution of the 1D gradient components of the unknown 1D residual components $u_x^i(x)$ $$\frac{\partial}{\partial x} u_x^i(x)$$

$G^TGu^i$: vector comprised of the finite difference approximations of the 1D distribution of the 1D Laplacians of the unknown 1D residual components $u_x^i(x)$ $$\frac{\partial^2}{\partial x^2} u_x^i(x)$$

$GG^TGu^i$: vector comprised of the finite difference approximations of the 1D distribution of the 1D gradient components of the 1D Laplacians of the unknown 1D residual components $u_z^i(x)$ $$\frac{\partial}{\partial x}\left(\frac{\partial^2}{\partial x^2} u_x^i(x)\right)$$

As $\|u^i\|^2, \|Gu^i\|^2, \|G^TGu^i\|^2, \|GG^TGu^i\|^2$ are positive definite, error ($u^i$) has one minimum value. Thus, by solving for the residual displacement component distribution $u_x^i(x)$ the simultaneous equations:

$$(F^TF + \alpha_{1i}I + \alpha_{2i}G^TG + \alpha_{3i}G^TGG^TG + \alpha_{4i}G^TGG^T GG^TG)u^i = F^Ta, \quad (78)$$

the estimate $\hat{u}_x^i(x)$ of the residual component distribution $u_x^i(x)$ is stably obtained. Thus, the estimation error is reduced of the residual component.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then the position of the unknown displacement component etc.

(Process 2: Update of the Estimate of the 1D Displacement Component Distribution)

The i−1 th estimate of the 1D displacement component distribution is updated using the i th estimate of the 1D residual component distribution.

$$dx^i(x) = \hat{d}_x^{i-1}(x) + \hat{u}_x^i(x) \quad (79)$$

Freely, this estimate can be 1D low pass filtered or 1D median filter to yield the estimate of the 1D displacement component distribution.

$$\hat{d}_x^i(x) = LPF[dx^i(x)], \text{ or } \hat{d}_x^i(x) = MED[dx^i(x)] \quad (80)$$

Hence, the phase matching of the process 1 of method 3-4 is performed using the 1D residual component data $u_x^i(x)$ obtained from eq. (78), or the 1D component data $dx^i(x)$ obtained from eq. (79), or smoothed estimate obtained from eq. (80).

[Process 3: Condition for Heightening the Spatial Resolution of the 1D Displacement Component Distribution Measurement (Condition for Making the Local Region Small)]

In order to make the spatial resolution high of the 1D displacement component distribution measurement, during the iterative estimation, the local region used for each point is made small, or the local region used over the ROI is made small.

The criteria for each point is described below. The processes 1 and 2 of method 3-4 are iteratively carried out till the criteria is satisfied with. When the criteria is satisfied with, the local region is made small, for instance, the length of the local region is made half. For instance, the criteria is (81) or (81') with respect to the threshold values Tratio or Tdiff.

$$\frac{\|\hat{u}_x^i(x)\|}{\|\hat{u}_x^{i-1}(x)\|} \leq Tratio \quad (81)$$

or $$\|\hat{u}_x^i(x) - \hat{u}_x^{i-1}(x)\| \leq Tdiff, \quad (81')$$

where $\|\hat{u}_x^i(x)\|$ and $\|\hat{u}_x^{i-1}(x)\|$ are respectively the norms (magnitudes) of the i th and i−1 th estimates of the residual components.

The criteria over the ROI is described below. The processes 1 and 2 of the method 3-4 are iteratively carried out till the criteria is satisfied with. When the criteria is satisfied with, the local region is made small, for instance, the length of the local region is made half. For instance, the criteria is (82) or (82') with respect to the threshold values Tratioroi or Tdiffroi.

$$\frac{\sum_{x \in ROI} \|\hat{u}_x^i(x)\|^2}{\sum_{x \in ROI} \|\hat{u}_x^{i-1}(x)\|^2} \leq Tratioroi \quad (82)$$

or $$\sum_{x \in ROI} \|\hat{u}_x^i(x) - \hat{u}_x^{i-1}(x)\| \leq Tdiffroi, \quad (82')$$

where $\|\hat{u}_x^i(x)\|$ and $\|\hat{u}_x^{i-1}(x)\|$ are respectively the norms (magnitudes) of the i th and i−1 th estimates of the residual components.

(Process 4: Condition for Terminating the Iterative Estimation of the 1D Displacement Component Distribution)

Described below is the criteria for terminating the iterative estimation of the 1D displacement component distribution. The processes 1, 2 and 3 of the method 3-4 are iteratively carried out till the criteria is satisfied with. For instance, the criteria is (83) or (83') with respect to threshold values aboveTratioroi or aboveTdiffroi.

$$\frac{\sum_{x \in ROI} \|\hat{u}_x^i(x)\|^2}{\sum_{x \in ROI} \|\hat{u}_x^{i-1}(x)\|^2} \leq aboveTratioroi \quad (83)$$

or $$\sum_{x \in ROI} \|\hat{u}_x^i(x) - \hat{u}_x^{i-1}(x)\| \leq aboveTdiffroi, \quad (83')$$

where $\|\hat{u}_x^i(x)\|$ and $\|\hat{u}_x^{i-1}(x)\|$ are respectively the norms (magnitudes) of the i th and i−1 th estimates of the residual components.

Final estimate is obtained from eq. (79) or eq. (80).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 3-5]

The flowchart of the method 3-5 is shown in FIG. 14. To prevent the phase matching from diverging at the process 1 of the method 3-1, the estimation error is reduced of the residual component. Possibility of the divergence is detected from the above-described condition (70) or (70'), and by effectively utilizing methods 3-1 and 3-4, even if the SNR of the ultrasound echo signals are low, accurate 1D displacement component measurement can be realized.

At first, the procedure of the iterative estimation is same as that of the method 3-4 (Processes 1, 2, 3, and 4). At the i th estimate, the following processes are performed.

The phase matching and estimation of the 1D residual displacement component are performed at every point x in the 1D ROI. That is, the process 1 of the method 3-1 is performed once at every point in the ROI. Moreover, using the regularization method, stably the estimate of the 1D residual component distribution is obtained.

i−1 th estimate $\hat{d}_x^{i-1}(x)$ of 1D displacement component distribution dx(x).

i th estimate $\hat{u}_x^i(x)$ of 1D residual component distribution $u_x^i(x)$.

During this estimation, if neither condition (70) nor (70') is satisfied with, the method 3-1 is used. If the condition (70) or (70') is satisfied with at the points or regions, in the process 2 of the method 3-4, over sufficiently large regions centered on the points or regions, or over the ROI, the estimate $dx^i(x)$ of the 1D displacement component dx(x) can be 1D low pass filtered or 1D median filtered as eq. (84).

$$\hat{d}_x^i(x) = LPF[dx^i(x)], \text{ or } \hat{d}_x^i(x) = MED[dx^i(x)] \quad (84)$$

Thus, the estimation error is reduced of the residual component.

The iterative estimation is terminated at the process 5 of the method 3-1 or the process 4 of the method 3-4. Hence, the final estimate is obtained from eq. (67), or eq. (79), or eq. (84).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

(IV) Method 4: Measurement of 2D Displacement Component Vector Distribution in 3D SOI

[Method 4-1]

The 2D displacement component vector distribution in 3D SOI can be measured by measuring the 2D displacement component vector distribution in each (x,y) plane by means of the method 2-1, or 2-2, or 2-3, or 2-4, or 2-5 (FIG. 21).

(Process 1)

In each (x,y) plane in 3D SOI, the method 2-1, or 2-2, or 2-3, or 2-4, or 2-5 is utilized. The initial estimate [eq. (29)] of the iterative estimation of the 2D displacement vector in the 3D SOI is set as zero vector if a priori data is not given about the displacement of body motion nor applied compression. Alternatively, the values accurately estimated at the neighborhood can be used (high correlation or least squares).

Moreover, the methods 4-2, 4-3, 4-4, and 4-5 are respectively based on the methods 2-2, 2-3, 2-4, and 2-5.

[Method 4-2]

The flowchart of the method 4-2 is shown in FIG. 22. As example, let's consider measurement of 2D displacement vector $d(x,y,z)$ $[=(dx(x,y,z), dy(x,y,z))^T]$ in 3D SOI. At the i th estimate ($i \geq 1$), the following processes are performed.

(Process 1: Estimation of the 2D Residual Displacement Component Vector Distribution in 3D SOI)

The phase matching and estimation of the 2D residual displacement vector are performed at every point (x,y,z) in the 3D SOI. That is, the processes 1 and 2 of the method 2-1 are performed once at every point in the 3D SOI. Thus, the i th estimate of the 2D residual component vector distribution $u^i(x,y,z)$ is obtained as $$\hat{u}^i(x,y,z)[=(\hat{u}_x^i(x,y,z), \hat{u}_y^i(x,y,z))^T].$$

(Process 2: Update of the Estimate of the 2D Displacement Component Vector Distribution in 3D SOI)

The i−1 th estimate of the 2D displacement component vector distribution in the 3D SOI is updated using the i th estimate of the 2D residual component vector distribution in the 3D SOI.

$$d^i(x,y,z) = \hat{d}^{i-1}(x,y,z) + \hat{u}^i(x,y,z) \tag{85}$$

Next, this estimate is 3D low pass filtered or 3D median filter to yield the estimate of the 2D displacement component vector distribution:

$$\hat{d}^i(x,y,z) = LPF[d^i(x,y,z)], \text{ or } \hat{d}^i(x,y,z) = MED[d^i(x,y,z)]. \tag{86}$$

Thus, the estimation error is reduced of the residual vector compared with process 2 of the method 2-1 [eq. (35)]. Hence, the phase matching of the process 1 of the method 4-2 is performed using the smoothed estimate $\hat{d}^i(x,y,z)$ of the 2D displacement component vector distribution in the 3D SOI

[Process 3: Condition for Heightening the Spatial Resolution of the 2D Displacement Component Vector Distribution Measurement in 3D SOI (Condition for Making the Local Region Small)]

In order to make the spatial resolution high of the 2D displacement component vector distribution measurement in the 3D SOI, during the iterative estimation, the local region used for each point is made small, or the local region used over the 3D SOI is made small.

The criteria for each point is described below. The processes 1 and 2 (method 4-2) are iteratively carried out till the criteria is satisfied with. When the criteria is satisfied with, the local region is made small, for instance, the length of each side is made half. For instance, the criteria is (87) or (87') with respect to the threshold values Tratio or Tdiff.

$$\frac{\|\hat{u}^i(x, y, z)\|}{\|\hat{u}^{i-1}(x, y, z)\|} \leq Tratio \tag{87}$$

or $$\|\hat{u}^i(x, y, z) - \hat{u}^{i-1}(x, y, z)\| \leq Tdiff, \tag{87'}$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (87) or (87') can be applied to each direction component, and in this case the side is shorten in each direction.

The criteria over the 3D SOI is described below. The processes 1 and 2 (method 4-2) are iteratively carried out till the criteria is satisfied with. When the criteria is satisfied with, the local region is made small, for instance, the length of each side is made half. For instance, the criteria is (88) or (88') with respect to the threshold values Tratioroi or Tdiffroi.

$$\frac{\sum_{(x,y,z) \in SOI} \|\hat{u}^i(x, y, z)\|^2}{\sum_{(x,y,z) \in SOI} \|\hat{u}^{i-1}(x, y, z)\|^2} \leq Tratioroi \tag{88}$$

or $$\sum_{(x,y,z) \in SOI} \|\hat{u}^i(x, y, z) - \hat{u}^{i-1}(x, y, z)\| \leq Tdiffroi, \tag{88'}$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (88) or (88') can be applied to each direction component, and in this case the side is shorten in each direction.

(Process 4: Condition for Terminating the Iterative Estimation of the 2D Displacement Component Vector Distribution in 3D SOI)

Described below is the criteria for terminating the iterative estimation of the 2D displacement component vector distribution in the 3D SOI. The processes 1, 2 and 3 of the method 4-2 are iteratively carried out till the criteria is satisfied with. For instance, the criteria is (89) or (89') with respect to the threshold values aboveTratioroi or aboveTdiffroi.

$$\frac{\sum_{(x,y,z) \in SOI} \|\hat{u}^i(x, y, z)\|^2}{\sum_{(x,y,z) \in SOI} \|\hat{u}^{i-1}(x, y, z)\|^2} \leq aboveTratioroi \tag{89}$$

or $$\sum_{(x,y,z) \in SOI} \|\hat{u}^i(x, y, z) - \hat{u}^{i-1}(x, y, z)\| \leq aboveTdiffroi, \tag{89'}$$

where $\|\hat{u}^i(x,y,z)\|$ and $\|\hat{u}^{i-1}(x,y,z)\|$ are respectively the norms (magnitudes) of the i th and i−1 th estimates of the residual vectors.

Final estimate is obtained from eq. (85) or eq. (86).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Method 4-3]

The flowchart of the method 4-3 is shown in FIG. 23. As example, let's consider measurement of the 2D displacement vector $d(x,y,z)$ $[=(dx(x,y,z), dy(x,y,z))^T]$ in 3D SOI.

Possibility of the divergence is detected from the above-described condition (42) or (42') in above-described process 1 of the method 4-2, and by effectively utilizing the method 4-1 based on the method 2-1, even if the SNR of the ultrasound echo signals are low, accurate 2D displacement vector measurement can be realized.

At first, the procedure of the iterative estimation is same as that of the method 4-2 (Processes 1, 2, 3, and 4). At the i th estimate, the following processes are performed.

The process 1 of the method 4-2 is performed. (The phase matching and estimation of the 2D residual displacement vector are performed at every point (x,y,z) in the 3D SOI.) That is, the processes 1 and 2 of the method 2-1 are performed once at every point in the 3D SOI. Thus, the estimate of the 2D residual component vector distribution is obtained.

During this estimation, if neither condition (42) nor (42') is satisfied with, the method 4-1 is used. If the condition (42) or (42') is satisfied with at the points or regions, in the process 2 of the method 4-2, over sufficiently large regions centered on the points or regions, or over the 3D SOI, the estimate $d^i(x,y,z)$ [eq. (85)] of the 2D displacement vector $d(x,y,z)$ can be 3D low pass filtered or 3D median filtered as eq. (90). Thus, the estimation error is reduced of the residual vector compared with the process 2 of the method 2-1 [eq. (35)].

$$\hat{d}^i(x,y,z)=LPF[\hat{d}^i(x,y,z)], \text{ or } \hat{d}^i(x,y,z)=MED[\hat{d}^i(x,y,z)] \quad (90)$$

Thus, the iterative estimation is terminated at the process 1 of the method 4-1 based on the method 2-1, or the process 4 of the method 4-2. Hence, the final estimate is obtained from eq. (39), or eq. (85), or eq. (90).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Method 4-4]

The flowchart of the method 4-4 is shown in FIG. 24. As example, let's consider measurement of the 2D displacement vector $d(x,y,z)$ [$=(dx(x,y,z), dy(x,y,z))^T$] in 3D SOI. At the i th estimate ($i \geq 1$), the following process 1 is performed.

(Process 1: Estimation of the 2D Residual Displacement Component Vector Distribution in 3D SOI)

The phase matching and estimation of the 2D residual displacement vector are performed at every point (x,y,z) in the 3D SOI. That is, the process 1 of the method 2-1 is performed once at every point in the 3D SOI.

To obtain the estimate $\hat{u}^i(x,y,z)$ [$=(\hat{u}_x^i(x,y,z), \hat{u}_y^i(x,y,z))^T$] of the 2D residual component vector distribution $u^i(x,y,z)$ [$=(u_x^i(x,y,z), u_y^i(x,y,z))^T$] in the 3D SOI, at every point the local 2D echo cross-spectrum [eq. (31)] is evaluated from the 2D Fourier's transforms of the pre-deformation local 2D ultrasound echo signal $r_1(l,m)$ and phase-matched post-deformation local 2D ultrasound echo signal $r'_2(l,m)$. Alternatively, when the pre-deformation local 2D ultrasound echo signal is phase-matched, at every point the cross-spectrum of $r'_1(l,m)$ and $r_2(l,m)$ is evaluated.

The least squares method is implemented on the gradient of the phase with utilization of each weight function, i.e., the squared cross-spectrum $|S_{2,1}^i(l,m)|^2$, where each weight function is normalized by the power of the cross-spectrum, i.e., $$\sum_{l,m} |S_{2,1}^i(l,m)|^2. \quad [\text{eq. (34)}]$$

Moreover, the regularization method is also implemented. That is, by minimizing the following functional with respect to the vector $u^i$ comprised of the 2D residual component vector distribution $u^i(x,y,z)$ in the 3D SOI.

$$\text{error}(u^i)=\|a-Fu^i\|^2+\alpha_{1i}\|u^i\|^2+\alpha_{2i}\|Gu^i\|^2+\alpha_{3i}\|G^T Gu^i\|^2+ \\ \alpha_{4i}\|GG^T Gu^i\|^2 \quad (91)$$

where a: vector comprised of (x,y,z) distribution of the cross-spectrum phase $\Theta^i(l,m)$ weighted with the cross-spectrum $|S_{2,1}^i(l,m)|$ normalized by the magnitude of the cross-spectrum $$\sqrt{\sum_{l,m} |S_{2,1}^i(l,m)|^2}$$

evaluated at every point in the 3D SOI.

F: matrix comprised of (x,y,z) distribution of the Fourier's coordinate value (l,m) weighted with the cross-spectrum $|S_{2,1}^i(l,m)|$ normalized by the magnitude of the cross-spectrum $$\sqrt{\sum_{l,m} |S_{2,1}^i(l,m)|^2}$$

evaluated at every point in the 3D SOI.

$\alpha_{1i}, \alpha_{2i}, \alpha_{3i}, \alpha_{4i}$: regularization parameter (at least larger than zero)

$Gu^i$: vector comprised of the finite difference approximations of the 3D distributions of the 3D gradient components of the unknown 2D residual vector $u^i(x,y,z)$ components $$\frac{\partial}{\partial x}u_x^i(x,y,z), \frac{\partial}{\partial y}u_x^i(x,y,z), \frac{\partial}{\partial z}u_x^i(x,y,z),$$

$$\frac{\partial}{\partial x}u_y^i(x,y,z), \frac{\partial}{\partial y}u_y^i(x,y,z), \frac{\partial}{\partial z}u_y^i(x,y,z)$$

$G^T Gu^i$: vector comprised of the finite difference approximations of the 3D distributions of the 3D Laplacian of the unknown 2D residual vector $u^i(x,y,z)$ components $$\frac{\partial^2}{\partial x^2}u_x^i(x,y,z)+\frac{\partial^2}{\partial y^2}u_x^i(x,y,z)+\frac{\partial^2}{\partial z^2}u_x^i(x,y,z)$$

$$\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)$$

$GG^T Gu^i$: vector comprised of the finite difference approximations of the 3D distributions of the 3D gradient components of the 3D Laplacians of the unknown 2D residual vector $u^i(x,y,z)$ components $$\frac{\partial}{\partial x}\left(\frac{\partial^2}{\partial x^2}u_x^i(x,y,z)+\frac{\partial^2}{\partial y^2}u_x^i(x,y,z)+\frac{\partial^2}{\partial z^2}u_x^i(x,y,z)\right),$$

$$\frac{\partial}{\partial y}\left(\frac{\partial^2}{\partial x^2}u_x^i(x,y,z)+\frac{\partial^2}{\partial y^2}u_x^i(x,y,z)+\frac{\partial^2}{\partial z^2}u_x^i(x,y,z)\right),$$

$$\frac{\partial}{\partial z}\left(\frac{\partial^2}{\partial x^2}u_x^i(x,y,z)+\frac{\partial^2}{\partial y^2}u_x^i(x,y,z)+\frac{\partial^2}{\partial z^2}u_x^i(x,y,z)\right),$$

-continued $$\frac{\partial}{\partial x}\left(\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)\right),$$

$$\frac{\partial}{\partial y}\left(\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)\right),$$

$$\frac{\partial}{\partial z}\left(\frac{\partial^2}{\partial x^2}u_y^i(x,y,z)+\frac{\partial^2}{\partial y^2}u_y^i(x,y,z)+\frac{\partial^2}{\partial z^2}u_y^i(x,y,z)\right)$$

As $\|u^i\|^2$, $\|Gu^i\|^2$, $\|G^TGu^i\|^2$, $\|GG^TGu^i\|^2$ are positive definite, error ($u^i$) has one minimum value. Thus, by solving for the 2D residual displacement component vector distribution $u^i(x,y,z)$ in the 3D SOI the simultaneous equations:

$$(F^TF+\alpha_{1i}I+\alpha_{2i}G^TG+\alpha_{3i}G^TGG^TG+\alpha_{4i}G^TGG^T GG^TG)u^i=F^Ta, \quad (92\text{-}1)$$

the estimate $\hat{u}^i(x,y,z)$ [=$(\hat{u}_x^i(x,y,z), \hat{u}_y^i(x,y,z))^T$] of the 2D residual component vector distribution $u^i(x,y,z)$ [=$(u_x^i(x,y,z), u_y^i(x,y,z))^T$] is stably obtained. Thus, the estimation error is reduced of the residual vector.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then the position of the unknown displacement vector, direction of the unknown displacement component, direction of the partial derivative, etc.

(Process 2: Update of the Estimate of the 2D Displacement Component Vector Distribution)

The i−1 th estimate of the 2D displacement component vector distribution is updated using the i th estimate of the 2D residual component vector distribution.

$$d^i(x,y,z)=\hat{d}^{i-1}(x,y,z)+\hat{u}^i(x,y,z) \quad (92\text{-}2)$$

Freely, this estimate can be 3D low pass filtered or 3D median filter to yield the estimate of the 2D displacement component vector distribution.

$$\hat{d}^i(x,y,z)=LPF[d^i(x,y,z)], \text{ or } \hat{d}^i(x,y,z)=MED[d^i(x,y,z)] \quad (93)$$

Hence, the phase matching of the process 1 of method 4-4 is performed using the 2D residual vector data $u^i(x,y,z)$ obtained from eq. (91), or the 2D vector data $d^i(x,y,z)$ obtained from eq. (92-2), or smoothed estimate obtained from eq. (93).

[Process 3: Condition for Heightening the Spatial Resolution of the 2D Displacement Component Vector Distribution Measurement in 3D SOI (Condition for Making the Local Region Small)]

In order to make the spatial resolution high of the 2D displacement component vector distribution measurement, during the iterative estimation, the local region used for each point is made small, or the local region used over the 3D SOI is made small.

The criteria for each point is described below. The processes 1 and 2 of the method 4-4 are iteratively carried out till the criteria is satisfied with. When the criteria is satisfied with, the local region is made small, for instance, the length of each side is made half. For instance, the criteria is (94) or (94') with respect to the threshold values Tratio or Tdiff.

$$\frac{\|\hat{u}^i(x,y,z)\|}{\|\hat{u}^{i-1}(x,y,z)\|} \leq Tratio \quad (94)$$

or $$\|\hat{u}^i(x,y,z)-\hat{u}^{i-1}(x,y,z)\| \leq Tdiff, \quad (94')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (94) or (94') can be applied to each direction component, and in this case the side is shorten in each direction.

The criteria over the 3D SOI is described below. The processes 1 and 2 of the method 4-4 are iteratively carried out till the criteria is satisfied with. When the criteria is satisfied with, the local region is made small, for instance, the length of each side is made half. For instance, the criteria is (95) or (95') with respect to the threshold values Tratioroi or Tdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq Tratioroi \quad (95)$$

or $$\sum_{(x,y,z)\in SOI}\|\hat{u}^i(x,y,z)-\hat{u}^{i-1}(x,y,z)\| \leq Tdiffroi, \quad (95')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The condition (95) or (95') can be applied to each direction component, and in this case the side is shorten in each direction.

(Process 4: Condition for Terminating the Iterative Estimation of the 2D Displacement Component Vector Distribution in 3D SOI)

Described below is the criteria for terminating the iterative estimation of the 2D displacement component vector distribution. The processes 1, 2 and 3 of the method 4-4 are iteratively carried out till the criteria is satisfied with. For instance, the criteria is (96) or (96') with respect to the threshold values aboveTratioroi or aboveTdiffroi.

$$\frac{\sum_{(x,y,z)\in SOI}\|\hat{u}^i(x,y,z)\|^2}{\sum_{(x,y,z)\in SOI}\|\hat{u}^{i-1}(x,y,z)\|^2} \leq aboveTratioroi \quad (96)$$

or $$\sum_{(x,y,z)\in SOI}\|\hat{u}^i(x,y,z)-\hat{u}^{i-1}(x,y,z)\| \leq aboveTdiffroi, \quad (96')$$

where $\|\hat{u}^i(x,y,z)\|$ and $\|\hat{u}^{i-1}(x,y,z)\|$ are respectively the norms (magnitudes) of the i th and i−1 th estimates of the residual vectors.

The final estimate is obtained from eq. (92-2) or eq. (93).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

[Method 4-5]

The flowchart of the method 4-5 is shown in FIG. 25. As example, let's consider measurement of the 2D displacement vector $d(x,y,z)$ [$=(dx(x,y,z), dy(x,y,z))^T$] in 3D SOI.

Possibility of the divergence is detected from the above-described condition (42) or (42') in the above-described process 1 of the method 4-4, and by effectively utilizing the method 4-1 based on the method 2-1, even if the SNR of the ultrasound echo signals are low, accurate 2D displacement vector measurement can be realized.

At first, the procedure of the iterative estimation is same as that of the method 4-4 (Processes 1, 2, 3, and 4). At the i th estimate, the following processes are performed.

The process 1 of the method 4-4 is performed. (The phase matching and estimation of the 2D residual displacement vector are performed at every point (x,y,z) in the 3D SOI.) That is, the process 1 of the method 2-1 is performed once at every point in the 3D SOI. Moreover, using the regularization method, stably the estimate of the 2D residual component vector distribution is obtained.

i−1 th estimate $\hat{d}^{i-1}(x,y,z)$ of 2D displacement component vector distribution $d(x,y,z)$.

i th estimate $\hat{u}^i(x,y,z)$ of 2D residual component vector distribution $u^i(x,y,z)$.

During this estimation, if neither condition (42) nor (42') is satisfied with, the method 4-1 based on the method 2-1 is used. If condition (42) or (42') is satisfied with at points or regions, in the process 2 of the method 4-4, over sufficiently large regions centered on the points or regions, or over the 3D SOI, the estimate $d^i(x,y,z)$ of the 2D displacement vector $d(x,y,z)$ can be 3D low pass filtered or 3D median filtered as eq. (97).

$$\hat{d}^i(x,y,z)=LPF[d^i(x,y,z)], \text{ or } \hat{d}^i(x,y,z)=MED[d^i(x,y,z)] \quad (97)$$

Thus, the estimation error is reduced of the residual vector.

The iterative estimation is terminated at the process 1 of the method 4-1 based on the method 2-1, or the process 4 of the method 4-4. Hence, the final estimate is obtained from eq. (39), or eq. (92-2), or eq. (97).

The initial estimate [eq. (29)] of the iterative estimation of the 2D displacement vector is set as zero vector if a priori data is not given about the displacement of body motion nor applied compression. Alternatively, the values accurately estimated at the neighborhood can be used (high correlation or least squares).

(V) Method 5: Measurement of 1D Displacement (One Direction) Component Distribution in 3D SOI

[Method 5-1]

The 1D x displacement component distribution in 3D SOI can be measured by measuring the 1D x displacement component distribution in each line being parallel to x axis by means of the method 3-1, or 3-2, or 3-3, or 3-4, or 3-5 (FIG. 21).

(Process 1)

In each line being parallel to the x axis in 3D SOI, the method 3-1, or 3-2, or 3-3, or 3-4, or 3-5 is utilized. The initial estimate [eq. (57)] of the iterative estimation of the 1D displacement component in the 3D SOI is set as zero if a priori data is not given about the displacement of body motion nor applied compression. Alternatively, the values accurately estimated at the neighborhood can be used (high correlation or least squares).

Moreover, the methods 5-2, 5-3, 5-4, and 5-5 are respectively based on the methods 3-2, 3-3, 3-4, and 3-5.

[Method 5-2]

The flowchart of the method 5-2 is shown in FIG. 22. As example, let's consider measurement of the 1D displacement component $dx(x,y,z)$ in 3D SOI. At the i th estimate ($i \geq 1$), the following processes are performed.

(Process 1: Estimation of the 1D Residual Displacement Component Distribution in 3D SOI)

The phase matching and estimation of the 1D residual displacement component are performed at every point (x,y,z) in the 3D SOI. That is, the processes 1 and 2 of the method 3-1 are performed once at every point in the 3D SOI. Thus, the i th estimate of the 1D residual component distribution $u_x^i(x,y,z)$ is obtained as $\hat{u}_x^i(x,y,z)$.

(Process 2: Update of the Estimate of the 1D Displacement Component Distribution in 3D SOI)

The i−1 th estimate of the 1D displacement component distribution in the 3D SOI is updated using the i th estimate of the 1D residual component distribution in the 3D SOI.

$$dx^i(x,y,z)=\hat{d}_x^{i-1}(x,y,z)+\hat{u}_x^i(x,y,z) \quad (98)$$

Next, this estimate is 3D low pass filtered or 3D median filter to yield the estimate of the 1D displacement component distribution:

$$\hat{d}_x^i(x,y,z)=LPF[dx^i(x,y,z)], \text{ or } \hat{d}_x^i(x,y,z)=MED[dx^i(x,y,z)]. \quad (99)$$

Thus, the estimation error is reduced of the residual component compared with the process 2 of the method 3-1 [eq. (63)]. Hence, the phase matching of the process 1 of the method 5-2 is performed using the smoothed estimate $\hat{d}_x^i(x,y,z)$ of the 1D displacement component distribution in the 3D SOI.

[Process 3: Condition for Heightening the Spatial Resolution of the 1D Displacement Component Distribution Measurement in 3D SOI (Condition for Making the Local Region Small)]

In order to make the spatial resolution high of the 1D displacement component distribution measurement in the 3D SOI, during the iterative estimation, the local region used for each point is made small, or the local region used over the 3D SOI is made small.

The criteria for each point is described below. The processes 1 and 2 (method 5-2) are iteratively carried out till the criteria is satisfied with. When the criteria is satisfied with, the local region is made small, for instance, the length of the local region is made half. For instance, the criteria is (87) or (87') with respect to the threshold values Tratio or Tdiff.

$$\frac{\|\hat{u}_x^i(x, y, z)\|}{\|\hat{u}_x^{i-1}(x, y, z)\|} \leq Tratio \quad (100)$$

or $$\|\hat{u}_x^i(x, y, z) - \hat{u}_x^{i-1}(x, y, z)\| \leq Tdiff, \quad (100')$$

where $\|\hat{u}_x^i(x,y,z)\|$ and $\|\hat{u}_x^{i-1}(x,y,z)\|$ are respectively the norms (magnitudes) of the i th and i−1 th estimates of the residual components.

The criteria over the 3D SOI is described below. The processes 1 and 2 (method 5-2) are iteratively carried out till the criteria is satisfied with. When the criteria is satisfied with, the local region is made small, for instance, the length of the local region is made half. For instance, the criteria is (101) or (101') with respect to the threshold values Tratioroi or Tdiffroi.

$$\frac{\sum_{(x,y,z)\in SOI} \|\hat{u}_x^i(x, y, z)\|^2}{\sum_{(x,y,z)\in SOI} \|\hat{u}_x^{i-1}(x, y, z)\|^2} \le Tratioroi \quad (101)$$

or $$\sum_{(x,y,z)\in SOI} \|\hat{u}_x^i(x, y, z) - \hat{u}_x^{i-1}(x, y, z)\| \le Tdiffroi, \quad (101')$$

where $\|\hat{u}_x^i(x,y,z)\|$ and $\|\hat{u}_x^{i-1}(x,y,z)\|$ are respectively the norms (magnitudes) of the i th and i−1 th estimates of the residual components.

(Process 4: Condition for Terminating the Iterative Estimation of the 1D Displacement Component Distribution in 3D SOI)

Described below is the criteria for terminating the iterative estimation of the 1D displacement component distribution in the 3D SOI. The processes 1, 2 and 3 of the method 5-2 are iteratively carried out till the criteria is satisfied with. For instance, the criteria is (102) or (102') with respect to the threshold values aboveTratioroi or aboveTdiffroi.

$$\frac{\sum_{(x,y,z)\in SOI} \|\hat{u}_x^i(x, y, z)\|^2}{\sum_{(x,y,z)\in SOI} \|\hat{u}_x^{i-1}(x, y, z)\|^2} \le aboveTratioroi \quad (102)$$

or $$\sum_{(x,y,z)\in SOI} \|\hat{u}_x^i(x, y, z) - \hat{u}_x^{i-1}(x, y, z)\| \le aboveTdiffroi, \quad (102')$$

where $\|\hat{u}_x^i(x,y,z)\|$ and $\|\hat{u}_x^{i-1}(x,y,z)\|$ are respectively the norms (magnitudes) of the i th and i−1 th estimates of the residual components.

The final estimate is obtained from eq. (98) or eq. (99).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 5-3]

The flowchart of the method 5-3 is shown in FIG. 23.

As example, let's consider measurement of the 1D displacement component dx(x,y,z) in 3D SOI.

Possibility of the divergence is detected from the above-described condition (70) or (70') in the above-described process 1 of the method 5-2, and by effectively utilizing the method 5-1 based on the method 3-1, even if the SNR of the ultrasound echo signals are low, accurate 1D displacement component measurement can be realized.

At first, the procedure of the iterative estimation is same as that of the method 5-2 (Processes 1, 2, 3, and 4). At the i th estimate, the following processes are performed.

The process 1 of the method 5-2 is performed. (The phase matching and estimation of the 1D residual displacement component are performed at every point (x,y,z) in the 3D SOI.) That is, the processes 1 and 2 of the method 3-1 are performed once at every point in the 3D SOI. Thus, the estimate of the 1D residual component distribution is obtained.

During this estimation, if neither condition (70) nor (70') is satisfied with, the method 5-1 is used. If the condition (70) or (70') is satisfied with at the points or regions, in the process 2 of the method 5-2, over sufficiently large regions centered on the points or regions, or over the 3D SOI, the estimate $dx^i$(x,y,z) [eq. (98)] of the 1D displacement component dx(x,y,z) can be 3D low pass filtered or 3D median filtered as eq. (102). Thus, the estimation error is reduced of the residual component compared with process 2 of the method 3-1 [eq. (63)].

$$\hat{d}_x^i(x,y,z) = LPF[dx^i(x,y,z)], \text{ or } \hat{d}_x^i(x,y,z) = MED[dx^i(x,y,z)] \quad (102)$$

Thus, the iterative estimation is terminated at the process 1 of the method 5-1 based on the method 3-1, or the process 4 of the method 5-2. Hence, the final estimate is obtained from eq. (67), or eq. (98), or eq. (102).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 5-4]

The flowchart of the method 5-4 is shown in FIG. 24. As example, let's consider measurement of the 1D displacement component dx(x,y,z) in 3D SOI. At the i th estimate (i≥1), the following process 1 is performed.

(Process 1: Estimation of the 1D Residual Displacement Component Distribution in 3D SOI)

The phase matching and estimation of the 1D residual displacement component are performed at every point (x,y,z) in the 3D SOI. That is, the process 1 of the method 3-1 is performed once at every point in the 3D SOI.

To obtain the estimate $\hat{u}_x^i(x,y,z)$ of the 1D residual component distribution $u_x^i(x,y,z)$ in the 3D SOI, at every point the local 1D echo cross-spectrum [eq. (59)] is evaluated from the 1D Fourier's transforms of the pre-deformation local 1D ultrasound echo signal $r_1(l)$ and phase-matched post-deformation local 1D ultrasound echo signal $r'_2(l)$. Alternatively, when the pre-deformation local 1D ultrasound echo signal is phase-matched, at every point the cross-spectrum of $r^i_1(l)$ and $r_2(l)$ is evaluated.

The least squares method is implemented on the gradient of the phase with utilization of each weight function, i.e., the squared cross-spectrum $|S_{2,1}^i(l)|^2$, where each weight function is normalized by the power of the cross-spectrum, i.e., $$\sum_l |S_{2,1}^i(l)|^2. \quad [\text{eq. } (62)]$$

Moreover, the regularization method is also implemented. That is, by minimizing the following functional with respect to the vector $u^i$ comprised of the 1D residual component distribution $u_x^i(x,y,z)$ in the 3D SOI.

$$\text{error}(u^i) = \|a - Fu^i\|^2 + \alpha_{1i}\|u^i\|^2 + \alpha_{2i}\|Gu^i\|^2 + \alpha_{3i}\|G^TGu^i\|^2 + \alpha_{4i}\|GG^TGu^i\|^2 \quad (103)$$

where a: vector comprised of (x,y,z) distribution of the cross-spectrum phase $\Theta^i(l)$ weighted with the cross-spectrum $|S_{2,1}^i(l)|$ normalized by the magnitude of the cross-spectrum $$\sqrt{\sum_l |S_{2,1}^i(l)|^2}$$

evaluated at every point in the 3D SOI.

F: matrix comprised of (x,y,z) distribution of the Fourier's coordinate value l weighted with the cross-spectrum $|S_{2,1}^i(l)|$ normalized by the magnitude of the cross-spectrum $$\sqrt{\sum_l |S_{2,1}^i(l)|^2}$$

evaluated at every point in the 3D SOI.

$\alpha_{1i}, \alpha_{2i}, \alpha_{3i}, \alpha_{4i}$: regularization parameter (at least larger than zero)

$Gu^i$: vector comprised of the finite difference approximations of the 3D distributions of the 3D gradient components of the unknown 1D residual component $u_x^i(x,y,z)$ $$\frac{\partial}{\partial x} u_x^i(x,y,z), \frac{\partial}{\partial y} u_x^i(x,y,z), \frac{\partial}{\partial z} u_x^i(x,y,z)$$

$G^T G u^i$: vector comprised of the finite difference approximations of the 3D distributions of the 3D Laplacian of the unknown 1D residual component $u^i(x,y,z)$ $$\frac{\partial^2}{\partial x^2} u_x^i(x,y,z) + \frac{\partial^2}{\partial y^2} u_x^i(x,y,z) + \frac{\partial^2}{\partial z^2} u_x^i(x,y,z)$$

$GG^T G u^i$: vector comprised of the finite difference approximations of the 3D distributions of the 3D gradient components of the 3D Laplacians of the unknown 1D residual component $u_x^i(x,y,z)$ $$\frac{\partial}{\partial x}\left(\frac{\partial^2}{\partial x^2} u_x^i(x,y,z) + \frac{\partial^2}{\partial y^2} u_x^i(x,y,z) + \frac{\partial^2}{\partial z^2} u_x^i(x,y,z)\right),$$

$$\frac{\partial}{\partial y}\left(\frac{\partial^2}{\partial x^2} u_x^i(x,y,z) + \frac{\partial^2}{\partial y^2} u_x^i(x,y,z) + \frac{\partial^2}{\partial z^2} u_x^i(x,y,z)\right),$$

$$\frac{\partial}{\partial z}\left(\frac{\partial^2}{\partial x^2} u_x^i(x,y,z) + \frac{\partial^2}{\partial y^2} u_x^i(x,y,z) + \frac{\partial^2}{\partial z^2} u_x^i(x,y,z)\right)$$

As $\|u^i\|^2, \|Gu^i\|^2, \|G^T G u^i\|^2, \|GG^T G u^i\|^2$ are positive definite, error ($u^i$) has one minimum value. Thus, by solving for the 1D residual displacement component distribution $u_x^i(x,y,z)$ in the 3D SOI the simultaneous equations:

$$(F^T F + \alpha_{1i} I + \alpha_{2i} G^T G + \alpha_{3i} G^T G G^T G + \alpha_{4i} G^T G G G^T G) u^i = F^T a, \quad (104)$$

the estimate $\hat{u}_x^i(x,y,z)$ of the 1D residual component distribution $u_x^i(x,y,z)$ is stably obtained. Thus, the estimation error is reduced of the residual component.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then the position of the unknown displacement component etc.

(Process 2: Update of the Estimate of the 1D Displacement Component Distribution)

The i−1 th estimate of the 1D displacement component distribution is updated using the i th estimate of the 1D residual component distribution.

$$dx^i(x,y,z) = \hat{d}_x^{i-1}(x,y,z) + \hat{u}_x^i(x,y,z) \quad (105)$$

Freely, this estimate can be 3D low pass filtered or 3D median filter to yield the estimate of the 1D displacement component distribution.

$$\hat{d}_x^i(x,y,z) = LPF[dx^i(x,y,z)], \text{ or } \hat{d}_x^i(x,y,z) = MED[dx^i(x,y,z)] \quad (106)$$

Hence, the phase matching of the process 1 of the method 5-4 is performed using the 1D residual component data $u_x^i(x,y,z)$ obtained from eq. (104), or the 1D component data $dx^i(x,y,z)$ obtained from eq. (105), or smoothed estimate obtained from eq. (106).

[Process 3: Condition for Heightening the Spatial Resolution of the 1D Displacement Component Distribution Measurement in 3D SOI (Condition for Making the Local Region Small)]

In order to make the spatial resolution high of the 1D displacement component distribution measurement, during the iterative estimation, the local region used for each point is made small, or the local region used over the 3D SOI is made small.

The criteria for each point is described below. The processes 1 and 2 of the method 5-4 are iteratively carried out till the criteria is satisfied with. When the criteria is satisfied with, the local region is made small, for instance, the length of the local region is made half. For instance, the criteria is (107) or (107') with respect to the threshold values Tratio or Tdiff.

$$\frac{\|\hat{u}_x^i(x,y,z)\|}{\|\hat{u}_x^{i-1}(x,y,z)\|} \leq Tratio \quad (107)$$

or $$\|\hat{u}_x^i(x,y,z) - \hat{u}_x^{i-1}(x,y,z)\| \leq Tdiff, \quad (107')$$

where $\|\hat{u}_x^i(x,y,z)\|$ and $\hat{u}_x^{i-1}(x,y,z)\|$ are respectively the norms (magnitudes) of the i th and i−1 th estimates of the residual components.

The criteria over the 3D SOI is described below. The processes 1 and 2 of the method 5-4 are iteratively carried out till the criteria is satisfied with. When the criteria is satisfied with, the local region is made small, for instance, the length of the local region is made half. For instance, the criteria is (108) or (108') with respect to the threshold values Tratioroi or Tdiffroi.

$$\frac{\sum_{(x,y,z) \in SOI} \|\hat{u}_x^i(x,y,z)\|^2}{\sum_{(x,y,z) \in SOI} \|\hat{u}_x^{i-1}(x,y,z)\|^2} \leq Tratioroi \quad (108)$$

or $$\sum_{(x,y,z) \in SOI} \|\hat{u}_x^i(x,y,z) - \hat{u}_x^{i-1}(x,y,z)\|^2 \leq Tdiffroi, \quad (108')$$

where $\|\hat{u}_x^i(x,y,z)\|$ and $\|\hat{u}_x^{i-1}(x,y,z)\|$ are respectively the norms (magnitudes) of the i th and i−1 th estimates of the residual components.

(Process 4: Condition for Terminating the Iterative Estimation of the 1D Displacement Component Distribution in 3D SOI)

Described below is the criteria for terminating the iterative estimation of the 1D displacement component distribution. The processes 1, 2 and 3 of the method 5-4 are iteratively carried out till the criteria is satisfied with. For instance, the criteria is (109) or (109') with respect to the threshold values aboveTratioroi or aboveTdiffroi.

$$\frac{\sum_{(x,y,z)\in SOI}\|\hat{u}_x^i(x,y,z)\|^2}{\sum_{(x,y,z)\in SOI}\|\hat{u}_x^{i-1}(x,y,z)\|^2} \le aboveTratioroi \quad (109)$$

or $$\sum_{(x,y,z)\in SOI}\|\hat{u}_x^i(x,y,z) - \hat{u}_x^{i-1}(x,y,z)\| \le aboveTdiffroi, \quad (109')$$

where $\|\hat{u}_x^i(x,y,z)\|$ and $\|\hat{u}_x^{i-1}(x,y,z)\|$ are respectively the norms (magnitudes) of the i th and i−1 th estimates of the residual components.

The final estimate is obtained from eq. (105) or eq. (106).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 5-5]

The flowchart of the method 5-5 is shown in FIG. 25. As example, let's consider measurement of the 1D displacement component dx(x,y,z) in 3D SOI.

Possibility of the divergence is detected from the above-described condition (70) or (70') in the above-described process 1 of the method 5-4, and by effectively utilizing the method 5-1 based on the method 3-1, even if the SNR of the ultrasound echo signals are low, accurate 1D displacement component measurement can be realized.

At first, the procedure of the iterative estimation is same as that of the method 5-4 (Processes 1, 2, 3, and 4). At the i th estimate, the following processes are performed.

The process 1 of the method 5-4 is performed. (The phase matching and estimation of the 1D residual displacement component are performed at every point (x,y,z) in the 3D SOI) That is, the process 1 of the method 3-1 is performed once at every point in the 3D SOI. Moreover, using the regularization method, stably the estimate of the 1D residual component distribution is obtained.

i−1 th estimate $\hat{d}_x^{i-1}(x,y,z)$ of 1D displacement component distribution dx(x,y,z).

i th estimate $\hat{u}_x^i(x,y,z)$ of 1D residual component distribution $u_x^i(x,y,z)$.

During this estimation, if neither condition (70) nor (70') is satisfied with, the method 5-1 based on the method 3-1 is used. If condition (70) or (70') is satisfied with at the points or regions, in the process 2 of the method 5-4, over sufficiently large regions centered on the points or regions, or over the 3D SOI, the estimate $dx^i(x,y,z)$ of the 1D displacement component dx(x,y,z) can be 3D lowpass filtered or 3D median filtered as eq. (110).

$$\hat{d}_x^i(x,y,z) = LPF[dx^i(x,y,z)], \text{ or } \hat{d}_x^i(x,y,z) = MED[dx^i(x,y,z)] \quad (110)$$

Thus, the estimation error is reduced of the residual component.

The iterative estimation is terminated at the process 1 of the method 5-1 based on the method 3-1, or the process 4 of the method 5-4. Hence, the final estimate is obtained from eq. (67), or eq. (105), or eq. (110).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

(VI) Method 6: Measurement of 1D Displacement (One Direction) Component Distribution in 2D ROI

[Method 6-1]

The 1D x displacement component distribution in 2D ROI can be measured by measuring the 1D x displacement component distribution in each line being parallel to x axis by means of the method 3-1, or 3-2, or 3-3, or 3-4, or 3-5 (FIG. 21).

(Process 1)

In each line being parallel to x axis in 2D ROI, the method 3-1, or 3-2, or 3-3, or 3-4, or 3-5 is utilized. The initial estimate [eq. (57)] of the iterative estimation of the 1D displacement component in the 2D ROI is set as zero if a priori data is not given about the displacement of body motion nor applied compression. Alternatively, the values accurately estimated at the neighborhood can be used (high correlation or least squares).

Moreover, the methods 6-2, 6-3, 6-4, and 6-5 are respectively based on the methods 3-2, 3-3, 3-4, and 3-5.

[Method 6-2]

The flowchart of the method 6-2 is shown in FIG. 22. As example, let's consider measurement of the 1D displacement component dx(x,y) in 2D ROI. At the i th estimate (i≥1), the following processes are performed.

(Process 1: Estimation of the 1D Residual Displacement Component Distribution in 2D ROI)

The phase matching and estimation of the 1D residual displacement component are performed at every point (x,y) in the 2D ROI. That is, the processes 1 and 2 of the method 3-1 are performed once at every point in the 2D ROI. Thus, the i th estimate of the 1D residual component distribution $u_x^i(x,y)$ is obtained as $\hat{u}_x^i(x,y)$.

(Process 2: Update of the Estimate of the 1D Displacement Component Distribution in 2D ROI)

The i−1 th estimate of the 1D displacement component distribution in the 2D ROI is updated using the i th estimate of the 1D residual component distribution in the 2D ROI.

$$dx^i(x,y) = \hat{d}_x^{i-1}(x,y) + \hat{u}_x^i(x,y) \quad (111)$$

Next, this estimate is 2D low pass filtered or 2D median filter to yield the estimate of the 1D displacement component distribution:

$$\hat{d}_x^i(x,y) = LPF[dx^i(x,y)], \text{ or } \hat{d}_x^i(x,y) = MED[dx^i(x,y)]. \quad (112)$$

Thus, the estimation error is reduced of the residual component compared with the process 2 of the method 3-1 [eq. (63)]. Hence, the phase matching of the process 1 of the method 6-2 is performed using the smoothed estimate $\hat{d}_x^i(x,y)$ of the 1D displacement component distribution in the 2D ROI.

[Process 3: Condition for Heightening the Spatial Resolution of the 1D Displacement Component Distribution Measurement in 2D ROI (Condition for Making the Local Region Small)]

In order to make the spatial resolution high of the 1D displacement component distribution measurement in the 2D ROI, during the iterative estimation, the local region used for each point is made small, or the local region used over the 2D ROI is made small.

The criteria for each point is described below. The processes 1 and 2 (method 6-2) are iteratively carried out till the criteria is satisfied with. When the criteria is satisfied with, the local region is made small, for instance, the length of the local region is made half. For instance, the criteria is (113) or (113') with respect to the threshold values Tratio or Tdiff.

$$\frac{\|\hat{u}_x^i(x, y)\|}{\|\hat{u}_x^{i-1}(x, y)\|} \leq Tratio \qquad (113)$$

or $$\|\hat{u}_x^i(x, y) - \hat{u}_x^{i-1}(x, y)\| \leq Tdiff, \qquad (113')$$

where $\|\hat{u}_x^i(x,y)\|$ and $\|\hat{u}_x^{i-1}(x,y)\|$ are respectively the norms (magnitudes) of the i th and i−1 th estimates of the residual components.

The criteria over the 2D ROI is described below. The processes 1 and 2 (method 6-2) are iteratively carried out till the criteria is satisfied with. When the criteria is satisfied with, the local region is made small, for instance, the length of the local region is made half. For instance, the criteria is (114) or (114') with respect to the threshold values Tratioroi or Tdiffroi.

$$\frac{\sum_{(x,y)\in ROI} \|\hat{u}_x^i(x, y)\|^2}{\sum_{(x,y)\in ROI} \|\hat{u}_x^{i-1}(x, y)\|^2} \leq Tratioroi \qquad (114)$$

or $$\sum_{(x,y)\in ROI} \|\hat{u}_x^i(x, y) - \hat{u}_x^{i-1}(x, y)\| \leq Tdiffroi, \qquad (114')$$

where $\|\hat{u}_x^i(x,y)\|$ and $\|\hat{u}_x^{i-1}(x,y)\|$ are respectively the norms (magnitudes) of the i th and i−1 th estimates of the residual components.

(Process 4: Condition for Terminating the Iterative Estimation of the 1D Displacement Component Distribution in 2D ROI)

Described below is the criteria for terminating the iterative estimation of the 1D displacement component distribution in the 2D ROI. The processes 1, 2 and 3 of the method 6-2 are iteratively carried out till the criteria is satisfied with. For instance, the criteria is (115) or (115') with respect to the threshold values aboveTratioroi or aboveTdiffroi.

$$\frac{\sum_{(x,y)\in ROI} \|\hat{u}_x^i(x, y)\|^2}{\sum_{(x,y)\in ROI} \|\hat{u}_x^{i-1}(x, y)\|^2} \leq aboveTratioroi \qquad (115)$$

or $$\sum_{(x,y)\in ROI} \|\hat{u}_x^i(x, y) - \hat{u}_x^{i-1}(x, y)\| \leq aboveTdiffroi, \qquad (115')$$

where $\|\hat{u}_x^i(x,y)\|$ and $\|\hat{u}_x^{i-1}(x,y)\|$ are respectively the norms (magnitudes) of the i th and i−1 th estimates of the residual components.

The final estimate is obtained from eq. (111) or eq. (112).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 6-3]

The flowchart of the method 6-3 is shown in FIG. 23. As example, let's consider measurement of the 1D displacement component dx(x,y) in 2D ROI.

Possibility of the divergence is detected from the above-described condition (70) or (70') in the above-described process 1 of the method 6-2, and by effectively utilizing the method 6-1 based on the method 3-1, even if the SNR of the ultrasound echo signals are low, accurate 1D displacement component measurement can be realized.

At first, the procedure of the iterative estimation is same as that of the method 6-2 (Processes 1, 2, 3, and 4). At the i th estimate, the following processes are performed.

The process 1 of the method 6-2 is performed. (The phase matching and estimation of the 1D residual displacement component are performed at every point (x,y) in the 2D ROI.) That is, the processes 1 and 2 of the method 3-1 are performed once at every point in the 2D ROI. Thus, the estimate of the 1D residual component distribution is obtained.

During this estimation, if neither condition (70) nor (70') is satisfied with, the method 6-1 is used. If condition (70) or (70') is satisfied with at the points or regions, in the process 2 of the method 6-2, over sufficiently large regions centered on the points or regions, or over the 2D ROI, the estimate $dx^i(x,y)$ [eq. (111)] of the 1D displacement component dx(x,y) can be 2D low pass filtered or 2D median filtered as eq. (116). Thus, the estimation error is reduced of the residual component compared with the process 2 of the method 3-1 [eq. (63)].

$$\hat{d}_x^i(x,y) = LPF[dx^i(x,y)], \text{ or } \hat{d}_x^i(x,y) = MED[dx^i(x,y)] \qquad (116)$$

Thus, the iterative estimation is terminated at the process 1 of the method 6-1 based on the method 3-1, or the process 4 of the method 6-2. Hence, the final estimate is obtained from eq. (67), or eq. (111), or eq. (116).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 6-4]

The flowchart of the method 6-4 is shown in FIG. 24. As example, let's consider measurement of the 1D displacement component dx(x,y) in 2D ROI. At the i th estimate (i≥1), the following process 1 is performed.

(Process 1: Estimation of the 1D Residual Displacement Component Distribution in 2D ROI)

The phase matching and estimation of the 1D residual displacement component are performed at every point (x,y) in the 2D ROI. That is, the process 1 of the method 3-1 is performed once at every point in the 2D ROI.

To obtain the estimate $\hat{u}_x^i(x,y)$ of the 1D residual component distribution $u_x^i(x,y)$ in the 2D ROI, at every point the local 1D echo cross-spectrum [eq. (59)] is evaluated from the 1D Fourier's transforms of the pre-deformation local 1D ultrasound echo signal $r_1(l)$ and phase-matched post-deformation local 1D ultrasound echo signal $r'_2(l)$. Alternatively, when the pre-deformation local 1D ultrasound echo signal is phase-matched, at every point the cross-spectrum of $r'_1(l)$ and $r_2(l)$ is evaluated.

The least squares method is implemented on the gradient of the phase with utilization of each weight function, i.e., the squared cross-spectrum $|S_{2,1}^i(l)|^2$, where each weight function is normalized by the power of the cross-spectrum, i.e., $$\sum_l |S_{2,1}^i(l)|^2. \qquad \text{[eq. (62)]}$$

Moreover, the regularization method is also implemented. That is, by minimizing the following functional with respect to the vector $u^i$ comprised of the 1D residual component distribution $u_x^i(x,y)$ in the 2D ROI.

$$\text{error}(u^i) = \|a - Fu^i\|^2 + \alpha_{1i}\|u^i\|^2 + \alpha_{2i}\|Gu^i\|^2 + \alpha_{3i}\|G^T Gu^i\|^2 + \alpha_{4i}\|GG^T Gu^i\|^2 \qquad (117)$$

where
a: vector comprised of (x,y) distribution of the cross-spectrum phase $\Theta^i(l)$ weighted with the cross-spectrum $|S_{2,1}^i(l)|$ normalized by the magnitude of the cross-spectrum $$\sqrt{\sum_l |S_{2,1}^i(l)|^2}$$

evaluated at every point in the 2D ROI.
F: matrix comprised of (x,y) distribution of the Fourier's coordinate value l weighted with the cross-spectrum $|S_{2,1}^i(l)|$ normalized by the magnitude of the cross-spectrum $$\sqrt{\sum_l |S_{2,1}^i(l)|^2}$$

evaluated at every point in the 2D ROI.
$\alpha_{1i}, \alpha_{2i}, \alpha_{3i}, \alpha_{4i}$: regularization parameter (at least larger than zero)
$Gu^i$: vector comprised of the finite difference approximations of the 2D distributions of the 2D gradient components of the unknown 1D residual component $u_x^i(x,y)$ $$\frac{\partial}{\partial x} u_x^i(x,y), \frac{\partial}{\partial y} u_x^i(x,y)$$

$G^T Gu^i$: vector comprised of the finite difference approximations of the 2D distributions of the 2D Laplacian of the unknown 1D residual component $u^i(x,y)$ $$\frac{\partial^2}{\partial x^2} u_x^i(x,y) + \frac{\partial^2}{\partial y^2} u_x^i(x,y)$$

$GG^T Gu^i$: vector comprised of the finite difference approximations of the 2D distributions of the 2D gradient components of the 2D Laplacians of the unknown 1D residual component $u_x^i(x,y)$ $$\frac{\partial}{\partial x}\left(\frac{\partial^2}{\partial x^2} u_x^i(x,y) + \frac{\partial^2}{\partial y^2} u_x^i(x,y)\right),$$

$$\frac{\partial}{\partial y}\left(\frac{\partial^2}{\partial x^2} u_x^i(x,y) + \frac{\partial^2}{\partial y^2} u_x^i(x,y)\right)$$

As $\|u^i\|^2, \|Gu^i\|^2, \|G^T Gu^i\|^2, \|GG^T Gu^i\|^2$ are positive definite, error$(u^i)$ has one minimum value. Thus, by solving for the 1D residual displacement component distribution $u_x^i(x,y)$ in the 2D ROI the simultaneous equations:

$$(F^T F + \alpha_{1i} I + \alpha_{2i} G^T G + \alpha_{3i} G^T GG^T G + \alpha_{4i} G^T GG^T GG^T G) u^i = F^T a, \qquad (118)$$

the estimate $\hat{u}_x^i(x,y)$ of the 1D residual component distribution $u_x^i(x,y)$ is stably obtained. Thus, estimation error is reduced of the residual component.

The regularization parameter of important information is set relatively large. Thus, the regularization parameters depend on the correlation of the local echo data (peak value of the cross-correlation function, sharpness of the cross-correlation function, width of the cross-correlation function), the SNR of the cross-spectrum power, etc.; then the position of the unknown displacement component etc.

(Process 2: Update of the Estimate of the 1D Displacement Component Distribution)

The i−1 th estimate of the 1D displacement component distribution is updated using i th estimate of the 1D residual component distribution.

$$dx^i(x,y) = \hat{d}_x^{i-1}(x,y) + \hat{u}_x^i(x,y) \qquad (119)$$

Freely, this estimate can be 2D low pass filtered or 2D median filter to yield the estimate of the 1D displacement component distribution.

$$\hat{d}_x^i(x,y) = LPF[dx^i(x,y)], \text{ or } \hat{d}_x^i(x,y) = MED[dx^i(x,y)] \qquad (120)$$

Hence, the phase matching of the process 1 of the method 6-4 is performed using the 1D residual component data $u_x^i(x,y)$ obtained from eq. (118), or the 1D component data $dx^i(x,y)$ obtained from eq. (119), or smoothed estimate obtained from eq. (120).

[Process 3: Condition for Heightening the Spatial Resolution of the 1D Displacement Component Distribution Measurement in 2D ROI (Condition for Making the Local Region Small)]

In order to make the spatial resolution high of the 1D displacement component distribution measurement, during the iterative estimation, the local region used for each point is made small, or the local region used over the 2D ROI is made small.

The criteria for each point is described below. The processes 1 and 2 of the method 6-4 are iteratively carried out till the criteria is satisfied with. When the criteria is satisfied with, the local region is made small, for instance, the length of the local region is made half. For instance, the criteria is (121) or (121') with respect to the threshold values Tratio or Tdiff.

$$\frac{\|\hat{u}_x^i(x,y)\|}{\|\hat{u}_x^{i-1}(x,y)\|} \leq Tratio \quad (121)$$

or $$\|\hat{u}_x^i(x,y) - \hat{u}_x^{i-1}(x,y)\| \leq Tdiff, \quad (121')$$

where $\|\hat{u}_x^i(x,y)\|$ and $\|\hat{u}_x^{i-1}(x,y)\|$ are respectively the norms (magnitudes) of the i th and i−1 th estimates of the residual components.

The criteria over the 2D ROI is described below. The processes 1 and 2 of the method 6-4 are iteratively carried out till the criteria is satisfied with. When the criteria is satisfied with, the local region is made small, for instance, the length of the local region is made half. For instance, the criteria is (122) or (122') with respect to the threshold values Tratioroi or Tdiffroi.

$$\frac{\sum_{(x,y)\in ROI}\|\hat{u}_x^i(x,y)\|^2}{\sum_{(x,y)\in ROI}\|\hat{u}_x^{i-1}(x,y)\|^2} \leq Tratioroi \quad (122)$$

or $$\sum_{(x,y)\in ROI}\|\hat{u}_x^i(x,y) - \hat{u}_x^{i-1}(x,y)\| \leq Tdiffroi, \quad (122')$$

where $\|\hat{u}_x^i(x,y)\|$ and $\|\hat{u}_x^{i-1}(x,y)\|$ are respectively the norms (magnitudes) of the i th and i−1 th estimates of the residual components.

(Process 4: Condition for Terminating the Iterative Estimation of the 1D Displacement Component Distribution in 2D ROI)

Described below is the criteria for terminating the iterative estimation of the 1D displacement component distribution. The processes 1, 2 and 3 of the method 6-4 are iteratively carried out till the criteria is satisfied with. For instance, the criteria is (123) or (123') with respect to the threshold values aboveTratioroi or aboveTdiffroi.

$$\frac{\sum_{(x,y)\in ROI}\|\hat{u}_x^i(x,y)\|^2}{\sum_{(x,y)\in ROI}\|\hat{u}_x^{i-1}(x,y)\|^2} \leq aboveTratioroi \quad (123)$$

or $$\sum_{(x,y)\in ROI}\|\hat{u}_x^i(x,y) - \hat{u}_x^{i-1}(x,y)\| \leq aboveTdiffroi, \quad (123')$$

where $\|\hat{u}_x^i(x,y)\|$ and $\|\hat{u}_x^{i-1}(x,y)\|$ are respectively the norms (magnitudes) of the i th and i−1 th estimates of the residual components.

The final estimate is obtained from eq. (119) or eq. (120).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

[Method 6-5]

The flowchart of the method 6-5 is shown in FIG. 25. As example, let's consider measurement of the 1D displacement component dx(x,y) in 2D ROI.

Possibility of the divergence is detected from the above-described condition (70) or (70') in the above-described process 1 of the method 6-4, and by effectively utilizing the method 6-1 based on the method 3-1, even if the SNR of the ultrasound echo signals are low, accurate 1D displacement component measurement can be realized.

At first, the procedure of the iterative estimation is same as that of the method 6-4 (Processes 1, 2, 3, and 4). At the i th estimate, the following processes are performed.

The process 1 of the method 6-4 is performed. (The phase matching and estimation of the 1D residual displacement component are performed at every point (x,y) in the 2D ROI.) That is, the process 1 of the method 3-1 is performed once at every point in the 2D ROI. Moreover, using the regularization method, stably the estimate of the 1D residual component distribution is obtained.

i−1 th estimate $\hat{d}_x^{i-1}(x,y)$ of 1D displacement component distribution dx(x,y).

i th estimate $\hat{u}_x^i(x,y)$ of 1D residual component distribution $u_x^i(x,y)$.

During this estimation, if neither condition (70) nor (70') is satisfied with, the method 6-1 based on the method 3-1 is used. If condition (70) or (70') is satisfied with at the points or regions, in the process 2 of the method 6-4, over sufficiently large regions centered on the points or regions, or over the 2D ROI, the estimate $dx^i(x,y)$ of the 1D displacement component dx(x,y) can be 2D low pass filtered or 2D median filtered as eq. (124).

$$\hat{d}_x^i(x,y) = LPF[dx^i(x,y)], \text{ or } \hat{d}_x^i(x,y) = MED[dx^i(x,y)] \quad (124)$$

Thus, the estimation error is reduced of the residual component.

The iterative estimation is terminated at the process 1 of the method 6-1 based on the method 3-1, or the process 4 of the method 6-4. Hence, the final estimate is obtained from eq. (67), or eq. (119), or eq. (124).

The initial estimate [eq. (57)] of the iterative estimation of the 1D displacement component is set as zero if a priori data is not given about the displacement of body motion nor applied compression. Alternatively, the values accurately estimated at the neighborhood can be used (high correlation or least squares).

In the 3D SOI, the 3D displacement vector distribution can also be measured using the method 4 or method 5 by changing the adapted direction. In the 2D ROI, the 2D displacement vector distribution can also be measured using the method 6 by changing the adapted direction. Except for the threshold value for terminating the iterative estimation, other threshold values can be updated. Estimation can also be performed non-iteratively.

When applying the regularization method, in addition to the magnitude of the unknown displacement vector, spatial continuity and differentiability of the unknown displacement vector distribution, mechanical properties of tissue (e.g., incompressibility), and compatibility conditions of displacement vector distribution and displacement component distribution, as the a priori knowledge, used is temporal continuity and differentiability of the unknown series of the displacement vector distribution and displacement component distribution. The regularization parameter depends on time-space dimension number, direction of the unknown displacement component, position of the unknown displacement vector, time, etc.

Thus, as the displacement vector can be measured accurately, consequently, in addition to 3D strain tensor, accurately measured can be 2D strain tensor, one strain component, 3D strain rate tensor, 2D strain rate tensor, one strain rate component, acceleration vector, velocity vector, etc.

(VII) Differential Filter

The strain tensor components can be obtained by spatial differential filtering with a suitable cutoff frequency in time domain or frequency domain the measured 3D, or 2D displacement vector components or measured 1D direction displacement component in the 3D, 2D, or 1D ROI. The strain rate tensor components, acceleration vector components or velocity vector components can be obtained by time differential filtering with a suitable cutoff frequency in time domain or frequency domain the measured time series of the displacement components or strain components. The strain rate tensor components can also be obtained from the strain tensor components directly measured by the below-described signal processing.

As above described, when measuring the displacement from the gradient of the echo cross-spectrum phase, to yield the more accurate measurement accuracy, the least squares method can be applied with utilization of the squares of the cross-spectrum usually normalized by the cross-spectrum power as the weight function. To stabilize the measurement, the regularization method can also be applied, by which a priori information can be incorporated, i.e., about within the ROI the magnitude of the unknown displacement vector, spatial continuity and differentiability of the unknown displacement vector distribution etc.

Next, in order to reduce the calculation amount and shorten the calculation time, other methods are also described below as the estimation methods of the displacements during the iterative estimation to update 3D, 2D or 1D displacement component. These estimation methods can also be used in combination, or one of them can also be used. To realize real-time measurement, the estimation can also be performed non-iteratively. Here, the transmitting/receiving of ultrasound is performed similarly as described above.

In order to reduce the calculation amount and shorten the calculation time, the calculation process is simplified. That is, as the cross-spectrum phase $\theta(\omega x, \omega y, \omega z)$ is represented as $\theta_2(\omega x, \omega y, \omega z) - \theta_1(\omega x, \omega y, \omega z)$ using the phases $\theta_1(\omega x, \omega y, \omega z)$ and $\theta_2(\omega x, \omega y, \omega z)$ respectively obtained from 3D Fourier's transforms $R_1(\omega x, \omega y, \omega z)$ and $R_2(\omega x, \omega y, \omega z)$ of the local echo signals under pre- and post-deformation, the displacement vector $u(=(ux,uy,uz)^T)$ is represented as $$\begin{pmatrix} ux \\ uy \\ uz \end{pmatrix} = grad(\arg[R_2^*(\omega x, \omega y, \omega z) R_1(\omega x, \omega y, \omega z)])$$

$$\left(\text{where } grad = \left(\frac{d}{d\omega x}, \frac{d}{d\omega y}, \frac{d}{d\omega z}\right)^T\right) = \begin{pmatrix} \frac{d}{d\omega x}\theta(\omega x, \omega y, \omega z) \\ \frac{d}{d\omega y}\theta(\omega x, \omega y, \omega z) \\ \frac{d}{d\omega z}\theta(\omega x, \omega y, \omega z) \end{pmatrix} =$$

$$\begin{pmatrix} \frac{d}{d\omega x}(\theta_1(\omega x, \omega y, \omega z) - \theta_2(\omega x, \omega y, \omega z)) \\ \frac{d}{d\omega y}(\theta_1(\omega x, \omega y, \omega z) - \theta_2(\omega x, \omega y, \omega z)) \\ \frac{d}{d\omega z}(\theta_1(\omega x, \omega y, \omega z) - \theta_2(\omega x, \omega y, \omega z)) \end{pmatrix} = \text{Im}[grad(\ln\{R_2^*(\omega x, \omega y, \omega z) R_1(\omega x, \omega y, \omega z)\})] =$$

$$\begin{pmatrix} -\frac{\text{Re}[R_2(\omega x, \omega y, \omega z)]\frac{d}{d\omega x}\text{Im}[R_2(\omega x, \omega y, \omega z)] - \frac{d}{d\omega x}\text{Re}[R_2(\omega x, \omega y, \omega z)]\text{Im}[R_2(\omega x, \omega y, \omega z)]}{|R_2(\omega x, \omega y, \omega z)|^2} + \\ \frac{\text{Re}[R_1(\omega x, \omega y, \omega z)]\frac{d}{d\omega x}\text{Im}[R_1(\omega x, \omega y, \omega z)] - \frac{d}{d\omega x}\text{Re}[R_1(\omega x, \omega y, \omega z)]\text{Im}[R_1(\omega x, \omega y, \omega z)]}{|R_1(\omega x, \omega y, \omega z)|^2} - \\ \frac{\text{Re}[R_2(\omega x, \omega y, \omega z)]\frac{d}{d\omega y}\text{Im}[R_2(\omega x, \omega y, \omega z)] - \frac{d}{d\omega y}\text{Re}[R_2(\omega x, \omega y, \omega z)]\text{Im}[R_2(\omega x, \omega y, \omega z)]}{|R_2(\omega x, \omega y, \omega z)|^2} + \\ \frac{\text{Re}[R_1(\omega x, \omega y, \omega z)]\frac{d}{d\omega y}\text{Im}[R_1(\omega x, \omega y, \omega z)] - \frac{d}{d\omega y}\text{Re}[R_1(\omega x, \omega y, \omega z)]\text{Im}[R_1(\omega x, \omega y, \omega z)]}{|R_1(\omega x, \omega y, \omega z)|^2} - \\ \frac{\text{Re}[R_2(\omega x, \omega y, \omega z)]\frac{d}{d\omega z}\text{Im}[R_2(\omega x, \omega y, \omega z)] - \frac{d}{d\omega z}\text{Re}[R_2(\omega x, \omega y, \omega z)]\text{Im}[R_2(\omega x, \omega y, \omega z)]}{|R_2(\omega x, \omega y, \omega z)|^2} + \\ \frac{\text{Re}[R_1(\omega x, \omega y, \omega z)]\frac{d}{d\omega z}\text{Im}[R_1(\omega x, \omega y, \omega z)] - \frac{d}{d\omega z}\text{Re}[R_1(\omega x, \omega y, \omega z)]\text{Im}[R_1(\omega x, \omega y, \omega z)]}{|R_1(\omega x, \omega y, \omega z)|^2} \end{pmatrix}$$

Then, using the phases of the high SNR frequency, the displacement vector u can be obtained by partially differentiating in the frequency directions $\omega x$, $\omega y$, $\omega z$ the difference between the phases $\theta_2(\omega x, \omega y, \omega z)$ and $\theta_1(\omega x, \omega y, \omega z)$, or by calculating the difference between partial derivatives in the frequency directions $\omega x$, $\omega y$, $\omega x$ of the phases $\theta_2(\omega x, \omega y, \omega z)$ and $\theta_1(\omega x, \omega y, \omega z)$, or by using Fourier's transform values $Re[R_2(\omega x, \omega y, \omega z)]$, $Im[R_2(\omega x, \omega y, \omega z)]$, $Re[R_1(\omega x, \omega y, \omega z)]$, $Im[R_1(\omega x, \omega y, \omega z)]$, and their partial derivatives in the frequency directions $\omega x$, $\omega y$, $\omega z$ without unwrapping the phase. These partial derivatives can be obtained by finite-difference approximation or differential filtering. Freely, the phases, the signal components, or numerator and denominator can be moving averaged or low-pass filtered in the frequency domain. The final estimate can be the mean vector calculated from the displacement data obtained at high SNR frequencies, for instance, by weighting using the spectra.

The 2D displacement vector and one direction displacement component can be respectively obtained in a similar way by calculating 2D and 1D Fourier's transforms.

The simultaneous equations of the above-described equation can be solved in the frequency domain, or spatial and temporal simultaneous equations of the above-described equation can be handled, where occasionally the above-described least squares method and regularization method can also be applied.

When performing 1D (one direction) calculation, in order to reduce the calculation amount and shorten the calculation time, the calculation process is simplified. That is, for instance, when performing x direction calculation, as the cross-spectrum phase $\theta(\omega x, \omega y, \omega z)$ is represented as $\theta(\omega x)=ux\cdot\omega x$, the displacement is obtained form the phase of the high SNR frequency (y direction calculation; $\theta(\omega y)=uy\cdot\omega y$, z direction calculation; $\theta(\omega z)=uz\cdot\omega z$). The final estimate can be the mean value calculated from the displacement data obtained at high SNR frequencies, for instance, by weighting using the spectra.

When large displacement needs to be handled, before estimating the gradient of the cross-spectrum phase, the phase was unwrapped, or the displacement was coarsely estimated by cross-correlation method. Thus, the measurement procedure had become complex one. Otherwise, to cope with these complexities, the measurement procedure is made simpler with no utilization of these processes by introducing the processes of thinning out data and remaking data interval original.

The simultaneous equations of the above-described equation can be solved in the frequency domain, or spatial and temporal simultaneous equations of the above-described equation can be handled, where the above-described least squares method and regularization method can also be applied.

Otherwise, echo signals are acquired at two different time, freely, the auto-correlation method (beam direction or scan direction) and the regularization method can also be equipped.

Otherwise, freely, ultrasound Doppler's method can also be equipped. The Doppler's shift can be detected in beam direction or scan direction.

Furthermore, occasionally the velocity measurement methods are equipped such as the below-described invented multidimensional methods, Doppler method, etc. for measuring the velocity in the beam and/or scan direction. As measurement of the beam direction is considerably accurate compared with that of the orthogonal scan direction, to yield high accuracy velocity vector measurement, mechanical scan and/or beam steering can be performed. That is, echo data are acquired by performing mechanical scan and/or beam steering such that ultrasound beams are transmitted in more than three different directions when measuring 3D velocity vector, in more than two different directions when measuring 2D velocity vector, and in more than one direction when measuring 1D velocity component. From two echo data acquired by transmitting the ultrasound beams in same direction, accurately the distribution of velocity component in the beam direction is measured, by which the accurate 3D or 2D velocity vector distribution is obtained. To obtain the final velocity vector distribution, the velocity vector distributions having the different discrete coordinates must be converted to ones having one new discrete coordinate. That is, by interpolating the velocity component distributions measured on the old discrete coordinates, the velocity component can be obtained at each point of the new discrete coordinate. For instance, the velocity component distribution is Fourier's transformed, which is multiplied with complex exponential such that the phase is shifted. That is, spatial shifting of the velocity component distribution is realized. Other velocity measurement methods can also be applied to the ultrasound echo in similar ways. The 1D axial velocity measurement can also be performed to yield the velocity vector instead of the multidimensional measurement. Otherwise, by using one element of the ultrasound array for transmitting ultrasound (during scan or not) and by using one or plural elements of the ultrasound array for receiving echo, beam forming is performed in more than three different directions when measuring 3D velocity vector, in more than two different directions when measuring 2D velocity vector, and in more than one direction when measuring 1D velocity component. The beam forming can also be performed only at receiving. From two echo data acquired by forming beams in same direction, accurately the distribution of velocity component in beam direction is measured, by which accurate 3D or 2D velocity vector distribution can be obtained. This enables to reduce the time for transmitting/receiving. The 1D axial velocity measurement can also be performed to yield the velocity vector instead of the multidimensional measurement. Otherwise, the velocity vector can be measured using the superimposed echo signals obtained by multi-directional beam forming. The 1D axial measurement can also be performed instead of the multidimensional measurement (the same below). Otherwise, the velocity vector can be measured using the quadrate-detected or enveloped-detected, superimposed echo signals. Otherwise, the velocity vector can be measured using the superimposed, quadrate-detected or enveloped-detected echo signals. Here, for transmitting described above, plural elements can also be used. Moreover, the beam can also be transmitted to different direction from that of the receiving. Moreover, beam forming may not be performed at transmitting, or only apodization may be performed. The apodization may also not be performed. When measuring the velocity components more than the unknown number of the velocity components, the least squares method is used. At the time, by incorporating the reliability of the measurements into the velocity vector measurement, a weighted least squares method is used together with the instantaneous or local power of the echo data.

There are many methods for detecting the Doppler's shift. From the phase distribution $\theta_{ZR}(x,y,z,t)=\tan^{-1}(Im[Z_R(x,y,z,t)]/Re[Z_R(x,y,z,t)])$ of the quadrate demodulation signal $Z_R(x,y,z,t)$ ($=Re[Z_R(x,y,z,t)]+jIm[Z_R(x,y,z,t)]$) or the phase distribution $\theta_A(x,y,z,t)=\tan^{-1}(Im[Z_A(x,y,z,t)]/Re[Z_A(x,y,z,t)])$ of the complex analytic signal $Z_A(x,y,z,t)$ ($=Re[Z_A(x,y,z,t)]+jIm[Z_A(x,y,z,t)]$) in R axis direction acquired at each position (x,y,z) in the ROI, for instance, the velocity component vx in x axis direction (R=x) at time t=T and at position (X,Y,Z) can be obtained as $$vx = -\frac{1}{s_x\pi}\frac{d}{dt}\left[\frac{c_x}{f_{0x}}\tan^{-1}\left(\frac{\text{Im}[Zx(x, y, z, t)]}{\text{Re}[Zx(x, y, z, t)]}\right)\right]\Big|_{x=X,y=Y,z=Z,t=T}$$

$$= -\frac{1}{s_x\pi}\left(\frac{c_x}{f_{0x}}\frac{\text{Re}[Zx(x, y, z, t)] \cdot \frac{d}{dt}[\text{Im}[Zx(x, , y, z, t)]] - \frac{d}{dt}[\text{Re}[Zx(x, y, z, t)]] \cdot \text{Im}[Zx(x, y, z, t)]}{\text{Re}[Zx(x, y, z, t)]^2 + \text{Im}[Zx(x, y, z, t)]^2}\right)\Big|_{x=X,y=Y,z=Z,t=T}.$$

$c_R$ is the ultrasound propagating velocity and 1.0 respectively when R axis is the beam axis and scan axis. $f_{0R}$ is the ultrasound carrier frequency (when laterally nonmodulated) and modulation frequency (when axial motion compensation is performed) respectively when R axis is the beam axis and scan axis. $s_R$ is 4.0 and 2.0 respectively when R axis is the beam axis and scan axis. As above-described, the temporal gradient of the phase $\theta_{ZR}(x,y,z,t)$ can also be obtained by finite difference approximation or differential filtering after obtaining the phase $\theta_{ZR}(x,y,z,t)$. Freely, the phases, the signal components, or numerator and denominator can be moving averaged or low-pass filtered in the time or spatial domain. Otherwise, the temporal gradient of the phase $\theta_{ZR}(x,y,z,t)$ can also be obtained as $\tan^{-1}(\text{Im}[Z_R*(x,y,z,t)Z_R(x,y,z,t+\Delta T)]/\text{Re}[Z_R*(x,y,z,t)Z_R(x,y,z,t+\Delta T)])/\Delta T$, where * is the conjugate. Occasionally, the phase difference, the signal components, or numerator and denominator can be moving averaged or low-pass filtered in the time or space domain. Thus, the velocity component distributions (series) can be obtained in the ROI.

The spatial and temporal simultaneous equations of the above-described equation can be handled, where the above-described least squares method and regularization method can be applied.

By multiplying pulse transmitting interval Ts to each velocity component distributions (series), the displacement component distribution (series) can be obtained. Alternatively, by integrating the velocity vector component distributions (series), the displacement vector distribution (series) can be obtained.

From temporal or spatial derivatives of the velocity vector component distributions (series) or displacement vector component distributions (series), obtained are the strain tensor component distributions (series), acceleration vector component distributions (series), and strain rate tensor component distributions (series).

Otherwise, freely, a method for directly obtaining the strain tensor components can be equipped, i.e., from spatial partial derivative of the phase of the quadrate demodulate signal (beam direction or scan direction) or the phase of the complex analytic signal (beam direction or scan direction) of the ultrasound echo signals.

From the phase distribution $\theta_{ZR}(x,y,z,t)=\tan^{-1}(\text{Im}[Z_R(x,y,z,t)]/\text{Re}[Z_R(x,y,z,t)])$ of the quadrate demodulation signal $Z_R(x,y,z,t)$ $(=\text{Re}[Z_R(x,y,z,t)]+j\text{Im}[Z_R(x,y,z,t)]$ or the phase distribution $\theta_A(x,y,z,t)=\tan^{-1}(\text{Im}[Z_A(x,y,z,t)]/\text{Re}[Z_A(x,y,z,t)])$ of the complex analytic signal $Z_A(x,y,z,t)$ $(=\text{Re}[Z_A(x,y,z,t)]+j\text{Im}[Z_A(x,y,z,t)])$ in R axis direction acquired at each position (x,y,z) in the ROI, for instance, the normal strain component $\epsilon xx$ in x axis direction (R=x) at time t=T and at position (X,Y,Z) can be obtained as $$\epsilon xx(X, Y, Z, T) = \frac{\partial}{\partial x}u_x(x, y, z, t)\Big|_{x=X,y=Y,z=Z,t=T}$$

$$= -\frac{1}{s_x\pi}\frac{d}{dx}\frac{d}{dt}\left[\frac{c_x}{f_{0x}}\tan^{-1}\left(\frac{\text{Im}[Zx(x, y, z, t)]}{\text{Re}[Zx(x, y, z, t)]}\right)\right]\Big|_{x=X,y=Y,z=Z,t=T}Ts$$

$$= -\frac{1}{s_x\pi}\frac{d}{dt}\left(\frac{c_x}{f_{0x}}\frac{\text{Re}[Zx(x, y, z, t)] \cdot \frac{d}{dx}[\text{Im}[Zx(x, y, z, t)]] - \frac{d}{dx}[\text{Re}[Zx(x, y, z, t)]] \cdot \text{Im}[Zx(x, y, z, t)]}{\text{Re}[Zx(x, y, z, t)]^2 + \text{Im}[Zx(x, y, z, t)]^2}\right)\Big|_{x=X,y=Y,z=Z,t=T}Ts$$

$$= -\frac{1}{s_x\pi}\frac{d}{dx}\left(\frac{c_x}{f_{0x}}\frac{\text{Re}[Zx(x, y, z, t)] \cdot \frac{d}{dt}[\text{Im}[Zx(x, y, z, t)]] - \frac{d}{dt}[\text{Re}[Zx(x, y, z, t)]] \cdot \text{Im}[Zx(x, y, z, t)]}{\text{Re}[Zx(x, y, z, t)]^2 + \text{Im}[Zx(x, y, z, t)]^2}\right)\Big|_{x=X,y=Y,z=Z,t=T}Ts.$$

$c_R$ is the ultrasound propagating velocity and 1.0 respectively when R axis is the beam axis and scan axis. $f_{0R}$ is the ultrasound carrier frequency (when laterally nonmodulated) and modulation frequency (when axial motion compensation is performed) respectively when R axis is the beam axis and scan axis. $s_R$ is 4.0 and 2.0 respectively when R axis is the beam axis and scan axis. As above-described, the spatial gradient of the phase $\theta_{ZR}(x,y,z,t)$ can also be obtained by finite difference approximation or differential filtering after obtaining the phase $\theta_{ZR}(x,y,z,t)$. Freely, the phases, the signal components, or numerator and denominator can be moving averaged or low-pass filtered in the space or time domain. Otherwise, the spatial gradient of the phase $\theta_{ZR}(x,y,z,t)$ can also be obtained, for instance, the partial derivative in x direction as $\tan^{-1}(\text{Im}[Z_x*(x,y,z,t)Z_R(x+\Delta x,y,z,t)]/\text{Re}[Z_x*(x,y,z,t)Z_x(x+\Delta x,y,z,t)])/\Delta x$, where * is the conjugate. Occasionally, the phase difference, the signal components, or numerator and denominator can be moving averaged or low-pass filtered in the space or time domain. For instance, the shear strain component $\varepsilon xy$ in x-y plane (R=x and y) at time t=T and at position (X,Y,Z) can be obtained as $$\varepsilon xy(X, Y, Z, T) = \frac{1}{2}\left(\frac{\partial}{\partial x}uy(x, y, z, t) + \frac{\partial}{\partial y}ux(x, y, z, t)\right)\bigg|_{x=X,y=Y,z=Z,t=T}$$

$$= \frac{1}{2}\begin{pmatrix} -\frac{1}{s_y\pi}\frac{d}{dx}\frac{d}{dt}\left[\frac{c_y}{f_{0y}}\tan^{-1}\left(\frac{\text{Im}[Zy(x,y,z,t)]}{\text{Re}[Zy(x,y,z,t)]}\right)\right] - \\ -\frac{1}{s_x\pi}\frac{d}{dy}\frac{d}{dt}\left[\frac{c_x}{f_{0x}}\tan^{-1}\left(\frac{\text{Im}[Zx(x,y,z,t)]}{\text{Re}[Zx(x,y,z,t)]}\right)\right] \end{pmatrix}\bigg|_{x=X,y=Y,z=Z,t=T} Ts$$

$$= \frac{1}{2}\left(-\frac{1}{s_y\pi}\frac{d}{dt}\left(\frac{c_y}{f_{0y}}\frac{\text{Re}[Zy(x,y,z,t)] \cdot \frac{d}{dx}[\text{Im}[Zy(x,y,z,t)]] - \frac{d}{dx}[\text{Re}[Zy(x,y,z,t)]] \cdot \text{Im}[Zy(x,y,z,t)]}{\text{Re}[Zy(x,y,z,t)]^2 + \text{Im}[Zy(x,y,z,t)]^2}\right) - \right.$$

$$\left. \frac{1}{s_x\pi}\frac{d}{dt}\left(\frac{c_x}{f_{0x}}\frac{\text{Re}[Zx(x,y,z,t)] \cdot \frac{d}{dy}[\text{Im}[Zx(x,y,z,t)]] - \frac{d}{dy}[\text{Re}[Zx(x,y,z,t)]] \cdot \text{Im}[Zx(x,y,z,t)]}{\text{Re}[Zx(x,y,z,t)]^2 + \text{Im}[Zx(x,y,z,t)]^2}\right)\right)\bigg|_{x=X,y=Y,z=Z,t=T} Ts$$

$$= \frac{1}{2}\left(-\frac{1}{s_y\pi}\frac{d}{dx}\left(\frac{c_y}{f_{0y}}\frac{\text{Re}[Zy(x,y,z,t)] \cdot \frac{d}{dt}[\text{Im}[Zy(x,y,z,t)]] - \frac{d}{dt}[\text{Re}[Zy(x,y,z,t)]] \cdot \text{Im}[Zy(x,y,z,t)]}{\text{Re}[Zy(x,y,z,t)]^2 + \text{Im}[Zy(x,y,z,t)]^2}\right) - \right.$$

$$\left. \frac{1}{s_x\pi}\frac{d}{dy}\left(\frac{c_x}{f_{0x}}\frac{\text{Re}[Zx(x,y,z,t)] \cdot \frac{d}{dt}[\text{Im}[Zx(x,y,z,t)]] - \frac{d}{dt}[\text{Re}[Zx(x,y,z,t)]] \cdot \text{Im}[Zx(x,y,z,t)]}{\text{Re}[Zx(x,y,z,t)]^2 + \text{Im}[Zx(x,y,z,t)]^2}\right)\right)\bigg|_{x=X,y=Y,z=Z,t=T} Ts$$

In this calculation, the conjugate product can also be used. Thus, the strain component distributions (series) can be obtained in the ROI.

The spatial and temporal simultaneous equations of the above-described equation can be handled, where above-described least squares method and regularization method can be applied.

By integrating the partial derivatives of displacement vector component distributions (series), the displacement vector distribution (series) can be obtained.

From the strain tensor component distributions (series) or temporal or spatial derivatives of the displacement vector component distributions (series), obtained are the strain rate tensor component distributions (series), and acceleration vector component distributions (series).

Freely, (I-1) complex cross-correlation method (phase in the beam direction or scan direction of the complex cross-correlation function signal obtained from the complex analytic signals or quadrate detection signals, or obtained from the cross-correlation of ultrasound echo signals) is utilized, or (I-2) both the complex cross-correlation method (beam direction or scan direction) and the regularization method are utilized, or (I-3) at least 2D distribution (including beam direction or not) of the phase of 3D, or 2D complex cross-correlation function signals or 1D complex cross-correlation function signal respectively obtained from 3D complex signals with single-octant spectra, 2D complex signals with single-quadrant spectra, and conventional 1D complex analytic signal (S. L. Hahn, "Multidimensional complex signals with single-orthant spectra," Proceedings of the IEEE, vol. 80, no. 8, pp. 1287-1300, 1992, where the 3D and 2D complex signals are not proven to be analytic in the formal sense) and the regularization method are utilized. That is, methods (I-1), (I-2), and (I-3) can be equipped. Occasionally, the conjugate product is simply used as the values of the complex cross-correlation function (Occasionally, the phase of the conjugate product, i.e., the phase difference, is used as the phase of the complex cross-correlation function). Occasionally, the conjugate products can be moving averaged or filtered by a low pass filter.

On the method (I-3), for instance, the following equation holds for unknown 3D displacement vector $(ux,uy,uz)^T$ at each point (X,Y,Z) at time t=T:

$$\theta_{cc}(0,0,0) + \frac{\partial}{\partial x}\theta_{cc}(x,y,z)\bigg|_{x=0,y=0,z=0}$$

$$ux + \frac{\partial}{\partial y}\theta_{cc}(x,y,z)\bigg|_{x=0,y=0,z=0} uy + \frac{\partial}{\partial z}\theta_{cc}(x,y,z)\bigg|_{x=0,y=0,z=0} uz = 0.$$

$\theta_{cc}(X,Y,Z;x,y,z)$ is the 3D phase distribution (x,y,z) of the complex cross-correlation function Cc(X,Y,Z;x,y,z) of the point (X,Y,Z) evaluated from rf echo signals with respect to transmitted ultrasound pulses at the time t=T and t=T+ΔT:

$$\theta_{cc}(X,Y,Z;x,y,z) = \tan^{-1}(Im[Cc(X,Y,Z;x,y,z)]/Re[Cc(X,Y,Z;x,y,z)]),$$

where the coordinate (x,y,z) has the origin at (X,Y,Z). In the SOI, occasionally also in time direction, these equations hold (simultaneous equations), and can be solved by least squares method, where, freely, the regularization method can also be applied (using a priori conditions such as the temporal and spatial magnitude of the unknown displacement vector distribution, temporal and spatial continuity and differentiability of the unknown displacement vector distribution). Thus, the displacement vector distribution (series) can be obtained. The gradients of the phase $\theta_{cc}(X,Y,Z;x,y,z)$ can be obtained by finite difference approximation or differential filtering. Otherwise, for instance, x partial derivative $\partial/\partial x \cdot \theta_{cc}(x,y,z)|_{x=0,y=0,z=0}$ can be obtained as: $\{Re[Cc(X,Y,Z;0,0,0)] \times \partial/\partial x \cdot Im[Cc(X,Y,Z;x,y,z)]|_{x=0, y=0, z=0} - \partial/\partial x \cdot Re[Cc(X,Y,Z;x,y,z)]|_{x=0, y=0, z=0} \times Im[Cc (X,Y,Z;0,0,0)]\}/\{Re[Cc(X,Y,Z;0,0,0)]^2 + Im[Cc(X,Y,Z;0,0,0)]^2\}$, where $\partial/\partial x \cdot Re[Cc(X,Y,Z;x,y,z)]|_{x=0, y=0, z=0}$ can be obtained by finite difference approximation or differential filtering. Otherwise, for instance, x partial derivative $\partial/\partial x \cdot \theta_{cc}(x,y,z)|_{x=0,y=0,z=0}$ can be obtained as: $\tan^{-1}(Im[Cc^*(X,Y,Z;0,0,0)Cc(X,Y,Z;\Delta x,0,0)]/Re[Cc^*(X,Y,Z;0,0,0)Cc(X,Y,Z;\Delta x,0,0)])$, where * is the conjugate.

For these calculations, freely, the phases, the signal components, or numerator and denominator can be moving averaged or low-pass filtered in the spatial and time domain.

When the unknown displacement vector is 2D one, for instance, when the unknown 2D displacement vector is $(ux, uy)^T$, the following equation holds for $(ux,uy)^T$ at each point (X,Y,Z) at time t=T:

$$\theta_{cc}(0, 0) + \frac{\partial}{\partial x}\theta_{cc}(x, y)\bigg|_{x=0,y=0} ux + \frac{\partial}{\partial y}\theta_{cc}(x, y)\bigg|_{x=0,y=0} uy = 0.$$

$\theta_{cc}(X,Y,Z;x,y)$ is the 2D phase distribution (x,y) of the complex cross-correlation function Cc (X,Y,Z;x,y) of the point (X,Y,Z) evaluated from rf echo signals with respect to transmitted ultrasound pulses at the time t=T and t=T+ΔT. Method (I-3) can also be applied to measurement of one displacement component distribution as Method (I-1).

On the method (I-1), utilized is the phase of the complex cross-correlation function signal in the beam direction or scan direction. The following equation holds for unknown displacement component ux at each point (X,Y,Z) at time t=T (the auto-correlation method's equation):

$$\theta_{cc}(0) + \frac{d}{dx}\theta_{cc}(x)\bigg|_{x=0} ux = 0.$$

$\theta_{cc}(X,Y,Z;x)$ is the 1D phase distribution (x) of the complex cross-correlation function Cc(X,Y,Z;x) of the point (X,Y,Z) evaluated from rf echo signals with respect to transmitted ultrasound pulses at the time t=T and t=T+ΔT.

In the ROI, by solving this equation for unknown displacement component ux at each point, the displacement component distribution (series) can be obtained.

On the method (I-2), in the ROI, occasionally also in the spatial and time direction, this equation holds in the beam direction or scan direction, and the derived simultaneous equations can be solved by the least squares method, where, freely, regularization method can also be applied (using a priori conditions such as the temporal and spatial magnitude of the unknown displacement component distribution, temporal and spatial continuity and differentiability of the unknown displacement component distribution). Thus, the displacement component distribution (series) can be obtained.

On the methods (I-1), (I-2) and (I-3), occasionally the unknown displacement vector and the unknown displacement component are dealt with as locally uniform ones. That is, occasionally, under the assumption that the local region uniformly moves, the simultaneous equations hold for the unknown local displacement vector or the unknown local displacement component. Otherwise, occasionally, the simultaneous equations hold under the assumption that the displacement is uniform for a finite temporal interval. Otherwise, in the above-described two cases where beam forming is performed in the plural directions, the equations derived from respective beam formings can be simultaneously solved for the unknown local displacement vector or the unknown local displacement component. Thus, the spatial distribution (series) can be obtained. Occasionally, the regularization method is not used.

Specifically, on the methods (I-2) and (I-3), when measuring the 2D displacement vector, the two 2D Complex signals with different single-quadrant spectra are obtained to derive the independent simultaneous two equations, whereas when measuring the 3D displacement vector, the three or four 3D complex signals with different single octant spectra are obtained to derive the independent simultaneous three or four equations (Here, the complex signals with the respective different single-quadrant or single-octant spectra exist two and four although there exist four and eight complex signals including those yield the dependent equations. Setting spectra at zeros in the frequency domain can also be performed for respective 1D Fourier's transforms). The independency can also be confirmed by the carrier frequencies. When the simultaneous four equations are dealt with, the least squares method is applied.

Moreover, on the methods (I-1), (I-2) and (I-3), the single-quadrant or single-octant spectra of the pre- and post-deformation echo data can be divided into plural spectra (for instance, using the carrier frequencies) to obtain the plural paired complex signals that yield independent simultaneous equations.

Moreover, on the methods (I-1), (I-2) and (I-3), the ultrasounds having different ultrasound frequencies can be transmitted to obtain the plural paired complex signals of the pre- and post-deformation echo data that yield independent simultaneous equations.

Moreover, on the methods (I-1), (I-2) and (I-3), when the lateral modulation is performed in the lateral directions, by yielding the plural paired complex signals of the pre- and post-deformation echo data having different modulation frequencies, independent simultaneous equations can be derived.

Moreover, on the methods (I-1), (I-2) and (I-3), by yielding the plural paired complex signals of the pre- and post-deformation echo data respectively having the basic and harmonic spectra, independent simultaneous equations can be derived.

Here, on the methods (I-1), (I-2) and (I-3), the spatial derivatives of the phase of the complex cross-correlation function can be set at the known values such as the nominal frequency, modulation frequency, pre-estimated values.

Moreover, on the methods (I-1), (I-2) and (I-3), the spatial derivatives of the phases of the complex cross-correlation functions can be set using the values evaluated from an arbitrary paired complex signals by changing their signs. Otherwise, the spatial derivatives of the phase of the complex cross-correlation function can be set using the values evaluated from a paired, averaged complex signals in the frequency domain or spatial domain. Otherwise, the spatial derivatives of the phase of the complex cross-correlation function can be set using the means of the absolute values evaluated from the plural paired complex signals by changing their signs. Thus, the spatial derivatives of the phase of the complex cross-correlation function can be set using more than one paired complex signals. In these cases, $\theta_{cc}(0,0,0)$ and $\theta_{cc}(0,0)$ can also be evaluated from the phase of the complex cross-correlation function of the quadrature-detected signals obtained by shifting the single-quadrant or single-octant spectra using the known frequencies (It is needless to say that the quadrature detection can also be performed respective for the 1D Fourier's transforms). Here, the quadrature detection can also be performed only in two or one directions for 3D measurement, whereas only in one direction for 2D measurement. In these cases, the spatial derivatives of the phase of the complex cross-correlation function can be obtained by the spatially differentiating the phase, and $\theta_{cc}(0,0,0)$, $\theta_{cc}(0,0)$ and $\theta_{cc}(0)$ can be obtained from the phase of the complex cross-correlation function. Here, the quadrature detection can also be realized in spatial domain (x,y,z). When detecting more than two directions, at least one complex signal is required to be quadrature-detected using the minus frequency. In this case, the detected complex signals in the fewer directions, after which the spectra in the remaining directions are set at zeros, can be dealt with in same ways as described above as well as the detected complex signals in all the directions.

Occasionally, the regularization method is not used above.

Furthermore, the envelope-detected signals obtained from the quadrature-detected complex signals can be respectively converted into images. Otherwise, the superimposed envelope-detected signals (i.e., mean) can be converted into an image. In this case, the PSF can also be designed as $\exp(-y^2/(2\sigma_y^2))\sin(2\pi f_y y)$ or $\exp((-y^2/(2\sigma_y^2))+(-z^2/(2\sigma_z^2)))\sin(2\pi f_y y)\sin(2\pi f_z z)$ using the sine functions.

The next method can also be equipped. That is, the strain tensor component can be directly obtained from the spatial derivative of the no time delay phase $\theta_{cc}(x,y,z;0,0,0)=\tan^{-1}(\text{Im}[Cc(x,y,z;0,0,0)]/\text{Re}[Cc(x,y,z;0,0,0)])$ of the 3D complex cross-correlation function, of the no time delay phase $\theta_{cc}(x,y,z;0,0)=\tan^{-1}(\text{Im}[Cc(x,y,z;0,0)]/\text{Re}[Cc(x,y,z;0,0)])$ of the 2D complex cross-correlation function (including beam direction or not), or of the no time delay phase $\theta_{cc}(x,y,z;0)=\tan^{-1}(\text{Im}[Cc(x,y,z;0)]/\text{Re}[Cc(x,y,z;0)])$ of the 1D complex cross-correlation function (beam direction or scan direction) of the point (x,y,z) evaluated from the rf echo signals with respect to the transmitted ultrasound pulses at the time t=T and t=T+ΔT.

For instance, the normal strain component εxx in x axis direction (R=x) at time t=T and at position (X,Y,Z) can be obtained as:

$$\varepsilon xx(X, Y, Z, T) = \frac{\partial}{\partial x} u_x(x, y, z, t)\Big|_{x=X, y=Y, z=Z, t=T}$$

$$= -\frac{1}{s_R \pi} \frac{d}{dx}\left[\frac{c_x}{f_{0x}} \theta_{cc}(x, y, z, t)\right]\Big|_{x=X, y=Y, z=Z, t=T}$$

-continued $$= -\frac{1}{s_R \pi} \frac{c_x}{f_{0x}} \left(\begin{array}{c} \text{Re}[Cc(x, y, z, t)] \cdot \\ \frac{d}{dx}[\text{Im}[Cc(x, y, z, t)]] - \\ \frac{d}{dx}[\text{Re}[Cc(x, y, z, t)]] \cdot \\ \text{Im}[Cc(x, y, z, t)] \\ \overline{\text{Re}[Cc(x, y, z, t)]^2 +} \\ \text{Im}[Cc(x, y, z, t)]^2 \end{array}\right)\Bigg|_{x=X, y=Y, z=Z, t=T}.$$

$c_R$ is the ultrasound propagating velocity and 1.0 respectively when R axis is the beam axis and scan axis. $f_{0R}$ is the ultrasound carrier frequency (when laterally nonmodulated) and modulation frequency (when axial motion compensation is performed) respectively when R axis is the beam axis and scan axis. $s_R$ is 4.0 and 2.0 respectively when R axis is the beam axis and scan axis. As above-described, the spatial gradient of the phase $\theta_{cc}(x,y,z,t)$ can also be obtained by finite difference approximation or differential filtering after obtaining the phase $\theta_{cc}(x,y,z,t)$. Freely, the phases, the signal components, or numerator and denominator can be moving averaged or low-pass filtered in the space or time domain. Otherwise, the spatial gradient of the phase $\theta_{cc}(x,y,z,t)$ can also be obtained, for instance, the partial derivative in x direction as $\tan^{-1}(\text{Im}[Cc^*(x,y,z,t)Cc(x+\Delta x,y,z,t)]/\text{Re}[Cc^*(x,y,z,t)Cc(x+\Delta x,y,z,t)])/\Delta x$, where * is the conjugate. Occasionally, the phase difference, the signal components, or numerator and denominator can be moving averaged or low-pass filtered in the space or time domain. Thus, the strain component distributions (series) can be obtained in the ROI.

The spatial and temporal simultaneous equations of the above-described equation can be handled, where the above-described least squares method and regularization method can be applied.

By integrating the partial derivatives of displacement vector component distributions (series), the displacement vector distribution (series) can be obtained.

From the strain tensor component distributions (series) or the temporal or spatial derivatives of displacement vector component distributions (series), obtained are the strain rate tensor component distributions (series), and acceleration vector component distributions (series).

Freely, (II-1) Doppler method (beam direction or scan direction) is utilized, or (II-2) both the Doppler method (beam direction or scan direction) and the regularization method are utilized, or (II-3) multidimensional Doppler method, i.e., at least 2D distribution (including beam direction or not) of the 3D, 2D phases, or 1D phase of respective of 3D complex signals with single-octant spectra, 2D complex signals with single-quadrant spectra and conventional 1D complex analytic signal, and the regularization method are utilized (Optical flow algorithm is applied to the phase of the complex signal). That is, methods (II-1), (II-2), and (II-3) can be equipped.

On the method (II-3), for instance, the following equation holds for unknown 3D displacement vector $(ux,uy,uz)^T$ at each point (X,Y,Z) at time t=T:

$$\frac{d}{dx}\theta_A(x, y, z, t)\Big|_{x=X, y=Y, z=Z, t=T}$$

$$ux + \frac{d}{dy}\theta_A(x, y, z, t)\Big|_{x=X, y=Y, z=Z, t=T} uy + \frac{d}{dz}\theta_A(x, y, z, t)\Big|_{x=X, y=Y, z=Z, t=T}$$

-continued $$uz + \frac{d}{dt}\theta_A(x, y, z, t)\bigg|_{x=X,y=Y,z=Z,t=T} \Delta t = 0$$

(or for unknown 3D velocity vector $(vx,vy,vz)^T$:

$$\frac{d}{dx}\theta_A(x, y, z, t)\bigg|_{x=X,y=Y,z=Z,t=T}$$

$$vx + \frac{d}{dy}\theta_A(x, y, z, t)\bigg|_{x=X,y=Y,z=Z,t=T} vy + \frac{d}{dz}\theta_A(x, y, z, t)\bigg|_{x=X,y=Y,z=Z,t=T}$$

$$vz + \frac{d}{dt}\theta_A(x, y, z, t)\bigg|_{x=X,y=Y,z=Z,t=T} = 0$$

$\theta_A(x,y,z,t)$ is the 3D phase distribution (x,y,z) of the complex signal A(x,y,z,t) (=Re[A(x,y,z,t)]+jIm[A(x,y,z,t)]) of the point (x,y,z) at the time t($\Delta$t: transmitted pulse interval):

$$\theta_A(x,y,z,t)=\tan^{-1}(Im[A(x,y,z,t)]/Re[A(x,y,z,t)]).$$

In the SOI, occasionally also in time direction, these equations hold (simultaneous equations), and can be solved by the least squares method, where, freely, the regularization method can also be applied [using a priori conditions such as the temporal and spatial magnitude of the unknown displacement (velocity) vector distribution, temporal and spatial continuity and differentiability of the unknown displacement (velocity) vector distribution]. Thus, the displacement (velocity) vector distribution (series) can be obtained. The temporal and spatial gradients of the phase $\theta_A(x,y,z,t)$ can be obtained by finite difference approximation or differential filtering. Otherwise, for instance, x partial derivative $\partial/\partial x\cdot\theta_A(x,y,z,t)|_{x=X,y=Y,z=Z,t=T}$ can be obtained as $\{Re[A(X,Y,Z,T)]\times \partial/\partial x\cdot Im[A(x,y,z,t)]|_{x=X, y=Y, z=Z, t=T}-\partial/\partial\cdot Re[A(x,y,z,t)]|_{x=X, y=Y, z=Z, t=T}\times Im[A(X,Y,Z,T)]\}/\{Re[A(X,Y,Z;T)]^2+Im[A(X,Y,Z,T)]^2\}$, where $\partial/\partial x\cdot Re[A(x,y,z,t)]|_{x=X,y=Y, z=Z, t=T}$ can be obtained by finite difference approximation or differential filtering. Otherwise, for instance, x partial derivative $\partial/\partial x\cdot\theta_A(x,y,z)|_{x=0,y=0,z=0}$ can be obtained as: $\tan^{-1}(Im[A^*(X,Y,Z;0,0,0)A(X,Y,Z;\Delta x,0,0)]/Re[A^*(X,Y,Z;0,0,0)A(X,Y,Z;\Delta x,0,0)])$, where * is the conjugate.

For these calculations, freely, the phases, the signal components, or numerator and denominator can be moving averaged or low-pass filtered in the spatial and time domain.

When the unknown displacement vector is 2D one, for instance, when the unknown 2D displacement vector is (ux, uy)$^T$, the following equation holds for $(ux,uy)^T$ at each point (X,Y,Z) at time t=T:

$$\frac{d}{dx}\theta_A(x, y, t)\bigg|_{x=X,y=Y,t=T} ux + \frac{d}{dy}\theta_A(x, y, t)\bigg|_{x=X,y=Y,t=T}$$

$$uy + \frac{d}{dt}\theta_A(x, y, t)\bigg|_{x=X,y=Y,t=T} \Delta t = 0$$

(or for unknown 2D velocity vector $(vx,vy)^T$:

$$\frac{d}{dx}\theta_A(x, y, t)\bigg|_{x=X,y=Y,t=T} vx + \frac{d}{dy}\theta_A(x, y, t)\bigg|_{x=X,y=Y,t=T}$$

$$vy + \frac{d}{dt}\theta_A(x, y, t)\bigg|_{x=X,y=Y,t=T} = 0\bigg).$$

$\theta_A(x,y,t)$ is the 2D phase distribution (x,y) of the complex signal A(x,y,t) (=Re[A(x,y,t)]+jIm[A(x,y,t)]) of the point (x,y) at the time t($\Delta$t: transmitted pulse interval):

$$\theta_A(x,y,t)=\tan^{-1}(Im[A(x,y,t)]/Re[A(x,y,t)]).$$

Method (II-3) can also be applied to measurement of one displacement component distribution.

On the method (II-1), utilized is the phase of the complex signal in the beam direction or scan direction. The following equation holds for the unknown displacement component ux at each point (X,Y,Z) at time t=T:

$$\frac{d}{dx}\theta_A(x, t)\bigg|_{x=X,t=T} ux + \frac{d}{dt}\theta_A(x, t)\bigg|_{x=X,t=T} \Delta t = 0$$

(or for unknown velocity component vx (the Doppler's equation):

$$\frac{d}{dx}\theta_A(x, t)\bigg|_{x=X,t=T} vx + \frac{d}{dt}\theta_A(x, t)\bigg|_{x=X,t=T} = 0\bigg).$$

$\theta_A(x,t)$ is the 1D phase distribution (x) of the complex signal A(x,t) of the point (x) at the time t($\Delta$T: transmitted pulse interval).

In the ROI, by solving this equation for unknown displacement component ux (unknown velocity component vx) at each point, the displacement (velocity) component distribution (series) can be obtained.

On the method (II-2), in the ROI, occasionally also in the spatial and time direction, this equation holds in beam direction or scan direction, and the derived simultaneous equations can be solved by least squares method, where, freely, regularization method can also be applied (using a priori conditions such as the temporal and spatial magnitude of the unknown displacement component distribution, temporal and spatial continuity and differentiability of the unknown displacement component distribution). Thus, the displacement component distribution (series) can be obtained.

On the methods (II-1), (II-2) and (II-3), occasionally the unknown displacement (velocity) vector and the unknown displacement (velocity) vector component are dealt with as locally uniform ones. That is, occasionally, under the assumption that the local region uniformly moves, the simultaneous equations hold for the unknown local displacement (velocity) vector or the unknown local displacement (velocity) component. Otherwise, occasionally, the simultaneous equations hold under the assumption that the displacement (velocity) is uniform for temporal finite interval. Otherwise, in the above-described two cases where beam forming is performed in the plural directions, the equations derived from respective beam formings can be simultaneously solved for the unknown local displacement (velocity) vector or the unknown local displacement (velocity) component. Thus, the spatial distribution (series) can be obtained. Occasionally, the regularization method is not used.

Specifically, on the methods (II-2) and (II-3), when measuring the 2D displacement vector, the two 2D Complex signals with different single-quadrant spectra are obtained to derive the independent simultaneous two equations, whereas when measuring the 3D displacement vector, the three or four 3D complex signals with different single octant spectra are obtained to derive the independent simultaneous three or four equations (Here, the complex signals with the respective different single-quadrant or single-octant spectra exist two and four although there exist four and eight complex signals including those yield the dependent equations. Setting spectra at zeros in the frequency domain can also be performed for respective 1D Fourier's transforms). The independency can also be confirmed by the carrier frequencies. When the simultaneous four equations are dealt with, the least squares method is applied.

Moreover, on the methods (II-1), (II-2) and (II-3), the single-quadrant or single-octant spectra of the pre- and post-deformation echo data can be divided into plural spectra, (for instance, using the carrier frequencies) to obtain the plural paired complex signals that yield independent simultaneous equations.

Moreover, on the methods (II-1), (II-2) and (II-3), the ultrasounds having different ultrasound frequencies can be transmitted to obtain the plural paired complex signals of the pre- and post-deformation echo data that yield independent simultaneous equations.

Moreover, on the methods (II-1), (II-2) and (II-3), when the lateral modulation is performed in the lateral directions, by yielding the plural paired complex signals of the pre- and post-deformation echo data having different modulation frequencies, independent simultaneous equations can be derived.

Moreover, on the methods (II-1), (II-2) and (II-3), by yielding the plural paired complex signals of the pre- and post-deformation echo data respectively having the basic and harmonic spectra, independent simultaneous equations can be derived.

Here, on the methods (II-1), (II-2) and (11-3), the spatial derivatives of the phase of the complex signal can be set at the known values such as the nominal frequency, modulation frequency, pre-estimated values.

Moreover, on the methods (I-1), (I-2) and (I-3), the spatial derivatives of the phases of the complex signals can be set using the values evaluated from an arbitrary paired complex signals by changing their signs. Otherwise, the spatial derivatives of the phase of the complex signal can be set using the values evaluated from a paired, averaged complex signals in the frequency domain or spatial domain. Otherwise, the spatial derivatives of the phase of the complex signal can be set using the means of the absolute values evaluated from the plural paired complex signals by changing their signs. Thus, the spatial derivatives of the phase of the complex signal can be set using more than one paired complex signals. In these cases, $$\frac{d}{dt} \cdot \theta_A(x, y, z, t)\Big|_{x=X, y=Y, z=Z, t=T} \Delta t,$$

$$\frac{d}{dt} \cdot \theta_A(x, y, t)\Big|_{x=X, y=Y, t=T} \Delta t \text{ and}$$

$$\frac{d}{dt} \cdot \theta_A(x, t)\Big|_{x=X, t=T} \Delta t$$

can also be evaluated from the phase difference of the quadrature-detected signals obtained by shifting the single-quadrant or single-octant spectra using the known frequencies (It is needless to say that the quadrature detection can also be performed respective for the 1D Fourier's transforms). The phase difference can also be directly obtained from the conjugate product of the quadrature-detected signals. Here, the quadrature detection can also be performed only in two or one directions for 3D measurement, whereas only in one direction for 2D measurement. In these cases, the spatial derivatives of the phase difference of the complex signal can be obtained by the spatially differentiating the phase difference, and $$\frac{d}{dt} \cdot \theta_A(x, y, z, t)\Big|_{x=X, y=Y, z=Z, t=T} \Delta t \text{ and}$$

$$\frac{d}{dt} \cdot \theta_A(x, y, t)\Big|_{x=X, y=Y, t=T} \Delta t$$

can be obtained from the phase difference between the complex signals. Here, the quadrature detection can also be realized in spatial domain (x,y,z). When detecting more than two directions, at least one complex signal is required to be quadrature-detected using the minus frequency. In this case, the detected complex signals in the fewer directions, after which the spectra in the remaining directions are set at zeros, can be dealt with in same ways as described above as well as the detected complex signals in all the directions.

Occasionally, the regularization method is not used above.

Furthermore, the envelope-detected signals obtained from the quadrature-detected complex signals can be respectively converted into images. Otherwise, the superimposed envelope-detected signals (i.e., mean) can be converted into an image. In this case, the PSF can also be designed as $\exp(-y^2/(2\sigma_y^2))\sin(2\pi f_y y)$ or $\exp((-y^2/(2\sigma y^2))+(-z^2/(2\sigma_z^2))\sin(2\pi f_y y)\sin(2\pi f_z z)$ using the sine function.

The displacement vector distribution (series) can also be obtained by integrating the obtained velocity vector component distributions (series), or by multiplying the transmitted pulse interval Ts to the obtained velocity vector component distributions (series).

From the temporal and spatial derivatives of the velocity vector distribution (series) or displacement vector distribution (series), obtained are the strain tensor component distributions (series), strain tensor rate component distributions (series), and acceleration vector component distributions (series).

There are other various methods for estimating the remaining estimation error vector. These methods can also be utilized in the same way. During the iterative estimation of the displacement vector and residual displacement vector, when estimation errors are detected a priori at the points of time-space magnitude and time-space continuity, for instance, the estimates can be truncated by compulsion such that the estimates range from the smallest value to the largest value set a priori, or such that the difference between the estimates of the neighboring points settles within the range set a priori.

As explained above, on this conduct form, by iterative estimation, the measurement accuracy can be improved of the displacement vector in the 3D SOI, particularly, 3D displacement vector, obtained from the cross-spectrum phase gradient etc of the ultrasound echo signals acquired as the responses to more than one time transmitted ultrasound. The local echo signal can be shifted by multiplying complex exponential, or interpolation can be performed after shifting the sampled ultrasound signal. The present invention can improve the measurement accuracies of lateral displacements (orthogonal directions to beam direction). Furthermore, the present invention can simplify calculation process such that the process does not require to unwrap the cross-spectrum phase nor utilizing the cross-correlation method, by which the calculation amount and calculation time are reduced.

Moreover, on this conduct form, a large displacement (vector) and a large strain (tensor) can be accurately measured by tracking the ultrasound echo signal of the target tissue using the echo signal phase as the index (the local echo signal can be shifted by multiplying complex exponential, or interpolation can be performed after shifting the sampled ultrasound signal) and by adding the successively estimated displacements or strains. Otherwise, such phase matching can also be realized by shifting the sampled echo data with the approximate displacements using the sampling intervals, by which the calculation amount and time can be significantly reduced.

Furthermore, on this conduct form, a high freedom of configurations of displacement (strain) sensors, mechanical sources, reference regions (mediums) can be realized; thus elastic constant and visco elastic constant can be accurately measured.

Next, explains are about the elasticity and visco-elasticity constants measurement apparatus related to one of the conduct forms of the present invention. The elasticity and visco-elasticity constants measurement apparatus related to this conduct form utilizes the apparatus shown in FIG. 1 (same as that of the above-explained displacement vector and strain measurement), and the apparatus measures the elastic constants and visco elastic constants from the displacement vector, strain tensor, etc. measured by using the displacement and strain measurement method.

At first, the assumptions are explained of the elasticity and visco-elasticity constants measurement apparatus related to this conduct form. The following constants are assumed to be measured only in the target ROI (SOI) set in the measurement object, the elastic constants such as shear modulus, Poisson's ratio, etc., visco elastic constants such as visco shear modulus, visco Poisson's ratio, etc., delay times or relaxation times relating these elastic constants and visco elastic constants, or density. All the mechanical sources are assumed to exist outside of the ROI. Then, if there exist other mechanical sources in addition to the set mechanical sources or if the mechanical sources are uncontrollable, the following constants can be measured in the target ROI (SOI), the elastic constants such as shear modulus, Poisson's ratio, etc., visco elastic constants such as visco shear modulus, visco Poisson's ratio, etc., delay times or relaxation times relating these elastic constants and visco elastic constants, or density. Any information is not needed about mechanical sources, such as positions, force directions, force magnitudes, etc. Moreover neither stress data nor strain data are needed at the target body surface. Only the ROI is modeled using the finite difference method or finite element method.

If the mechanical sources originally exist near the ROI, only the mechanical sources may be utilized. In the case of the observation of living tissues, for instance, the mechanical sources include the uncontrollable mechanical sources such as heart motion, respiratory motion, blood vessel motion, body motion. In general, lung, air, blood vessel, blood are included in the ROI. In this case, without disturbing the deformation field, the following constants can be measured, i.e., the elastic constants such as shear modulus, Poisson's ratio, etc., visco elastic constants such as visco shear modulus, visco Poisson's ratio, etc., delay times or relaxation times relating these elastic constants and visco elastic constants, or density. This is effective particularly when the ROI is deeply situated.

When solving the first order partial differential equations, as initial conditions the following can be utilized if necessary, i.e., the reference shear modulus and reference Poisson's ratio, reference visco shear modulus and reference visco Poisson's ratio, reference density. In this case, the reference mediums or reference regions are set in the original ROI or near the original ROI, after which the final ROI is set such that the final ROI includes the original ROI as well as the references. By measuring in the ROI including the reference regions the strain tensor field, strain rate tensor field, and acceleration vector field, the references are realized.

The size and position of the reference mediums or reference regions should be set such that they should widely cross the direction of the dominant tissue deformation. For instance, if the mechanical source has large a contact surface, a large reference region should be set. Otherwise, if the mechanical source has a small contact surface, by setting the reference region near the mechanical source, a small reference region may be used. The estimates can also be used as their references.

The present invention can provide the absolute shear modulus distribution, relative shear modulus distribution, absolute Poisson's ratio distribution, relative Poisson's ratio distribution, absolute visco shear modulus distribution, relative visco shear modulus distribution, absolute visco Poisson's ratio distribution, relative visco Poisson's ratio distribution, absolute or relative delay time distributions relating these elastic constants and visco elastic constants, absolute or relative relaxation time distributions relating these elastic constants and visco elastic constants, absolute density distribution, or relative density distribution. Here, distributions of the reference Poisson's ratio, reference visco Poisson's ratio and reference density must be distributions of absolute values, while distributions of the other reference elastic constants, and reference visco elastic constants may be distributions of relative values.

As the numerical solution method of the first order partial differential equations, the finite difference method or finite element method can be utilized. By utilizing the regularized algebraic equations, if the strain tensor field data is contaminated with errors (noises), or if the reference medium or reference region is small, or if the reference position is ill-conditioned, the following distribution can be stably estimated, i.e., the shear modulus distribution, Poisson's ratio distribution, visco shear modulus distribution, visco Poisson's ratio, density, etc.

Referring to FIG. 1 again, next explain is about the means of data processing 1, i.e., the calculation method of the shear modulus distribution, Poisson's ratio distribution, visco shear modulus distribution, visco Poisson's ratio distribution, delay time distributions, relaxation time distributions, or density distribution, etc. When the 3D strain tensor, the 3D strain rate tensor, the 3D acceleration vector, etc. are measured, for instance, on the Cartesian coordinate system (x,y,z), the following simultaneous first order partial equations from (125) to (137″) are dealt with, where the shear modulus distribution, $\mu$; the Poisson's ratio distribution, $\nu$; the visco shear modulus distribution, $\mu'$; the visco Poisson's ratio distribution, $\nu'$; the delay time distributions, $\tau$; the relaxation time distributions, $\tau'$; the strain tensor field, $\epsilon$; the strain rate tensor field, $\epsilon'$.

That is, when the 3D strain tensor is measured, and only the shear modulus distribution $\mu$ is unknown, the following equations are dealt with, $$\{\phi \varepsilon_{\alpha\alpha} \delta_{ij} + \varepsilon_{ij}\}(\ln\mu)_{,j} + \{\phi \varepsilon_{\alpha\alpha} \delta_{ij} + \varepsilon_{ij}\}_{,j} = 0, \tag{125}$$

$$\text{where } \phi = \frac{\nu}{1-2\nu}, \tag{125'}$$

or $$\{\phi \varepsilon_{\alpha\alpha} \delta_{ij} + \varepsilon_{ij}\}\mu_{,j} + \{\phi \varepsilon_{\alpha\alpha} \delta_{ij} + \varepsilon_{ij}\}_{,j}\mu = 0, \tag{126}$$

$$\text{where } \phi = \frac{\nu}{1-2\nu}. \tag{126'}$$

When the 3D strain tensor is measured, and the shear modulus distribution μ and Poisson's ratio distribution ν are unknown, the following equations are dealt with, $$\{\varepsilon_{aa}\delta_{ij}\}\lambda_{,j} + \{\varepsilon_{aa}\delta_{ij}\}_{,j}\lambda + 2\varepsilon_{ij}\mu_{,j} + 2\varepsilon_{ij,j}\mu = 0, \quad (127)$$

$$\text{where } \lambda = \frac{2\nu}{1-2\nu}\mu. \quad (127')$$

When the 3D strain tensor and 3D strain rate tensor are measured, and the shear modulus distribution μ and visco shear modulus distribution μ' are unknown, the following equations are dealt with, $$\{\phi\varepsilon_{aa}\delta_{ij} + \varepsilon_{ij}\}\mu_{,j} + \{\phi\varepsilon_{aa}\delta_{ij} + \varepsilon_{ij}\}_{,j}\mu + \quad (128)$$
$$\{\phi'\varepsilon'_{aa}\delta_{ij} + \varepsilon'_{ij}\}\mu'_{,j} + \{\phi'\varepsilon'_{aa}\delta_{ij} + \varepsilon'_{ij}\}_{,j}\mu' = 0,$$

$$\text{where } \phi = \frac{\nu}{1-2\nu}, \quad (128')$$

$$\phi' = \frac{\nu'}{1-2\nu'}, \quad (128'')$$

or $$\left[\int_{t'}^{t}\phi(t-\tau)\mu(t-\tau)\exp\left\{-\frac{\phi(t-\tau)\mu(t-\tau)}{\phi'(t-\tau)\mu'(t-\tau)}(t-\tau)\right\}\varepsilon'_{aa}(\tau)d\tau\delta_{ij}\right]_{,j} + \quad (128''')$$
$$\left[\int_{t'}^{t}\mu(t-\tau)\exp\left\{-\frac{\mu(t-\tau)}{\mu'(t-\tau)}(t-\tau)\right\}\varepsilon'_{ij}(\tau)d\tau\right]_{,j} = 0$$

where t' is the initial time. If either shear modulus distribution μ or visco shear modulus distribution μ' is given, instead of (128'''), the following equations can be dealt with, $$\{\phi\epsilon_{aa}\delta_{ij} + \epsilon_{ij}\}\mu = \{\phi'\epsilon'_{aa}\delta_{ij} + \epsilon'_{ij}\}\mu'. \quad (128'''')$$

If both the shear modulus distribution μ and visco shear modulus distribution μ' are unknown, from (128''''), the relaxation time μ'(t)/μ(t) can be calculated, and can be utilized in the above equations (128''').

When the 3D strain tensor and 3D strain rate tensor are measured, and the shear modulus distribution μ, Poisson's ratio distribution ν, visco shear modulus distribution μ', and visco Poisson's ratio distribution ν' are unknown, the following equations are dealt with, $$\{\varepsilon_{aa}\delta_{ij}\}\lambda_{,j} + \{\varepsilon_{aa}\delta_{ij}\}_{,j}\lambda + 2\varepsilon_{ij}\mu_{,j} + 2\varepsilon_{ij,j}\mu + \quad (129)$$
$$\{\varepsilon'_{aa}\delta_{ij}\}\lambda'_{,j} + \{\varepsilon'_{aa}\delta_{ij}\}_{,j}\lambda' + 2\varepsilon'_{ij}\mu'_{,j} + 2\varepsilon'_{ij,j}\mu' = 0,$$

$$\text{where } \lambda = \frac{2\nu}{1-2\nu}\mu, \quad (129')$$

$$\lambda' = \frac{2\nu'}{1-2\nu'}\mu', \quad (129'')$$

or $$\left[\int_{t'}^{t}\lambda(t-\tau)\exp\left\{-\frac{\lambda(t-\tau)}{\lambda'(t-\tau)}(t-\tau)\right\}\varepsilon'_{aa}(\tau)d\tau\delta_{ij}\right]_{,j} + \quad (129''')$$
$$2\left[\int_{t'}^{t}\mu(t-\tau)\exp\left\{-\frac{\mu(t-\tau)}{\mu'(t-\tau)}(t-\tau)\right\}\varepsilon'_{ij}(\tau)d\tau\right]_{,j} = 0$$

where t' is the initial time. Either both the shear modulus distribution μ and visco shear modulus distribution μ' or both the Poisson's ratio distribution ν and visco Poisson's ratio distribution ν' are given, instead of (129''') the following equations can be dealt with, $$\lambda\epsilon_{aa}\delta_{ij} + 2\epsilon_{ij}\mu = \lambda'\epsilon'_{aa}\delta_{ij} + 2\epsilon'_{ij}\mu'. \quad (129'''')$$

From (129''''), the relaxation time μ'(t)/μ(t) can always be calculated. Then if either shear modulus distribution μ or visco shear modulus distribution μ', is given, the obtained shear modulus distribution μ and visco shear modulus distribution μ' can be utilized in the above equations (129'''). Otherwise, if either Poisson's ratio distribution ν or visco Poisson's ratio distribution ν' is given, the obtained Poisson's ratio distribution ν, visco Poisson's ratio distribution ν', and relaxation time λ'(t)/λ(t) can be utilized in the above equations (129''').

Equations (128'''), (128''''), (129'''), and (129'''') can be dealt with when the target is fluid such as water, secretions, blood, etc., or tissue includes the fluid much. The equations can also be dealt with after first order temporal partial differentiation or partial integration. Theoretically, the elastic constant distributions and visco elastic constant distributions need to be invariant from the initial time t' to time t.

When the 2D strain tensor, 2D strain rate tensor, etc. are measured, the simultaneous first order partial equations (125) to (129'''') [i, j=1,2] or the following simultaneous first order partial differential equations (130) to (134'''') [i, j=1,2] are dealt with. The equations (125) to (129'''') [i, j=1,2] are dealt with approximately under plane strain condition, while the equations (130) to (134'''') [i, j=1,2] are dealt with approximately under plane stress condition.

When the 2D strain tensor is measured, and only the shear modulus distribution μ is unknown, the following equations are dealt with, $$\{\varphi\varepsilon_{aa}\delta_{ij} + \varepsilon_{ij}\}(\ln\mu)_{,j} + \{\varphi\varepsilon_{aa}\delta_{ij} + \varepsilon_{ij}\}_{,j} = 0, \quad (130)$$

$$\text{where } \varphi = \frac{\nu}{1-\nu}, \quad (130')$$

or $$\{\varphi\varepsilon_{aa}\delta_{ij} + \varepsilon_{ij}\}\mu_{,j} + \{\varphi\varepsilon_{aa}\delta_{ij} + \varepsilon_{ij}\}_{,j}\mu = 0, \quad (131)$$

$$\text{where } \varphi = \frac{\nu}{1-\nu}. \quad (131')$$

When the 2D strain tensor is measured, and the shear modulus distribution μ and Poisson's ratio distribution ν are unknown, the following equations are dealt with, $$\{\varepsilon_{aa}\delta_{ij}\}\gamma_{,j} + \{\varepsilon_{aa}\delta_{ij}\}_{,j}\gamma + \varepsilon_{ij}\mu_{,j} + \varepsilon_{ij,j}\mu = 0, \quad (132)$$

$$\text{where } \gamma = \frac{\nu}{1-\nu}\mu. \quad (132')$$

When the 2D strain tensor and 2D strain rate tensor are measured, and the shear modulus distribution μ and visco shear modulus distribution μ' are unknown, the following equations are dealt with, $$\{\varphi\varepsilon_{aa}\delta_{ij} + \varepsilon_{ij}\}\mu_{,j} + \{\varphi\varepsilon_{aa}\delta_{ij} + \varepsilon_{ij}\}_{,j}\mu + \quad (133)$$
$$\{\varphi'\varepsilon'_{aa}\delta_{ij} + \varepsilon'_{ij}\}\mu'_{,j} + \{\varphi'\varepsilon'_{aa}\delta_{ij} + \varepsilon'_{ij}\}_{,j}\mu' = 0,$$

$$\text{where } \varphi = \frac{\nu}{1-\nu}, \quad (133')$$

$$\varphi' = \frac{v'}{1-v'}, \tag{133''}$$

or $$\left[\int_{t'}^{t} \varphi(t-\tau)\mu(t-\tau)\exp\left\{-\frac{\varphi(t-\tau)\mu(t-\tau)}{\varphi'(t-\tau)\mu'(t-\tau)}(t-\tau)\right\}\varepsilon'_{aa}(\tau)d\tau\delta_{ij}\right]_{,j} + \tag{133'''}$$

$$\left[\int_{t'}^{t} \mu(t-\tau)\exp\left\{-\frac{\mu(t-\tau)}{\mu'(t-\tau)}(t-\tau)\right\}\varepsilon'_{ij}(\tau)d\tau\right]_{,j} = 0,$$

where t' is the initial time. If either shear modulus distribution μ or visco shear modulus distribution μ' is given, the following equations can be dealt with, $$\{\phi\varepsilon_{\alpha\alpha}\delta_{ij}+\varepsilon_{ij}\}\mu=\{\phi'\varepsilon'_{\alpha\alpha}\delta_{ij}+\varepsilon'_{ij}\}\mu'. \tag{133''''}$$

If both the shear modulus distribution μ and visco shear modulus distribution μ' are unknown, from (133''''), the relaxation time μ'(t)/μ(t) can be calculated, and can be utilized in the above equations (133''').

When the 2D strain tensor and 2D strain rate tensor are measured, and the shear modulus distribution μ, Poisson's ratio distribution ν, visco shear modulus distribution μ', and visco Poisson's ratio distribution ν' are unknown, the following equations are dealt with, $$\{\varepsilon_{\alpha\alpha}\delta_{ij}\}\gamma_{,j} + \{\varepsilon_{\alpha\alpha}\delta_{ij}\}_{,j}\gamma + \varepsilon_{ij}\mu_{,j} + \varepsilon_{ij,j}\mu + \tag{134}$$

$$\{\varepsilon'_{\alpha\alpha}\delta_{ij}\}\gamma'_{,j} + \{\varepsilon'_{\alpha\alpha}\delta_{ij}\}_{,j}\gamma' + \varepsilon'_{ij}\mu'_{,j} + \varepsilon'_{ij,j}\mu' = 0,$$

where $\gamma = \frac{v}{1-v}\mu,$ (134')

$$\gamma' = \frac{v'}{1-v'}\mu', \tag{134''}$$

or $$\left[\int_{t'}^{t} \gamma(t-\tau)\exp\left\{-\frac{\gamma(t-\tau)}{\gamma'(t-\tau)}(t-\tau)\right\}\varepsilon'_{aa}(\tau)d\tau\delta_{ij}\right]_{,j} + \tag{134'''}$$

$$\left[\int_{t'}^{t} \mu(t-\tau)\exp\left\{-\frac{\mu(t-\tau)}{\mu'(t-\tau)}(t-\tau)\right\}\varepsilon'_{ij}(\tau)d\tau\right]_{,j} = 0,$$

where t' is the initial time. Either both the shear modulus distribution μ and visco shear modulus distribution μ' or both the Poisson's ratio distribution ν and visco Poisson's ratio distribution ν' are given, the following equations can be dealt with, $$\gamma\varepsilon_{\alpha\alpha}\delta_{ij}+\varepsilon_{ij}\mu=\gamma'\varepsilon'_{\alpha\alpha}\delta_{ij}+\varepsilon'_{ij}\mu'. \tag{134''''}$$

From (134''''), the relaxation time μ'(t)/μ(t) can always be calculated. Then if either shear modulus distribution μ or visco shear modulus distribution μ' is given, the obtained shear modulus distribution μ and visco shear modulus distribution μ' can be utilized in the above equations (134'''). Otherwise, if either Poisson's ratio distribution ν or visco Poisson's ratio distribution ν' is given, the obtained Poisson's ratio distribution ν, visco Poisson's ratio distribution ν', and relaxation time γ'(t)/γ(t) can be utilized in the above equations (134''').

Equations (133'''), (133''''), (134'''), and (134'''') can be dealt with when the target is fluid such as water, secretions, blood, etc., or tissue includes the fluid much. The equations can also be dealt with after first order temporal partial differentiation or partial integration. Theoretically, the elastic constant distributions and visco elastic constant distributions need to be invariant from the initial time t' to time t.

When the 1D strain tensor, the 1D strain rate tensor, etc. are measured, the simultaneous first order partial differential equations from (135) to (137'') are dealt with.

When the 1D strain tensor is measured, and only the shear modulus distribution μ is unknown, the following equations are dealt with, $$\varepsilon_{11}(\ln\mu)_{,1}+\varepsilon_{11,1}=0, \tag{135}$$

or $$\varepsilon_{11}\mu_{,1}+\varepsilon_{11,1}\mu=0. \tag{136}$$

When the 1D strain tensor and 1D strain rate tensor are measured, and the shear modulus distribution μ and visco shear modulus distribution μ' are unknown, the following equations are dealt with, $$\varepsilon_{11}\mu_{,1} + \varepsilon_{11,1}\mu + \varepsilon'_{11}\mu'_{,1} + \varepsilon'_{11,1}\mu' = 0, \tag{137}$$

or $$\left[\int_{t'}^{t} \mu(t-\tau)\exp\left\{-\frac{\mu(t-\tau)}{\mu'(t-\tau)}(t-\tau)\right\}\varepsilon'_{11}(\tau)d\tau\right]_{,1} = 0, \tag{137'}$$

where t' is the initial time. If either shear modulus distribution μ or visco shear modulus distribution μ' is given, the following equations can be dealt with, $$\varepsilon_{11}\mu=\varepsilon'_{11}\mu'. \tag{137''}$$

If both the shear modulus distribution μ and visco shear modulus distribution μ' are unknown, from (137''), the relaxation time μ'(t)/μ(t) can be calculated, and can be utilized in the above equations (137').

Equations (137') and (137'') can be dealt with when the target is fluid such as water, secretions, blood, etc., or tissue includes the fluid much. The equations can also be dealt with after first order temporal partial differentiation or partial integration. Theoretically, the shear modulus distribution and visco shear modulus distribution need to be invariant from the initial time t' to time t.

In the equations (125), (130), (135), the signs of the terms not including (ln μ),j can be changed and together (ln μ),j can be changed by {ln(1/μ)},j, then the resultant partial differential equations can be dealt with for the unknown ln(1/μ). Although regarding with equations (125), (130), (135), the unknown ln μ cases are explained below, in unknown ln(1/μ) cases, ln μ or μ can be estimated after ln(1/μ) or (1/μ) are estimated in similar ways.

In the equations (126), (131), (136), the signs of the terms not including μ,j can be changed and together μ can be changed by (1/μ), then the resultant partial differential equations can be dealt with for the unknown (1/μ). Although regarding with equations (126), (131), (136), the unknown μ cases are explained below, in the unknown (1/μ) cases, μ or ln μ can be estimated after (1/μ) or ln(1/μ) are estimated in similar ways.

These can be effective when the ROI includes extremely high shear modulus object such as bone, interstitial needle (for biopsy and treatment), etc.

When the target is fluid such as water, secretions, blood, etc., or tissue includes the fluid much, in the equations (125), (126), (127), (130), (131), (132), (135), (136) the elastic constants can be changed by the corresponding visco elastic constants, and the strain tensor can be changed by the strain rate tensor. Also in this case, in the equations (125), (130), (135), the signs of the terms not including (ln μ'),j can be changed and together (ln μ'),j can be changed by {ln(1/μ')},j, then the resultant partial differential equations can be dealt with for the unknown $\ln(1/\mu')$. Although regarding with equations (125), (130), (135), the unknown $\ln \mu'$ cases are explained below, in the unknown $\ln(1/\mu')$ cases, $\ln \mu'$ or $\mu'$ can be estimated after $\ln(1/\mu')$ or $(1/\mu')$ are estimated in similar ways.

In the equations (126), (131), (136), the signs of the terms not including $\mu',j$ can be changed and together $\mu'$ can be changed by $(1/\mu')$, then the resultant partial differential equations can be dealt with for the unknown $(1/\mu')$. Although regarding with equations (126), (131), (136), the unknown $\mu'$ cases are explained below, in the unknown $(1/\mu')$ cases, $\mu'$ or $\ln \mu'$ can be estimated after $(1/\mu')$ or $\ln(1/\mu')$ are estimated in similar ways.

These can be effective when the ROI includes extremely high visco shear modulus object.

Here, in (127), by dealing with the mean normal stress p instead of $\lambda \epsilon_{\alpha\alpha}$, i.e., $p_{,j}\delta_{ij}$ instead of $\{\epsilon_{\alpha\alpha}\delta_{ij}\}\lambda_{,j}+\{\epsilon_{\alpha\alpha}\delta_{ij}\}_{,j}\lambda$; in (129), by dealing with the mean normal stress p and stress p' instead of $\lambda \epsilon_{\alpha\alpha}$ and $\lambda'\epsilon'_{\alpha\alpha}$, respectively, i.e., $p_{,j}\delta_{ij}+p'_{,j}\delta_{ij}$ instead of $\{\epsilon_{\alpha\alpha}\delta_{ij}\}\lambda_{,j}+\{\epsilon_{\alpha\alpha}\delta_{ij}\}_{,j}\lambda+\{\epsilon'_{\alpha\alpha}\delta_{ij}\}\lambda'_{,j}+\{\epsilon'_{\alpha\alpha}\delta_{ij}\}_{,j}\lambda'$; in (132), by dealing with the stress p instead of $\gamma\epsilon_{\alpha\alpha}$, i.e., $p_{,j}\delta_{ij}$ instead of $\{\epsilon_{\alpha\alpha}\delta_{ij}\}\gamma_{,j}+\{\epsilon_{\alpha\alpha}\delta_{ij}\}_{,j}\gamma$; in (134), by dealing with the stress p and p' instead of $\gamma\epsilon_{\alpha\alpha}$ and $\gamma'\epsilon'_{\alpha\alpha}$, respectively, i.e., $p_{,j}\delta_{ij}+p'_{,j}\delta_{ij}$ instead of $\{\epsilon_{\alpha\alpha}\delta_{ij}\}\gamma_{,j}+\{\epsilon_{\alpha\alpha}\delta_{ij}\}_{,j}\gamma+\{\epsilon'_{\alpha\alpha}\delta_{ij}\}\gamma'_{,j}+\{\epsilon'_{\alpha\alpha}\delta_{ij}\}_{,j}\gamma'$, by dealing with such stresses as unknown together with the unknown elastic constants or visco elastic constants in the remaining terms, obtained can be $\lambda$, $\lambda'$, $\gamma$, $\gamma'$, $\nu$ or $\nu'$.

When the elasticity or visco elasticity is anisotropic, the correspondingly derived equations (125) to (137") can be dealt with.

Regarding the density distribution $\rho$, the measured acceleration vector field a is used. Specifically, in equations (126), (128), (128'''), (131), (132), (133), (133'''), (134), (134'''), ($\frac{1}{2}$)$\rho a_i$ is added to the right terms, in equations (127), (129), (129''')$\rho a_i$ is added to the right terms, and in equations (136), (137), (137') ($\frac{1}{3}$)$\rho a_i$ is added to the right term. The known density distribution is used in the region, and the unknown density distribution is estimated together with the unknown shear modulus distribution $\mu$, unknown Poisson's ratio distribution $\nu$, unknown visco shear modulus distribution $\mu'$, and unknown visco Poisson's ratio distribution $\nu'$. When the target is fluid such as water, secretions, blood, etc., or tissue includes the fluid much, in the equations (126), (127), (131), (132), (136) the elastic constants can be changed by the corresponding visco elastic constants, and the strain tensor can be changed by the strain rate tensor. Otherwise, by deleting the inertia term (i.e., term including the accelerations) from the simultaneous equations and by solving the equations for the remaining elastic constants or visco elastic constants, the accelerations can be obtained (In this case, the reference regions should be set such that the reference regions widely extend in the direction that cross the characteristic curves determined by the inhomogeneous coefficients of the first order partial differential equations). Here, the density can not be dealt with when the partial differential equations (126), (131), (136) are directly solved for $\ln(1/\mu)$, $(1/\mu)$, $\ln(1/\mu')$ or $(1/\mu')$.

Specifically, according to the measured deformation fields, i.e., the strain tensor field, the strain rate tensor field [when dealing with the density $\rho$ (below omitted), the acceleration vector field, the temporal first derivative of the acceleration vector field, the strain tensor field or the strain rate tensor field] and/or the accuracy of the measured deformation fields, dealt with all over the 3D SOI 7 are the simultaneous first order partial differential equations (125) to (129""), or dealt with in the plural 3D SOIs, plural 2D ROIs, plural 1D ROIs set in the 3D SOI 7 are respectively the simultaneous first order partial differential equations (125) to (129""), the simultaneous first order partial differential equations (125) to (134""), the first order partial differential equations from (135) to (137"). When the plural independent deformation fields are measured, according to the accuracy of the measured deformation fields, freely one of the equations (125) to (137") or the plural equations (125) to (137") can be dealt with at each point of interest. That is, these equations are solved individually or simultaneously. The plural independent deformation fields can be generated under the different positions and conditions of the mechanical sources and the reference regions, when, for instance, their positions or conditions are changed artificially or not. These 3D SOIs, 2D ROIs, and 1D ROIs can include same regions in the 3D SOI 7.

The Poisson's ratio and visco Poisson's ratio can respectively be approximated from ratios of the principal values of the strain tensor and strain rate tensor (on 3D measurement, one of three ratios of the principle values, or means of the three or two ratios). When plural deformation fields are measured, the Poisson's ratio and the visco Poisson's ratio can respectively be approximated as the means of the ratios calculated from the plural fields. Typical values can also be utilized for the Poisson's ratio and the visco Poisson's ratio. For instance, the object is assumed to be incompressible, then the values are approximated as the value of about 0.5. Particularly, on equations from (130) to (134""), the object can be assumed to be completely incompressible, then the values are approximated as 0.5.

As initial conditions, at least at one reference point, or at least in properly set one reference region, the reference shear modulus, reference Poisson's ratio, reference visco shear modulus, or reference visco Poisson's ratio, etc. should be given.

That is, the reference shear moduli (absolute or relative values) may be given at least in one reference region $\overline{\omega}_{\mu,l}(l=1\sim N_\mu)$.

$$\ln \mu(x,y,z)=\ln \hat{\mu}(x,y,z), \overline{\omega}_{\mu,l} \in (x,y,z) \quad (138)$$

$$\mu(x,y,z)=\hat{\mu}(x,y,z), \overline{\omega}_{\mu,l} \in (x,y,z) \quad (138')$$

That is, the reference Poisson's ratios (absolute values) may be given at least in one reference region $\overline{\omega}_{\nu,l}(l=1\sim N_\nu)$.

$$\nu(x,y,z)=\hat{\nu}(x,y,z), \overline{\omega}_{\nu,l} \in (x,y,z) \quad (139)$$

That is, the reference visco shear moduli (absolute or relative values) may be given at least in one reference region $\overline{\omega}_{\mu',l}(l=1\sim N_{\mu'})$.

$$\mu'(x,y,z)=\hat{\mu}'(x,y,z), \overline{\omega}_{\mu',l} \in (x,y,z) \quad (140)$$

That is, the reference visco Poisson's ratios (absolute values) may be given at least in one reference region $\overline{\omega}_{\nu',l}(l=1\sim N_{\nu'})$.

$$\nu'(x,y,z)=\hat{\nu}'(x,y,z), \overline{\omega}_{\nu',l} \in (x,y,z) \quad (141)$$

Here, in (127), when dealing with the mean normal stress p instead of $\lambda \epsilon_{\alpha\alpha}$, i.e., $p_{,j}\delta_{ij}$ instead of $\{\epsilon_{\alpha\alpha}\delta_{ij}\}\lambda_{,j}+\{\epsilon_{\alpha\alpha}\delta_{ij}\}_{,j}\lambda$; in (129), when dealing with the mean normal stress p and stress p' instead of $\lambda\epsilon_{\alpha\alpha}$ and $\lambda'\epsilon'_{\alpha\alpha}$, respectively, i.e., $p_{,j}\delta_{ij}+p'_{,j}\delta_{ij}$ instead of $\{\epsilon_{\alpha\alpha}\delta_{ij}\}\lambda_{,j}+\{\epsilon_{\alpha\alpha}\delta_{ij}\}_{,j}\lambda+\{\epsilon'_{\alpha\alpha}\delta_{ij}\}\lambda'_{,j}+\{\epsilon'_{\alpha\alpha}\delta_{ij}\}_{,j}\lambda'$; in (132), when dealing with the stress p instead of $\gamma\epsilon_{\alpha\alpha}$, i.e., $p_{,j}\delta_{ij}$ instead of $\{\epsilon_{\alpha\alpha}\delta_{ij}\}\gamma_{,j}+\{\epsilon_{\alpha\alpha}\delta_{ij}\}_{,j}\gamma$; in (134), when dealing with the stress p and p' instead of $\gamma\delta_{\alpha\alpha}$ and $\gamma'\epsilon'_{\alpha\alpha}$, respectively, i.e., $p_{,j}\delta_{ij}+p'_{,j}\delta_{ij}$ instead of $\{\epsilon_{\alpha\alpha}\delta_{ij}\}\gamma_{,j}+\{\epsilon_{\alpha\alpha}\delta_{ij}\}_{,j}\gamma+\{\epsilon'_{\alpha\alpha}\delta_{ij}\}\gamma'_{,j}+\{\epsilon'_{\alpha\alpha}\delta_{ij}\}_{,j}\gamma'$, the initial conditions of p or p' should be given together with those of the remaining unknown elastic constants and visco elastic constants in the equations. Otherwise, when none of p, p', λ, λ', γ, γ', ν, ν' are targets, the conditions of p and p' are not required (When using the iterative method to solve the equations, the estimations p, p', λ, λ', γ, γ' become dependent results on the initial estimates).

When the elasticity or visco elasticity is anisotropic, the correspondingly derived equations from (125) to (137'') and correspondingly derived initial conditions from (138) to (141) can be dealt with.

When the target is fluid such as water, secretions, blood, etc., by measuring the strain rate tensor $\epsilon'_{ij}$ and acceleration vector $a_i$, the Navier-Stokes equations $\rho a_i = [-p-(2/3)\mu\epsilon'_{\alpha\alpha}]_{,j}\delta_{ij} + [2\mu\epsilon'_{ij}]_{,j}$ (when the fluid is completely incompressible, $\epsilon'_{\alpha\alpha}=0$) are solved for the viscosity μ (shear viscosity), density ρ or mean normal stress p (Some may be given in advance). Thus, the initial condition (reference) of the viscosity μ, density ρ or mean normal stress p may be given (More than one reference may be given) similarly as in the elastic constant measurement case. Here, when it is difficult to set the initial condition of the mean normal stress p or the mean normal stress p is not target, the initial condition of p is not required similarly as in the elastic constant measurement case (When using the iterative method to solve the equations, the estimation p becomes a dependent result on the initial estimate). Moreover, when the fluid is nearly incompressible, the term of $-(2/3)\mu\epsilon'_{\alpha\alpha}$ is ignored by setting at zero. Otherwise, the term $-(2/3)\mu\epsilon'_{\alpha\alpha}$ is dealt with as q and by giving the initial condition of q, q is reconstructed. Otherwise, the term $-(2/3)\mu\epsilon'_{\alpha\alpha}$ is dealt with as q and under the condition that the initial condition of q is not given, q is not reconstructed (When using the iterative method to solve the equations, the estimation q becomes a dependent result on the initial estimate). Otherwise, the terms $-p-(2/3)\mu\epsilon'_{\alpha\alpha}$ is dealt with as q and under the condition that the initial condition of q is given or not, q is reconstructed or not (When the initial condition is not used, the estimation q becomes a dependent result on the initial estimate).

Without dealing with the above Navier-Stokes equations (which assumes the mean normal stress equals to the pressure for compressible fluid as like for complete incompressible fluid), the bulk viscosity $\mu_v$ can also be estimated by dealing with $\rho a_i = [-p+(\mu_v-(2/3)\mu)\epsilon'_{\alpha\alpha}]_{,j}\delta_{ij} + [2\mu\epsilon'_{ij}]_{,j}$. Here, $\mu_v-(2/3)\mu$ can be expressed by λ. Thus, the initial condition (reference) of the viscosity μ, $\mu_v$, λ, density ρ or stress p may be given (More than one reference may be given) similarly as in the elastic constant measurement case. Here, when it is difficult to set the initial condition of the stress p or the stress p is not target, the initial condition of p is not required similarly as in the elastic constant measurement case (When using the iterative method to solve the equations, the estimation p becomes a dependent result on the initial estimate). Moreover, when the fluid is nearly incompressible, the term of $(\mu_v-(2/3)\mu)\epsilon'_{\alpha\alpha}$ is ignored by setting at zero. Otherwise, the term $(\mu_v-(2/3)\mu)\epsilon'_{\alpha\alpha}$ is dealt with as q and under the condition that the initial condition of q is given or not, q is reconstructed or not (When the initial condition is not used, the estimation q becomes a dependent result on the initial estimate). Otherwise, the term $-p+(\mu_v-(2/3)\mu)\epsilon'_{\alpha\alpha}$ is dealt with as q and under the condition that the initial condition of q is given or not, q is reconstructed or not (When the initial condition is not used, the estimation q becomes a dependent result on the initial estimate).

The kinematic viscosity $\mu_s$ can be obtained from μ/ρ.

Here, the temporal derivative can be realized by the Euler or Lagrange differentiation. Below, although the elastic constant and visco elastic constant measurements are described, the measurement of fluid is also realized in similar ways.

On the discrete Cartesian coordinate (x,y,z)~(IΔx, JΔy, KΔz) in the ROI 7 the finite difference approximation or finite element method based on the Galerkin's method or the variation principle is applied to the shear modulus distribution μ, Poisson's ratio distribution ν, elastic constant distribution φ, elastic constant distribution λ, elastic constant distribution φ, elastic constant distribution γ, visco shear modulus distribution μ', Poisson's ratio distribution ν', visco elastic constant distribution φ', visco elastic constant distribution λ', visco elastic constant distribution φ', visco elastic constant distribution γ', displacement distribution, strain distribution, or strain rate distribution. Then algebraic equations are derived from the first order partial differential equations and initial conditions, and usually the algebraic equations are normalized, for instance, by the root square of the summation of the powers of the spatially inhomogeneous coefficients (or the distributions) multiplied to the shear modulus (distribution) μ, Poisson's ratio (distribution) ν, elastic constant (distribution) φ, elastic constant (distribution) λ, elastic constant (distribution) φ, elastic constant (distribution) γ, visco shear modulus (distribution) μ', Poisson's ratio (distribution) ν', visco elastic constant (distribution) φ', visco elastic constant (distribution) λ', visco elastic constant (distribution) φ', or visco elastic constant (distribution) γ'. Furthermore, the algebraic equations can be regularized. Here, the elastic constants λ and μ are called as Lame's constants, while visco elastic constants λ' and μ' are called as visco Lame's constants.

For instance, when the finite difference method is utilized, the simultaneous equations are derived.

$$EGs = e \quad (142)$$

s is the unknown vector comprised of the unknown shear modulus distribution μ, unknown elastic constant distribution λ, unknown elastic constant distribution γ, unknown visco shear modulus distribution μ', unknown visco elastic constant distribution λ', unknown visco elastic constant distribution γ', etc. G is the coefficients matrix comprised of the finite approximations of the 3D, 2D or 1D partial derivatives. E and e are respectively the matrix and vector comprised of the strain tensor data, strain rate tensor data, their derivatives, and given elastic constants or visco elastic constants.

Equations (142) is solved by least squares method, where in order to reduce the noises of the measured strain tensor data and strain rate tensor data, the spatially, temporally, or spatio-temporally low pass filtered strain distribution and the strain rate distribution are used (Here, when solving the equations iteratively and further the eigens of the local matrixes multiplied to the respective unknown distributions differs significantly each other, to reduce the iteration number, the suitable constants are multiplied to the respective matrix). However, the inverse of EG amplifies the high frequency noises filled with e. Then, s becomes unstable. Thus, to stabilize s the regularization method is applied. Utilizing the regularization parameters α1 and α2 (≥0), the following equation (143) is minimized with respect to s, where T indicates transpose.

$$\text{error}(s) = |e - EGs|^2 + \alpha 1 |Ds|^2 + \alpha 2 |D^T Ds|^2 \quad (143)$$

D and $D^T D$ are respectively 3D, 2D, or 1D gradient and Laplacian operator of the unknown shear modulus distribution μ, unknown elastic constant distribution λ, unknown elastic constant distribution γ, unknown visco shear modulus distribution μ', unknown visco elastic constant distribution λ', unknown visco elastic constant distribution γ', etc. That is, with respect to each unknown distribution, the regularization method can be applied over the 3D SOI, plural 3D SOIs, 2D ROIs or 1D ROIs in the 3D SOI. As Ds and $D^T D$ are positive definite, error (s) absolutely has one minimum value. By minimizing error (s), the following regularized normal equations are derived.

$$(G^TE^TEG+\alpha 1D^TD+\alpha 2D^TDD^TD)s=G^TE^Te \qquad (144)$$

Therefore, the solution is obtained as $$s=(G^TE^TEG+\alpha 1D^TD+\alpha 2D^TDD^TD)^{-1}G^TE^Te \qquad (145)$$

When the finite element method is utilized, in similar ways, the least squares method and the regularization method are applied to the derived simultaneous equations. In this case, G is comprised of the basis functions of the unknown nodal elastic modulus distributions and unknown nodal visco elastic modulus distributions. Moreover, utilizing the regularization parameter $\alpha 0$ ($\geq 0$), $\alpha 0|s|^2$ or $\alpha 0|Gs|^2$ can be added to the equation (143). Furthermore, instead of $\alpha 1|Ds|^2$ and $\alpha 2|D^TDs|$, the respective $\alpha 1|DGs|$ and $\alpha 2|D^TDGs|$ can also be utilized.

The regularization parameter of important information is set relatively large. Thus, the regularization parameter utilized for each unknown constant distribution depends on the deformation measurement accuracy (SNR), deformation state, configurations of mechanical sources and reference regions, number of the utilized independent deformation fields, etc.; then the position of the unknown constant, direction of the partial derivative, etc.

From the ratio of each elastic constant E with respect to the corresponding visco elastic constant E', i.e., (E'/E), for instance, when measured are the shear modulus, the Poisson's ratio, the Lame constants, etc. and their corresponding visco elastic modulus, estimated can be the time delay distribution $\tau$ [case when visco elastic modulus is determined from (128), (129), (133), (134), (136), or (137)] or relaxation time distribution $\tau'$ [case when visco elastic modulus is determined from (128'''), (128''''), (129'''), (129''''), (133'''), (133''''), (134'''), (134''''), (136'''), (136''''), (137'), or (137''), or case when visco elastic modulus is determined from (125), (126), (127), (130), (131), (132), (135), or (136) where the elastic moduli and strain tensor components are respectively changed by the corresponding visco elastic mouli and the strain rate tensor components]. Moreover, from the strain tensor data and elastic moduli data, the elastic energy distribution can be obtained, while from the strain rate tensor data and visco elastic moduli data, the consumed energy distribution can be obtained.

These elastic constants and visco elastic constants can be temporally changed. Thus, the spatial and temporal simultaneous equations of the above-described equation can be handled, where above-described regularization method can be applied spatially and temporally.

If the time sequence of the elastic modulus distribution or the visco elastic modulus distribution is estimated, by the spectrum analysis, the distribution of the frequency variance of the elastic modulus or the visco elastic modulus can be obtained. Moreover, if the time sequence of the time delay distribution or the relaxation time distribution is estimated, by the spectrum analysis, the distribution of the frequency variance of the time delay or the relaxation time can be obtained. When estimating the distributions of the frequency variances of these elastic modulus, visco elastic modulus, time delay, relaxation time, the deformation fields are measured with changing the frequency of the mechanical source, or with utilizing a broadband mechanical source. Furthermore, at each time, from the strain tensor data and elastic moduli data, the elastic energy distribution can be obtained, while from the strain rate tensor data and visco elastic moduli data, the consumed energy distribution can be obtained.

When solving the equations (143) to (145) derived from equations (125) to (137'') for each unknown elastic modulus distribution or visco elastic modulus distribution by the iterative method such as the conjugate gradient method, as explained below, if necessary the reference regions are newly set in the ROI in addition to the pre-described reference regions, and properly initial values of the estimates are set in the unknown region. In general, each initial value is set based on the a priori information such as homogeneity, inhomogeneity etc. Thus, calculation amount can be reduced.

Regarding with the elasticity distribution, for instance, on the 1D measurement based on the partial differential equation (135) or (136), by analytically solving the equation, the relative shear modulus of the point x=X with respect to the point x=A can be estimated from the ratio of the strains $\epsilon(A)/\epsilon(X)$ (Japanese Patent Application Publication JP-7-55775). This is effective when the tissue dominantly deforms in x direction. (Moreover, regarding with the visco elasticity distribution, for instance, on the 1D measurement based on the partial differential equation (135) or (136), by analytically solving the equation, the relative visco shear modulus of the point x=X with respect to the point x=A can be estimated from the ratio of the strain rates $\epsilon'(A)/\epsilon'(X)$. Below, the shear modulus is dealt with, for instance.)

However, for instance, in the singular points or the singular regions where the strain is numerically zero or the sign of the strain changes, the shear modulus can be stably estimated by using the above-described regularization method and the absolute reference values or relative reference values (i.e., reference values obtained from the strain ratios in addition to the given reference values). Otherwise, in the unknown points or the unknown regions where the absolute strain is less than the positive value A (threshold), in a similar way, the shear modulus can be stably estimated by using the above-described regularization method and the absolute reference values or relative reference values (i.e., reference values obtained from the strain ratios in addition to the given reference values). In these cases, the initial values [of the singular points, singular regions, unknown points or unknown regions] utilized for solving the equations from (143) to (145) can be determined by various interpolation methods (quadrature interpolation, cosine interpolation, Lagrange's interpolation, spline interpolation, etc.) such that the values become spatially continuous with the reference values (i.e., the reference values set by the strain ratios and the given reference values) or the initial values determined from the above-mentioned a priori information. The threshold A depends on the power or the accuracy (SNR) of the strain data at each point, and then the threshold can be spatio-temporally changeable. The threshold can be set small when or where the SNR of the strain is high, while the threshold can be set large when or where the SNR of the strain is low. Otherwise, in the unknown points or the unknown regions where the relative shear modulus values obtained from stain ratios with respect to the reference values are larger than the relative value B (threshold), in a similar way, the shear modulus can be stably estimated by using the above-described regularization method and the absolute reference values or relative reference values (i.e., reference values obtained from the strain ratios in addition to the given reference values). Also in this case, the initial values can be determined with various interpolation methods such that the values are spatially continuous with the reference values (i.e., the reference values set by the strain ratios and the given reference values) or the initial values determined from the above-mentioned a priori information. The threshold B depends on the power or the accuracy (SNR) of the strain data at each point, and then the threshold can be spatio-temporally changeable. The threshold can be set high when or where the SNR of the strain is high, while the threshold can be set low when or where the SNR of the strain is low. The strain distribution data to determine the reference regions can be moving-averaged with the spatio-temporally changeable window. Otherwise, to properly set the reference values (regions) and the initial values, as the reference values and initial values should be spatio-temporally continuous, the initial values can be calculated by various interpolation methods (including linear interpolation) using the reference values (i.e., the reference values set by the strain ratios and the given reference values) or the initial values determined from the above-mentioned a priori information, and freely the reference values and initial values can be spatio-temporally low pass filtered. However, the given reference $\mu(A)$ is unchangeable. Also for other equations, the reference regions should be widely set in similar ways, and the initial values, singular points, singular regions, unknown points or unknown regions can be dealt with in similar ways. The method for setting the reference regions explained here can also be adopted when the direct method is utilized.

When newly setting the reference values (regions) or initial values of each unknown elastic constant or visco elastic constant, for instance, when the reference shear modulus value or the initial value at x=X is calculated, by calculating the strain ratio utilizing the averaged strain $\epsilon_{ave}$ in the finite region in the original reference region, i.e., $\epsilon_{ave}/\epsilon(X)$, the reference value or the initial value can be obtained using the averaged reference shear modulus $\mu_{ave}$ as $\mu(X)/\mu_{ave}$ or $\mu(X)$. When the original reference region is homogeneous, $\mu_{ave}$ is the original shear modulus of the reference region. Otherwise, as the strain of the original reference point x=A, instead of the averaged strain $\epsilon$ave, the moving-averaged strain $\epsilon(A)$, low-pass filtered strain $\epsilon(A)$ or strain $\epsilon(A)$ obtained using the differential filter with a cutoff frequency can be utilized. That is, by calculating the strain ratio $\epsilon(A)/\epsilon(X)$, the reference values or initial values can be obtained as $\mu(X)/\mu(A)$ or $\mu(X)$. As described above, strain can also be spatio-temporal low-pass filtered. In similar ways, the strain rate can be dealt with. Thus, the strain or strain rate whose spatial or temporal resolutions are lowered can be used.

The reference or initial values or the estimates obtained using the reference or initial values can also be used as the initial estimates for solving others equations.

Moreover, as the final estimate, the distributions of the strain ratios or strain rate ratios can also be presented. Moreover, the reference or initial values can also be presented together with the original reference values (low-pass filtered or not).

When solving equations (143) to (145) derived from the equations (125) to (137″) by the iterative method for each unknown elastic modulus distribution and each unknown visco elastic modulus distribution, by properly setting the initial values of the estimates, the calculation amount can be reduced. For instance, when solving equation (135) or (136) for the unknown shear modulus distribution, the initial values can be determined from the above-described strain ratios. In the above-described singular points, singular regions, points or regions where the absolute strain is less than the positive value A (threshold), or the points or regions where the relative shear modulus values obtained from stain ratios with respect to the reference values are larger than the relative value B (threshold), the initial values can be determined by various interpolation methods (quadrature interpolation, cosine interpolation, Lagrange's interpolation, spline interpolation) such that the values are spatially continuous with the reference values and the initial values (i.e., the initial values determined from the a priori information or strain ratios). Otherwise, in the above-described singular points, singular regions, points or regions where the absolute strain is less than the positive value A (threshold) or the points or regions where the relative shear modulus values obtained from the stain ratios with respect to the reference values are larger than the relative value B (threshold), to properly set the initial values, the initial values can be calculated by various interpolation methods (including linear interpolation) using the reference values and the initial values (i.e., the initial values determined from the a priori information or strain ratios), and freely the reference values and the initial values can be spatio-temporally low pass filtered. However, the given reference $\mu(A)$ is unchangeable. These thresholds depend on the power or the accuracy (SNR) of the strain data at each point, and then these thresholds can be spatio-temporally changeable. The thresholds A and B can respectively be set small and high when or where the SNR of the strain is high, while the thresholds A and B can respectively be set large and low when or where the SNR of the strain is low. Regarding with other elastic modulus distributions or other visco elastic modulus distributions, in similar ways, the initial values can be dealt with.

When setting the initial values of each unknown elastic constant or visco elastic constant, for instance, when the initial value at x=X is calculated, by calculating the strain ratio utilizing the averaged strain $\epsilon_{ave}$ in the finite region in the original reference region, i.e., $\epsilon_{ave}/\epsilon(X)$, the initial value can be obtained using the averaged reference shear modulus $\mu_{ave}$ as $\mu(X)/\mu_{ave}$ or $\mu(X)$. When the reference region is homogeneous, $\mu_{ave}$ is the original shear modulus of the reference region. Otherwise, as the strain of the reference point x=A, instead of the averaged strain $\epsilon$ave, the moving-averaged strain $\epsilon(A)$, low-pass filtered strain $\epsilon(A)$ or strain $\epsilon(A)$ obtained using the differential filter with a cutoff frequency can be utilized. That is, by calculating the strain ratio $\epsilon(A)/\epsilon(X)$, the initial values can be obtained as $\mu(X)/\mu(A)$ or $\mu(X)$. As described above, strain can also be spatio-temporal low-pass filtered. In similar ways, the strain rate can be dealt with. Thus, the strain or strain rate whose spatial or temporal resolutions are lowered can be used.

The initial values or the estimates obtained using the initial values can also be used as the initial estimates for solving others equations.

Moreover, as the final estimate, the distributions of the strain ratios or strain rate ratios can also be presented. Moreover, the initial values can also be presented together with the original reference values (low-pass filtered or not).

Regarding with some elastic moduli and visco elastic moduli, as explained above, the reference regions (reference values) and the initial estimates are set and utilized, and simultaneously other elastic moduli and visco elastic moduli can also be dealt with.

These can also be similarly applied when the ROI is 2D or 1D, in which plural 2D or 1D ROIs may be set.

During the iterative estimation, if the elastic modulus, visco elastic modulus, time delay, relaxation time, density are estimated as the values out of the a priori known ranges, they are corrected such that they are satisfied with the a priori data. For instance, the (visco) elastic moduli are positive values. The (visco) Poisson's ratio is less than 0.5. Then, for instance, if the (visco) elastic moduli are estimated as negative values, they are corrected as positive values but nearly equals to zero. If the (visco) Poisson's ratio are estimated to be larger than 0.5, they are corrected to be smaller than 0.5 but nearly equals to 0.5. However, if a plane stress condition is assumed, the (visco) Poisson's ratio can be corrected to be 0.5.

On the 1D or 2D measurement of the elastic constants such as the shear modulus, Poisson's ratio, etc., and the visco elastic constants such as the visco shear modulus, visco Poisson's ratio, etc., they are estimated to be smaller than the original values when the point of interest gets far from the mechanical source. In this case, by utilizing the same shape model having homogeneous elastic modulus and visco elastic modulus and the same mechanical source model, the analytically or numerically estimated strain data and strain rate data can be utilized to correct the measured strain data and strain rate data. Otherwise, on this model the analytically or numerically estimated stress data can be utilized to correct the measured elastic modulus distribution and visco elastic modulus distribution. Otherwise, on this model the elastic modulus and visco elastic modulus are estimated from the analytically or numerically estimated strain data and strain rate data, and the estimates can be utilized to correct the measured elastic modulus distribution and visco elastic modulus distribution.

The temporal absolute change of the elastic constants such as the shear modulus, Poisson's ratio, etc., visco elastic constants such as the visco shear modulus, visco Poisson's ratio, etc., time delay, relaxation time can be obtained as the difference of the estimated absolute values. The temporal relative change of the elastic constants, visco elastic constants, time delay, relaxation time can be obtained as the ratio of the estimated absolute or relative values. Otherwise, regarding with the elastic constants or visco elastic constants, the temporal relative change can be obtained as the difference of the estimated logarithms of them. In this way, for the signal processing of the elastic constants or visco elastic constants, the logarithm can also be utilized.

When iteratively solving the equations (143) to (145), the previously obtained estimate can be used as the initial estimate; reducing the calculation amount. During the iterative estimation, if the elastic modulus, visco elastic modulus, time delay, relaxation time, density are estimated as the values out of the a priori known ranges, they are corrected such that they are satisfied with the a priori data. For instance, the (visco) elastic moduli are positive values. The (visco) Poisson's ratio is less than 0.5. Then, for instance, if the (visco) elastic moduli are estimated as negative values, they are corrected as positive values but nearly equals to zero. If the (visco) Poisson's ratio are estimated to be larger than 0.5, they are corrected to be smaller than 0.5 but nearly equals to 0.5. If a plane stress condition is assumed, the (visco) Poisson's ratio can be corrected to be 0.5.

The above-explained regularization parameter can be set larger when the point of interest gets far from the reference region along dominant tissue deformation direction.

The equations (125) to (137") can also be solved by using the singular value decomposition (SVD) method. In this case, the equations are regularized or nonregularized.

On the equations (125) to (137"), the spectrum of the unknown elastic constants and unknown visco elastic constants can be dealt with, where the regularization method can be applied not only in the above-described spatio-temporal directions but also in the frequency direction.

For instance, in the 1D ROI (x axis), when measurement target are frequency variances (spectrum component distributions and phase distributions) of the sequence of shear modulus distribution μ(x,t) and sequence of visco shear modulus distribution μ'(x,t), the discrete sequence μ(x,j) [j=t/Δt (=0~n)] of μ(x,t) can be expressed as $$\mu(x, j) = \frac{1}{n+1}\sum_{l=0}^{n}[\mu(x, l)\exp(j\theta_\mu(x, l))][\cos(2\pi l\Delta f j\Delta t) + j\sin(2\pi l\Delta f j\Delta t)]$$

where μ(x,l) and θ$_\mu$(x,l) are respectively the spectrum component of the frequency l and the phase of the frequency l. j expresses imaginary unit. l (=0~n) is the discrete frequency coordinate (f=lΔf).

The discrete sequence μ'(x,j) [j=t/Δt (=0~n)] of μ'(x,t) can be expressed as $$\mu'(x, j) =$$

$$\frac{1}{n+1}\sum_{l=0}^{n}[\mu'(x, l)\exp(j\theta_{\mu'}(x, l))][\cos(2\pi l\Delta f j\Delta t) + j\sin(2\pi l\Delta f j\Delta t)]$$

where μ'(x,l) and θ$_{\mu'}$(x,l) are respectively the spectrum component of the frequency l and the phase of the frequency l.

Then, the first order partial differential equation (137) can be expressed as $$\sum_{l=0}^{n}\left[\left(\varepsilon_{xx}(x, j)\frac{\partial}{\partial x}\mu(x, l) + \frac{\partial}{\partial x}\varepsilon_{xx}(x, j)\mu(x, l)\right)\exp(j\theta_\mu(x, l)) + \right. \quad (146)$$

$$\left.\left(\varepsilon'_{xx}(x, j)\frac{\partial}{\partial x}\mu'(x, l) + \frac{\partial}{\partial x}\varepsilon'_{xx}(x, j)\mu'(x, l)\right)\exp(j\theta_{\mu'}(x, l))\right]$$

$$\{\cos(2\pi l\Delta f j\Delta t) + j\sin(2\pi l\Delta f j\Delta t)\} = 0$$

Thus, with respect to each frequency l, the following simultaneous first order partial differential equations hold.

$$\left(\varepsilon_{xx}(x, j)\frac{\partial}{\partial x}\mu(x, l) + \frac{\partial}{\partial x}\varepsilon_{xx}(x, j)\mu(x, l)\right)\cos(\theta_\mu(x, l)) + \quad (146')$$

$$\left(\varepsilon'_{xx}(x, j)\frac{\partial}{\partial x}\mu'(x, l) + \frac{\partial}{\partial x}\varepsilon'_{xx}(x, j)\mu'(x, l)\right)\cos(\theta_{\mu'}(x, l)) = 0$$

$$\left(\varepsilon_{xx}(x, j)\frac{\partial}{\partial x}\mu(x, l) + \frac{\partial}{\partial x}\varepsilon_{xx}(x, j)\mu(x, l)\right)\sin(\theta_\mu(x, l)) + \quad (146'')$$

$$\left(\varepsilon'_{xx}(x, j)\frac{\partial}{\partial x}\mu'(x, l) + \frac{\partial}{\partial x}\varepsilon'_{xx}(x, j)\mu'(x, l)\right)\sin(\theta_{\mu'}(x, l)) = 0$$

Therefore, the simultaneous first order partial differential equations (146') and (146") can be finite difference approximated or finite element approximated in the same way as the case where the equation (137) is dealt with at each time j (=0~n).

By substituting the known nodal distribution of the real components and imaginary components of the spectrum of the frequency l (=0~n) of the elastic constant and visco elastic constant [μ(l,l)cos θ$_\mu$(l,l), μ(l,l)sin θ$_\mu$(l,l), μ'(l,l)cos θ$_{\mu'}$(l,l), μ'(l,l)sin θ$_{\mu'}$(l,l)], at each time j (j=0~n), the simultaneous equations (142) are derived respectively for real components μ(l,l)cos θ$_\mu$(l,l) and μ'(l,l)cos θ$_{\mu'}$(l,l), and imaginary components μ(l,l)sin θ$_\mu$(l,l) and μ'(l,l)sin θ$_{\mu'}$(l,l).

Thus, on the equations (125) to (137"), the simultaneous equations are derived respectively for real components of the spectrum of the elastic constants and visco elastic constants, and imaginary components of the spectrum of the elastic constants and visco elastic constants. When the respective simultaneous equations are regularized, as above-explained, usually, the derived algebraic equations are normalized by the root square of the summation of the powers of the spatially inhomogeneous coefficient distributions multiplied to the unknown distributions.

(A) Two equations derived on each frequency l (=0~n) of each time j (=0~n) of each sequence i (=1~M) are respectively solved for the real component distributions and imaginary component distributions of the frequency l of the spectrum of the unknown parameters, and are solved. Occasionally, the spatial regularization is applied.

(B) Respective two equations derived for the different sequence i (=1~M) or different time j (=0~n) are simultaneously set for the real component distributions and imaginary component distributions of the frequency l of the spectrum of the unknown parameters, and are respectively solved.

(C) Respective two equations derived for the different sequence i (=1~M) or different time j (=0~n) are simultaneously set for the real component distributions and imaginary component distributions of the frequency l of the spectrum of the unknown parameters, and by applying the spatial regularization, the respective simultaneous equations are stably solved.

(D) Respective two equations derived for the different sequence i (=1~M) or different time j (=0~n) are simultaneously set for the real component distributions and imaginary component distributions of the frequency l of the spectrum of the unknown parameters, and by applying the temporal regularization, the respective simultaneous equations are stably solved.

(E) Respective two equations derived for an arbitrary time j (=0~n) of an arbitrary sequence i (=1~M) are simultaneously set for the real component distributions and imaginary component distributions of the spectrum of the unknown parameters, and by applying the frequency regularization, the equations are stably solved. Spatial, and temporal regularization can also simultaneously be applied.

As explained above, by one of (A), (B), (C), (D), (E), the frequency variances of the unknown elastic constants and visco elastic constants can be obtained.

The sequences of the nodal elastic constant distributions and nodal visco elastic constant distributions can be obtained by the inverse Fourier's transform of the spectrums. For instance, the sequence of the nodal shear modulus distribution is $$\mu(I, j) = \frac{1}{n+1} \sum_{j=0}^{n} [\mu(I, l) \exp(j\theta_\mu(I, l))][\cos(2\pi l \Delta f j \Delta t) + j\sin(2\pi l \Delta f j \Delta t)],$$

from which the sequence of the shear modulus distribution $\mu(x,t)$ can be obtained.

For the equations (125) to (137"), when the ROI is 3D, 2D or 1D, the sequences of the nodal elastic constant distributions and nodal visco elastic constant distributions can be similarly obtained by the inverse Fourier's transform of the spectrums.

When the frequency variance is the measurement target, the deformation fields are measured with changing the frequency of the mechanical source, or by utilizing a broadband mechanical source. Here, the variance can also be obtained by the Fourier's transform of the measured sequence of the parameter.

Here, when an instantaneous frequency of the deformation data can be measured, the frequency l can be dealt with as the instantaneous frequency.

The Fourier's transform can be applied not only for the time direction but also the spatial direction.

For the equations (126), (127), (128), (129), (131), (132), (133), (134), (136), (137) and (128'''), (128''''), (129'''), (129''''), (133'''), (133''''), (134'''), (134''''), (137'), (137''), in order to deal with the frequency variances of the sequences of the elastic constants and visco elastic constants, (126), (127), (128), (128''''), (129), (129''''), (131), (132), (133), (133''''), (134), (134''''), (136), (137), (137'') can be approximated utilizing the convolute integration as like (128'''), (129'''), (133'''), (134'''), (137'). For instance, the equation (137) can be approximated as $$\left[\int_{t'}^{t} \mu(t-\tau)\varepsilon'_{11}(\tau)d\tau\right]_{,1} + \left[\int_{t'}^{t} \mu'(t-\tau)\varepsilon''_{11}(\tau)d\tau\right]_{,1} = 0 \quad (137''')$$

where t' is the initial time, $\varepsilon''_{11}(t)$ is the first order derivative of the strain rate $\varepsilon'_{11}(t)$.

As like on (128'''), (129'''), (133'''), (134'''), (137'), the regularization can be performed temporally and spatially.

After the Fourier's transform, the regularization can also be performed in the spatial direction, time direction, in frequency domain. For instance, equation (137'''):

$$[N(I,l)E'_{11}(I,l)]_{,1} + [N'(I,l)E''_{11}(I,l)]_{,1} = 0,$$

where $E'_{11}(I,l)$ is the Fourier's transform of the strain rate $\varepsilon'_{11}(I,j)$, and $E''_{11}(I,l)$ is the Fourier's transform of the first order derivative of the strain rate $\varepsilon''_{11}(I,j)$. From the Fourier's transforms $E_{11}(I,l)$ and $E'_{11}(I,l)$ respective of the strain $\varepsilon(I,j)$ and the strain rate $\varepsilon_{11}(I,j)$, $E'_{11}(I,l)$ and $E''_{11}(I,l)$ can be obtained as $$E'_{11}(x, l) = (j2\pi l \Delta f) E_{11}(x, l) \quad (137'''')$$

$$E''_{11}(x, l) = (j2\pi l \Delta f) E'_{11}(x, l)$$
$$= (j2\pi l \Delta f)^2 E_{11}(x, l).$$

As described above, the regularization can also be applied in the frequency direction.

When dealing with the density ρ, the measured acceleration vector field a is used (after low-pass filtered) Specifically, as described above, in equations (125) to (137'), the inertia term is added to the right terms (Here, the density can not be dealt with when the partial differential equations (126), (131), (136) are directly solved for ln(1/μ), (1/μ), ln(1/μ') or (1/μ')). The density distribution is finite difference approximated or finite element approximated, and is regularized as the elastic constants or visco elastic constants, where the reference density is required when neither reference elastic constants nor reference visco elastic constants are given, whereas the reference density is not required when either or both of the reference elastic constants or visco elastic constants are given. Otherwise, by deleting the inertia term from the equations (occasionally, plural fields can also be used) and by solving the equations for the remaining elastic constants or visco elastic constants, the accelerations can be obtained.

In order to determine the unknown elastic constant distributions, unknown visco elastic constant distributions, unknown density distribution, the equations (125) to (137'') can also be solved utilizing the elastic constant data, visco elastic constant data, density data obtained by solving the equations (125) to (137'') together with other deformation data.

Figure 26:
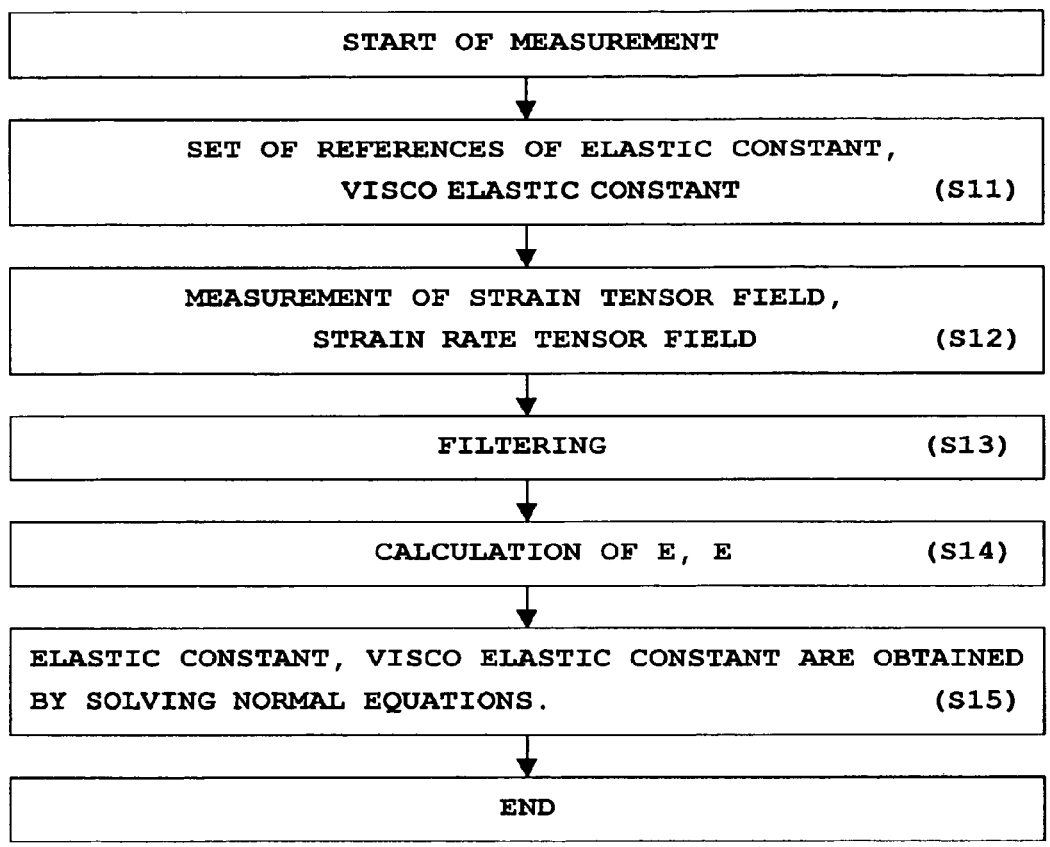
FIG. 26 shows flowchart of measurement procedure of elasticity constants, and visco-elasticity constants utilizing the elasticity and visco-elasticity constants measurement apparatus (FIG. 1)

Next, utilizing the flowchart of FIG. 26, explained is the measurement procedure of the elastic constant distributions such as the shear modulus, Poisson's ratio, etc., the visco elastic constant distributions such as the visco shear modulus, visco Poisson's ratio, etc., the time delay distributions, the relaxation time distributions, and the density distributions. At first, the reference regions are properly set for the unknown elastic constants, the unknown visco elastic constants or the unknown density (S11). Otherwise, as the reference region, reference points are set in the ROI 7. A reference point has at least a known elastic constant, a known visco elastic constant or a known density. Otherwise, the reference point has the a priori set reference unity value, or other finite reference values.

To obtain with a high accuracy the elastic constants, the visco elastic constants and the density, the reference regions should be set such that they should widely cross the direction of the dominant tissue deformation. The reference region has at least a known elastic constant distribution, a known visco elastic constant distribution, a known density distribution, or the a priori assumed distributions. When measuring the absolute elastic constant distributions, the absolute visco elastic constant distributions or the absolute density distribution, the given reference values must be absolute values.

Occasionally, by assuming the stress distribution in the reference region, from measured strain values the reference elastic constant can be obtained. (For instance, by assuming the stress distribution to be constant, from strain ratio the reference elastic constant can be obtained). Moreover, by assuming the stress distribution in the reference region, from strain rate values the reference visco elastic constant can be obtained. (For instance, by assuming the stress distribution to be constant, from strain rate ratio the reference visco elastic constant can be obtained).

When there exist neither reference point nor reference regions, if a reference medium can be directly contacted onto the object, the deformations (strain tensor field, strain rate tensor field, acceleration vector field) are measured over the ROI including the reference (S12). In this case, the shear modulus value of the reference should be larger than that of the target. The reference medium should be put between the mechanical source 8 and the ROI.

As the object is deformed in 3D space, the 3D reconstruction should be carried out. However, when estimating in the superficial tissues the elastic constants, the visco elastic constants or the density, the 1D reconstruction method [from (135) to (137")] is also useful since the accurately measured strain data, strain rate data or acceleration data in the beam direction can be used. In contrast, when estimating in the deeply situated tissues the elastic constants, the visco elastic constants or the density, the multi-dimensional reconstruction method is useful since the freedom of the configurations can be high of mechanical sources and reference regions (mediums).

However, on 2D reconstruction, when a 2D strain distribution approximately occurs, the equations (125) to (129"") can be utilized. Alternatively, when a 2D stress distribution approximately occurs, the equations (130) to (134"") can be utilized. To measure the independent deformation fields (strain tensor fields, strain rate tensor fields, acceleration vector fields), the position of the mechanical source 8 is changed. Since the measurement accuracy of the strains, strain rates, acceleration vectors rely on their magnitudes, to measure the elastic constants, visco elastic constants or density with a uniform accuracy over the ROI, the position of the mechanical source 8 should be variously changed. This measurement accuracy has a trade off with respect to the measurement time and cost. As already described, when the object is spontaneously deformed due to the mechanical sources 8' and 8", the mechanical source 8 may not be required.

The measurement controller 3 controls the positions of the object 6 and displacement (strain) sensor 5, and further inputs the position information and echo signals into the data storage 2. At the data processor 1, the measured strain data, strain rate data or acceleration data is filtered to reduce the measurement noises (S13), by which spatially smoothed coefficients E and e are obtained (S14). Subsequently, the elastic constant distributions, visco elastic constant distributions or density distribution s is obtained from the normal equations (144) (S15). Thus, the measurement results are, at each time, the displacement vector distribution, strain tensor distribution, gradient distribution of the strain tensor, strain tensor rate distribution, gradient distribution of the strain rate tensor, elastic constant distributions such as shear modulus, Poisson's ratio, Lame constants, etc., visco elastic constant distributions such as visco shear modulus, visco Poisson's ratio, visco Lame constants, etc., time delay distributions or relaxation time distributions relating these elastic constants and visco elastic constants, density distribution, gradient distributions of these results, Laplacian distributions of these results, temporal first order derivatives of these results, temporal second order derivatives of these results. To store the time series of these measurement results, these measurement results (output of the data processor 1) are input into the storage 2. To display in real time these measurement results on the display equipment such as a CRT (color or gray), the output of the data processor 1 can be input into the display equipment. Freeze image can also be displayed. When displaying these measurement results, each measurement result can be truncated by respectively set upper value or lower value. When displaying the elastic constant distributions or visco elastic constant distributions, the reciprocal can also be displayed. Moreover, the direct current can be added to the measurement results, or subtracted from the measurement results. When displaying the strain tensor distribution, to make the sign of the strain invariant, the direct current can be added (the brightness should be assigned such that the strain image has correlation with the elastic constant image). When it is a priori known that the compression is generated, the value can be controlled to be negative, whereas that the elongation is generated, the value can be controlled to be positive. By calculating the ratio of such biased strains or strain rates, the (visco) shear modulus or the reciprocal etc. can also be estimated. The results obtained from the biased deformation data can also be used as the initial estimates of the estimation of the (visco) shear modulus or the reciprocal, where the original nonbiased deformation data are used. Furthermore, above-described each measurement result can also be displayed in a log scaled. The measurement results are, in addition to the displacement vector distribution, strain tensor distribution, gradient distribution of the strain tensor, strain tensor rate distribution, gradient distribution of the strain rate tensor, elastic constants such as shear modulus, Poisson's ratio, Lame constants, etc., visco elastic constants such as visco shear modulus, visco Poisson's ratio, visco Lame constants, etc., time delay distributions or relaxation time distributions relating these elastic constants and visco elastic constants, density distribution, gradient distributions of these results, Laplacian distributions of these results, temporal first order derivatives of these results, temporal second order derivatives of these results (at each time) and time series of these results, the time series of relative (ratio) or absolute (subtraction) changes of these results, frequency variance distributions of these results, elastic energy at each time or accumulations, consumed energy at each time or accumulations, time series of elastic energy at each time or accumulations, consumed energy at each time or accumulations, time series of relative (ratio) or absolute (subtraction) changes of these energy. When there exist the points or regions of no strain data, the elastic constants etc. are interpolated or extrapolated from the measured data. These results can also be stored at storage 2, and can be displayed.

These results can be obtained through spatial filtering of the absolute elastic constant distributions, absolute visco elastic constant distributions, absolute time delay distributions, absolute relaxation time distributions, absolute density distributions, or the relative distributions obtained from the normal equations (144). Otherwise, these results can be directly spatially filtered. Otherwise, these results can be obtained through temporal, spatial or temporal-spatial filtering of the elastic constant distributions, visco elastic constant distributions, time delay distributions, relaxation time distributions, density distributions. Otherwise, these results can be directly, temporally, spatially or temporal-spatially filtered. These results can be stored at storage 2, and can be displayed. The spatial filter, temporal filter and temporal-spatial filter are high pass type, band pass type, or low pass type. These filters can be freely utilized at data processor 1.

For these measurement results, the values of the region include the singular points/regions or the regions where the calculations are unstable etc. can be set at the values based on the a priori information. Moreover, the distributions of such regions can also be dealt with by signal processing. Otherwise, the values of the region include the singular points/regions or the regions where the calculations are unstable etc. can also be truncated by their respectively set upper or lower values. Moreover, the distributions of such regions can also be dealt with by signal processing. Otherwise, the values of the region include the singular points/regions or the regions where the calculations are unstable etc. can also be interpolated or extrapolated using the values of the neighborhoods by the various methods (linear interpolation, quadrature interpolation, cosine interpolation, Lagrange's interpolation, spline interpolation, etc). Moreover, the distributions of such regions can also be dealt with by signal processing. The elastic or visco elastic constant distributions obtained by the strain ratios or strain rate ratios can also be similarly dealt with.

Moreover, the reciprocals or the logarithms of the measured values can also be dealt with by the signal processing. Also in these cases, the values can be set at the values based on the a priori information. Moreover, the values (distributions) can also be dealt with by signal processing. Otherwise, the values can also be truncated by their respectively set upper or lower values. Moreover, the values (distributions) can also be dealt with by signal processing. Otherwise, the values can also be interpolated or extrapolated using the values of the neighborhoods by the various methods (linear interpolation, quadrature interpolation, cosine interpolation, Lagrange's interpolation, spline interpolation, etc). Moreover, the values (distributions) can also be dealt with by signal processing. The elastic or visco elastic constant distributions obtained by the strain ratios or strain rate ratios can also be similarly dealt with.

Here, as described above, the strain ratio can also be calculated by utilizing the averaged strain $\epsilon_{ave}$ in the finite region in the reference region, i.e., $\epsilon_{ave}/\epsilon(X)$, as the relative shear modulus with respect to the averaged reference shear modulus $\mu_{ave}$ as $\mu(X)/\mu_{ave}$ or the absolute shear modulus $\mu(X)$. When the reference shear modulus is homogeneous, $\mu_{ave}$ is the original reference shear modulus. Otherwise, the strain ratio can also be calculated by utilizing the moving-averaged or low-pass filtered strain $\epsilon(A)$ (or obtained by using the differential filter with a cutoff frequency), i.e., $\epsilon(A)/\epsilon(X)$, as the relative value $\mu(X)/\mu(A)$ or absolute value $\mu(X)$.

From equations (125) to (137"), the unknown elastic constant distribution, unknown visco elastic constant distribution, unknown density distribution can also be obtained using the measured elastic constant distribution, visco elastic constant distribution, density distribution using another deformation field data, or using their typical value distributions.

By utilizing the ultrasonic diagnosis equipment together, the spatial variations of the bulk modulus and density can be measured together, and can be displayed together. In this case, utilized together are the data processor 1, data storage 2, measurement controller 3, displacement (strain) sensor 5, transmitting/output controller 5' etc (FIG. 1). By utilizing the magnetic nuclear imaging equipment together, the atomic density distribution can also be measured together, and can be displayed together.

As described above (FIG. 1), using the displacement (strain) sensor, the strain tensor field, strain rate tensor field, acceleration vector field can be remotely measured. By solving by the finite difference method or finite element method the first order partial differential equations whose coefficients are derived from the measured data, the followings are estimated, i.e., the absolute elastic constant distributions, relative elastic constant distributions with respect to the reference elastic constants, absolute visco elastic constant distributions, relative visco elastic constant distributions with respect to the reference elastic constants, absolute density distribution, relative density distribution with respect to the reference density.

By using the regularized algebraic equations, the errors (measurement noises) of the measured strain data, strain rate data, acceleration data can be coped with. Moreover, ill-conditioned reference regions (e.g., ill-conditioned short region, ill-conditioned position) can also be coped with.

By the above-described conduct form, when the mechanical sources 8, 8' and 8" exist outside the SOI (ROI), only using the measured data of the strain tensor fields, strain rate tensor fields or acceleration vector fields in the SOI (ROI) [using the ultrasound scattered signals detected by the displacement/strain sensor 5], the distributions of the elastic constants, visco elastic constants or density can be estimated in the SOI (ROI). Particularly, the present invention is effective when the object spontaneously deforms, because the distributions of the elastic constant, visco elastic constants or density can be estimated without disturbing the deformation fields. Otherwise, the present invention is also effective when the SOI (ROI) exists in the deep position in the target because it is difficult to generate deformations artificially.

Elasticity and visco-elasticity constants measurement apparatus, related to this conduct form, is useful to monitor the treatment effectiveness of the radiation therapy since the degeneration and change of temperature have high correlations with the change of elastic constants such as shear modulus, Poisson's ratio, Lame constants, etc., visco elastic constants such as visco shear modulus, visco Poisson's ratio, visco Lame constants, etc., delay times or relaxation times relating these elastic constants and visco elastic constants, and density.

On the conduct form of FIG. 1, as an example, the ultrasound transducer is utilized as the displacement (strain) sensor 5 to measure the strain tensor, strain rate tensor, acceleration vector. In the present invention, however, strain tensor, strain rate tensor, acceleration vector can also be measured by signal processing of the magnetic nuclear resonance signals or electromagnetic wave (transmitted, reflected, scattered waves, including light), and from these measured deformation data, the followings can be measured, i.e., the elastic constants such as shear modulus, Poisson's ratio, Lame constants, etc., visco elastic constants such as visco shear modulus, visco Poisson's ratio, visco Lame constants, etc., delay times or relaxation times relating these elastic constants and visco elastic constants or density.

The next explanation is the treatment apparatus related to one of the conduct forms of the present invention. This treatment apparatus utilizes for the ultrasound therapy the above-explained measurement techniques of displacement vector field/strain tensor field and measurement techniques of elastic constants, visco elastic constants or density.

The aim of the measurement of the followings is to quantitatively examine statically or dynamically the objects, substances, materials, living things, etc., i.e., displacement vector distribution, the strain tensor distribution, the strain rate tensor distribution, the acceleration vector distribution, the velocity vector distribution, elastic constant distributions, visco elastic constant distributions. For instance, on human soft tissues, the tissues can be differentiated by extracorporeally applying pressures or low frequency vibrations, i.e., by focusing on the change of the elasticity due to the growth of the lesion or change of the pathological state. Instead of the pressures and vibrations, the spontaneous hear motion or pulse can also be utilized to measure the tissue deformations, and the tissues can be differentiated using the values and distributions of the tissue elastic constants and visco elastic constants. Blood velocity can also be observed.

Figure 27:
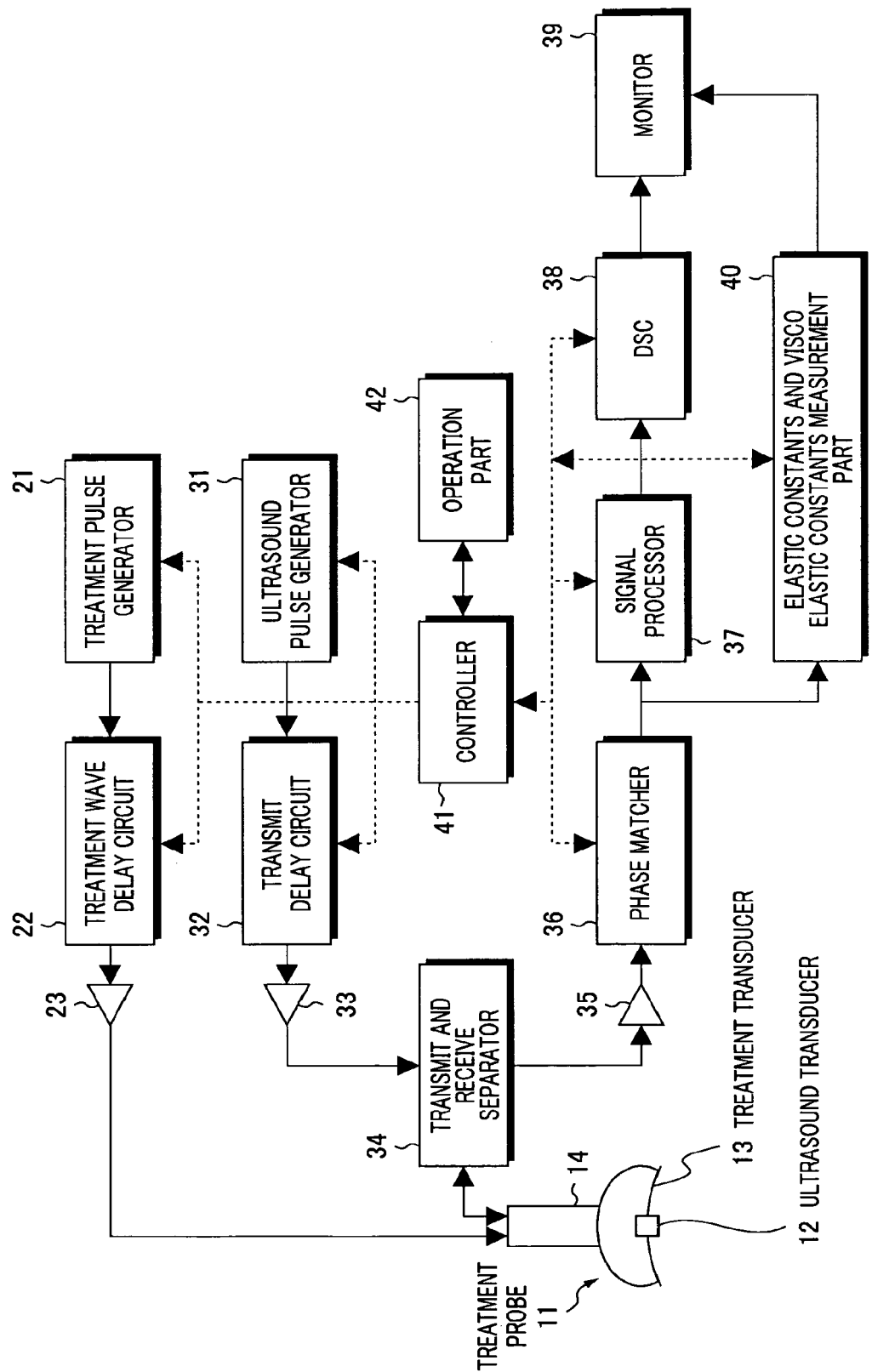
FIG. 27 shows a schematic representation of a global frame of elasticity and visco-elasticity constants measurement apparatus-based treatment apparatus related to one of conduct forms of the present invention.

FIG. 27 shows the global structure of the treatment apparatus related to this conduct form. In the therapy field, lesions can be treated by applying a high intensity ultrasound, a laser, an electromagnetic RF wave, a electromagnetic micro wave, or by a cryotherapy. By these low invasive treatments, degeneration occurs, a composition rate in weight changes, and a temperature changes. For instance, in living tissues, the protein degenerates, and the tissue coagulates. The degeneration, change of composition rate, and change of temperature occur together with the changes of the elastic constants such as shear modulus, Poisson's ratio, etc., visco elastic constants such as visco shear modulus, visco Poisson's ratio, etc., delay times or relaxation times relating these elastic constants and visco elastic constants or density.

Thus, by measuring the lesion's absolute or relative shear modulus, absolute or relative Poisson's ratio, absolute or relative visco shear modulus, absolute or relative visco Poisson's ratio, absolute or relative delay times or absolute or relative relaxation times, or absolute or relative density, etc., and by observing these time courses or these frequency variances, the effectiveness of the treatments can be low invasively monitored. Based on the conversion data for each tissue obtained from theories, simulations, and measurements, the changes of the measured shear modulus, Poisson's ratio, visco shear modulus, visco Poisson's ratio, delay time, relaxation time, density, strain, strain rate, electric impedance, thermal properties can be converted into the consumed electric energy, time course of electric energy, temperature, or time course of temperature. From the measured consumed electric energy, time course of electric energy, temperature or time course of the temperature, the effectiveness of the treatment can be confirmed.

The consumed electric energy and time course of the consumed electric energy can also be measured by using an electric power meter and tissue physical parameters (tissue electric impedance, mechanical impedance, etc). The temperature or the time course of the temperature can also be measured by using a usual temperature monitoring method, thermocoupler, etc. By measuring these spatial distributions, not only the effectiveness of treatment can be monitored, but also the safety and reliability can be obtained. These monitoring data can be utilized for the dynamic electronic digital control or mechanical control of the beam focus position, treatment term, treatment interval, ultrasound beam power, ultrasound beam strength, transmit term, transmit interval, beam shape (apodization), etc. Thus, these monitoring data can also be utilized to improve the efficiency of the treatment.

FIG. 27 shows the treatment apparatus that transmits high intensity ultrasounds to the lesion. The treatment apparatus can be equipped with an ultrasound diagnosis equipment and an elasticity and visco-elasticity constants measurement apparatus. As shown in FIG. 27, the treatment probe 11 possesses the ultrasound transducer 12 and treatment transducer 13 (The ultrasound and treatment transducer can also serve as the treatment and ultrasound transducer, respectively), the supporter 14 of the probe. As utilized in the ultrasonic diagnosis equipment, for instance, a convex type transducer, the ultrasound transducer 12 arrays plural oscillators. The treatment transducer 13 also arrays plural oscillators. In the figure, a concavity type treatment probe 11 is shown. The supporter 14 can be held by a hand or the position controller 4, by which the position of the treatment probe 11 can be controlled.

To the treatment transducer 13, the electric pulse generated by the treatment pulse generator 21 is provided through the treatment wave delay circuit 22 and amplifier 23. That is, at the treatment wave delay circuit 22 the delay time of the transmit ultrasound pulse is controlled for each oscillator, by which the focus position of the synthesized ultrasound beam is controllable.

Moreover, to the oscillators of the ultrasound transducer 12, the electric pulse generated by the ultrasound pulse generator 31 is provided through the transmit and receive separator 34 after being focused by the transmit delay circuit and amplified by the amplifier 33. The echo signals received by the oscillators of the ultrasound transducer 12 are amplified by the amplifier 35 after passing through the transmit and receive separator, and the phases of the echo signals are matched at the phase matcher 36. The outputs of the phase matcher 36 are used to reconstruct image by the signal processor 37, and the image data is converted to the diagnosis image by the DSC (digital scan converter) 38, and the diagnosis image is displayed by the monitor 39. A conventional ultrasound diagnosis equipment can be used for this diagnosis equipment.

The elastic constants and visco elastic constants measurement part 40 related to this conduct form can measure the shear modulus, Poisson's ratio, visco shear modulus, visco Poisson's ratio, delay times or relaxation times relating these elastic constants and visco elastic constants, density, etc., using the echo signals output from the phase matcher 36. The measured data and calculated results are stored at the data storage equipped with 40, ultrasound diagnosis equipment or displacement/strain measurement equipment.

Commands from the controller 41 control the treatment pulse generator 21, treatment wave delay circuit 22, ultrasound pulse generator 31, transmit delay circuit 32, phase matcher 36, signal processor 37, DSC 38, and elastic constants and visco elastic constants measurement part 40. The operator can input the commands and conditions from the operation part 42 into the controller 41, by which the operator can set various operation conditions and treatment conditions. The signal processor 37, elastic constants and visco elastic constants measurement part 40, operation part 42, controller 41 are comprised of computers.

Next explanation is how this like ultrasound treatment equipment is utilized. The treatment probe 11 is contacted onto body surface, and is supported such that the ROI include the target lesion. Occasionally, by using water tank, the treatment probe 11 is supported without contacting onto the body surface. At first, to image the lesion part, the command to start the imaging is input from the operation part 42, by which as the response the controller 41 outputs the commands into the ultrasound pulse generator 31 and transmit delay circuit 32. Then, the ultrasound beam is transmitted from the ultrasound transducer 12 into the body. This ultrasound beam scans the ROI. The echo signals are received by the oscillators of the ultrasound transducer, the phases of the received echo signals are matched by the phase matcher 36. The outputs of the phase matcher 36 are used to reconstruct the image by the signal processor 37 and DSC (digital scan converter) 38, i.e., a 2D diagnosis image is generated, and the diagnosis image is displayed by the monitor 39. Thus, during observing the images and diagnosing the tissues, when the lesion part can be detected, the treatment can be carried out.

When the treatment transducer 13 and ultrasound transducer 12 are utilized together or realized as one transducer (i.e., The ultrasound and treatment transducer can also serve as the treatment and ultrasound transducer, respectively), the treatment pulse generator 21 can also be used as the ultrasound pulse generator 31, the treatment wave delay circuit 22 can also be used as the transmit delay circuit 32, the amplifier 23 can also be used as the amplifier 33. The output of the amplifier 23 or 33 can be sent to the treatment transducer 13 and the ultrasound transducer 12 through the transmit and receive separator 34. In this case, when transmitting the treatment beam, the followings to the transmit and receive separator 34 can also be used. That is, by the phase matcher 36 or signal processor 37, the phase aberrations of the received echo signals by the neighboring elements are calculated using the above-described displacement vector measurement method, and by controlling the treatment wave delay circuit 22 and transmit delay circuit 32, not only the correction of the phase aberrations of the received echo signals but also the improvement of the accuracy of the focus point of the treatment is performed.

That is, when the lesion is detected, the treatment probe 11 is held at the present position. From the image memorized by the DSC 38, the controller 41 obtains the delay time to provide the drive pulse to each oscillator of the treatment transducer 13. Then, the controller outputs the obtained time delays into the treatment wave delay circuit 22, by which the lesion part is focused. The strength of the ultrasound beam can be controlled. The lesion part is heated. The lesion part degenerates. The treatment can also be carried out by observing 3D ultrasound image using a 3D ultrasound equipment. Controlled of the treatment ultrasound beam can be the beam focus position, treatment term, treatment interval, ultrasound beam power, ultrasound beam strength, transmit term, transmit interval, beam shape (apodization), etc.

Here, the region to be treated can be controlled by the diffusion length of the generated thermal waves, i.e., by using the target thermal diffusivity $\kappa$ and the frequency f (of the thermal source/sink or the generated thermal wave) as $\sqrt{\kappa/(\pi f)}$ in a homogeneous case, whereas in the inhomogeneous case the length is estimated using the thermal conductivity, thermal capacity and frequency. Thus, the frequency f is suitably set by modulating the strength, treatment term, treatment interval, transmit term, transmit interval, etc. of the continuous or repetitive pulse HIFU waves. However, for reconstructions of the thermal properties [US patent by this inventor], almost nonmodulated continuous or pulse HIFU waves (i.e., static heat source) are used to obtain a region of reconstruction, although generally the reconstruction accuracies of the thermal properties are considered to be improved using a high-frequency thermal wave. Alternatively, after stopping modulated or nonmodulated heating, the reconstruction is performed.

Figure 28:
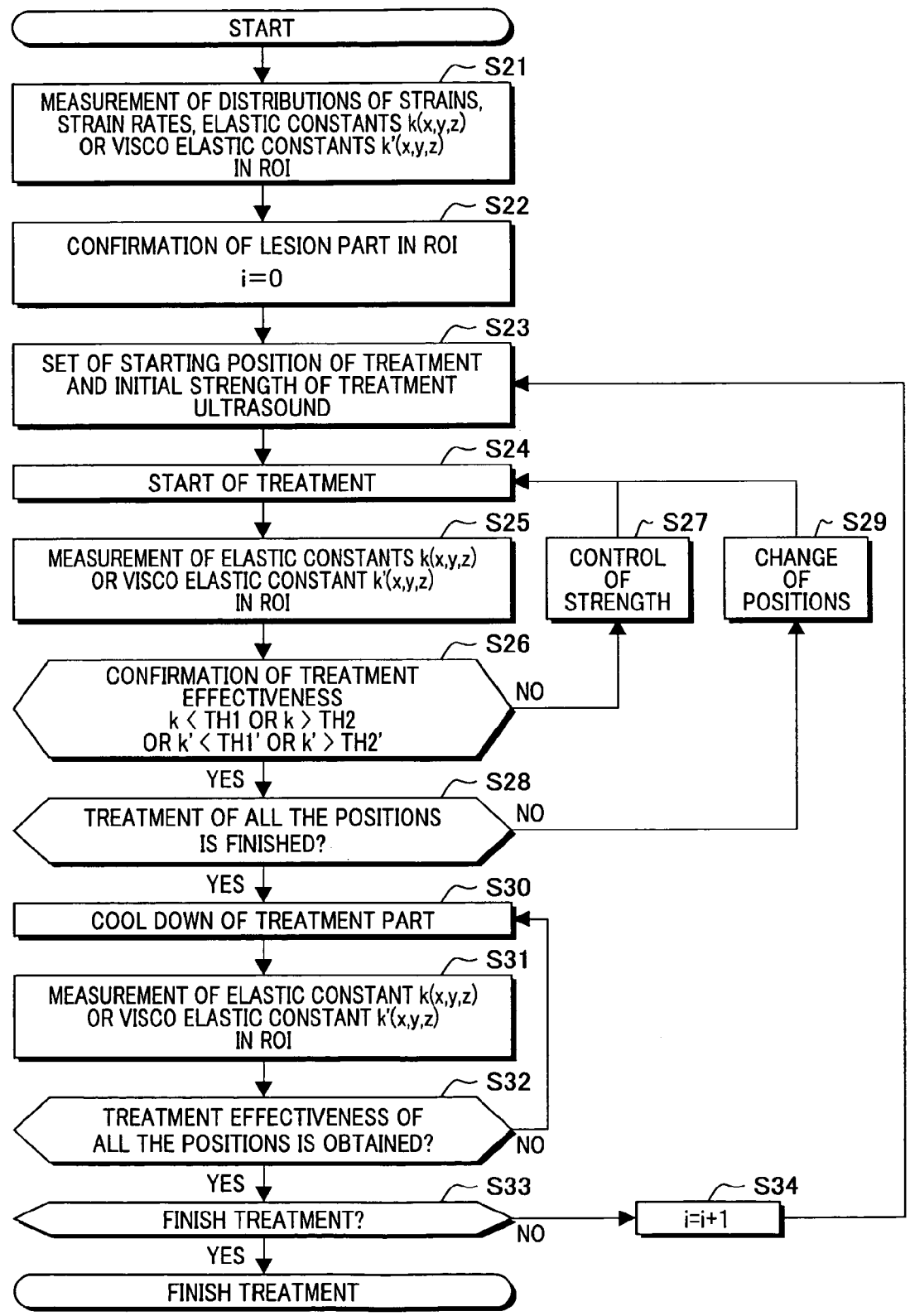
FIG. 28 shows flowchart of control procedure of the elasticity and visco-elasticity constants measurement apparatus-based treatment apparatus (FIG. 27).

Next explanation is the procedure of the treatment and measurement of the shear modulus, Poisson's ratio, visco shear modulus, visco Poisson's ratio, time delay, relaxation time density, etc. for monitoring the treatment effectiveness. Flowchart of FIG. 28 is referred to. At first, before the treatment, measured in the ROI are the shear modulus distribution $\mu(x,y,z)$, Poisson's ratio $\nu(x,y,z)$, visco shear modulus $\mu'(x,y,z)$, visco Poisson's ratio $\nu'(x,y,z)$, delay time $\tau(x,y,z)$, relaxation time $\tau'(x,y,z)$, density $\rho(x,y,z)$ (S21). The commands are sent from the operator part 42 to the controller 41, after which the ultrasounds are transmitted from the ultrasound transducer 12. Subsequently, the controller 41 sends commands to the elastic constants and visco elastic constants measurement part 40, by which using the echo signals output from the phase matcher 36 the strain tensor field, strain rate tensor field, etc. are measured. From the measured strain tensor field, strain rate tensor field, etc., calculated are the shear modulus distribution $\mu(x,y,z)$, Poisson's ratio $\nu(x,y,z)$, visco shear modulus $\mu'(x,y,z)$, visco Poisson's ratio $\nu'(x,y,z)$, delay time $\tau(x,y,z)$, relaxation time $\tau'(x,y,z)$, density $\rho(x,y,z)$, etc.

Next, if the lesion part is confirmed, the treatment process counter I is initialized (I=0) (S22). The starting position of the treatment and the initial strength of the treatment ultrasound are set (S23), and the treatment is started (S24). At every treatment, measured are the shear modulus distribution $\mu(x,y,z)$, Poisson's ratio distribution $\nu(x,y,z)$, visco shear modulus distribution $\mu'(x,y,z)$, visco Poisson's ratio distribution $\nu'(x,y,z)$, delay time distribution $\tau(x,y,z)$, relaxation time distribution $\tau'(x,y,z)$, density distribution $\rho(x,y,z)$, etc. (S25). The measured elastic constants, visco elastic constants, delay times, relaxation times can be absolute values, spatially relative values, temporally relative values, etc. Then, to confirm the effectiveness of the treatment, the comparison can be carried out between the shear modulus value $\mu(x,y,z)$, Poisson's ratio value $\nu(x,y,z)$, visco shear modulus value $\mu'(x,y,z)$, visco Poisson's ratio value $\nu'(x,y,z)$, etc., and their respective thresholds TH1 (softened case) and TH2 (hardened case), etc. (S26). Moreover, the comparison can be carried out between the delay time value $\tau(x,y,z)$, relaxation time value $\tau'(x,y,z)$, density value $\rho(x,y,z)$ and their respective thresholds. The thresholds TH1, TH2, etc., can be set from the information of the tissue properties etc. The thresholds TH1, TH2, etc. are the functions of the time t, the position (x,y,z), the ultrasound parameters such as shooting counter etc., the degeneration information about tissues, etc. The thresholds can be set before the treatment, or can be updated during the treatment. If desired effectiveness cannot be confirmed, the ultrasound strength is controlled to be higher (S27), after which the treatment is carried out again (S24). If the desired effectiveness can be confirmed, it is judged if the treatments of all the positions are finished (S28). If the treatments of all the positions are not finished yet, the treatment position is changed (S29), and the treatment is carried out again (S24).

If the treatments of all the positions are finished, the treated part can be naturally or compulsively cooled down (S30). After the treatment, measured are the shear modulus distribution $\mu(x,y,z)$, Poisson's ratio distribution $\nu(x,y,z)$, visco shear modulus distribution $\mu'(x,y,z)$, visco Poisson's ratio distribution $\nu'(x,y,z)$, delay time distribution $\tau(x,y,z)$, relaxation time distribution $\tau'(x,y,z)$, density distribution $\rho(x,y,z)$, etc. (S31). It is judged if desired effectiveness can be obtained at all the positions (S32). If the desired effectiveness can not be confirmed at all the positions, till the effectiveness can be confirmed, the treated part is cooled down (S30 to S32). If the desired effectiveness is confirmed at all the positions, it is judged if this treatment process is finished (S33). When the treatment process is not finished, the treatment process counter I is incremented, and steps from S23 to S33 are iteratively carried out. The maximum number of the treatment process can be set. The treatment position can be set in order from the deep position or central position of the lesion, or the treatment position can also be set where the treatment effectiveness is not confirmed yet.

As described above, using the treatment apparatus of FIG. 27, during the ultrasound treatment, we can observe the treatment effectiveness in real time and then we can properly carry out the treatment. Moreover, by confirming the treatment effectiveness in real time, the ultrasound strength, the shoot number, etc. can be controlled.

The treatment apparatus of FIG. 27 can also be used for other treatments such as a laser treatment, an electromagnetic RF wave treatment, an electromagnetic micro wave treatment, or a cryotherapy etc. In this case, the low invasive treatment modalities are substituted for the treatment probe 11, treatment pulse generator 21, treatment wave delay circuit 22, amplifier 23.

As the ultrasound transducer 12, for instance, utilized can be a 2D or 1D array type (linear, convex, etc.), a 2D array aperture type applicator, a 1D array aperture type applicator, a concavity type applicator. For instance, when carrying out the cryotherapy or radio therapeutics (applying high intensity focus ultrasound, laser, electromagnetic RF wave, micro wave, etc.) on the living things or the in vitro tissues through skin, mouth, vagina, anus, opened body, body surface, monitored can be the degeneration, change of composition rate in weight, and change of temperature. The measured shear modulus, Poisson's ratio, visco shear modulus, visco Poisson's ratio delay time, relaxation time, density, electric impedance, thermal properties, etc., can be utilized as indexes to dynamically control the beam position (focus), treatment term, treatment interval, beam power, beam strength, transmit term, transmit interval, beam shape (apodization), etc.

Before, during, after the treatment, the followings can be displayed by the monitor 39 as the static, motion or time course (difference) image, the values of arbitrary points, the time course (graph), etc., i.e., not only the elastic constant or visco elastic constant distributions and electric or thermal property distributions but also the displacement vector distribution, displacement vector component distributions, strain tensor component distributions, strain gradient component distributions, strain rate tensor component distributions, strain rate gradient component, acceleration vector component distributions, or velocity vector component distributions, etc.

Moreover, by utilizing ultrasound diagnosis apparatus together, the spatial variations of bulk modulus and density of tissues can be measured and displayed in real-time. On the ultrasound image, as the measurement results, superimposed and displayed can be the static, motion or time course (difference) image of the measured elastic constant distribution, visco elastic constant distribution, density distribution, displacement vector distribution, displacement vector component distributions, strain tensor component distributions, strain gradient component distributions, strain rate tensor component distributions, strain rate gradient component, acceleration vector component distributions, velocity vector component distributions, etc. The vector can also be displayed using the vector line.

Particularly, when the applicator has an arrayed aperture, the beam focus position, treatment term, treatment interval, beam power, beam strength, transmit term, transmit interval, beam shape (apodization), etc. are electronically digital controlled, while when the applicator has a concavity aperture, the focus position is mechanically controlled. The flowchart of FIG. 28 can be applied as the control program, for instance. That is, to dynamically control the beam focus position, treatment term, treatment interval, beam power, beam strength, transmit term, transmit interval, beam shape (apodization), etc, utilized can be the absolute or relative shear modulus distribution, absolute or relative Poisson's ratio distribution, absolute or relative visco shear modulus distribution, absolute or relative visco Poisson's ratio distribution, absolute or relative delay time distributions, absolute or relative relaxation time distributions, absolute or relative density distribution, absolute or relative electric property distributions, absolute or relative thermal property distributions, temporally absolute or relative changes of these, etc. measured before, during, after transmitting the energies.

The above-explained measurement techniques of displacement vector field, strain tensor field, etc., and measurement techniques of elastic constants, visco elastic constants, density, etc., can be utilized together with the interstitial needle, catheter, etc. when carrying out a cryotherapy or radio therapeutics (applying a high intensity focus ultrasound, a laser, an electromagnetic RF wave, a micro wave, etc.) or when nondestructive examining living things or substances or materials (cases including during producing or growing of the target).

For instance, on the interstitial cryotherapy, interstitial radio therapeutics (applying high intensity focus ultrasound, laser, electromagnetic RF wave, micro wave, etc. utilizing needles and a plate, only needles, mono needle, etc.), etc., the followings can also be displayed by the monitor before, during, after the treatment as the static, motion or time course (difference image) image, the values of arbitrary points, the time course (graph), etc., i.e., not only the elastic or visco elastic constant distributions and electric or thermal property distributions but also the displacement vector distribution, displacement vector component distributions, strain tensor component distributions, strain gradient component distributions, strain rate tensor component distributions, strain rate gradient component, acceleration vector component distributions, or velocity vector component distributions, etc. Moreover, by utilizing the ultrasound diagnosis apparatus together, the spatial variations of bulk modulus and density of tissues can also be measured and displayed in real-time. On the ultrasound image, as the measurement results, superimposed and displayed can also be the static, motion or time course (difference) image of the elastic constant distribution, visco elastic constant, density distribution, electric property distribution, thermal property distribution, displacement vector distribution, displacement vector component distributions, strain tensor component distributions, strain gradient component distributions, strain rate tensor component distributions, strain rate gradient component, acceleration vector component distributions, velocity vector component distributions, etc. The followings can be displayed in vector style as well, i.e., the displacement vector distribution, acceleration vector, velocity vector.

To obtain the safety when carrying out the treatment, by setting the upper values and lower values of shear modulus, Poisson's ratio, visco shear modulus, visco Poisson's ratio, delay times, relaxation times, density, electric impedance, thermal properties, etc., and by setting the upper values of absolute or relative changes of these, the beam position (focus), treatment term, treatment interval, beam power, beam strength, transmit term, transmit interval, beam shape (apodization), etc. should be controlled such that these physical parameter values do not change more than necessary.

As explained above, the treatment effectiveness can also be evaluated by measuring the temperature and temporal change of the temperature using the strain (tensor) distribution, strain rate (tensor) distribution, shear modulus distribution, Poisson's ratio distribution, visco shear modulus distribution, visco Poisson's ratio distribution, density distribution, electric or thermal property distributions, temporal changes of these, etc. measured before, during, after transmitting the energies. In this case, to obtain the safety, by setting the upper values of the temperature or change of the temperature, the beam position (focus), treatment term, treatment interval, beam power, beam strength, transmit term, transmit interval, beam shape (apodization), etc. should be controlled such that the temperature does not change more than necessary. These can also be controlled utilizing the shear modulus value $\mu$, Poisson's ratio value $\nu$, visco shear modulus value, visco Poisson's ratio value, density value, delay time values, relaxation time values, strain values, strain rate values, electric or thermal property values, etc., which can be converted values from the upper values. The temperature and change of the temperature can also be measured utilizing the conventional temperature measurement method or thermocoupler.

In the cases where no mechanical source exists or mechanical sources are not utilized, the degeneration, change of composition rate in weight and change of the temperature can also be detected from the strain (tensor) distribution, strain rate (tensor) distribution, shear modulus distribution, Poisson's ratio distribution, visco shear modulus distribution, visco Poisson's ratio distribution, density distribution, electric or thermal property distribution, temporal changes of these, etc. measured before, during, after transmitting the energies. Directly the expansion and shrink of the tissues can also be detected by measuring the strain (tensor) distribution or strain rate (tensor) distribution.

The elasticity and visco-elasticity constants measurement apparatus of the present invention can be utilized to monitor the degeneration, change of composition rate in weight, change of temperature due to the injection of medicine, putting of medicine, giving of medicine. To control the amount of the medicine, term, interval, position, etc., utilized can be the absolute or relative shear modulus distribution, absolute or relative Poisson's ratio distribution, absolute or relative visco shear modulus distribution, absolute or relative visco Poisson's ratio distribution, absolute or relative electric property distributions, absolute or relative thermal property distributions, absolute or relative delay time distributions, absolute or relative relaxation time distributions, absolute or relative density distribution, temporally absolute or relative changes of these, etc. measured before, during, after the treatment. For instance, anticancer drug can be utilized as the medicine.

That is, to monitor the treatment effectiveness (including the change of temperature) of the anticancer drug and to control the treatment, the followings can also be displayed by the monitor before, during, after the treatment as the static, motion or time course (difference) image, the values of arbitrary points, the time course (graph), etc., i.e., not only the elastic or visco elastic constant distributions and electric or thermal property distributions but also the displacement vector distribution, displacement vector component distributions, strain tensor component distributions, strain gradient component distributions, strain rate tensor component distributions, strain rate gradient component, acceleration vector component distributions, or velocity vector component distributions, etc. Moreover, by utilizing the ultrasound diagnosis apparatus together, the spatial variations of bulk modulus and density of the tissues can also be measured and displayed in real-time. On the ultrasound image, as the measurement results, superimposed and displayed can also be the static, motion or time course (difference) image of the elastic or visco elastic constant distributions, electric or thermal property distribution, displacement vector distribution, displacement vector component distributions, strain tensor component distributions, strain gradient component distributions, strain rate tensor component distributions, strain rate gradient component, acceleration vector component distributions, velocity vector component distributions, etc. The followings can be displayed in vector style as well, i.e., the displacement vector distribution, acceleration vector, velocity vector. In cases where no mechanical source exists or mechanical sources are not utilized, the degeneration, expansion or shrink, and change of temperature, etc. can also be detected from the measured displacement vector, strain (tensor) distribution, strain rate (tensor) distribution, etc.

The elastic constants, visco elastic constants, density, high order data expressed from the elastic constants, visco elastic constants, density are utilized to obtain the non-linear properties of tissues by the linear approximation of non-linear phenomena in an infinitesimal time space or spatial space. Thus, the estimated non-linear elastic constants data, non-linear visco elastic constants data, high order data expressed from the non-linear data can also be utilized for the diagnosis and treatment.

As explained above, as the measurement techniques or methods of temperature, there exist the techniques or methods that utilize the measurements of elastic or visco elastic constant, electric impedance, thermal properties in addition to the conventional ultrasound (detection of the change of the ultrasound speed or volume) or magnetic resonance (chemical shift) techniques or methods. To enhance the safety, reliability and efficiency of the above low-invasive treatments, the reconstructed thermal properties [US patent invented by this inventor] can be used to predict the temperature distribution together with the measurements or knowledges about the conversions of the various thermal energies to the temperature. On the basis of the prediction, controlled of the treatment ultrasound beam can be the beam focus position, treatment term, treatment interval, ultrasound beam power, ultrasound beam strength, transmit term, transmit interval, beam shape (apodization), etc. Otherwise, the power etc. of the above-described other thermal energies can be controlled. As described above, the elastic or visco elastic constant reconstructions can also be used for the controlling the treatments.

Here, the region to be treated can be controlled by the diffusion length of the generated thermal waves, i.e., by using the target thermal diffusivity $\kappa$ and the frequency f (of the thermal source/sink or the generated thermal wave) expressed as $\sqrt{\kappa/(\pi f)}$ in a homogeneous case, whereas in the inhomogeneous case the length is estimated using the thermal conductivity, thermal capacity and frequency. Thus, the frequency f is suitably set by modulating the strength, treatment term, treatment interval, transmit term, transmit interval, etc. of the continuous or repetitive pulse HIFU waves. Otherwise, those of other thermal source/sinks are modulated. However, for reconstructions of the thermal properties [US patent by this inventor], almost nonmodulated continuous or pulse waves (i.e., static heat source) are used to obtain a region of reconstruction, although generally the reconstruction accuracies of the thermal properties are considered to be improved using a high-frequency thermal wave. Alternatively, after stopping modulated or nonmodulated heating, the reconstruction is performed. Thus, minimum-invasive treatment is realized.

Occasionally, the data (e.g., the distributions, time sequences, etc.) of the mechanical sources such as a heat, blood vessel are given in the ROI or outside the ROI. Also in this case, by adding the source term to the differential equations, the distributions or time sequences etc. of the mechanical properties, stresses, pressures can be estimated. A high intensity (focus) vibration can also be used as a mechanical source, e.g., the treatment ultrasound, etc.

Otherwise, the distributions or time sequences etc. of such mechanical sources (heat, blood vessel, vibration, compression, etc.) can also be estimated together with the distributions or time sequences etc. of the mechanical properties, stresses, pressures. Moreover, by using the measured deformation data or other measured deformation data together with the reconstructed mechanical properties, the distributions or time sequences of the mechanical sources, stresses or pressures can also be measured. Of course, the elastic body and fluid are dealt with together. Thus, accurately, the internal pressure of the heat or blood pressure can be measured. These measured distributions of the mechanical sources, stresses, pressures can be displayed by CRT etc. similarly with other mechanical properties and mechanical quantities. The viscosities etc. of the fluid can also be displayed.

When there exist a priori known homogeneous region or a region assumed to be homogeneous in the SOI (ROI), the derivatives in the equations can be ignored.

Thus, as explained above, the present invention can realize the accurate measurement in 3D space of interest (SOI) or 2D region of interest (ROI) or 1D ROI of the displacement vector distribution, strain tensor distribution, the spatio or temporal derivatives of these, generated due to arbitrary mechanical sources. If the target naturally deforms, the elastic constant or visco elastic constant can be estimated in the SOI or ROI from the measured deformation data without disturbing the deformation field. Moreover, even if there exist another mechanical sources and uncontrollable mechanical sources in the object, for instance, the elastic constant and visco elastic constant measurement apparatus can be utilized, which is applicable for diagnosing the part of interest in the object and for monitoring the treatment effectiveness. Furthermore, such low-invasive treatment apparatuses can be realized, which are equipped with the elastic constant and visco elastic constant measurement apparatuses.

The invention claimed is:

1. A clinical apparatus comprising:
   at least one sensor which is configured to sense one selected from a group consisting of an ultrasound signal, a magnetic nuclear resonance signal, an electromagnetic wave, and light;
   a storage which is configured to store at least one of strain tensor component data, strain rate tensor component data, and acceleration vector component data measured in a ROI (region of interest) set in a target by using said at least one sensor; and
   a data processor which is configured to calculate at least one of a stress and a pressure of at least one arbitrary point within the ROI by utilizing first reference data representing at least one reference value about at least one of the stress and the pressure and at least one reference position that has said at least one reference value, the pressure being a mean of normal stress tensor components, and each of the stress and the pressure being expressed using at least one product of at least one elastic constant and a volume strain, at least one product of at least one visco elastic constant and a volume strain rate, or at least one product of at least one viscosity and a volume strain rate;
   wherein said data processor is configured to linearly and directly calculate said at least one of the stress and the pressure while setting to unknown a Poisson's ratio or at least one of said at least one elastic constant, said at least one visco elastic constant, and said at least one viscosity, which expresses said at least one of the stress and the pressure, based on at least said first reference data and at least one equation representing a relation between (i) said at least one of the stress and the pressure, (ii) at least one of other stresses that is at least one stress tensor component expressed using at least one product of said at least one elastic constant or other elastic constants and the measured strain tensor component data, at least one product of said at least one visco elastic constant or other visco elastic constants and the measured strain rate tensor component data, or at least one product of said at least one viscosity or other viscosities and the measured strain rate tensor component data, (iii) when the arbitrary point within the ROI has a non-zero acceleration vector, at least one inertia vector component expressed using a product of a density and the measured acceleration vector component data, and (iv) when the arbitrary point within the ROI has a mechanical source, the mechanical source.

2. The clinical apparatus according to claim 1, wherein said data processor is configured to simultaneously calculate said at least one elastic constant or said other elastic constants, said at least one visco elastic constant or said other visco elastic constants, said at least one viscosity or said other viscosities, said density, said at least one stress tensor component, said at least one inertia vector component, or said mechanical source in addition to said at least one of the stress and the pressure of said at least one arbitrary point within the ROI.

3. The clinical apparatus according to claim 2, wherein said at least one reference value is measured in advance or set in advance.

4. The clinical apparatus according to claim 2, wherein said at least one reference value is set in advance and has a unity or one of arbitrary finite values.

5. The clinical apparatus according to claim 2, wherein said data processor is configured to utilize the stress, the pressure, said at least one elastic constant or said other elastic constants, said at least one visco elastic constant or said other visco elastic constants, said at least one viscosity or said other viscosities, said density, said at least one stress tensor component, said at least one inertia vector component, or said mechanical source, which is measured over said ROI or partially in advance or set in advance, as a coefficient of said at least one equation.

6. The clinical apparatus according to claim 2, wherein said at least one equation is solved by using an iterative method together with at least an initial estimate about the stress, the pressure, said at least one elastic constant or said other elastic constants, said at least one visco elastic constant or said other visco elastic constants, said at least one viscosity or said other viscosities, said density, said at least one stress tensor component, said at least one inertia vector component, or said mechanical source, which is obtained by measuring over said ROI or partially in advance or setting in advance.

7. The clinical apparatus according to claim 2, wherein said data processor is configured to calculate the stress, the pressure, said at least one elastic constant or said other elastic constants, said at least one visco elastic constant or said other visco elastic constants, said at least one viscosity or said other viscosities, said density, said at least one stress tensor component, said at least one inertia vector component, or said mechanical source by using simultaneous equations, inertia vector component terms of which are deleted, and using at least one of the measured strain tensor component data, the measured strain rate tensor component data, and the measured acceleration vector component data.

8. The clinical apparatus according to claim 2, wherein said data processor is configured to calculate the stress, the pressure, said at least one elastic constant or said other elastic constants, said at least one visco elastic constant or said other visco elastic constants, said at least one viscosity or said other viscosities, said density, said at least one stress tensor component, said at least one inertia vector component, or said mechanical source, by using the stress, the pressure, said at least one elastic constant or said other elastic constants, said at least one visco elastic constant or said other visco elastic constants, said at least one viscosity or said other viscosities, said density, said at least one stress tensor component, said at least one inertia vector component, or said mechanical source, at least a part of the measured strain tensor component data, at least a part of the measured strain rate tensor component data, or at least a part of the measured acceleration vector component data, which is measured over said ROI or partially in advance or set in advance.

9. The clinical apparatus according to claim 2, wherein said data processor is configured to perform calculation by using motion or deformation data, a spatial resolution of which at least in a reference position is made low.

10. The clinical apparatus according to claim 2, wherein calculated values can be set at values based on a priori information, or truncated by respectively set upper or lower values, or interpolated, or extrapolated during the calculation or when the calculation is finalized.

11. The clinical apparatus according to claim 2, wherein motion or deformation data added or subtracted by a direct current is used when a sign of a value changes in the ROI.

12. The clinical apparatus according to claim 2, wherein said at least one elastic constant or said other elastic constants, said at least one visco elastic constant or said other visco elastic constants, said at least one viscosity or said other viscosities, or said density has a property of anisotropy or nonlinearity.

13. The clinical apparatus according to claim 2, further comprising an output unit which is configured to output at least one of a treatment effect and degeneration information on a part including lesion based on a measured displacement, a displacement vector, a displacement vector component, a strain, a strain tensor, a strain tensor component, a strain rate, a strain rate tensor, a strain rate tensor component, a velocity, a velocity vector, a velocity vector component, an acceleration, an acceleration vector, an acceleration vector component, the calculated stress, the pressure, said mechanical source, said at least one elastic constant or said other elastic constants, said at least one visco elastic constant or said other visco elastic constants, said at least one viscosity or said other viscosities, said density, said at least one stress tensor component, or said at least one inertia vector component.

14. The clinical apparatus according to claim 2, wherein said data processor is configured to estimate at least one of consumed or elastic energy, a time course of consumed or elastic energy, a temperature, a time course of temperature, a composition rate in weight, and a time course of composition rate in weight based on conversion data about said at least one elastic constant or said other elastic constants, said at least one visco elastic constant or said other visco elastic constants, said at least one viscosity or said other viscosities, said density, a delay time, a relaxation time, the stress, the pressure, said mechanical source, said at least one stress tensor component, said at least one inertia vector component, a strain, a strain tensor, a strain tensor component, a strain rate, a strain rate tensor, a strain rate tensor component, an expansion or shrink, changes thereof versus consumed or elastic energy, a change of consumed or elastic energy, a temperature, a change of temperature, a composition rate in weight, or a change of composition rate in weight.

15. The clinical apparatus according to claim 2, further comprising a display which is configured to display, as one of a static image and a motion image and one of a color image and a gray image, an image of a measured displacement, a displacement vector, a displacement vector component, a velocity, a velocity vector, a velocity vector component, a strain, a strain tensor, a strain tensor component, a strain rate, a strain rate tensor, a strain rate tensor component, an acceleration, an acceleration vector, an acceleration vector component, the calculated stress, the pressure, said mechanical source, said at least one elastic constant or said other elastic constants, said at least one visco elastic constant or said other visco elastic constants, said at least one viscosity or said other viscosities, said density, a delay time, a relaxation time, said at least one stress tensor component, said at least one inertia vector component, elastic energy, consumed energy, accumulation of energy, a temperature, a composition rate in weight, gradient, Laplacian, a first temporal derivative, a second temporal derivative, frequency variance, relative change, absolute change, truncated one by an upper or lower limit value, direct-current-added one, direct-current-subtracted one, reciprocal one, log-scaled one, or one of those superimposed on one of an ultrasound image and an NMR (nuclear magnetic resonance) image.

16. The clinical apparatus according to claim 2, wherein said data processor is configured to calculate the stress, the pressure, said mechanical source, said at least one elastic constant or said other elastic constants, said at least one visco elastic constant or said other visco elastic constants, said at least one viscosity or said other viscosities, said density, said at least one stress tensor component, or said at least one inertia vector component under an assumption or condition of a local homogeneity of at least one calculation target within the ROI.

17. The clinical apparatus according to claim 2, wherein said data processor is configured to simultaneously calculate said at least one elastic constant or said other elastic constants, said at least one visco elastic constant or said other visco elastic constants, said at least one viscosity or said other viscosities, said density, said at least one stress tensor component, said at least one inertia vector component, or said mechanical source in addition to said at least one of the stress and the pressure of said at least one arbitrary point within the ROI by further utilizing second reference data representing (i) at least one second reference value about said mechanical source, said at least one elastic constant or said other elastic constants, said at least one visco elastic constant or said other visco elastic constants, said at least one viscosity or said other viscosities, or said density, and (ii) at least one reference position that has said at least one second reference value, said second reference data, except for said mechanical source, being provided in at least one region that crosses a dominant deformation direction of the ROI.

18. The clinical apparatus according to claim 17, wherein said at least one second reference value is set in advance and has a unity or one of arbitrary finite values.

19. The clinical apparatus according to claim 1, further comprising a high intensity focus vibrator as a mechanical source configured to generate at least one of a motion, a deformation, and a vibration in the target.

20. The clinical apparatus according to claim 1, further comprising at least one of a treatment modality and a use of medicine.

21. The clinical apparatus according to claim 1, wherein said at least one sensor includes an ultrasound transducer which is configured to serve as at least one of:
   a diagnosis transducer configured to observe the target,
   a high intensity focus vibrator configured to generate a deformation, and
   a high intensity focus ultrasound applicator for a thermal treatment.

22. The clinical apparatus according to claim 1, further comprising a controller which is configured to control a frequency of at least one of a thermal source and a thermal sink to set one of a thermal-treatment region and a cryo-treatment region.

23. The clinical apparatus according to claim 22, wherein the controller is configured to also use at least one thermal property of the target to set one of the thermal-treatment region and the cryo-treatment region.

24. The clinical apparatus according to claim 1, wherein said data processor is configured to calculate said Poisson's ratio or said at least one of said at least one elastic constant, said at least one visco elastic constant, and said at least one viscosity, which expresses said at least one of the stress and the pressure, using a measured volume strain or a measured volume strain rate expressing said at least one of the stress and the pressure after completing the linear and direct calculation of said at least one of the stress and the pressure of said at least one arbitrary point within the ROI.

25. The clinical apparatus according to claim 1, wherein said at least one of the stress and the pressure is combined with each other, or the stress is combined with at least one of a different stress and a pressure, or the pressure is combined with at least one of a different pressure and a stress.

26. A clinical apparatus comprising:
   at least one sensor which is configured to sense one selected from a group consisting of an ultrasound signal, a magnetic nuclear resonance signal, an electromagnetic wave, and light;
   a storage which is configured to store at least one of strain tensor component data, strain rate tensor component data, and acceleration vector component data measured in a ROI (region of interest) set in a target by using said at least one sensor; and
   a data processor which is configured to calculate at least one of a stress and a pressure of at least one arbitrary point within the ROI without utilizing reference data representing at least one reference value about at least one of the stress and the pressure and at least one reference position that has said at least one reference value, the pressure being a mean of normal stress tensor components, and each of the stress and the pressure being expressed using at least one product of at least one elastic constant and a volume strain, at least one product of at least one visco elastic constant and a volume strain rate, or at least one product of at least one viscosity and a volume strain rate;
   wherein said data processor is configured to linearly and directly calculate said at least one of the stress and the pressure while setting to unknown a Poisson's ratio or at least one of said at least one elastic constant, said at least one visco elastic constant, and said at least one viscosity, which expresses said at least one of the stress and the pressure, by implementing one of an iterative method and a finite element method on at least one equation representing a relation between (i) said at least one of the stress and the pressure, (ii) at least one of other stresses that is at least one stress tensor component expressed using at least one product of said at least one elastic constant or other elastic constants and the measured strain tensor component data, at least one product of said at least one visco elastic constant or other visco elastic constants and the measured strain rate tensor component data, or at least one product of said at least one viscosity or other viscosities and the measured strain rate tensor component data, (iii) when the arbitrary point within the ROI has a non-zero acceleration vector, at least one inertia vector component expressed using a product of a density and the measured acceleration vector component data, and (iv) when the arbitrary point within the ROI has a mechanical source, the mechanical source.

27. The clinical apparatus according to claim 26, wherein said data processor is configured to simultaneously calculate said at least one elastic constant or said other elastic constants, said at least one visco elastic constant or said other visco elastic constants, said at least one viscosity or said other viscosities, said density, said at least one stress tensor component, said at least one inertia vector component, or said mechanical source in addition to said at least one of the stress and the pressure of said at least one arbitrary point within the ROI by utilizing given reference data representing (i) at least one given reference value about said mechanical source, said at least one elastic constant or said other elastic constants, said at least one visco elastic constant or said other visco elastic constants, said at least one viscosity or said other viscosities, or said density, and (ii) at least one reference position that has said at least one given reference value, said given reference data, except for said mechanical source, being provided in at least one region that crosses a dominant deformation direction of the ROI.

28. The clinical apparatus according to claim 27, wherein said at least one given reference value is set in advance and has a unity or one of arbitrary finite values.

29. The clinical apparatus according to claim 26, wherein said at least one of the stress and the pressure is combined with each other, or the stress is combined with at least one of a different stress and a pressure, or the pressure is combined with at least one of a different pressure and a stress.

* * * * *